US010653791B2

(12) United States Patent
Lonberg et al.

(10) Patent No.: US 10,653,791 B2
(45) Date of Patent: May 19, 2020

(54) ANTIBODIES COMPRISING MODIFIED HEAVY CONSTANT REGIONS

(71) Applicant: BRISTOL-MYERS SQUIBB COMPANY, Princeton, NJ (US)

(72) Inventors: Nils Lonberg, Woodside, CA (US); Alan J. Korman, Piedmont, CA (US); Mark J. Selby, San Francisco, CA (US); Bryan C. Barnhart, Philadelphia, PA (US); Aaron P. Yamniuk, Lawrenceville, NJ (US); Mohan Srinivasan, Cupertino, CA (US); Karla A. Henning, Milpitas, CA (US); Michelle Minhua Han, Piedmont, CA (US); Ming Lei, Princeton, NJ (US); Liang Schweizer, Shanghai (CN); Sandra V. Hatcher, Hillsborough, NJ (US); Arvind Rajpal, San Francisco, CA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 282 days.

(21) Appl. No.: 15/520,954

(22) PCT Filed: Nov. 19, 2015

(86) PCT No.: PCT/US2015/061632
§ 371 (c)(1),
(2) Date: Apr. 21, 2017

(87) PCT Pub. No.: WO2016/081746
PCT Pub. Date: May 26, 2016

(65) Prior Publication Data
US 2018/0333502 A1 Nov. 22, 2018

Related U.S. Application Data

(60) Provisional application No. 62/083,021, filed on Nov. 21, 2014.

(51) Int. Cl.
*C07K 16/00* (2006.01)
*C07K 16/28* (2006.01)
*C07K 16/30* (2006.01)
*A61K 47/68* (2017.01)
*A61K 39/395* (2006.01)

(52) U.S. Cl.
CPC ...... *A61K 47/6803* (2017.08); *A61K 39/3955* (2013.01); *C07K 16/00* (2013.01); *C07K 16/2878* (2013.01); *C07K 16/2896* (2013.01); *C07K 16/30* (2013.01); *C07K 2317/522* (2013.01); *C07K 2317/524* (2013.01); *C07K 2317/53* (2013.01); *C07K 2317/71* (2013.01); *C07K 2317/72* (2013.01); *C07K 2317/75* (2013.01); *C07K 2317/77* (2013.01); *C07K 2317/92* (2013.01)

(58) Field of Classification Search
CPC .............. C07K 16/00; C07K 2317/524; C07K 2317/53; C07K 2317/522; C07K 2317/77; C07K 2317/75; C07K 2317/66; C07K 2317/71; C07K 2317/73; C07K 2317/732; C07K 2317/734
See application file for complete search history.

(56) References Cited

U.S. PATENT DOCUMENTS

| 5,624,821 | A  | 4/1997  | Winter et al.   |
|-----------|-----|---------|-----------------|
| 5,677,425 | A  | 10/1997 | Bodmer et al.   |
| 6,737,056 | B1 | 5/2004  | Presta          |
| 6,861,225 | B1 | 3/2005  | Bertha et al.   |
| 6,896,885 | B2 | 5/2005  | Hanna           |
| 7,148,321 | B2 | 12/2006 | Gillies et al.  |
| 7,247,302 | B1 | 7/2007  | Rosok et al.    |

(Continued)

FOREIGN PATENT DOCUMENTS

| CN | 103278634 A  | 9/2013  |
|----|--------------|---------|
| EP | 0347433 A1   | 12/1989 |

(Continued)

OTHER PUBLICATIONS

Mayes et al., Nature reviews Drug Discovery 17: 509-527 (Year: 2018).*
Sult, E. et al., "Checkpoint inhibitor combinations in a human mixed leukocyte reaction," Proceedings of the 106th Annual Meeting of the American Association for Cancer Research? Apr. 18-22, 2015? Philadelphia, PA. Philadelphia (PA): AARC 2015, Abstract No. 272, 2 pages.
Tao, MH et al., "Structural features of human immunoglobulin G that determine isotype-specific differences in complement activation," J Exp Med, vol. 178(2), pp. 661-667 (1993).

(Continued)

*Primary Examiner* — Phuong Huynh
(74) *Attorney, Agent, or Firm* — Nelson Mullins Riley & Scarborough LLP; Jane E. Remillard, Esq.; Jeanne M. DiGiorgio, Esq.

(57) ABSTRACT

Provided herein are heavy chain constant regions (referred to as "modified heavy chain constant regions"), or functionally equivalent fragments thereof, that enhance biological properties of antibodies relative to the same antibodies in unmodified form. An exemplary modified heavy chain constant region includes an IgG2 hinge and three constant domains (i.e., CH1, CH2, and CH3 domains), wherein one or more of the constant region domains are of a non-IgG2 isotype (e.g., IgG1, IgG3 or IgG4). The heavy chain constant region may comprise wildtype human IgG domain sequences, or variants of these sequences. Also provided herein are methods for enhancing certain biological properties of antibodies that comprise a non-IgG2 hinge, such as internalization, agonism and antagonism, wherein the method comprises replacing the non-IgG2 hinge of the antibody with an IgG2 hinge.

6 Claims, 38 Drawing Sheets

Specification includes a Sequence Listing.

(56) References Cited

U.S. PATENT DOCUMENTS

| | | |
|---|---|---|
| 7,597,889 B1 | 10/2009 | Armour et al. |
| 7,741,072 B2 | 6/2010 | Idusogie et al. |
| 7,927,594 B2 | 4/2011 | Rosenthal et al. |
| 8,066,994 B2 | 11/2011 | Gillies et al. |
| 8,101,720 B2 | 1/2012 | Lazar et al. |
| 8,399,618 B2 | 3/2013 | Lazar et al. |
| 8,562,986 B2 | 10/2013 | Goodman et al. |
| 8,637,641 B2 * | 1/2014 | Dahiyat ............... C07K 16/00 530/387.1 |
| 8,728,469 B2 | 5/2014 | Thompson et al. |
| 8,735,553 B1 | 5/2014 | Li et al. |
| 8,883,147 B2 | 11/2014 | Lazar et al. |
| 8,961,967 B2 | 2/2015 | Strohl et al. |
| 9,605,080 B2 | 3/2017 | Lonberg et al. |
| 10,100,129 B2 | 10/2018 | Lonberg et al. |
| 10,167,343 B2 | 1/2019 | Lonberg et al. |
| 2003/0109690 A1 | 6/2003 | Ruben et al. |
| 2004/0031072 A1 | 2/2004 | La Rosa et al. |
| 2004/0146516 A1 | 7/2004 | Roben et al. |
| 2006/0134105 A1 | 6/2006 | Lazar et al. |
| 2006/0263856 A1 * | 11/2006 | Gillies ............... C07K 16/30 435/69.7 |
| 2007/0042392 A1 | 2/2007 | Tang et al. |
| 2007/0184444 A1 | 8/2007 | Abbas et al. |
| 2009/0203538 A1 | 8/2009 | Sugioka et al. |
| 2010/0209942 A1 | 8/2010 | Jalkanen et al. |
| 2010/0226925 A1 * | 9/2010 | Dillon ............... C07K 16/00 424/141.1 |
| 2010/0298542 A1 | 11/2010 | Igawa et al. |
| 2011/0059078 A1 | 3/2011 | Coyle et al. |
| 2011/0212087 A1 | 9/2011 | Strohl et al. |
| 2011/0229459 A1 | 9/2011 | Kuramochi et al. |
| 2011/0245090 A1 | 10/2011 | Abbas et al. |
| 2011/0245473 A1 | 10/2011 | Igawa et al. |
| 2012/0065379 A1 | 3/2012 | Igawa et al. |
| 2012/0071634 A1 | 3/2012 | Igawa et al. |
| 2012/0128677 A1 | 5/2012 | Domon et al. |
| 2012/0238729 A1 | 9/2012 | Kuramochi et al. |
| 2013/0052160 A1 | 2/2013 | Zitvogel et al. |
| 2013/0101581 A1 | 4/2013 | Kuramochi et al. |
| 2013/0144041 A1 | 6/2013 | Dillon et al. |
| 2013/0156790 A1 | 6/2013 | Zitvogel et al. |
| 2013/0217033 A1 | 8/2013 | Jalkanen et al. |
| 2013/0317201 A1 | 11/2013 | Ishii et al. |
| 2013/0317203 A1 | 11/2013 | Igawa et al. |
| 2014/0235833 A1 | 8/2014 | Sugioka et al. |
| 2014/0371427 A1 | 12/2014 | Dillon et al. |
| 2015/0030534 A1 | 1/2015 | Howell et al. |
| 2015/0071948 A1 | 3/2015 | Lazar et al. |
| 2016/0129108 A1 | 5/2016 | Sachsenmeier et al. |
| 2016/0145350 A1 | 5/2016 | Lonberg et al. |
| 2017/0253665 A1 | 9/2017 | Lonberg et al. |
| 2018/0127513 A1 | 5/2018 | Lonberg et al. |
| 2019/0055320 A1 | 2/2019 | Lonberg et al. |
| 2019/0062456 A1 | 2/2019 | Lonberg et al. |
| 2019/0284293 A1 | 9/2019 | Lonberg et al. |

FOREIGN PATENT DOCUMENTS

| | | |
|---|---|---|
| EP | 1068241 A1 | 1/2001 |
| EP | 1075496 A1 | 2/2001 |
| EP | 1283722 A1 | 2/2003 |
| EP | 1366067 A2 | 12/2003 |
| EP | 1746107 A2 | 1/2007 |
| EP | 2014675 A1 | 1/2009 |
| EP | 2078732 A1 | 7/2009 |
| EP | 2182006 A2 | 5/2010 |
| EP | 2194066 A1 | 6/2010 |
| EP | 2197911 A2 | 6/2010 |
| EP | 2201376 A1 | 6/2010 |
| EP | 2206775 A1 | 7/2010 |
| EP | 2409991 A1 | 1/2012 |
| EP | 2481752 A1 | 8/2012 |
| EP | 2503338 A2 | 9/2012 |
| EP | 2506871 A1 | 10/2012 |
| EP | 2561088 A1 | 2/2013 |
| EP | 2784091 A1 | 10/2014 |
| EP | 2788097 A2 | 10/2014 |
| WO | 8901974 A1 | 3/1989 |
| WO | 99/51642 A1 | 10/1999 |
| WO | 99/58572 A1 | 11/1999 |
| WO | 00/42072 A2 | 7/2000 |
| WO | 00067796 A1 | 11/2000 |
| WO | 01/46261 A1 | 6/2001 |
| WO | 2001/46232 A2 | 6/2001 |
| WO | 2001/46261 A1 | 6/2001 |
| WO | 01/074388 A1 | 10/2001 |
| WO | 01090493 A1 | 11/2001 |
| WO | 02/04613 A2 | 1/2002 |
| WO | 02072605 A2 | 9/2002 |
| WO | 2004/079013 A1 | 9/2004 |
| WO | 05/007809 A2 | 1/2005 |
| WO | 2005/016962 A2 | 2/2005 |
| WO | 2005/019258 A2 | 3/2005 |
| WO | 05073732 A2 | 8/2005 |
| WO | 06/047350 A2 | 5/2006 |
| WO | 06047340 A2 | 5/2006 |
| WO | 06075668 A1 | 7/2006 |
| WO | 07148417 A1 | 12/2007 |
| WO | 08/007648 A1 | 1/2008 |
| WO | 2008/070593 A2 | 6/2008 |
| WO | 09010290 A2 | 1/2009 |
| WO | 09036209 A2 | 3/2009 |
| WO | 09041613 A1 | 4/2009 |
| WO | 09053523 A1 | 4/2009 |
| WO | 2009041613 A1 | 4/2009 |
| WO | 2009041621 A1 | 4/2009 |
| WO | 2009053368 A1 | 4/2009 |
| WO | 10107110 A1 | 9/2010 |
| WO | 11037158 A1 | 3/2011 |
| WO | 11052799 A1 | 5/2011 |
| WO | 2011066501 A1 | 6/2011 |
| WO | 2011/120134 A1 | 10/2011 |
| WO | 11131246 A1 | 10/2011 |
| WO | 11131472 A1 | 10/2011 |
| WO | 12007783 A1 | 1/2012 |
| WO | 2012012736 A2 | 1/2012 |
| WO | 12031320 A1 | 3/2012 |
| WO | 13086448 A2 | 6/2013 |
| WO | 2013/112986 A1 | 8/2013 |
| WO | 2014003553 A1 | 1/2014 |
| WO | 2014153424 A1 | 9/2014 |
| WO | 2015/145360 A1 | 10/2015 |
| WO | 2015/164573 A1 | 10/2015 |
| WO | 2015/187835 A2 | 12/2015 |
| WO | 16055609 A1 | 4/2016 |
| WO | 2016/081746 A2 | 5/2016 |
| WO | 2016/081748 A2 | 5/2016 |
| WO | 16075099 A1 | 5/2016 |
| WO | 16075176 A1 | 5/2016 |
| WO | 2017/152085 A1 | 9/2017 |
| WO | 2019/200256 A1 | 10/2019 |

OTHER PUBLICATIONS

Tao, MH., "The differential ability of human IgG1 and IgG4 to activate complement is determined by the COOH-terminal sequence of the CH2 domain," J Exp Med., vol. 173(4), pp. 1025-1028 (1991).

Terp, M.G. et al.,"Anti-Human CD73 Monoclonal Antibody Inhibits Metastasis Formation in Human Breast Cancer by Inducing Clustering and Internalization of CD73 Expressed on the Surface of Cancer Cells," The Journal of Immunology, vol. 191(8):4165-4173.

Third Party Observation, PCT/US2015/061632, dated Mar. 21, 2017, 8 pages.

Thomson, L. et al., "Purification of 5'-nucleotidase from human placenta after release from plasma membranes by phosphatidylinositol-specific phospholipase C," Biochem Biophys Res Commun, vol. 145(1), pp. 118-125 (1987).

Thomson, L.F. et al., "Production and characterization of monoclonal antibodies to the glycosyl phosphatidylinositol-anchored lym-

(56) References Cited

OTHER PUBLICATIONS phocyte differentiation antigen ecto-5'-nucleotidase (CD73)," Tissue Antigens, vol. 35(1), pp. 9-19 (1990).
Vafa, O. et al., "An engineered Fc variant of an IgG eliminates all immune effector functions via structural perturbations," Methods, vol. 65(1):95-110 (2014).
White, A. et al., "Conformation of the human immunoglobulin G2 hinge imparts superagonistic properties to immunostimulatory anti-cancer antibodies," Cancer Cell., vol. 27(1), pp. 138-148 (2015).
Whiteside et al., "Disarming suppressor cells to improve immunotherapy," Cancer Immunol. Immunother, vol. 61, pp. 283-288 (2012).
Xu, Y. et al., "Residue at position 331 in the IgG1 and IgG4 CH2 domains contributes to their differential ability to bind and activate complement," Journal of Biological Chemistry, vol. 269(5): 3469-3474 (1994).
Xu, Y. et al., The N-Terminal Sequence of the CH2 Domain Controls the Differential Ability of Human IgG 1 and IgG2 to Activate Complement, J. of Immunol., vol. 150, Abstract 862, p. 152A (1993).
Young, A. et al., "Targeting Cancer-Derived Adenosine: New Therapeutic Approaches," Cancer Discovery, vol. 4, pp. 879-888 (2014).
Zhang , B., "CD73: A novel target for cancer immunotherapy," Cancer Res., vol. 70(16), pp. 6407-6411 (2010).
Zhang, B., "Opportunities and challenges for anti-CD73 cancer therapy," Immunotherapy, vol. 4(9), pp. 861-865 (2012).
Zhi, X. et al., "RNA interference of ecto-5'-nucleotidase (CD73) inhibits human breast cancer cell growth and invasion," Clin. Exp. Metastasis, vol. 24, pp. 439-448 (2007).
Allard, B. et al., "Targeting CD73 and downstream adenosine receptor signaling in triple-negative breast cancer," Expert Opinion Ther Targets, vol. 18 (Issue 7), pp. 1-19 (2014).
Allard, B. et al., "Targeting CD73 enhances the antitumor activity of anti-PD-1 and anti-CTLA-4 mAbs," Clin Cancer Res, pp. 5626-5635 (Oct. 15, 2013 ).
Allen, M. et al., "Interchain disulfide bonding in human IgG2 antibodies probed by site-directed mutagenesis," Biochemistry, vol. 48 (17), pp. 3755-3766 (Mar. 2009).
Armour, K. et al., "Recombinant Human IgG Molecules lacking FCy receptor I binding and monocyte triggering activiites," Eur. J. Immunol., vol. 29, pp. 2613-2624 (1999).
Barnhart, B. et al., "A Therapeutic Antibody that Inhibits CD73 Activity by Dual Mechanisms," Bristol-Myers Squibb, AACR Annual Meeting 2016, Apr. 16-20, 2016, New Orleans, Louisiana, USA, Abstract No. 1476, 1 page.
Barnhart, B., "Antibody Inhibition of CD73 Activity by Multiple Mechanisms for Tumor Therapy," Bristol-Myers Squibb, Apr. 14, 2016, Presentation Slides, 19 pages.
Beavis et al. "CD73: a potent suppressor of antitumor immune responses," Trends in Immunol., vol. 33(5), pp. 231-237 (2012).
Beavis, P. et al., "A2A blockade enhances anti-metastatic immune responses," OncoImmunology, vol. 2(12), e26705-1-e26705-3 (2013).
Brekke, O. et al., "Human IgG isotype-specific amino acid residues affecting complement-mediated cell lysis and phagocytosis," Eur. J. Immunol, vol. 24, pp. 2542-2547 (1994).
Buisseret, L. et al., "CD73 Expression on Tumor-infiltrating Breast Cancer Leukocytes," Proceedings of the 106th Annual Meeting of the American Association for Cancer Research? Apr. 18-22, 2015? Philadelphia, PA. Philadelphia (PA): AARC 2015, Poster Presentation, Abstract No. 3361, 1 page.
Canfield, S. et al., "The binding affinity of human IgG for its high affinity Fc receptor is determined by multiple amino acids in the CH2 domain and is modulated by the hinge region.," J. Exp. Med., vol. 173, pp. 1483-1491 (1991).
Chappel, S. et al., "Identification of the Fcy receptor class I binding site in human IgG through the use of recombinant IgG1/IgG2 hybrid and point-mutated antibodies," PNAS, vol. 88, pp. 9036-9040 (1991).
Dillon, T.et al., "Development of an analytical reversed-phase high-performance liquid chromatography-electrospray ionization mass spectrometry method for characterization of recombinant antibodies," J. Chromatogr. A, vol. 1053, pp. 299-305 (2004).
Fukunaga, Y. et al., "Increased density of ecto 5' nucleotidase antigen on leukemic T cells from patients with cutaneous T-cell lymphoma and adult T-cell leukemia/lymphoma," Blood, vol. 74(7), pp. 2486-2492 (1989).
Geoghegan, JC et al., "Inhibition of CD73 AMP hydrolysis by a therapeutic antibody with a dual, non-competitive mechanism of action," MAbs, vol. 8 (3): 454-467 (2016) doi: 10.1080/19420862. 2016.1143182. Epub Feb 8, 2016.
Greenwood, J. et al., "Structural motifs involved in human IgG antibody effector functions," Eur J Immol, vol. 23 (5), pp. 1098-1104 (1993).
Gross, J. et al., "TACI-Ig neutralizes molecules critical for B cell development and autoimmune disease. impaired B cell maturation in mice lacking BLyS.," Immunity, vol. 15, pp. 289-302 (2001).
Gutensohn, W. et al., "Production and properties of monoclonal Abs against human ecto-5'-nucloeotidase," Advances in Exp. Med. & Biol., vol. 195, pp. 385-389 (1986).
Hausler, SF., et al., "Anti-CD39 and anti-CD73 antibodies A1 and 7G2 improve targeted therapy in ovarian cancer by blocking adenosine-dependent immune evasion," Am J Transl Res., vol. 6(2), pp. 129-139 (2014).
Hay, C. et al., MEDI9447: enhancing anti-tumor immunity by targeting CD73 in the tumor microenvironment, Proceedings of the 106th Annual Meeting of the American Association for Cancer Research? Apr. 18-22, 2015? Philadelphia, PA. Philadelphia(PA): AARC 2015, Abstract No. 285, 2 pages.
Huang, Q. et al., "Levels and enzyme activity of CD73 in primary samples from cancer patients," Proceedings of the 106th Annual Meeting of the American Association for Cancer Research? Apr. 18-22, 2015?Philadelphia, PA. Philadelphia(PA): AARC 2015,Poster Presentation, Abstract No. 1538, 2 pages.
International Preliminary Report on Patentability, PCT/US2015/061632, dated May 23, 2017, 17 pages.
International Preliminary Report on Patentability, PCT/US2015/061639, dated May 23, 2017, 18 pages.
International Search Report and Written Opinion, PCT/US2015/061632, dated Jul. 7, 2016, 26 pages.
International Search Report and Written Opinion, PCT/US2017/020714, dated Jul. 11, 2017, 21 pages.
International Search Report, PCT/US2015/061639, dated Jul. 18, 2018, 31 pages.
Jin, D. et al., "CD73 on tumor cells impairs antitumor T-cell responses: a novel mechanism of tumor-induced immune suppression," Cancer Res., vol. 70(6), 2245-2255 (2 page Supplement data) (2010).
Kai, M. et al., "Switching Constant Domains Enhances Agonist Activities of Antibodies to a Thrombopoietin Receptor," Nature Biotechnology, vol. 26(2), pp. 209-211 (2008).
Klemens, M. et al., "Characterization of soluble vs membrane-bound human placental 5'-nucleotidase," Biochem Biophys Res Commun.,vol. 172(3), pp. 1371-1377 (1990).
Kummer, U. et al. "Development and properties of a monoclonal Ab specific for human Ecto-5'-nucleotidase," Immunobiology, vol. 166, pp. 203-211 (1984).
Lau, C. et al., "Chimeric Anti-CD14 IGG2/4 Hybrid Antibodies for Therapeutic Intervention in Pig and Human Models of Inflammation," The Journal of Immunology, vol. 191(9):4769-4777 (2013).
Lightle, S. et al., "Mutations within a human IgG2 antibody form distinct and homogeneous disulfide isomers but do not affect Fc gamma receptor or C1q binding," Protein Sci, vol. 19(4), pp. 753-762 (2010).
Martinez, T. et al., "Disulfide connectivity of human immunoglobulin G2 structural isoforms," Biochemistry, vol. 47(26), pp. 7496-7508 (May 2008).
Misumi, Y., et al., "Primary structure of human placental 5'-nucleotidase and identification of the glycolipid anchor in the mature form," (Fukuoka Univ., Jp), Eur J Biochem., vol. 191(3), pp. 563-569. (1990).
Mittal, D. et al., "Antimetastatic effects of blocking PD-1 and the adenosine A2A receptor," vol. 74(14) Cancer Res, pp. 3652-3658 (Jul. 2014).

(56) References Cited

OTHER PUBLICATIONS

Morgan, A. et al., "The N-terminal end of the CH2 domain of chimeric human IgG1 anti-HLA-DR is necessary for C1q, Fc gamma RI and Fc gamma RIII binding," Immunology, vol. 86 (2), pp. 319-324 (1995).
Morrison, S. et al., "Structural Determinants of Human IgG Function," Immunologist, vol. 2, pp. 119-124 (1994).
Moulard, M. et al., "How Validated Receptor Occupancy Flow Cytometry Assays Can Impact Decisions and Support Drug Development," Cytometry Part B (Clinical Cytometry, vol. 90B (2):150-158 (2015), XP055383541, US ISSN: 1552-4949, DOI: 10.1002/cyto.b.21320.
NCBI Reference Sequence NP_001191742.1, 4 pages (2012).
Nielsen, UB et al., "Internalizing antibodies and targeted cancer therapy: direct selection from phage display libraries," PSTT, vol. 3(8), pp. 282-291 (2000).
Resta, R. et al., "Murine ecto-5'-nucleotidase (CD73): cDNA cloning and tissue distribution," Gene, vol. 133(2), pp. 171-177 (1993) Abstract.
Resta, R. et al., "T cell signalling through CD73," Cell Signal, vol. 9(2), pp. 131-139 (1997).
Rother, R. et al., "Discovery and Development of the Complement Inhibitor Exulizmab for the Treatment of Paroxysmal Nocturnal Hemoglobinuria," Nature Biotechnology, vol. 25(11):1256-1264 (2007).
Rust, S. et al., "Combining phenotypic and proteomic approaches to identify membrane targets in a 'triple negative' breast cancer cell type," Molecular Cancer, vol. 12(11), pp. 1-11 (2013).
Sachsenmeier, K. et al., "Development of a Novel Ectonucleotidase Assay Suitable for High-Throughput Screening," Journal of Biomolecular Screening, vol. 17(7), pp. 993-998 (2012).
Shields, RL., "High resolution mapping of the binding site on human IgG1 for Fc gamma RI, Fc gamma RII, Fc gamma RIII, and FcRn and design of IgG1 variants with improved binding to the Fc gamma R," J Biol Chem, vol. 276 (9), pp. 6591-6604 (2001).
Spychala J., "Tumor-promoting functions of adenosine," Pharmacology and Therapeutics, vol. 87 (2-3) pp. 161-173 (2000).
Stagg, J. et al., "Anti-CD73 Antibody therapy inhibits breast tumor growth and metastasis," PNAS, vol. 107(4), pp. 1547-1552 (2010).
Stagg, J. et al., "Extracellular adenosine triphosphate and adenosine in cancer," Oncogene, vol. 29 (39), pp. 5346-5358 (2010).
Strater, N. et al., "Ecto-5'-nucleotidase: Structure function Relationships," Purinergic Signalling, vol. 2, pp. 343-350 (2006).
U.S. Appl. No. 16/113,061, filed Aug. 27, 2018, Nils Lonberg.
U.S. Appl. No. 16/117,183, filed Aug. 30, 2018, Nils Lonberg.
U.S. Appl. No. 16/081,115, filed Aug. 30, 2018, Nils Lonberg.
U.S. Appl. No. 15/520,638, filed Apr. 20, 2017, Nils Lonberg.
U.S. Appl. No. 15/432,180, filed Feb. 14, 2017, Nils Lonberg.
U.S. Appl. No. 14/994,828, filed Jan. 13, 2016, Nils Lonberg.
U.S. Appl. No. 14/994,828, Jan. 27, 2017.
U.S. Appl. No. 14/994,828, Nov. 7, 2016.
U.S. Appl. No. 14/994,828, Jul. 14, 2016.
U.S. Appl. No. 14/994,828, May 23, 2016.
International Preliminary Report on Patentability, PCT/US2017/020714, dated Sep. 4, 2018, 11 pages.
International Search Report and Written Opinion, PCT/US2015/061639, dated Jul. 18, 2016, 31 pages.
International Search Report and Written Opinion, PCT/US2018/034446, dated Oct. 15, 2018, 27 pages.
Siu, L. et al., "Preliminary phase 1 profile of BMS-986179, an anti-CD73 antibody, in combination with Nivolumab in Patients with Advanced Solid Tumors," AACR: 2018—first disclosure, 2 pages.
Invitation to Pay Applicable Fees, and, Where Applicable, Protest Fee, PCT/US2018/034446, dated Aug. 21, 2018, 24 pages.
Siu, L. et al., "Preliminary phase 1 profile of BMS-986179, an anti-CD73 antibody, in combination with Nivolumab in Patients with Advanced Solid Tumors," AACR, (CT180), 17 pages (2018).
U.S. Appl. No. 15/432,180, Feb. 16, 2018.
U.S. Appl. No. 15/520,638, Feb. 7, 2018.
Allard B. et al., "The ectonucleotidases CD39 and CD73: Novel checkpoint inhibitor targets," HHS Public Access Author manuscript, pp. 1-47 (2017).
Fong L. et al., "Safety and clinical activity of adenosine A2a receptor (A2aR) antagonist, CPI-444, in anti-PD1/PDL1 treatment-refractory renal cell (RCC) and non-small cell lung cancer (NSCLC) patients," ASCO Annual meeting 2017, 17 pages (2017) Retrieved from the Inter-net:URL:https://www.corvuspharma.com/file.cfm/23/docs/FongASC0173004.FINAL_6.05.2017.pdf.
International Search Report and Written Opinion, PCT/US2019/027219, dated Sep. 2, 2019, 13 pages.
Morello S et al., "Soluble CD73 as biomarker in patients with metastatic melanoma patients treated with nivolumab," Journal of Translation Medicine, vol. 15 (1):pp. 1-9 (2017).
Topalian, S.L. et al., "Survival, Durable Tumor Remission, and Long-Term Safety in Patients With Advanced Melanoma Receiving Nivolumab," Journal of Clinical Oncology, vol. 32(10):1020-1030 (2014).

* cited by examiner

SEC-MALS data for CD73/mAb complexes

| Target | mAb | Molar ratio target:mAb | [mAb] (uM) | [target] (uM) | UV elution time (min) Peak 1 | Peak 2 | Peak 3 | Peak 4 | SEC UV integration by % Peak 1 | Peak 2 | Peak 3 | Peak 4 | MW (kDa) Peak 1 | Peak 2 | Peak 3 | Peak 4 |
|---|---|---|---|---|---|---|---|---|---|---|---|---|---|---|---|---|
| | CD73.10-IgG1.1f | 0:1 | 4 | | ~2.0 | ~14.0 | ~17.3 | | 0.3 | 0.3 | 99.4 | | n/a | 62 | 140 | |
| | CD73.10-IgG2-C219S | 0:1 | 4 | | ~2.0 | ~17.5 | | | 0.1 | 99.5 | | | 73 | 150 | | |
| | CD73.3-IgG1.1f | 0:1 | 4 | | ~16.3 | | | | 100.0 | | | | 150 | | | |
| | 11F11-Fab | 0:1 | 8 | | ~2.0 | ~17.7 | ~20.2 | | 0.8 | 0.6 | 98.7 | | n/a | 19 | 47 | |
| hCD73-his | | 1.0 | | 4 | ~17.1 | ~18.4 | | | 2.8 | 97.2 | | | 280 | 120 | | |
| N-hCD73-his | | 1.0 | | 8 | ~19.3 | | | | 100.0 | | | | 38 | | | |
| hCD73-his | CD73.10-IgG1.1f | 1:1 | 4 | 4 | ~11.7 | ~12.7 | ~16.9 | | 34.2 | 67.2 | 3.0 | | 1100 | 540 | 180 | |
| hCD73-his | CD73.10-IgG2-C219S | 1:1 | 4 | 4 | ~10.3 | ~11.1 | | | 6.4 | 93.3 | | | 110000 | 3400 | | |
| hCD73-his | CD73.3-IgG1.1f | 1:1 | 4 | 4 | ~12.0 | ~13.0 | ~14.8 | | 17.5 | 78.3 | 4.0 | | 960 | 530 | 260 | |
| hCD73-his | 11F11-Fab | 1:2 | 4 | 8 | ~12.6 | ~14.7 | ~16.8 | ~20.1 | 0.9 | 90.7 | 0.8 | 7.7 | 300 | 310 | 85 | 40 |
| N-hCD73-his | CD73.10-IgG1.1f | 2:1 | 4 | 8 | ~14.6 | ~17.1 | | | 86.5 | 13.5 | | | 210 | 140 | | |
| hCD73-his | CD73.10-IgG2-C219S | 2:1 | 4 | 8 | ~14.7 | ~17.3 | | | 87.1 | 12.9 | | | 210 | 150 | | |
| N-hCD73-his | CD73.3-IgG1.1f | 2:1 | 4 | 8 | ~15.3 | ~16.2 | ~19.3 | | 6.4 | 68.7 | 24.9 | | 170 | 160 | 42 | |
| N-hCD73-his | 11F11-Fab | 1:1 | 8 | 8 | ~17.4 | ~20.0 | | | 95.3 | 4.7 | | | 84 | 44 | | |
| hCD73 | | 1.0 | | 2.5 | ~16.9 | | | | 100.0 | | | | 120 | | | |
| hCD73 | CD73.4-hybrid | 1:0.25 | 0.625 | 2.5 | ~11.8 | ~13.4 | ~17.1 | | 42.0 | 21.6 | 36.4 | | 1200 | 520 | 120 | |
| hCD73 | CD73.4-hybrid | 1:0.5 | 1.25 | 2.5 | ~11.7 | ~13.4 | ~17.1 | | 71.9 | 15.8 | 13.4 | | 1900 | 540 | 130 | |
| hCD73 | CD73.4-hybrid | 1:1 | 2.5 | 2.5 | ~11.5 | ~13.4 | ~17.1 | | 95.3 | 1.9 | 2.8 | | 3300 | 1000 | 530 | |
| hCD73 | CD73.4-hybrid | 1:2 | 5 | 2.5 | ~11.7 | ~13.4 | ~15.3 | ~17.1 | 52.5 | 17.7 | 0.6 | 29.3 | 1700 | 500 | 220 | 140 |
| hCD73 | CD73.4-hybrid | 1:4 | 10 | 2.5 | ~11.7 | ~13.4 | ~15.3 | ~17.1 | 24.1 | 16.2 | 1.2 | 58.6 | 1300 | 500 | 200 | 140 |
| hCD73 | | 1.0 | | 2.5 | ~16.9 | ~18.2 | | | 97.6 | 2.4 | | | 120 | 73 | | |
| hCD73 | CD73.4-IgG1.1f | 1:0.25 | 0.625 | 2.5 | ~12.3 | ~13.1 | ~17.1 | | 11.8 | 49.5 | 38.6 | | 830 | 530 | 120 | |
| hCD73 | CD73.4-IgG1.1f | 1:0.5 | 1.25 | 2.5 | ~12.3 | ~13.1 | ~17.1 | ~17.1 | 31.1 | 54.8 | 3.3 | 10.7 | 890 | 540 | 120 | 81 |
| hCD73 | CD73.4-IgG1.1f | 1:1 | 2.5 | 2.5 | ~12.1 | ~12.3 | ~13.1 | ~17.0 | 55.2 | 44.5 | 2.1 | 2.2 | 1100 | 560 | 280 | 160 |
| hCD73 | CD73.4-IgG1.1f | 1:2 | 5 | 2.5 | ~12.3 | ~13.1 | ~15.3 | ~17.0 | 22.3 | 44.1 | 2.8 | 30.7 | 910 | 530 | 210 | 140 |
| hCD73 | CD73.4-IgG1.1f | 1:4 | 10 | 2.5 | ~12.3 | ~13.2 | ~15.3 | ~17.0 | 9.1 | 31.0 | 2.4 | 57.4 | 810 | 510 | 200 | 140 |
| hCD73 | CD73.4-hybrid | 1:1 | 2.5 | 2.5 | ~13.9 | ~14.7 | ~15.9 | ~17.0 | 0.7 | 88.3 | 8.1 | 2.8 | 390 | 210 | 180 | 150 |
| N-hCD73 | CD73.4-IgG1.1f | 1:1 | 2.5 | 2.5 | ~13.4 | ~14.7 | | | 1.7 | 98.3 | | | 360 | 210 | | |
| N-hCD73 | CD73.4-hybrid | 0:1 | 5 | 0 | ~15.9 | ~16.9 | | | 0.4 | 99.6 | | | 290 | 140 | | |
| | CD73.4-IgG1.1f | 0:1 | 5 | 0 | ~14.2 | ~15.9 | ~17.1 | | 0.6 | 1.2 | 98.2 | | 81 | 120 | 140 | |
| hCD73 | CD73.4-IgG2-C219S | 1:1 | 2.5 | 2.5 | ~11.5 | ~13.4 | ~17.3 | | 95.0 | 2.1 | 2.8 | | 3400 | 970 | 480 | |
| hCD73 | CD73.4-IgG2-C219S-IgG1.1f | 1:1 | 2.5 | 2.5 | ~11.5 | ~13.4 | ~17.3 | | 94.7 | 2.3 | 3.0 | | 3600 | 1100 | 580 | |
| hCD73 | CD73.4-IgG1.1f | 1:1 | 2.5 | 2.5 | ~11.7 | ~13.0 | ~15.1 | ~17.0 | 60.0 | 35.3 | 2.3 | 2.5 | 1300 | 550 | 270 | 160 |
| hCD73 | CD73.10-IgG2-C219S | 1:1 | 2.5 | 2.5 | ~11.8 | ~16.9 | | | 96.2 | 3.2 | | | 2000 | 310 | | |
| hCD73 | CD73.10-IgG1.1f | 1:1 | 2.5 | 2.5 | ~11.8 | ~16.9 | | | 95.6 | 2.5 | 0.9 | | 2000 | 320 | 390 | |
| hCD73 | CD73.10-IgG2CS-1.1 | 1:1 | 2.5 | 2.5 | ~12.1 | ~13.0 | ~16.5 | | 35.1 | 62.1 | 2.7 | | 1000 | 530 | 170 | |
| hCD73 | | 1.0 | | 2.5 | ~17.3 | ~18.4 | | | 97.2 | 2.8 | | | 120 | 60 | | |
| hCD73 | CD73.4-IgG2-C219S-IgG1.1f | 1:1 | 5 | 5 | ~11.5 | ~13.4 | ~17.3 | | 93.9 | 2.6 | 3.5 | | 4800 | 1300 | 740 | |
| hCD73 | CD73.4-IgG2-C219S-IgG1.1f | 1:1 | 1 | 1 | ~11.5 | ~13.4 | ~15.0 | ~17.3 | 84.4 | 7.6 | 2.5 | 5.4 | 2900 | 660 | 460 | 240 |

* Molar concentrations are defined as N-hCD73 monomer, 11F11-Fab monomer, hCD73-his dimer, and (bivalent) mAb DLS data for CD73/mAb complexes:

Figure 6

| Target | mAb | Molar ratio target:[uM][mAb] (uM) | | | DLS | | | | | |
|---|---|---|---|---|---|---|---|---|---|---|
| | | | | | Rh | Rh SD | %Pd | %Pd SD | %Mass | %Mass SD |
| hCD73-his | CD73.10-IgG1.1f | 0:1 | | 4 | 5.0 | 0.6 | 11.0 | 6.0 | 100.0 | 0.0 |
| | CD73.10-IgG2-C219S | 0:1 | | 4 | 5.2 | 0.1 | 11.9 | 2.3 | 100.0 | 0.0 |
| | CD73.3-IgG1.1f | 0:1 | | 4 | 5.1 | 0.5 | 11.6 | 6.9 | 100.0 | 0.0 |
| | 11F11-Fab | 0:1 | | 8 | 3.4 | 0.2 | 22.0 | 5.3 | 100.0 | 0.1 |
| hCD73-his | | 1:0 | 4 | | 4.3 | 0.3 | 10.6 | 5.2 | 99.8 | 0.2 |
| N-hCD73-his | | 1:0 | 8 | | 2.3 | 0.2 | 19.3 | 12.3 | 99.9 | 0.2 |
| hCD73-his | CD73.10-IgG1.1f | 1:1 | 4 | 4 | 12.8 | 0.7 | 32.4 | 6.7 | 100.0 | 0.0 |
| hCD73-his | CD73.10-IgG2-C219S | 1:1 | 4 | 4 | 2.9 | 1.5 | 7.5 | 0.8 | 73.9 | 11.5 |
| hCD73-his | CD73.3-IgG1.1f | 1:1 | 4 | 4 | 10.8 | 0.1 | 28.2 | 0.6 | 100.0 | 0.0 |
| hCD73-his | 11F11-Fab | 1:2 | 4 | 8 | 6.4 | 0.1 | 15.1 | 4.3 | 100.0 | 0.0 |
| N-hCD73-his | CD73.10-IgG1.1f | 2:1 | 8 | 4 | 6.6 | 0.3 | 15.3 | 6.5 | 100.0 | 0.0 |
| N-hCD73-his | CD73.10-IgG2-C219S | 2:1 | 8 | 4 | 6.5 | 0.2 | 15.7 | 5.7 | 100.0 | 0.1 |
| N-hCD73-his | CD73.3-IgG1.1f | 2:1 | 8 | 4 | 5.8 | 0.3 | 12.8 | 5.3 | 100.0 | 0.0 |
| N-hCD73-his | 11F11-Fab | 1:1 | 8 | 8 | 4.2 | 0.1 | 12.6 | 4.7 | 100.0 | 0.0 |
| hCD73 | | 1:0 | 2.5 | 0 | 4.5 | 0.1 | 12.3 | 4.3 | 99.9 | 0.2 |
| hCD73 | CD73.4-hybrid | 1:0.25 | 2.5 | 0.625 | 13.2 | 1.7 | 46.5 | 5.9 | 99.9 | 0.1 |
| hCD73 | CD73.4-hybrid | 1:0.5 | 2.5 | 1.25 | 17.5 | 1.0 | 31.7 | 8.8 | 62.6 | 25.8 |
| hCD73 | CD73.4-hybrid | 1:1 | 2.5 | 2.5 | 29.9 | 1.0 | 25.1 | 2.1 | 22.3 | 4.9 |
| hCD73 | CD73.4-hybrid | 1:2 | 2.5 | 5 | 14.4 | 0.1 | 31.3 | 5.5 | 68.7 | 25.8 |
| hCD73 | CD73.4-hybrid | 1:4 | 2.5 | 10 | 11.4 | 0.9 | 42.9 | 3.5 | 90.2 | 17.5 |
| hCD73 | CD73.4-hybrid | 1:0 | 2.5 | 0 | 4.7 | 0.1 | 18.6 | 3.3 | 99.8 | 0.1 |
| hCD73 | CD73.4-IgG1.1f | 1:0.25 | 2.5 | 0.625 | 10.4 | 1.5 | 38.6 | 15.9 | 81.3 | 37.1 |
| hCD73 | CD73.4-IgG1.1f | 1:0.5 | 2.5 | 1.25 | 12.9 | 0.6 | 35.5 | 5.4 | 88.3 | 23.2 |
| hCD73 | CD73.4-IgG1.1f | 1:1 | 2.5 | 2.5 | 14.7 | 0.5 | 34.3 | 3.9 | 100.0 | 0.0 |
| hCD73 | CD73.4-IgG1.1f | 1:2 | 2.5 | 5 | 11.6 | 0.4 | 24.9 | 8.5 | 65.0 | 32.5 |
| hCD73 | CD73.4-IgG1.1f | 1:4 | 2.5 | 10 | 8.1 | 4.0 | 33.0 | 16.9 | 84.2 | 31.7 |
| hCD73 | CD73.4-IgG1.1f | 1:1 | 5 | 2.5 | 6.7 | 0.3 | 13.9 | 7.0 | 100.0 | 0.0 |
| hCD73 | CD73.4-IgG1.1f | 1:1 | 5 | 2.5 | 6.5 | 0.1 | 7.4 | 3.2 | 100.0 | 0.0 |
| N-hCD73 | CD73.4-hybrid | 0:1 | 0 | 5 | 5.4 | 0.2 | 15.7 | 5.7 | 99.9 | 0.1 |
| N-hCD73 | CD73.4-IgG1.1f | 0:1 | 0 | 5 | 5.3 | 0.4 | 13.6 | 7.9 | 100.0 | 0.0 |
| hCD73 | CD73.4-IgG2-C219S-IgG1.1f | 1:1 | 2.5 | 2.5 | 31.7 | 2.4 | 31.6 | 11.4 | 19.3 | 12.2 |
| hCD73 | CD73.4-IgG1.1f | 1:1 | 2.5 | 2.5 | 31.2 | 0.9 | 30.8 | 3.8 | 17.5 | 11.4 |
| hCD73 | CD73.10-IgG2-C219S | 1:1 | 2.5 | 2.5 | 15.6 | 1.2 | 32.7 | 8.0 | 100.0 | 0.0 |
| hCD73 | CD73.10-IgG2CS-1.1 | 1:1 | 2.5 | 2.5 | 23.9 | 1.2 | 26.7 | 4.4 | 36.3 | 5.3 |
| hCD73 | CD73.10-IgG1.1f | 1:1 | 2.5 | 2.5 | 25.6 | 2.3 | 30.1 | 8.8 | 35.9 | 9.1 |
| hCD73 | | 1:0 | 2.5 | 0 | 13.5 | 1.2 | 31.6 | 12.0 | 83.2 | 31.5 |
| hCD73 | | 1:1 | 2.5 | 2.5 | 4.2 | 0.8 | 24.4 | 12.8 | 99.1 | 0.7 |
| hCD73 | CD73.4-IgG2-C219S-IgG1.1f | 1:1 | 5 | 5 | 35.3 | 3.8 | 35.2 | 13.9 | 6.7 | 4.4 |
| hCD73 | CD73.4-IgG2-C219S-IgG1.1f | 1:1 | 1 | 1 | 25.5 | 3.2 | 32.9 | 2.9 | 60.7 | 27.5 |

* Molar concentrations are defined as N-hCD73 monomer, 11F11-Fab monomer, hCD73-his dimer, and (bivalent) mAb

Figure 7

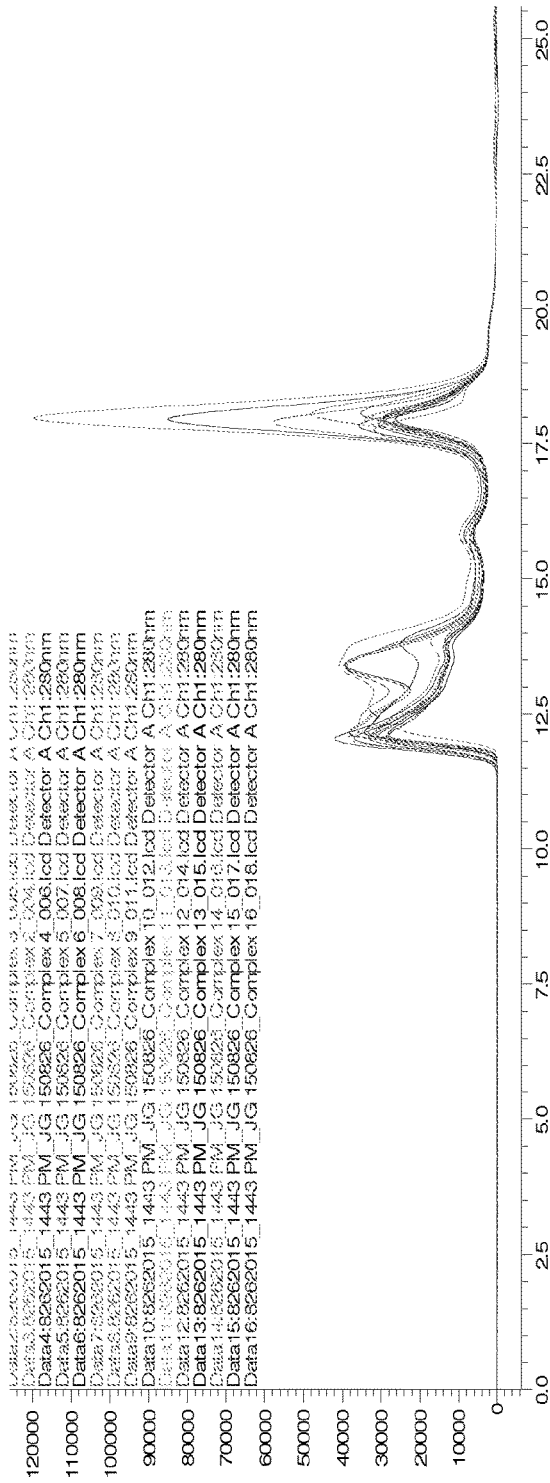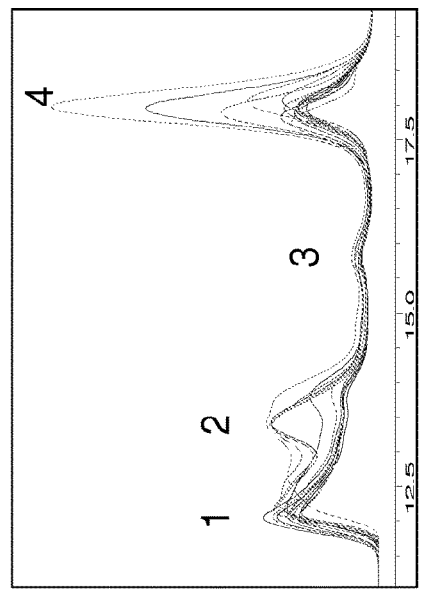
Figure 11

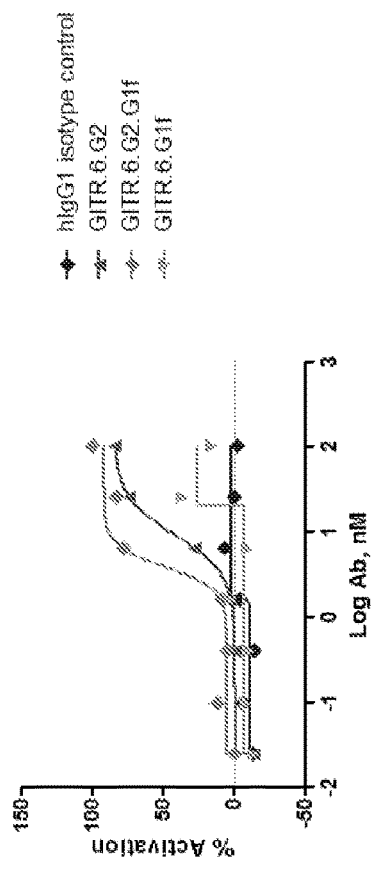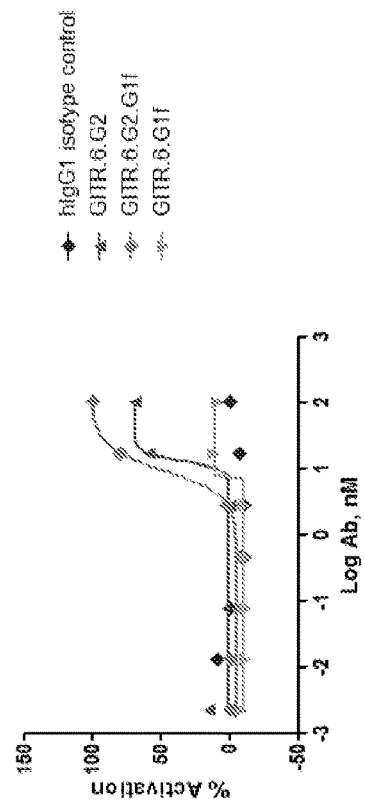
Figure 17

ANTIBODIES COMPRISING MODIFIED HEAVY CONSTANT REGIONS

CROSS-REFERENCE TO RELATED APPLICATIONS

This application claims priority to U.S. Provisional Application No. 62/083,021, filed Nov. 21, 2014. The contents of any patents, patent applications, and references cited throughout this specification are hereby incorporated by reference in their entireties.

SEQUENCE LISTING

The instant application contains a Sequence Listing which has been submitted in ASCII format via EFS-Web, and is hereby incorporated by reference in its entirety. Said ASCII copy, created on Dec. 21, 2017, is named MXI-539US_Sequence_Listing.txt and is 328,732 bytes in size.

BACKGROUND

Antibody therapeutics is one of the fastest growing areas in the treatment of disease, such as cancer and immune disorders. Nevertheless, efficiently targeting an antigen by a therapeutic antibody remains a major challenge in health care. Therefore, antibody engineering has become a major focus in the pharmaceutical world. From this focus, a myriad of new engineered antibodies have emerged, such as antibody fragments, antibody drug conjugates (ADCs), antibodies with modified effector regions, and bispecific antibodies.

Antibodies facilitate their therapeutic properties through many different mechanisms. Antibodies may directly inhibit or activate a target antigen, thus regulating cell signaling. Antibodies may inhibit the binding of a ligand to a receptor. Antibodies may also induce or inhibit an immune response, for example, by boosting the subject's immune system to fight infection or cancer (e.g., as costimulators in the activation of T cells).

Furthermore, antibody-mediated internalization of a cell surface receptor/antigen is recognized as a major mechanism of action for therapeutic antibodies. In this instance, an antibody removes the target from the cell surface and from performing its function by inducing internalization into the cell. Indeed, one of the forerunners of antibody therapeutics is trastuzumab for the treatment of breast cancer. Trastuzumab targets the ErbB2 receptor and induces receptor/antibody internalization, thus inhibiting EGFR signaling. However, antibodies do not always display efficient internalization qualities, thus there is an ongoing need for antibodies with improved internalization functions. Accordingly, methods for improving the internalization of known therapeutic antibodies are highly desirable.

SUMMARY

The invention provides heavy chain constant regions (referred to as "modified heavy chain constant regions"), or functionally equivalent fragments thereof, that enhance biological properties of antibodies relative to the same antibodies in unmodified form. For example, antibodies comprising such modified constant regions exhibit increased internalization and/or agonistic or antagonistic activity. Accordingly, antibodies of the invention are optimized versions of the original unmodified antibody. Specifically, the modified heavy chain constant region includes an IgG2 hinge and three constant domains (i.e., CH1, CH2, and CH3 domains), wherein one or more of the constant region domains is a non-IgG2 human isotype (e.g., IgG1, IgG3 or IgG4), or functionally equivalent fragments thereof. The modified constant region can include the corresponding wildtype amino acid sequence, or a variant thereof, e.g., one or more (e.g., between 1-10, or more) amino acid substitutions or deletions within the hinge or the CH1, CH2, CH3 domains relative to the wildtype amino acid sequence. Accordingly, the amino acid sequence of the hinge and/or each constant domain is at least about 80%, 85%, 90%, 95%, or more (i.e., 96%, 97%, 98%, 99%, or 100%) identical to the corresponding wildtype amino acid sequence.

In one embodiment, the modified heavy chain constant region includes a wildtype human IgG2 hinge, or an amino acid sequence that is at least 95% identical to the amino acid sequence of a wildtype human IgG2 hinge. The hinge can further contain additional modifications, for example, to reduce disulfide bond formation. In one embodiment, the hinge includes the amino acid substitution C219S, relative to the wildtype human IgG2 hinge. In certain embodiments, the hinge comprises the amino acid sequence set forth in any of SEQ ID NO: 8, 21-23, 126-132 and 134-147 or one of these sequences that comprises 1-3 amino acids inserted between CVE and CPP.

In certain embodiments, the modified heavy chain constant region includes an IgG2 CH1 domain, e.g., a wildtype human IgG2 CH1 domain, or an amino acid sequence that is at least 95% identical to the amino acid sequence of a wildtype human IgG2 CH1 domain (SEQ ID NO: 7).

In certain embodiments, the modified heavy chain constant region includes an IgG1 CH2 domain, e.g., a wildtype human IgG1 CH2 domain, or an amino acid sequence that is at least 95% identical to the amino acid sequence of a wildtype human IgG1 CH2 domain. The CH2 domain may contain additional modifications (e.g., to reduce or eliminate effector functions). In certain embodiments, the CH2 domain comprises the amino acid substitutions A330S and P331S, relative to wildtype full-length human IgG1 CH2. In certain embodiments, the CH2 domain comprises SEQ ID NO: 24.

In certain embodiments, the modified heavy chain constant region includes an IgG1 CH3 domain, e.g., a wildtype human IgG1 CH3 domain, or an amino acid sequence that is at least 95% identical to the amino acid sequence of a wildtype human IgG1 CH3 domain. The CH3 domain can further contain additional modifications to confer a particular allotype. In one embodiment, the CH3 domain contains the amino acid residue E at position 356 and the amino acid M at position 358, relative to wildtype full-length human IgG1 of a different allotype. In certain embodiments, the CH3 domain comprises SEQ ID NO: 5.

In a particular embodiment, the antibody comprises a modified heavy chain constant region wherein (a) the CH1 domain is a wildtype human IgG2 CH1 domain or a wildtype IgG1 CH1 domain, with or without additional modification, (b) the hinge is a wildtype IgG2 hinge with or without a C219S substitution, (c) the CH2 domain is a wildtype human IgG1 CH2 domain or a wildtype IgG2 CH2 domain, with or without additional modifications, and (d) the CH3 domain is a wildtype human IgG1 CH3 domain or a wildtype human IgG2 CH3 domain, with or without amino acid E at position 356 and amino acid M at position 358. In a specific embodiment, the modified heavy chain constant region comprises an amino acid sequence described herein, e.g., set forth in any one of SEQ ID NOs: 26-37 and 78-93.

Antibodies of the invention (i.e., antibodies having a modified constant region) may be fully human antibodies or humanized antibodies, and further exhibit one or more enhanced or altered features, compared to the same antibodies without a modified heavy chain constant region. These features may include increased or altered internalization by a cell, agonistic activity, formation of large cross-linked complexes, ADCC, receptor mediated signaling, antagonist activity, immuno-modulating activity and anti-tumor activity; or introduction of a new property, e.g., agonist activity.

Bispecific molecules and immunoconjugates containing modified constant regions of the invention are also provided, as well as compositions which contain the antibodies, bispecifics, or immunoconjugates and an acceptable pharmaceutical carrier. Such compositions also may include one or more additional therapeutic agents, e.g., an agent that stimulates the immune system, such as a checkpoint inhibitor, a co-stimulatory molecule, an anti-CD39 antibody, or an anti-A2AR antibody.

Methods for preparing an antibody comprising a modified heavy chain constant region are also provided. Certain methods provided herein include methods of increasing internalization of an antibody by a cell, and methods for increasing the agonist activity of an antibody, compared to the same antibody comprising a hinge of a non-IgG2 isotype. Such methods comprise the steps of providing an antibody having a hinge that is not an IgG2 hinge, and replacing the hinge with an IgG2 hinge (such as a hinge that is a wildtype human IgG2 hinge, a hinge having an amino acid sequence that is at least 95% identical to the amino acid sequence of a wildtype human IgG2 hinge, or a hinge that is modified to reduce disulfide bond formation, e.g., a hinge that comprises amino acid substitution C219S). In one embodiment, internalization of the antibody is enhanced or increased by at least 10%, 30%, 50%, 75%, 2 fold, 3 fold, 5 fold or more, resulting in a reduction of the $T_{1/2}$ by at least 10%, 30%, 50%, 75%, 2 fold, 3 fold, 5 fold or more. In certain embodiments, agonist activity is increased or enhanced by at least 10%, 30%, 50%, 75%, 2 fold, 3 fold, 5 fold or more as defined by increased cytokine release or increased proliferation in effector T cells; reduced T regulatory cell activity if engagement on Tregs reduces Treg function; or increased depletion of Tregs.

In certain embodiments, the method further includes the step of replacing at least one of the CH1, CH2, or CH3 domains with a CH1, CH2, or CH3 domain of a different isotype. Such replacements include, for example: (a) replacing the CH1 domain with an IgG1 CH1 domain or an IgG2 CH1 domain; (b) replacing the CH2 domain with an IgG1 CH2 domain or an IgG2 CH2 domain; and/or (b) replacing the CH3 domain with an IgG1 CH3 domain or an IgG2 CH3 domain, wherein the replacement domain has the wildtype sequence or at least 95% identity the wildtype sequence. In certain embodiments, the CH1 domain comprises the amino acid sequence as set forth in SEQ ID NO: 7. In certain embodiments, the CH2 domain is modified to reduce or eliminate effector functions, e.g., the CH2 domain comprises amino acid substitutions A330S and P331S (SEQ ID NO:24). In certain embodiments, the CH3 domain comprises the amino acid residue E at position 356 and the amino acid M at position 358 (SEQ ID NO: 5).

Methods provided herein include methods of treating a subject by administering an antibody, bispecific molecule or immunoconjugate comprising a modified heavy chain constant region. One or more additional therapeutic agents, e.g., a therapeutic agent that stimulates the immune system, such as a checkpoint inhibitor, a co-stimulatory molecule also can be co-administered.

Provided herein are antibodies comprising a modified heavy chain constant region comprising a CH1 domain, a hinge, a CH2 domain, and a CH3 domain in order from N- to C-terminus, and wherein (a) the CH1 domain comprises the amino acid sequence of SEQ ID NO: 7 or an amino acid sequence that differs therefrom in at most 5 amino acids or which is at least 95% identical to SEQ ID NO: 7, and wherein at least one of C131, R133, E137, S138 or R217 are not substituted or deleted; (b) a hinge comprising any one of SEQ ID NO: 8, 21-23, 126-132 or 134-147 or a sequence that comprises 1-3 amino acids inserted between CVE and CPP, or which differs therefrom in at most 5 amino acids, wherein the hinge does not comprise a substitution or deletion at both C219 and C220; (c) the antibody has at least one enhanced property or a new introduced property relative to the same antibody that comprises an IgG1 hinge and CH1 domain; and (d) the modified heavy chain constant region is not a wildtype IgG2 constant region or an IgG2 constant region comprising C219S and/or C220S. The hinge may comprise the amino acid sequence ERKXCVECPPCPAP (SEQ ID NO: 129) or ERKCXVECPPCPAP (SEQ ID NO: 130), wherein X is any amino acid except cysteine. For example, the hinge may comprise the amino acid sequence ERKSCVECPPCPAP (SEQ ID NO: 131) or ERKCSVECPPCPAP (SEQ ID NO: 132). In certain embodiments at least one of, or all of, amino acid residues P233, V234, A235 and G237 are deleted or substituted with another amino acid residue, e.g, the corresponding amino acid in an IgG1 hinge. In certain embodiments, none of amino acid residues R133, E137, S138 and R217 or none of C131, R133, E137, S138 and R217 are substituted or deleted. In certain embodiments, N192 and/or F193 are substituted with another amino acid. The antibody may comprise a CH2 domain that is at least 95% identical to that of wildtype IgG1. The antibody may comprise a CH3 domain that is at least 95% identical to that of wildtype IgG1. In certain embodiments, the CH2 and/or CH3 domain is not a wildtype IgG1 CH2 and/or CH3 domain, and the antibody has an effector function that is more potent than that of wildtype IgG1. In certain embodiments, the CH2 and/or CH3 domain is not a wildtype IgG1 CH2 and/or CH3 domain, and the antibody has an effector function that less potent than that of wildtype IgG1. In certain embodiments, the antibody comprises a CH2 domain and/or CH1 domain that is at least 95% identical to that of wildtype IgG1 or IgG4. In certain embodiments, the antibody has at least one enhanced property selected from agonist activity, antibody mediated receptor internalization, ADCC, receptor mediated signaling, antagonist activity, immuno-modulating activity or anti-tumor activity; or a newly introduced property, which is agonist activity.

In certain embodiments, an antibody comprises a modified heavy chain constant region, wherein (a) the CH1 domain is a wildtype human IgG2 CH1 domain; (b) the hinge comprises SEQ ID NO: any one of SEQ ID NO: 8, 21-23, 126-132 or 134-147 or a sequence that comprises 1-3 amino acids inserted between CVE and CPP; (c) the CH2 domain is a wildtype human IgG1 CH2 domain or a modified CH2 domain conferring enhanced or reduced effector function to the antibody; and (d) the CH3 domain is a wildtype human IgG1 CH3 domain or a modified CH3 domain conferring enhanced or reduced effector function to the antibody. A modified heavy chain constant domain may comprise the amino acid sequence set forth in any one of SEQ ID NOs: 26-37, 54-56, 78-125 and 152-168, or an amino acid sequence that is at least 95% identical to SEQ ID NOs: 26-37, 54-56, 78-125 and 152-168.

In certain embodiments, an antibody comprises a modified heavy chain constant region, wherein the heavy chain constant region comprises a CH1 domain and a hinge comprising the sequence (SEQ ID NO: 133)
ASTKGPSVFPLAPCSRSTSESTAALGCLVKDYFPEPVTVSWNSGALTSGV HTFPAVLQSSGLYSLSSVVTVPSS*NF*GTQTYTCNVDHKPSNTKVDKTV<u>ER</u>

<u>KCCVECPPCPAP</u>*PVAG*, or an amino acid sequence that differs from SEQ ID NO: 133 in at most 10 amino acids or is at least 90% identical to SEQ ID NO: 133, wherein (i) at least one of C131, R133, E137, S138 and R217 is not substituted with another amino acid or deleted; (ii) C219 and C220 may be substituted with another amino acid or deleted, but C219 and C220 may not both be substituted or deleted; (iii) 1-3 amino acids may be inserted between CVE and CPP in the hinge; (iv) the hinge optionally comprises an additional amino acid at the C-terminus, e.g., G; (v) one or more of amino acids P233, V234, A235 and G237 may be substituted with another amino acid (e.g., the corresponding amino acid from IgG1) or deleted; (vi) the CH2 and CH3 domains may be wildtype or modified IgG1, IgG2, IgG3 or IgG4 CH2 and CH3 domains; (vii) the modified heavy chain constant region is not a wildtype IgG2 heavy chain constant region or a wildtype IgG2 heavy constant domain with C219S or C220S; and (viii) the antibody has at least one enhanced property or a new introduced property relative to the same antibody that comprises an IgG1 hinge and CH1 domain. In certain embodiments, the antibody has at least one enhanced property selected from agonist activity, antibody mediated receptor internalization, ADCC, receptor mediated signaling, antagonist activity, immuno-modulating activity or anti-tumor activity; or a newly introduced property, which is agonist activity. In certain embodiments, none of amino acids C131; R133; E137; S138; R217 are substituted with another amino acid or deleted. In certain embodiments, N192 and/or F193 are not substituted or are N192S and/or F193L, respectively. In certain embodiments, C219 is C219S, C220 is C220S, P233-G237 are substituted or deleted; V234-G237 are substituted or deleted; A235-G237 are substituted or deleted; G237 is substituted or deleted; P233 is substituted or deleted; P233-V234 are substituted or deleted; or P233-A235 are substituted or deleted. The antibody may have effector function, or be deprived of effector function. The antibody may comprise a wildtype or modified IgG1 CH2 domain and or a wildtype or modified IgG1 CH3 domain.

In certain embodiments, an antibody comprises a modified heavy chain constant region, wherein the heavy chain constant region comprises a CH1 domain comprising the sequence ASTKGPSVFPLAPCSRSTSESTAALG-CLVKDYFPEPVTVSWNSGALTSGVHTFPAVLQSS GLYSLSSVVTVPSSNFGTQTYTCNVDHKPSNTKVDK-TVE (SEQ ID NO: 7), or an amino acid sequence that differs from SEQ ID NO: 7 in at most 10 amino acids or is at least 90% identical to SEQ ID NO: 7, wherein (i) at least one of C131, R133, E137, S138 and R217 is not substituted or deleted; (ii) the modified heavy chain constant region is not a wildtype IgG2 heavy chain constant region or a wildtype IgG2 heavy constant domain with C219S or C220S; and (iii) the antibody has at least one enhanced property or a new introduced property relative to the same antibody that comprises an IgG1 hinge and CH1 domain. The antibody may have at least one enhanced property selected from agonist activity, antibody mediated receptor internalization, ADCC, receptor mediated signaling, antagonist activity, immuno-modulating activity or anti-tumor activity; or a newly introduced property, which is agonist activity. In certain embodiments, none of amino acids C131; R133; E137 and S138 are substituted with another amino acid or deleted. In certain embodiments, N192 and/or F193 are not substituted or are N192S and/or F193L, respectively. The antibody may have effector function, or be deprived of effector function. The antibody may comprise a wildtype or modified IgG1 CH2 domain and or a wildtype or modified IgG1 CH3 domain.

An antibody may comprise a modified heavy chain constant region, wherein the heavy chain constant region comprises a hinge comprising the sequence (SEQ ID NO: 8)
<u>ERKCCVECPPCPAP</u>*PVAG*, or an amino acid sequence that differs from SEQ ID NO: 8 in at most 5 amino acids, wherein (i) C219 and C220 may be substituted with another amino acid or deleted, but C219 and C220 may not both be substituted or deleted; (ii) one or more of amino acids P233, V234, A235 and G237 may be substituted or deleted; (iii) 1-3 amino acids may be inserted between CVE and CPP in the hinge; (iv) the hinge optionally comprises an additional amino acid at the C-terminus, e.g., G; (v) the CH2 and CH3 domains may be wildtype or modified IgG1, IgG2, IgG3 or IgG4 CH2 and CH3 domains; (vi) the modified heavy chain constant region is not a wildtype IgG2 heavy chain constant region or a wildtype IgG2 heavy constant domain with C219S or C220S; and (vii) the antibody has at least one enhanced property or a new introduced property relative to the same antibody that comprises an IgG1 hinge and CH1 domain. The antibody may have at least one enhanced property selected from agonist activity, antibody mediated receptor internalization, ADCC, receptor mediated signaling, antagonist activity, immuno-modulating activity or anti-tumor activity; or a newly introduced property, which is agonist activity. In certain embodiments, C219 is C219S, C220 is C220S, P233-G237 are substituted or deleted; V234-G237 are substituted or deleted; A235-G237 are substituted or deleted; G237 is substituted or deleted; P233 is substituted or deleted; P233-V234 are substituted or deleted; or P233-A235 are substituted or deleted. The antibody may have effector function, or be deprived of effector function. The antibody may comprise a wildtype or modified IgG1 CH2 domain and or a wildtype or modified IgG1 CH3 domain.

Also provided are antibodies comprising a modified heavy chain constant region, wherein the heavy chain constant region comprises an IgG1 or IgG2 hinge, and wherein the hinge is lacking 1-7 amino acids, and wherein the antibody has at least one enhanced property or a new introduced property relative to the same antibody that comprises an IgG1 hinge and CH1 domain. The antibody may have at least one enhanced property selected from agonist activity, antibody mediated receptor internalization, ADCC, receptor mediated signaling, antagonist activity, immuno-modulating activity or anti-tumor activity; or a newly introduced property, which is agonist activity. The hinge may be an IgG2 hinge that is lacking 1-4 amino acids, e.g., amino acids C219, C220, V222 and E224. The hinge is an IgG1 hinge that is lacking amino acids S219, C220, D221, K222, T223, H224 and T225. The antibody may comprise an IgG2 CH1 domain that is wildtype or modified; an IgG1 CH1 domain that is wildtype or modified, and an IgG1, IgG2 or IgG4 CH2 domain and an IgG1, IgG2 or IgG4 CH3 domain.

Antibodies with modified heavy chain constant regions may be human or humanized antibodies, or antigen binding portions thereof. In certain embodiments, the antibody binds specifically to an antigen that is involved in immune regulation. The antibody may be an agonist of a costimulatory receptor or an antagonist of an inhibitory receptor. For example, the antibody may bind to a costimulatory receptor, e.g., selected from the group of B7-1, B7-2, CD28, 4-1BB, GITR, OX40, ICOS, CD70, CD27, CD40, DR3 or CD28H, or the antibody may bind to an inhibitory receptor, e.g., selected from the group of CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1 and TIM-4. The antigen may be an antigen that is required to be internalized, e.g., CD73. The antigen may be CD39.

In certain embodiments, an antibody comprising a modified heavy chain constant region binds specifically to a costimulatory receptor, e.g, GITR, OX40, 4-1BB, CD28, ICOS, CD40, CD27 or any other TNFR superfamily member, and comprises a modified heavy chain constant region selected from the group of SEQ ID NOs: 26-37, 54-56, 78-125 and 152-168. In certain embodiments, the antibody exhibits enhanced or altered agonist activity relative to an antibody having the same variable regions and light chain, but comprising an IgG1 heavy chain constant region.

In certain embodiments, an antibody comprising a modified heavy chain constant region binds specifically to a cell surface molecule, e.g., CD73, and triggers antibody mediated internalization of the cell surface molecule, and comprises a modified heavy chain constant region selected from the group of SEQ ID NOs: 26-37, 54-56, 78-125 and 152-168. In certain embodiments, the antibody possesses enhanced or altered internalization properties relative to an antibody having the same variable regions and light chain, but comprising an IgG1 heavy chain constant region.

In certain embodiments, an antibody comprising a modified heavy chain constant region binds specifically to an inhibitory receptor, e.g., CTLA-4, PD-1, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1 and TIM-4, and comprises a modified heavy chain constant region selected from the group of SEQ ID NOs: 26-37, 54-56, 78-125 and 152-168. In certain embodiments, the antibody exhibits more potent or altered antagonist activity or introduces a new activity relative to the same antibody having an IgG1 heavy chain constant region.

In certain embodiments, an antibody comprising a modified heavy chain constant region binds specifically to a cell surface molecule and triggers intracellular signaling, wherein the antibody comprises a modified heavy chain constant region selected from the group of SEQ ID NOs: 26-37, 54-56, 78-125 and 152-168. In certain embodiments, intracellular signaling mediates agonist activity, antagonist activity, internalization of the cell surface molecule, or ADCC. In certain embodiments, the antibody triggers more potent intracellular signaling relative to an antibody having the same variable regions and light chain, but comprising an IgG1 heavy chain constant region.

In certain embodiments, an antibody comprising a modified heavy chain constant region binds specifically to a cell surface molecule and triggers formation of high molecular weight antibody-cell surface molecule complexes, wherein the antibody comprises a modified heavy chain constant region selected from the group of SEQ ID NOs: 26-37, 54-56, 78-125 and 152-168. In certain embodiments, the antibody triggers formation of higher molecular weight complexes relative to an antibody having the same variable regions and light chain, but comprising an IgG1 heavy chain constant region.

In certain embodiments, an antibody comprising a modified heavy chain constant region binds specifically to a cell surface molecule and triggers clustering or oligomerization of the cell surface molecule, wherein the antibody comprises a modified heavy chain constant region selected from the group of SEQ ID NOs: 26-37, 54-56, 78-125 and 152-168. In certain embodiments, the antibody triggers more clustering or oligomerization of the cell surface molecule relative to an antibody having the same variable regions and light chain, but comprising an IgG1 heavy chain constant region.

Also provided herein are bispecific molecule comprising an antibody comprising a modified heavy chain constant region linked to a molecule having a second binding specificity. Also provided herein are immunoconjugates comprising an antibody comprising a modified heavy chain constant region, linked to a second agent. Composition comprising an antibody, bispecific or immunoconjugate described herein and a carrier are also provided. Compositions may comprise one or more additional therapeutic agents, e.g., a therapeutic agent stimulates the immune system, and is, e.g., an antagonist of a checkpoint inhibitor or a co-stimulatory receptor.

Also provided herein are methods of preparing an antibody comprising a modified heavy chain constant region, wherein the antibody comprises a CH1 domain, a hinge, a CH2 domain, and a CH3 domain in order from N- to C-terminus, comprising the steps of: (a) providing an antibody comprising a hinge and/or a CH1 domain that is not an IgG2 hinge and/or IgG2 CH1 domain; and (b) replacing the hinge and/or the CH1 domain with an IgG2 hinge and/or IgG2 CH1 domain, respectively. Further provided herein are methods of increasing internalization of an antibody by a cell, comprising: (a) providing an antibody comprising a hinge and/or a CH1 domain that is not an IgG2 hinge and/or IgG2 CH1 domain; and (b) replacing the hinge and/or the CH1 domain with an IgG2 hinge and/or IgG2 CH1 domain, respectively. Internalization of the antibody may be increased compared to internalization of the same antibody comprising a hinge of a non-IgG2 isotype, e.g., an antibody comprising an IgG1 constant region. Also provided are methods of increasing the agonist activity of an antibody, comprising: (a) providing an antibody comprising a hinge and/or a CH1 domain that is not an IgG2 hinge and/or IgG2 CH1 domain; and (b) replacing the hinge and/or the CH1 domain with an IgG2 hinge and/or IgG2 CH1 domain, respectively. The agonist activity may be increased compared to agonist activity of the same antibody comprising a hinge of a non-IgG2 isotype, e.g., an antibody comprising an IgG1 constant region. An IgG2 hinge may be a wildtype human IgG2 hinge, or comprises an amino acid sequence that is at least 95% identical to the amino acid sequence of a wildtype human IgG2 hinge and may comprise, e.g., a sequence set forth in Table 4. A method may comprise the step of replacing at least one of the CH1, CH2, or CH3 domains with a CH1, CH2, or CH3 domain of a different isotype, respectively. A method may comprise the steps of (a) replacing the CH1 domain with an IgG2 CH1 domain; (b) replacing the CH2 domain with an IgG1 CH2 domain; and/or (b) replacing the CH3 domain with an IgG1 CH3 domain. A method may comprise the steps of (a) replacing the CH1 domain with a wildtype human IgG2 CH1 domain, or a domain at least 95% identical thereto; (b) replacing the CH2 domain with a wildtype human IgG1 CH2 domain, or a domain at least 95% identical thereto; and/or (b) replacing the CH3 domain with a wildtype human IgG1 CH3 domain, or a domain at least 95% identical thereto. A method may comprise the step of replacing the heavy chain constant region with a modified heavy chain constant region comprising any one of SEQ ID NOs: 26-37, 54-56, 78-125 and 152-168 or a region at least 95% identical to SEQ ID NOs: 26-37, 54-56, 78-125 and 152-168. The hinge may be modified to reduce or alter disulfide bond formation. Te hinge may comprise amino acid substitution C219S. The hinge may comprise an amino acid sequence set forth in any one of SEQ ID NO: 8, 21-23, 126-132 or 134-147 or a sequence that comprises 1-3 amino acids inserted between CVE and CPP. The CH1 domain may comprise the amino acid sequence ASTKGPSVFPLAPCSRSTSESTAALGCLVKDYFPEPVTVSWNSGALTSGVHTFPAVLQSS GLYSLSSVVTVPSSNFGTQTYTCNVDHKPSNTKVDKTV (SEQ ID NO: 7). The CH2 domain may be modified to reduce or eliminate effector functions. The CH2 domain may comprise amino acid substitutions A330S and P331S. The CH2 domain may comprise the amino acid sequence PSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAK (SEQ ID NO: 4). The CH2 domain may comprise amino acid substitutions A330S and P331S. The CH3 domain may comprise the amino acid sequence (SEQ ID NO: 5)
GQPREPQVYTLPPSR<u>EE</u>MTKNQVSLTCLVKGFYPSDIAVEWESNGQPENN

YKTTPPVLDSDGSFFLYSKLTVDKSRWQQGNVFSCSVMHEALHNHYTQKS

LSLSPGK.

Also provided are antibodies, or antigen binding portion thereof, produced by the methods described herein, e.g., set forth above, e.g., human or humanized antibodies. Methods of treating a subject, e.g., a subject having cancer, with any of the antibodies described herein are also encompassed herein. The methods may comprise administering one or more additional therapeutic agents, e.g., therapeutic agents that stimulate the immune system. For example, a therapeutic agent may target a checkpoint inhibitor or a co-stimulatory molecule. Methods may include administering a composition, bispecific molecule, or immunoconjugate described herein.

BRIEF DESCRIPTION OF THE DRAWINGS

FIG. 3A shows IFN-γ secretion from donor CD4 T cells stimulated with OKT3 expressing CHO cells and various concentrations of anti-human GITR antibodies with an IgG2-IgG1 constant region. FIG. 3B shows IL-2 secretion from donor CD4 T cells stimulated with OKT3 expressing CHO cells and various concentrations of an IgG1 heavy chain constant domain or an IgG2-IgG1 hybrid heavy chain constant domain. FIG. 3C shows IL-2 secretion from donor CD4 T cells stimulated with OKT3 expressing CHO cells and various concentrations of effectorless versions (IgG1.1) of the antibodies in FIGS. 3A and B.

FIGS. 5A-C show SEC chromatogram data, DLS data and MALS data, for complexes of hCD73-his with the antibody CD73.4 containing different constant regions. FIG. 5D shows a schematic model of the hCD73-his/mAb complexes derived from the MALS-determined masses in FIG. 5C.

FIG. 6 shows SEC-MALS data for CD73/mAb complexes.

FIG. 7 shows DLS data for CD73/mAb complexes.

FIG. 11A shows overlay of SEC chromatogram data for 1:1 molar complexes of hCD73-his with 16 different CD73.4 antibodies containing different constant region sequences.

FIG. 11B shows an expansion of the chromatogram data from 11-19.5 min of the chromatogram of FIG. 10A, with 4 distinct elution species indicated.

FIG. 17A shows NFkB signaling activation in CD8+ T cells treated with the indicated anti-GITR antibodies.

FIG. 17B shows NFkB signaling activation in CD4+ T cells treated with the indicated anti-GITR antibodies.

DETAILED DESCRIPTION

Figure 1A:
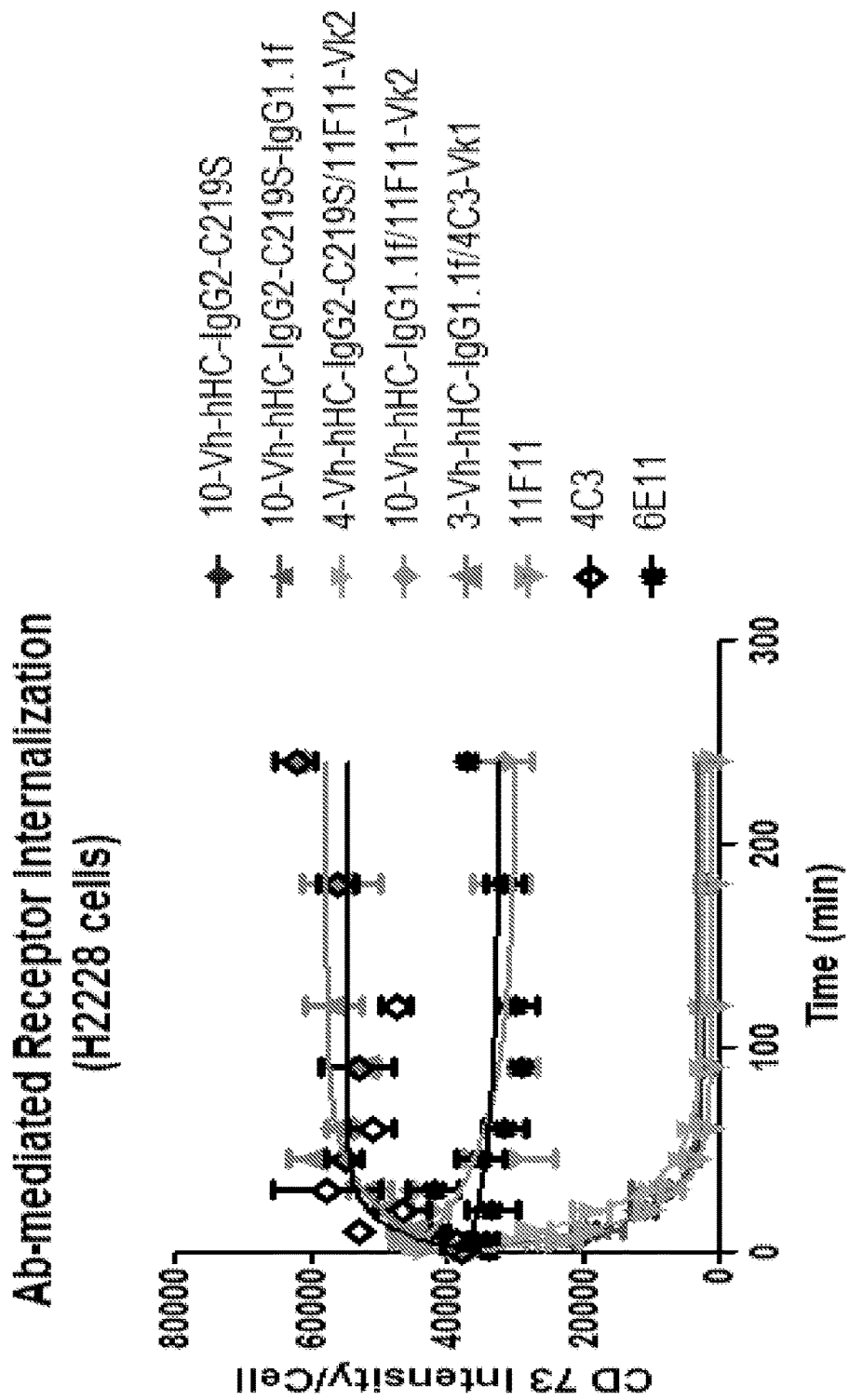
FIG. 1A shows the kinetics of antibody mediated internalization of CD73 in H2228 cells (non-small cell lung carcinoma cell line) by the following antibodies: 11F11, 4C3, 6D11, CD73.3-IgG1.1f with the 4C3Vk1 light chain ("3-Vh-hHC-IgG1.1f/4C3Vk1"), CD73.4-IgG2CS with the 11F11 Vk2 light chain ("4-Vh-hHC-IgG2-C219S/11F11-Vk2"), CD73.10-IgG2CS ("CD73.10-Vh-hHC-IgG2-C219S"), CD73.10-IgG2CS-IgG1.1f ("CD73.10-Vh-hHC-IgG2-C219S-IgG1.1f"), and CD73.10-IgG1.1f ("CD73.10-Vh-hHC-IgG1.1f") antibodies in H2228 cells. The 11F11 (which is of an IgG2 isotype), CD73.4-IgG2CS, CD73.10-IgG2CS and CD73.10-IgG2CS-IgG1.1f antibodies are internalized faster and to a higher degree than the other tested antibodies, which are of an IgG1 isotype.
Figure 1B:
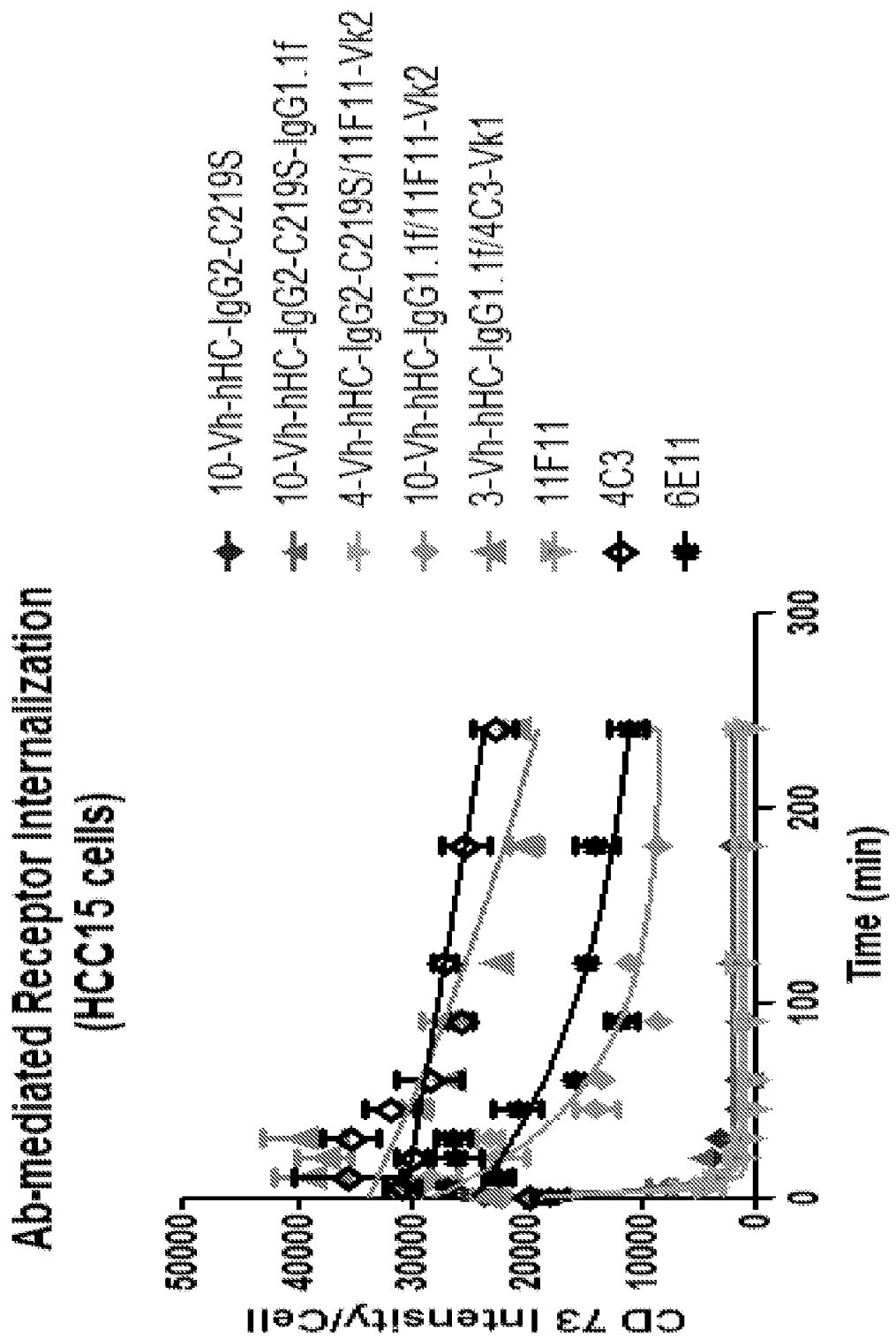
FIG. 1B shows the kinetics of antibody mediated CD73 internalization of the same antibodies as those shown in FIG. 1A in HCC15 cells (non-small cell lung carcinoma cell line), showing similar results to those obtained in H2228 cells.
Figure 1C:
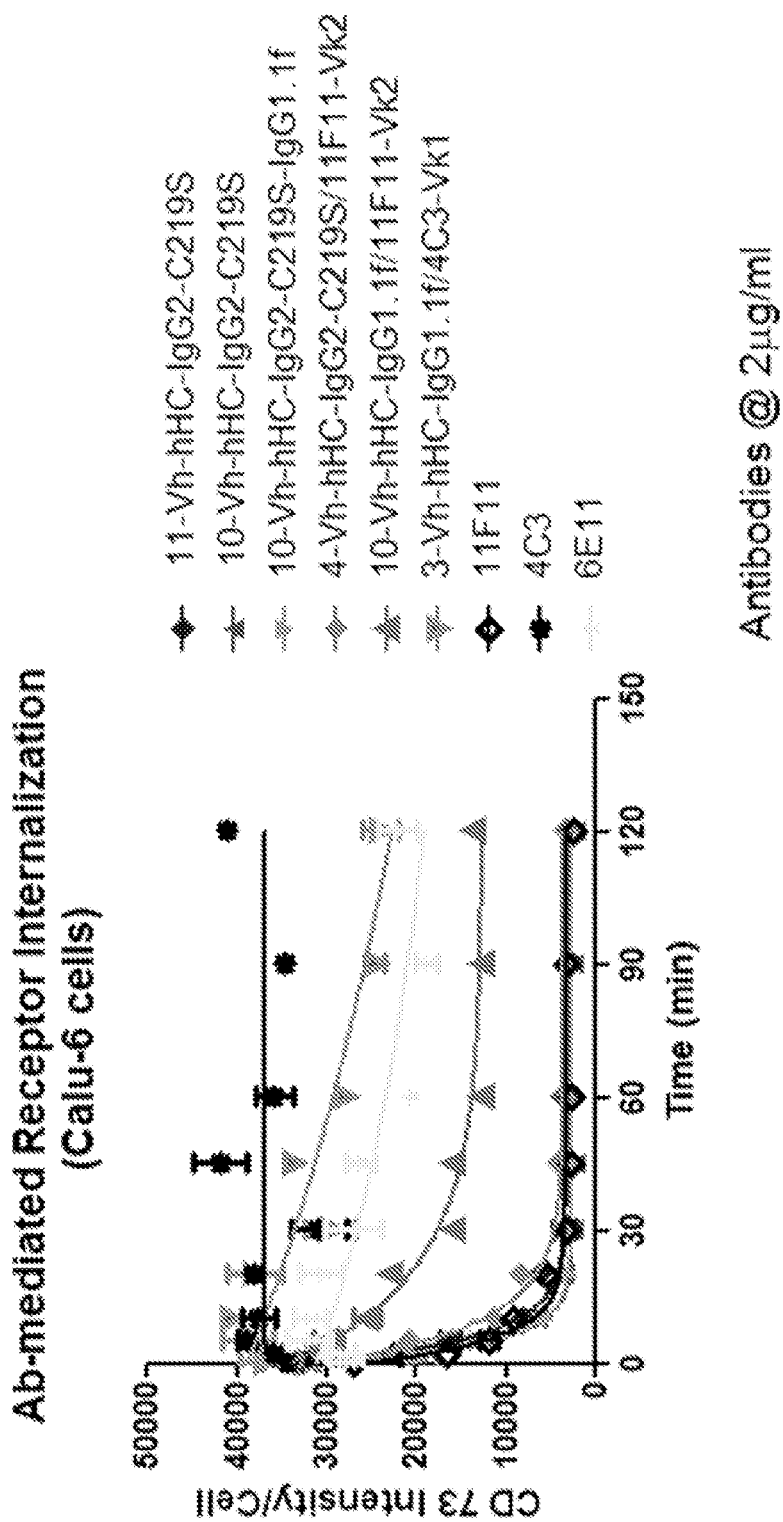
FIG. 1C shows the kinetics of antibody mediated CD73 internalization of the same antibodies as those shown in FIGS. 1A and 1B, as well as CD73.11-IgG2CS ("11-Vh-hVC-IgG2-C219S"), in Calu6 cells, showing similar results to those obtained in H2228 and HCC15 cells.
Figure 1D:
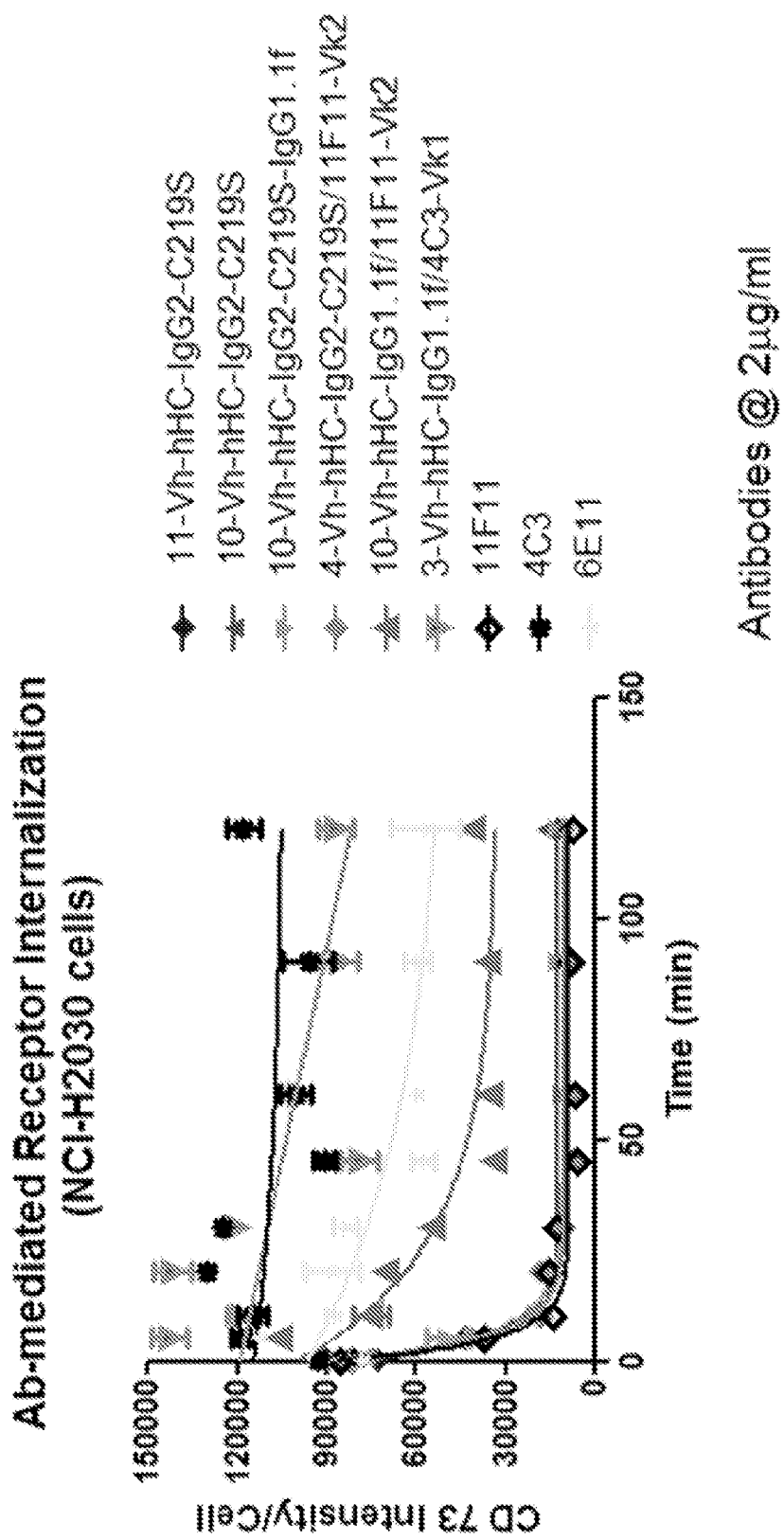
FIG. 1D shows the kinetics of antibody mediated CD73 internalization of the same antibodies as those shown in FIG. 1C in NCI-2030 cells (non-small cell lung carcinoma cell line), showing similar results to those obtained in H2228, HCC15, and Calu6 cells.

The invention is based, at least in part, on the findings that the following properties of antibodies are enhanced or altered when the antibodies comprise an IgG2 hinge relative to the same antibodies that comprise a non-IgG2 hinge (or relative to the same antibodies comprising an IgG1 constant region): (i) internalization; (ii) agonist function; (iii) receptor mediated intracellular signaling; (iv) ADCC; and (v) weight of antibody/antigen complexes. In addition, these enhanced or altered features of antibodies are further enhanced or altered when the antibodies comprise, in addition to an IgG2 hinge, an IgG2 CH1 domain. It has also been observed that antibodies having an IgG2 CH1 domain, but not an IgG2 hinge, have enhanced or altered activities compared to the same antibodies having an IgG1 CH1 domain. Without wanting to be limited to a particular mechanism of action, the enhancing effects of an IgG2 hinge has been found to correlate with an increase in size of antibody/antigen complexes. The enhanced size of antibody/antigen complexes when the antibody has an IgG2 hinge may result from a higher rigidity of IgG2 hinges relative to that of other isotypes. Furthermore, it has been shown that specific regions or amino acid residues of the IgG2 hinge and CH1 domain may be modified, whereas others are preferably not modified, to preserve the enhanced or altered activities.

As further described herein, these modified heavy chain constant regions conferring onto antibodies (or antigen binding regions thereof) enhanced or modified activities may have effector function. Thus, it was shown that antibodies may be created that have the advantageous properties conferred by an IgG2 hinge and/or CH1 domain and also have effector function.

The invention is also based at least in part on the finding that deletion of certain portions of a hinge in an IgG1 or IgG2 antibody results in the antibody having enhanced or altered properties relative to the antibody with an IgG1 constant region.

Accordingly, provided herein are (i) antibodies having modified heavy chain constant regions conferring to the antigen binding regions of the antibodies enhanced or altered properties and methods of using them, and (ii) methods for enhancing or altering certain biological properties of antibodies that comprise a non-IgG2 hinge and/or CH1 domain, such as internalization, agonism and antagonism, wherein the method comprises replacing the non-IgG2 hinge and/or CH1 domain of the antibody with an IgG2 hinge and/or IgG2 CH1 domain or portion thereof.

Provided herein are "modified heavy chain constant regions" that enhance certain biological properties of antibodies, e.g., antibodies that have a non-IgG2 hinge and/or a non-IgG2 CH1 domain, relative to the same antibodies having different constant regions. Exemplary modified heavy chain constant regions include an IgG2 hinge, a CH1 domain, a CH2 domain and a CH3 domain, wherein at least one of these constant domains is not of the IgG2 isotype and may be, e.g., of an IgG1, IgG3 or IgG4. In certain embodiments, a modified heavy chain constant region comprises an IgG2 hinge and IgG1 CH2 and CH3 domains. In certain embodiments, a modified heavy chain constant region comprises an IgG2 CH1 domain and an IgG2 hinge. In certain embodiments, a modified heavy chain constant region comprises an IgG2 CH1 domain, an IgG2 hinge, an IgG1 CH2 domain and an IgG1 CH3 domain. A modified heavy chain constant region may have effector function similar to that of wild-type IgG1, or may be engineered to have reduced or enhanced effector function relative to that of the wildtype IgG. A modified heavy chain constant region may comprise a wildtype CH1, hinge, CH2 and/or CH3 domain, or a variant thereof, e.g., a CH1, hinge, CH2 and/or CH3 domain having one or more amino acid substitutions, deletions or additions relative to the corresponding wildtype domain, and/or having an amino acid sequence that is at least 90% identical, or more, to the corresponding wildtype sequence.

Definitions

In order that the present description may be more readily understood, certain terms are first defined. Additional definitions are set forth throughout the detailed description.

The term "antibody" as used herein may include whole antibodies and any antigen binding fragments (e.g., an antigen binding fragment that includes a hinge, an antigen binding fragment that includes a hinge and a CH1 domain, an antigen binding fragment that includes a hinge and CH2 domain, or an antigen binding fragment that includes a hinge, a CH2 domain and a portion of a CH3 domain) or single chains thereof. In one embodiment, an "antibody" refers to a protein, e.g., a glycoprotein, comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. In certain naturally occurring IgG, IgD and IgA antibodies, the heavy chain constant region is comprised of a hinge, a CH1 domain, a CH2 domain and a CH3 domain. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. In certain embodiments, the antibodies described herein are of the human IgG1 or IgG2 subtype. Immunoglobulins, e.g., human IgG1, exist in several allotypes, which differ from each other in at most a few amino acids. "Antibody" may include, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

In certain embodiments, a heavy chain of an antibody comprises a C-terminal lysine; a C-terminal glycine (having lost the C-terminal lysine), or is lacking GK or is lacking K. When referring to antibodies comprising a modified heavy chain constant region described herein, the antibody may comprise a provided sequence having the C-terminal GK or K, or alternatively, lacking GK or K.

Amino acid numbering is according to the EU index as in Kabat. Kabat et al. (1991) *Sequences of Proteins of Immunological Interest*, National Institutes of Health, Bethesda, Md., and according to FIGS. 3c-3f of U.S. Pat. App. Pub. No. 2008/0248028.

The term "antigen-binding portion" of an antibody, as used herein, refers to one or more fragments of an antibody that retain the ability to specifically bind to an antigen. An antigen-binding portion of an antibody can be a "hinge containing antigen binding portion." It has been shown that the antigen-binding function of an antibody can be performed by fragments of a full-length antibody. Examples of binding fragments encompassed within the term "antigen-binding portion" of an antibody described herein, include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These and other potential constructs are described at Chan & Carter (2010) *Nat. Rev. Immunol.* 10:301. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "CDR" of a variable domain are amino acid residues within the hypervariable region that are identified in accordance with the definitions of the Kabat, Chothia, the combination of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As used herein, "isotype" refers to the antibody class (e.g., IgG1, IgG2, IgG3, IgG4, IgM, IgA1, IgA2, IgD, and IgE antibody) that is encoded by the heavy chain constant domain genes. The full-length amino acid sequence of each wild type human IgG constant region (including all domains, i.e., CH1 domain, hinge, CH2 domain, and CH3 domain) is cataloged in the UniProt database available on-line, e.g., as P01857 (IgG1), P01859 (IgG2), P01860 (IgG3), and P01861 (IgG4), or different allotypes thereof (SEQ ID NOs: 1, 6, 11, and 16, respectively). As used herein, a domain of a heavy chain constant region, e.g., the hinge, is of an "IgG1 isotype," "IgG2 isotype," "IgG3 isotype," or "IgG4 isotype," if the domain comprises the amino acid sequence of the corresponding domain of the respective isotype, or a variant thereof (that has a higher homology to the corresponding domain of the respective isotype than it does to that of the other isotypes).

"Allotype" refers to naturally occurring variants within a specific isotype group, which variants differ in a few amino acids (see, e.g., Jefferies et al. (2009) mAbs 1:1). Antibodies described herein may be of any allotype.

A "wildtype" protein or portion thereof is a version of the protein as it is found in nature. An amino acid sequence of a wildtype protein, e.g., a heavy chain constant region, is the amino acid sequence of the protein as it occurs in nature. Due to allotypic differences, there can be more than one amino acid sequence for a wildtype protein. For example, there are several allotypes of naturally occurring human IGg1 heavy chain constant regions (see, e.g., Jeffries et al. (2009) mAbs 1:1).

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region of an antibody of isotype IgG comprises the heavy chain constant region of the antibody excluding the first constant region immunoglobulin domain (CH1). In IgG, IgA and IgD antibody isotypes, the Fc region comprises $C_{H2}$ and $C_{H3}$ constant domains in each of the antibody's two heavy chains; IgM and IgE Fc regions comprise three heavy chain constant domains ($C_H$ domains 2-4) in each polypeptide chain. For IgG, the Fc region comprises immunoglobulin domains consisting of the hinge, CH2 and CH3. For purposes herein, the Fc region is defined as starting at amino acid 216 and ending at amino acid 447, wherein the numbering is according to the EU index as in Kabat. Kabat et al. (1991) *Sequences of Proteins of Immunological Interest*, National Institutes of Health, Bethesda, Md., and according to FIGS. 3c-3f of U.S. Pat. App. Pub. No. 2008/0248028. The Fc may be a native (or naturally-occurring or wildtype) Fc, including any allotypic variant, or a variant Fc (e.g., a non-naturally occurring Fc), comprising, e.g., 1, 2, 3, 4, 5, 1-5, 1-10 or 5-10 or more amino acid mutations, e.g., substitutions, additions or deletions. For example, a variant Fc may comprise an amino acid sequence that is at least 75%, 80%, 85%, 90%, 95%, 96%, 97%, 98% or 99% identical to a wildtype Fc. Modified or mutated Fcs may have enhanced or reduced effector function and/or half-life. The CH2 and CH3 regions are the primary site of effector functions and FcRn binding. Fc may refer to this region in isolation or in the context of an Fc-comprising protein polypeptide such as a "binding protein comprising an Fc region," also referred to as an "Fc fusion protein" (e.g., an antibody or immunoadhesin).

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Various properties of human FcγRs are summarized in Table 1. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

TABLE 1

Properties of human FcγRs

| Fcγ | Allelic variants | Affinity for human IgG | Isotype preference | Cellular distribution |
|---|---|---|---|---|
| FcγRI | None described | High ($K_D$ ~10 nM) | IgG1 = 3 > 4 >> 2 | Monocytes, macrophages, activated neutrophils, dendritic cells? |
| FcγRIIA | H131 | Low to medium | IgG1 > 3 > 2 > 4 | Neutrophils, monocytes, macrophages, eosinophils, |
|  | R131 | Low | IgG1 > 3 > 4 > 2 | dendritic cells, platelets |
| FcγRIIIA | V158 | Medium | IgG1 = 3 >> 4 > 2 | NK cells, monocytes, |
|  | F158 | Low | IgG1 = 3 >> 4 > 2 | macrophages, mast cells, eosinophils, dendritic cells? |
| FcγRIIB | I232 | Low | IgG1 = 3 = 4 > 2 | B cells, monocytes, |
|  | T232 | Low | IgG1 = 3 = 4 > 2 | macrophages, dendritic cells, mast cells |

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al. J. Immunol. 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 J Immunol 161:4083). The sequences of wildtype IgG1, IgG2, IgG3 and IgG4 hinges are show in Table 2.

substitutions, deletions or additions. Exemplary IgG2 hinge variants include IgG2 hinges in which 1, 2, 3 or all 4 cysteines (C219, C220, C226 and C229) are changed to another amino acid. In a specific embodiment, an IgG2 hinge comprises a C219X or C220X substitution, wherein X is any amino acid, except cysteine. An IgG2 hinge may comprise a substitution, which alone, or together with one or more substitutions in other regions of the heavy or light chain will cause the antibody comprising the hinge to adopt form A or B (see, e.g., Allen et al. (2009) Biochemistry 48:3755). In certain embodiments, a hinge is a hybrid hinge that comprises sequences from at least two isotypes. For example, a hinge may comprise the upper, middle or lower hinge from one isotype and the remainder of the hinge from one or more other isotypes. For example, a hinge can be an

TABLE 2

Hinge region amino acids

| Ig Type | C-terminal $C_H1$* | Upper Hinge | Middle Hinge | Lower Hinge |
|---|---|---|---|---|
| IgG1 | VDKRV (SEQ ID NO: 57) | EPKSCDKTHT (SEQ ID NO: 59) | CPPCP (SEQ ID NO: 64) | APELLGG (SEQ ID NO: 70) |
| IgG2 | VDKTV (SEQ ID NO: 58) | ERK (SEQ ID NO: 60) | CCVECPPCP (SEQ ID NO: 65) | APPVAG (SEQ ID NO: 71) |
| IgG3 (17-15-15-15) | VDKRV | ELKTPLGDTTHT (SEQ ID NO: 61) | CPRCP (SEQ ID NO: 66) (EPKSCDTPPCPRCP)$_3$ (SEQ ID NO: 67) | APELLGG |
| IgG3 (17-15-15) | VDKRV | ELKTPLGDTTHT | CPRCP (EPKSCDTPPCPRCP)$_2$ | APELLGG |
| IgG3 (17-15) | VDKRV | ELKTPLGDTTHT | CPRCP (EPKSCDTPPCPRCP)$_1$ | APELLGG |
| IgG3 (15-15-15) | VDKRV | EPKS (SEQ ID NO: 62) | CDTPPPCPRCP (SEQ ID NO: 68) (EPKSCDTPPCPRCP)$_2$ | APELLGG |
| IgG3 (15) | VDKRV | EPKS | CDTPPPCPRCP | APELLGG |
| IgG4 | VDKRV | ESKYGPP (SEQ ID NO: 63) | CPSCP (SEQ ID NO: 69) | APEFLGG |

*C-terminal amino acid sequences of the CH1 domains.

The term "hinge" includes wildtype hinges (such as those set forth in Table 3), as well as variants thereof (e.g., non-naturally-occurring hinges or modified hinges). For example, the term "IgG2 hinge" includes wildtype IgG2 hinge, as shown in Table 3, and variants having 1, 2, 3, 4, 5, 1-3, 1-5, 3-5 and/or at most 5, 4, 3, 2, or 1 mutations, e.g., IgG2/IgG1 hinge, and may comprise, e.g., the upper and middle hinges of IgG2 and the lower hinge of IgG1. A hinge may have effector function or be deprived of effector function. For example, the lower hinge of wildtype IgG1 provides effector function.

A "non-IgG2" hinge refers to a hinge that is not of the IgG2 isotype.

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains (such as having SEQ ID NO: 2 for IgG1 and SEQ ID NO: 7 for IgG2; Table 3), as well as variants thereof (e.g., non-naturally-occurring CH1 domains or modified CH1 domains). For example, the term "CH1 domain" includes wildtype CH1 domains and variants thereof having 1, 2, 3, 4, 5, 1-3, 1-5, 3-5 and/or at most 5, 4, 3, 2, or 1 mutations, e.g., substitutions, deletions or additions. Exemplary CH1 domains include CH1 domains with mutations that modify a biological activity of an antibody, such as ADCC, CDC or half-life. Modifications to the CH1 domain that affect a biological activity of an antibody are provided herein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains (such as having SEQ ID NO: 4 for IgG1; Table 3), as well as variants thereof (e.g., non-naturally-occurring CH2 domains or modified CH2 domains). For example, the term "CH2 domain" includes wildtype CH2 domains and variants thereof having 1, 2, 3, 4, 5, 1-3, 1-5, 3-5 and/or at most 5, 4, 3, 2, or 1 mutations, e.g., substitutions, deletions or additions. Exemplary CH2 domains include CH2 domains with mutations that modify a biological activity of an antibody, such as ADCC, CDC or half-life. In certain embodiments, a CH2 domain comprises the substitutions A330S/P331S that reduce effector function. Other modifications to the CH2 domain that affect a biological activity of an antibody are provided herein.

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains (such as having SEQ ID NO: 5 for IgG1; Table 3), as well as variants thereof (e.g., non-naturally-occurring CH3 domains or modified CH3 domains). For example, the term "CH3 domain" includes wildtype CH3 domains and variants thereof having 1, 2, 3, 4, 5, 1-3, 1-5, 3-5 and/or at most 5, 4, 3, 2, or 1 mutations, e.g., substitutions, deletions or additions. Exemplary CH3 domains include CH3 domains with mutations that modify a biological activity of an antibody, such as ADCC, CDC or half-life. Modifications to the CH3 domain that affect a biological activity of an antibody are provided herein.

TABLE 3

| Domain | Amino acid sequence | SEQ ID NO: |
|---|---|---|
| IgG1 CH1 | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KV | 2 |
| IgG1 Hinge | EPKSCDKTHTCPPCPAPELLGG | 3 |
| IgG1 CH2 | PSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPI EKTISKAK | 4 |
| IgG1 CH3 | GQPREPQVYTLPPSREEMTKNQVSLTCLVKGFYPSDIAVEWESNGQPE NNYKTTPPVLDSDGSFFLYSKLTVDKSRWQQGNVFSCSVMHEALHNH YTQKSLSLSPGK | 5 |
| IgG2 CH1 | ASTKGPSVFPLAPCSRSTSESTAALGCLVKDYFPEPVTVSWNSGALTSG VHTFPAVLQSSGLYSLSSVVTVPSSNFGTQTYTCNVDHKPSNTKVDKTV | 7 |
| IgG2 Hinge | ERKCCVECPPCPAPPVAG | 8 |
| IgG2 CH2 | PSVFLFPPKPKDTLMISRTPEVTCVVVDVSHEDPEVQFNWYVDGVEVH NAKTKPREEQFNSTFRVVSVLTVVHQDWLNGKEYKCKVSNKGLPAPI EKTISKTK | 9 |
| IgG2 CH3 | GQPREPQVYTLPPSREEMTKNQVSLTCLVKGFYPSDIAVEWESNGQPE NNYKTTPPMLDSDGSFFLYSKLTVDKSRWQQGNVFSCSVMHEALHNH YTQKSLSLSPGK | 10 |
| IgG3 CH1 | ASTKGPSVFPLAPCSRSTSGGTAALGCLVKDYFPEPVTVSWNSGALTS GVHTFPAVLQSSGLYSLSSVVTVPSSSLGTQTYTCNVNHKPSNTKVDK RV | 12 |
| IgG3 Hinge | ELKTPLGDTTHTCPRCPE | 13 |
| IgG3 CH2 | PKSCDTPPPCPRCPEPKSCDTPPPCPRCPEPKSCDTPPPCPRCPAPELLGG PSVFLFPPKPKDTLMISRTPEVTCVVVDVSHEDPEVQFKWYVDGVEVH NAKTKPREEQYNSTFRVVSVLTVLHQDWLNGKEYKCKVSNKALPAPI EKTISKTK | 14 |
| IgG3 CH3 | GQPREPQVYTLPPSREEMTKNQVSLTCLVKGFYPSDIAVEWESSGQPE NNYNTTPPMLDSDGSFFLYSKLTVDKSRWQQGNIFSCSVMHEALHNR FTQKSLSLSPGK | 15 |

TABLE 3-continued

| Domain | Amino acid sequence | SEQ ID NO: |
|---|---|---|
| IgG4 CH1 | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRV | 17 |
| IgG4 Hinge | ESKYGPPCPSCPAPEFLGG | 18 |
| IgG4 CH2 | PSVFLFPPKPKDTLMISRTPEVTCVVVDVSQEDPEVQFNWYVDGVEVH NAKTKPREEQFNSTYRVVSVLTVLHQDWLNGKEYKCKVSNKGLPSSI EKTISKAK | 19 |
| IgG4 CH3 | GQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNH YTQKSLSLSLGK | 20 |

The term "monoclonal antibody," as used herein, refers to an antibody that displays a single binding specificity and affinity for a particular epitope or a composition of antibodies in which all antibodies display a single binding specificity and affinity for a particular epitope. Typically such monoclonal antibodies will be derived from a single cell or nucleic acid encoding the antibody, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell obtained from a transgenic or transchromosomal non-human animal (e.g., a transgenic mouse having a genome comprising a human heavy chain transgene and a light chain transgene), to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations that occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid sequences that encode the light chain and heavy chain immunoglobulin polypeptides in response to an antigen may not be identical to the original germline sequences, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

A "bispecific" or "bifunctional antibody" is an artificial hybrid antibody having two different heavy/light chain pairs, giving rise to two antigen binding sites with specificity for different antigens. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

The phrases "an antibody recognizing an antigen" and "an antibody specific for an antigen" are used interchangeably herein with the term "an antibody which binds specifically to an antigen."

An "isolated antibody," as used herein, is intended to refer to an antibody that is substantially free of other antibodies having different antigenic specificities (e.g., an isolated antibody that specifically binds to antigen "x" is substantially free of antibodies that specifically bind antigens other than antigen "x"). An isolated antibody that specifically binds to an epitope of antigen "x" may, however, have cross-reactivity to other antigen "x" proteins from different species.

As used herein, an "agonist antibody" refers to an antibody that is an agonist of a co-stimulatory receptor, e.g., an antibody that is capable of boosting the immune system (or an immune response) of a subject by stimulating the activity of a protein that, in turn, stimulates an immune cell, e.g., a T cell, such as a B7-1, B7-2, CD28, 4-1BB (CD137), 4-1BBL, GITR, ICOS, ICOS-L, OX40, OX40L, CD70, or CD27, DR3, or CD28H protein. In certain embodiments, an agonist antibody is an antibody that enhances the activity of an inhbibitory receptor, e.g., CTLA-4, PD-1, PD-L1, PD-L2, or LAG-3, TIM-3, Galectin 9, CEACAM-1, BTLA, CD69, Galectin-1, TIGIT, CD113, GPR56, VISTA, 2B4, CD48, GARP, CD73, PD1H, LAIR1, TIM-1, or TIM-4, and thereby inhibits an immune response.

As used herein, an "antagonist antibody" refers to an antibody that is an antagonist of an inhibitory signal on an immune cell, e.g., a T cell, e.g., an antibody that is capable of inhibiting or blocking a protein that inhibits T cell activation (e.g., immune checkpoint inhibitors), such as a CTLA-4, PD-1, PD-L1, PD-L2, or LAG-3, TIM-3, Galectin 9, CEACAM-1, BTLA, CD69, Galectin-1, TIGIT, CD113, GPR56, VISTA, 2B4, CD48, GARP, CD73, PD1H, LAIR1, TIM-1, or TIM-4, and thereby stimulates an immune response. In certain embodiments, an antagonist antibody is an antibody that inhibits the activity of a stimulatory receptor, e.g., B7-1, B7-2, CD28, 4-1BB (CD137), 4-1BBL, GITR, ICOS, ICOS-L, OX40, OX40L, CD70, or CD27, DR3, or CD28H, and thereby inhibits an immune response.

Both agonist and antagonist antibodies result in amplifying antigen-specific T cell responses, or in inhibiting antigen-specific T cell responses (immune checkpoint regulators).

The term "epitope" or "antigenic determinant" refers to a site on an antigen (e.g., GITR) to which an immunoglobulin or antibody specifically binds. Epitopes within protein antigens can be formed both from contiguous amino acids (usually a linear epitope) or noncontiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from are tested for reactivity with a given antibody. Methods of determining spatial conformation of epitopes include techniques in the art and those described herein, for example, x-ray crystallography, 2-dimensional nuclear magnetic resonance and HDX-MS (see, e.g., *Epitope Mapping Protocols in Methods in Molecular Biology*, Vol. 66, G. E. Morris, Ed. (1996)).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" may comprise one or more polypeptides.

The term "nucleic acid molecule," as used herein, is intended to include DNA molecules and RNA molecules. A nucleic acid molecule may be single-stranded or double-stranded, and may be cDNA.

Also provided are "conservative sequence modifications" of the sequences set forth herein include, for example, conservative nucleotide and amino acid substitutions, as well as, nucleotide and amino acid additions and deletions. For example, modifications can be introduced into SEQ ID NOs: 1-74 by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

In one embodiment, amino acid sequence modifications to a heavy chain constant region or domain thereof do not modify or abrogate certain properties of the heavy chain constant region. These properties include, e.g., the rigidity or stiffness of the hinge, as well as agonist or antagonist activity of the antibody. In certain embodiments, amino acid sequence modifications to a heavy chain constant region or domain thereof do modify or abrogate certain properties of the heavy chain constant region.

Methods of identifying amino acid conservative substitutions that do and do not abrogate antibody and/or constant region properties are well-known in the art, e.g., as described herein in the Examples section.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences when the sequences are optimally aligned (i.e., % homology=# of identical positions/total # of positions×100), with optimal alignment determined taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

As used herein, the term "antigen" refers to any natural or synthetic immunogenic substance, such as a protein, peptide, or hapten. An antigen may be a full-length or mature protein, or a fragment thereof.

An "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4+ or CD8+ T cell, or the inhibition of a Treg cell.

An "immunomodulator" or "immunoregulator" refers to an agent, e.g., a component of a signaling pathway, that may be involved in modulating, regulating, or modifying an immune response. "Modulating," "regulating," or "modifying" an immune response refers to any alteration in a cell of the immune system or in the activity of such cell (e.g., an effector T cell). Such modulation includes stimulation or suppression of the immune system which may be manifested by an increase or decrease in the number of various cell types, an increase or decrease in the activity of these cells, or any other changes which can occur within the immune system. Both inhibitory and stimulatory immunomodulators have been identified, some of which may have enhanced function in a tumor microenvironment. In preferred embodiments, the immunomodulator is located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with, or at risk of contracting or suffering a recurrence of, a disease by a method comprising inducing, enhancing, suppressing or otherwise modifying an immune response.

"Immunostimulating therapy" or "immunostimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

"T effector" ("$T_{\mathit{eff}}$") cells refers to T cells (e.g., CD4+ and CD8+ T cells) with cytolytic activities as well as T helper (Th) cells, which secrete cytokines and activate and direct other immune cells, but does not include regulatory T cells (Treg cells).

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the term "T cell-mediated response" refers to a response mediated by T cells, including effector T cells (e.g., $CD8^+$ cells) and helper T cells (e.g., $CD4^+$ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by $CD8^+$ T cells.

As used herein, the terms "inhibits" or "blocks" (e.g., referring to inhibition/blocking of a ligand to its receptor or to a subsequent intracellular response) are used interchangeably and encompass both partial and complete inhibition/blocking. In some embodiments, the antibody inhibits binding by at least about 50%, for example, at least about 60%, 70%, 80%, 90%, 95%, 99%, or 100%, determined, e.g., as further described herein.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Prophylaxis refers to administration to a subject who does not have a disease, to prevent the disease from occurring or minimize its effects if it does.

A "hematological malignancy" includes a lymphoma, leukemia, myeloma or a lymphoid malignancy, as well as a cancer of the spleen and the lymph nodes. Exemplary lymphomas include both B cell lymphomas and T cell lymphomas. B-cell lymphomas include both Hodgkin's lymphomas and most non-Hodgkin's lymphomas. Non-limiting examples of B cell lymphomas include diffuse large B-cell lymphoma, follicular lymphoma, mucosa-associated lymphatic tissue lymphoma, small cell lymphocytic lymphoma (overlaps with chronic lymphocytic leukemia), mantle cell lymphoma (MCL), Burkitt's lymphoma, mediastinal large B cell lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological malignancies also include leukemia, such as, but not limited to, secondary leukemia, chronic lymphocytic leukemia, acute myelogenous leukemia, chronic myelogenous leukemia, and acute lymphoblastic leukemia. Hematological malignancies further include myelomas, such as, but not limited to, multiple myeloma and smoldering multiple myeloma. Other hematological and/or B cell- or T-cell-associated cancers are encompassed by the term hematological malignancy.

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent is a drug that slows cancer progression or promotes cancer regression in a subject. In preferred embodiments, a therapeutically effective amount of a drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. Pharmacological effectiveness refers to the ability of the drug to promote cancer regression in the patient. Physiological safety refers to an acceptably low level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In other preferred embodiments described herein, tumor regression may be observed and may continue for a period of at least about 20 days, more preferably at least about 40 days, or even more preferably at least about 60 days.

The terms "patient" and "subject" refer to any human or non-human animal that receives either prophylactic or therapeutic treatment. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

Various aspects described herein are described in further detail in the following subsections.

I. Modified Heavy Chain Constant Regions

Described herein are "modified heavy chain constant regions," which, when present in antibodies, enhance or alter certain biological properties or features of the antibodies, relative to the same antibodies that do not have a modified heavy chain constant region, such as antibodies that contain a non-IgG2 hinge, e.g., IgG1 antibodies. Enhanced or altered biological properties of antibodies include:

(a) increased or altered internalization by a cell;
(b) increased or altered agonist activity;
(c) increased or altered antagonist or blocking activity;
(d) enhanced ADCC;
(d) generation of a new property;
(e) increased or altered signal transduction;
(f) formation of larger antibody/antigen cross-linked complexes;
(g) increased clustering or oligomerization of the target cell surface molecule;
(h) increased stimulation or enhancement of an immune response; and/or
(i) increased inhibition of an immune response.

In certain embodiments, an antibody comprising a modified heavy chain constant region mediates antibody dependent receptor (or ligand or surface molecule) internalization more effectively, e.g., the antibody internalizes a target or surface molecule (e.g., a receptor or ligand) and/or is internalized itself with a higher rate and/or extent of internalization into a cell after the antibody binds to its target on the cell membrane, relative to the same antibody that does not comprise a modified heavy chain constant region, and comprises, e.g., an IgG1 heavy chain. The rate and extent of internalization of an antibody can be determined, e.g., as shown in the Examples. The rate of internalization, as measured, e.g., by $T_{1/2}$ of internalization, e.g., as shown in the Examples, can be enhanced or increased by at least 10%, 30%, 50%, 75%, 2 fold, 3 fold, 5 fold or more, resulting in a reduction of the $T_{1/2}$ by at least 10%, 30%, 50%, 75%, 2 fold, 3 fold, 5 fold or more. For example, instead of having a $T_{1/2}$ of 10 minutes, a modified heavy chain constant region may increase the rate of internalization and thereby reduce the $T_{1/2}$ to 5 minutes (i.e., a two fold increase in rate of internalization or a two-fold decrease in $T_{1/2}$). "$T_{1/2}$" is defined as the time at which half of the maximal internalization is achieved, as measured from the time the antibody is added to the cells. In certain embodiments, $T_{1/2}$ is reduced by at least 10 minutes, 30 minutes, or 1 hour. The maximal level of internalization can be the level of internalization at the plateau of a graph representing the internalization plotted against antibody concentrations or time. A modified heavy chain constant region may increase the maximal level of internalization of an antibody by at least 10%, 30%, 50%, 75%, 2 fold, 3 fold, 5 fold or more. Another way of comparing internalization efficacies of different antibodies, such as an antibody with, and the same antibody without, a modified heavy chain constant region, is by comparing their level of internalization at a given antibody concentration (e.g., 100 nM) and/or at a given time (e.g., 2 minutes, 5 minutes, 10 minutes or 30 minutes). Comparing levels of internalization can also be done by comparing the $EC_{50}$ levels of internalization. The level of internalization of one antibody can be defined relative to that of a given (reference) antibody, e.g., an antibody described herein, e.g., 11F11 or CD73.4-IgG2CS-IgG1, and, can be indicated as a percentage of the value obtained with the given (reference) antibody. The extent of internalization can be enhanced by at least 10%, 30%, 50%, 75%, 2 fold, 3 fold, 5 fold or more, as compared by any one of these methods.

In certain embodiments, an antibody comprising a modified heavy chain constant region has more potent agonist activity, relative to the same antibody that does not comprise a modified heavy chain constant region, and comprises, e.g., an IgG1 heavy chain. In certain embodiments, the enhanced agonist activity enhances the stimulatory activity of a target molecule, e.g., GITR, or other moleceules that stimulate or co-stimulate an immune response, e.g., T cell activity. In certain embodiments, the enhanced agonist activity enhances the inhibitory activity of a target molecule that inhibits an immune response, e.g., T cell activity (e.g., a checkpoint inhibitor). The enhanced agonist activity of an antibody that modulates T cell activity can be determined, e.g., as shown in the Examples, e.g., by measuring the level of IFN-γ or IL-2 secretion from T cells that are contacted with the antibody. The agonist activity of an antibody that binds to a stimulatory target may be enhanced by at least 10%, 30%, 50%, 75%, 2 fold, 3 fold, 5 fold or more as defined by increased cytokine release or increased proliferation of effector T cells; reduced T regulatory cell activity if engagement on Tregs reduces Treg function; or increased depletion of Tregs. For example, the amount of IFN-γ or IL-2 secreted from T cells stimulated with an antibody that binds to a stimulatory target comprising a modified heavy chain constant region may be at least 10%, 30%, 50%, 75%, 2 fold, 3 fold, 5 fold or more higher than that of T cells simulated with the same antibody that does not comprise a modified heavy chain constant region. The agonist activity of an antibody that binds to an inhibitory target may be enhanced by at least 10%, 30%, 50%, 75%, 2 fold, 3 fold, 5 fold or more as defined by reduced cytokine release or reduced proliferation of effector T cells; increased T regulatory cell activity; or decreased depletion of Tregs. For example, the amount of IFN-γ or IL-2 secreted from T cells stimulated with an antibody that binds to an inhibitory target comprising a modified heavy chain constant region may be at least 10%, 30%, 50%, 75%, 2 fold, 3 fold, 5 fold or more lower than that of T cells simulated with the same antibody that does not comprise a modified heavy chain constant region.

In certain embodiments, an antibody comprising a modified heavy chain constant region has more potent antagonist or blocking activity, relative to the same antibody that does not comprise a modified heavy chain constant region, and comprises, e.g., an IgG1 heavy chain. The enhanced antagonist activity of an antibody can be determined, e.g., by measuring cytokine release and/or proliferation in contexts that include conditions of T cell activation. The antagonist activity may be enhanced by at least 10%, 30%, 50%, 75%, 2 fold, 3 fold, 5 fold or more.

In certain embodiments, an antibody comprising a modified heavy chain constant region has enhanced ADCC activity, relative to the same antibody that does not comprise a modified heavy chain constant region, and comprises, e.g., an IgG1 heavy chain. Enhanced ADCC may be determined according to methods known in the art. ADCC may be enhanced by at least 10%, 30%, 50%, 2 fold, 5 fold or more.

In certain embodiments, an antibody comprising a modified heavy chain constant region has the ability to form larger antibody/antigen cross-linked complexes, relative to the same antibody that does not comprise a modified heavy chain constant region, and comprises, e.g., an IgG1 heavy chain. The ability to form complexes can be determined as described, e.g., in the Examples. Antibody/antigen complexes formed with an antibody that comprises a modified heavy chain constant region may be at least 50%, 2 fold, 3 fold, 5 fold or 10 folder larger than complexes formed with the same antibody that does not comprise a modified heavy chain constant region. In certain embodiments, complexes of at least 2,000 kDa; 3,000 kDa; 5000 kDa; 10,000 kDa, 50,000 kDa or 100,000 kDa are formed with antibodies having a modified heavy chain constant region.

In certain embodiments, an antibody comprising a modified heavy chain constant region triggers more clustering or oligomerization of the target molecule on the cell surface, relative to the same antibody that does not comprise a modified heavy chain constant region, and comprises, e.g., an IgG1 heavy chain. The extent of clustering an oligomerization can be determined, e.g., by measuring the size of antibody/antigen complexes.

In certain embodiments, an antibody comprising a modified heavy chain constant region transduces a higher level or different type of signaling or signal transduction, relative to the same antibody that does not comprise a modified heavy chain constant region, and comprises, e.g., an IgG1 heavy chain. Signal transduction can be monitored by determining the level of activation of one or more proteins in signal transduction pathways. In certain embodiments, signal transduction is determined by measuring the activity (or phosphorylation) of a signal transduction protein, e.g., NKkB or p38, as described, e.g., in the Examples. Signal transduction triggered by an antibody that comprises a modified heavy chain constant region may be higher or lower by at least 10%, 20%, 50%, 2 fold, 5 fold or more than signal transduction with the same antibody that does not comprise a modified heavy chain constant region. For example, signal transduction triggered by an antibody that binds to a stimulatory molecule (e.g, GITR) and comprises a modified heavy chain constant region may be enhanced by at least 10% relative to that obtained with the same antibody having an IgG1 heavy chain. For example, $EC_{50}$ of NKkB or p38 activity (e.g., phosphorylation) may be reduced by at least 50%, 2 fold, 5 fold or more.

In certain embodiments, an antibody comprising a modified heavy chain constant region has an increased ability to stimulate or enhance an immune response or the immune system, relative to the same antibody that does not comprise a modified heavy chain constant region, and comprises, e.g., an IgG1 heavy chain. An increased ability to stimulate an immune response or the immune system, can result from an enhanced agonist activity of T cell costimulatory receptors and/or an enhanced antagonist activity of inhibitory receptors. An increased ability to stimulate an immune response or the immune system may be reflected by a fold increase of the $EC_{50}$ or maximal level of activity in an assay that measures an immune response, e.g., an assay that measures changes in cytokine or chemokine release, cytolytic activity (determined directly on target cells or indirectly via detecting CD107a or granzymes) and proliferation. The ability to stimulate an immune response or the immune system activity may be enhanced by at least 10%, 30%, 50%, 75%, 2 fold, 3 fold, 5 fold or more.

In certain embodiments, an antibody comprising a modified heavy chain constant region has an increased anti-proliferative or anti-tumor activity, relative to the same antibody that does not comprise a modified heavy chain constant region, and comprises, e.g., an IgG1 heavy chain. The enhanced anti-tumor activity of an antibody can be determined, e.g., by the growth of a tumor in an animal that has been treated with the antibody. The anti-tumor activity may be enhanced by at least 10%, 30%, 50%, 75%, 2 fold, 3 fold, 5 fold or more. Anti-tumor activity can be measured, e.g., as a decrease in tumor burden, e.g., manifested by decreased tumor growth kinetics and complete tumor regressions.

In certain embodiments, an antibody comprising a modified heavy chain constant region has an increased ability to inhibit or suppress an immune response or the immune system, relative to the same antibody that does not comprise a modified heavy chain constant region, and comprises, e.g., an IgG1 heavy chain. An increased ability to inhibit or suppress an immune response or the immune system, can result from an enhanced antagonist activity of T cell costimulatory receptors and/or an enhanced agonist activity of inhibitory receptors. An increased ability to stimulate an immune response or the immune system may be reflected by a fold increase of the $EC_{50}$ or maximal level of activity in an assay that measures an immune response, e.g., an assay that measures changes in cytokine or chemokine release, cytolytic activity (determined directly on target cells or indirectly via detecting CD107a or granzymes) and proliferation. The ability to inhibit or suppress an immune response or the immune system activity may be enhanced by at least 10%, 30%, 50%, 75%, 2 fold, 3 fold, 5 fold or more.

In certain embodiments, a modified heavy chain constant region or portion thereof, e.g., the hinge, is more rigid, compared to other heavy chain constant regions, e.g., IgG1, IgG2, IgG3 and/or IgG4 heavy chain constant regions. For example, a modified heavy chain constant region is a non-naturally occurring heavy chain constant region that is more rigid than, or has a portion, e.g., the hinge, that is more rigid than a naturally-occurring heavy chain constant region or hinge thereof. The rigidity of a heavy chain constant region or portion thereof, such as the hinge, can be determined by e.g., by computer modeling, electron microscopy, spectroscopy such as Nuclear Magnetic Resonance (NMR), X-ray crystallography (B-factors), or Sedimentation Velocity Analytical ultracentrifugation (AUC) to measure or compare the radius of gyration of antibodies comprising the hinge. Alternatively, the rigidity of a heavy chain constant region or portion thereof can be determined by measuring the sizes of antibody/antigen complexes, e.g., as further described herein.

An antibody comprising a modified heavy chain constant region and exhibiting an enhanced functional property as determined according to methodologies known in the art and described herein, will be understood to relate to a statistically significant difference in the particular activity relative to that seen in the same antibody but with a different heavy chain constant region.

In certain embodiments, a modified heavy chain constant region comprises a hinge of the IgG2 isotype (an "IgG2 hinge") and a CH1, CH2 and CH3 domain. In certain embodiments, a modified heavy chain constant region comprises an IgG2 hinge and a CH1, CH2 and CH3 domain, wherein at least one of the CH1, CH2 and CH3 domains is not of the IgG2 isotype. In certain embodiments, a modified heavy chain constant region comprises an IgG2 hinge and a CH1, CH2 and CH3 domain, wherein the heavy chain constant domain is not a wild-type IgG2 constant region or is not an IgG2 constant region with a mutation at amino acid 219 or 220. The IgG2 hinge may be a wildtype IgG2 hinge, e.g., a wildtype human IgG2 hinge (e.g., having SEQ ID NO: 8) or a variant thereof, provided that the IgG2 hinge retains the ability to confer to the antibody an enhanced activity relative to that of the same antibody that comprises a non-IgG2 hinge or comprises an IgG1 heavy chain. In certain embodiments, an IgG2 hinge variant retains similar rigidity or stiffness to that of a wildtype IgG2 hinge. The rigidity of a hinge can be determined, e.g., by computer modeling, electron microscopy, spectroscopy such as Nuclear Magnetic Resonance (NMR), X-ray crystallography (B-factors), or Sedimentation Velocity Analytical ultracentrifugation (AUC) to measure or compare the radius of gyration of antibodies comprising the hinge. A hinge has similar or higher rigidity relative to that of another hinge if an antibody comprising the hinge has a value obtained from one of the tests described in the previous sentence that differs from the value of the same antibody with a different hinge, e.g., an IgG1 hinge, in less than 5%, 10%, 25%, 50%, 75%, or 100%. A person of skill in the art would be able to determine from the tests whether a hinge has at least similar rigidity to that of another hinge by interpreting the results of these tests.

An exemplary human IgG2 hinge variant is an IgG2 hinge that comprises a substitution of one or more of the four cysteine residues (i.e., C219, C220, C226 and C229) with another amino acid. A cysteine may be replaced by a serine. An exemplary IgG2 hinge is a human IgG2 hinge comprising a C219X mutation ro a C220X mutation, wherein X is any amino acid exept serine. In a certain embodiments, an IgG2 hinge does not comprise both a C219X and a C220X substitution. In certain embodiments, an IgG2 hinge comprise C219S or C220S, but not both C219S and C22S. Other IgG2 hinge variants that may be used include human IgG2 hinges comprising a C220, C226 and/or C229 substitution, e.g., a C220S, C226S or C229S mutation (which may be combined with a C219S mutation). An IgG2 hinge may also be an IgG2 hinge in which a portion of the hinge is that of another isotype (i.e., it is a chimeric or hybrid hinge), provided that the rigidity of the chimeric hinge is at least similar to that of a wildtype IgG2 hinge. For example, an IgG2 hinge may be an IgG2 hinge in which the lower hinge (as defined in Table 2) is of an IgG1 isotype, and is, e.g., a wildtype IgG1 lower hinge.

A "hybrid" or "chimeric" hinge is referred to as being of a specific isotype if more than half of the consecutive amino acids of the hinge are from that isotype. For example, a hinge having an upper and middle hinge of IgG2 and the lower hinge of IgG1 is considered to be an IgG2 hybrid hinge.

In certain embodiments, an antibody comprises a modified heavy chain constant region that comprises an IgG2 hinge comprising a sequence set forth in Table 4, e.g., one of the following amino acid sequences: 8, 21, 22, 23, 126-129, and 134-147. In certain embodiments, the hinge comprises SEQ ID NO: 8, 21, 126, 134 or 135, wherein 1, 2, 3 or all 4 amino acids P233, V234, A235 and G237 (corresponding to the C-terminal 4 amino acids "PVAG" (SEQ ID NO: 148) are deleted or substituted with another amino acid, e.g., the amino acids of the C-terminus of the IgG1 hinge (ELLG (SEQ ID NO: 149) or ELLGG (SEQ ID NO: 150). In certain embodiments, the hinge comprises SEQ ID NO: 8, 21, 126, 134 or 135, wherein V234, A235 and G237 are deleted or substituted with another amino acid. In certain embodiments, the hinge comprises SEQ ID NO: 8, 21, 126, 134 or 135, wherein A235 and G237 are deleted or substituted with another amino acid. In certain embodiments, the hinge comprises SEQ ID NO: 8, 21, 126, 134 or 135, wherein G237 is deleted or substituted with another amino acid. In certain embodiments, the hinge comprises SEQ ID NO: 8, 21, 126, 134 or 135, wherein V234 and A235 are deleted or substituted with another amino acid. Substitution of PVAG (SEQ ID NO: 143) in an IgG2 with the corresponding amino acids of an IgG1 hinge, i.e., (ELLG (SEQ ID NO: 144) or ELLGG (SEQ ID NO: 145)) to obtain a hybrid hinge having SEQ ID NO: 22 or 138 or variants thereof (see, e.g., Table 4) provides a hinge having the advantages of an IgG2 hinge and the effector function of IgG1 hinges.

In certain embodiments, a modified heavy chain constant region comprises a hinge that consists of or consists essentially of one of the sequences in Table 4, e.g., SEQ ID NOs: 8, 21, 22, 23, 127-132, and 134-141, and, in certain embodiments, does not comprise additional hinge amino acid residues.

TABLE 4

Exemplary IgG2 hinges

| IgG2 Hinge description | Amino acid sequence | SEQ ID NO: |
|---|---|---|
| Wildtype IgG2 | ERKCCVECPPCPAPPVAG | 8 |
| IgG2 with C219S | ERKSCVECPPCPAPPVAG | 21 |
| IgG2 with C220S | ERKCSVECPPCPAPPVAG | 126 |
| IgG2 with C219X | ERKXCVECPPCPAPPVAG | 134 |
| IgG2 with C220X | ERKCXVECPPCPAPPVAG | 135 |
| Wildtype IgG2 with C-terminal X | ERKCCVECPPCPAPPVAGX | 143 |
| IgG2 with C219S with C-terminal X | ERKSCVECPPCPAPPVAGX | 144 |
| IgG2 with C220S with C-terminal X | ERKCSVECPPCPAPPVAGX | 145 |
| IgG2 with C219X with C-terminal X | ERKXCVECPPCPAPPVAGX | 146 |
| IgG2 with C220X with C-terminal X | ERKCXVECPPCPAPPVAGX | 147 |
| IgG2/IgG1 hybrid | ERKCCVECPPCPAPELLGG | 22 |
| IgG2/IgG1 hybrid with C219S | ERKSCVECPPCPAPELLGG | 23 |
| IgG2/IgG1 hybrid with C220S | ERKCSVECPPCPAPELLGG | 127 |

TABLE 4-continued

Exemplary IgG2 hinges

| IgG2 Hinge description | Amino acid sequence | SEQ ID NO: |
|---|---|---|
| IgG2/IgG1 hybrid with C219X | ERKXCVECPPCPAPELLGG | 136 |
| IgG2/IgG1 hybrid with C220X | ERKCXVECPPCPAPELLGG | 137 |
| IgG2/IgG1 hybrid deltaG | ERKCCVECPPCPAPELLG | 138 |
| IgG2/IgG1 hybrid with C219S deltaG | ERKSCVECPPCPAPELLG | 139 |
| IgG2/IgG1 hybrid with C220S deltaG | ERKCSVECPPCPAPELLG | 140 |
| IgG2/IgG1 hybrid with C219X deltaG | ERKXCVECPPCPAPELLG | 141 |
| IgG2/IgG1 hybrid with C220X deltaG | ERKCXVECPPCPAPELLG | 142 |
| Truncated wiltype IgG2 | ERKCCVECPPCPAP | 128 |
| Truncated wiltype IgG2 with C219S | ERKSCVECPPCPAP | 129 |
| Truncated wiltype IgG2 with C220S | ERKCSVECPPCPAP | 130 |
| Truncated wiltype IgG2 with C219X | ERKXCVECPPCPAP | 131 |
| Truncated wiltype IgG2 with C220X | ERKCXVECPPCPAP | 132 |

X is any amino acid, except cysteine.

In certain embodiments, a modified heavy chain constant region comprises an IgG2 hinge set forth in Table 4, in which 1-5, 1-3, 1-2 or 1 amino acid is inserted between amino acid residues CVE and CPP. In certain embodiments, THT or GGG is inserted. In certain embodiments, 1, 1-2 or 1-3 amino acids may be inserted between the hinge and CH2 domain. For example, an additional glycine may be inserted between the hinge and the CH2 domain.

In certain embodiments a modified heavy chain constant region is an IgG1 or IgG2 constant region, wherein the hinge comprises a deletion of 1-10 amino acids. As shown in the Examples, an IgG1 antibody lacking amino acid residues SCDKTHT (S219, C220, D221, K222, T223, H224 and T225; SEQ ID NO: 151) conferred antibody mediated CD73 internalization more effectively than the same antibody having a wildtype IgG1 constant region. Similarly, in the context of an IgG2 antibody, an IgG2 antibody lacking amino acid residues CCVE (C219, C220, V222, and E224; SEQ ID NO: 152) conferred antibody mediated CD73 internalization more effectively than the same antibody having a wildtype IgG1 constant region. Accordingly, provided herein are modified heavy chain constant region in which the hinge comprises a deletion of 1, 2, 3, 4, 5, 6, or 7 amino acid residues, selected from residues S219, C220, D221, K222, T223, H224 and T225 for an IgG1 antibody, and residues C219, C220, V222, and E224 for an IgG2 antibody.

In certain embodiments, a modified heavy chain constant region comprises a CH1 domain that is a wildtype CH1 domain of the IgG1 or IgG2 isotype ("IgG1 CH1 domain" or "IgG2 CH1 domain," respectively). CH1 domains of the isotypes IgG3 and IgG4 ("IgG3 CH1 domain and "IgG2 CH1 domain," respectively) may also be used. A CH1 domain may also be a variant of a wildtype CH1 domain, e.g., a variant of a wildtype IgG1, IgG2, IgG3 or IgG4 CH1 domain. Exemplary variants of CH1 domains include A114C, C131S and/or T173C. A CH1 domain, e.g., an IgG2 CH1 domain, may comprise the substitution C131S, which substitution confers onto an IgG2 antibody or antibody having IgG2 CH1 and hinge the B form (or conformation).

In certain embodiments, a modified heavy chain constant region comprises a CH1 domain that is of the IgG2 isotype. In certain embodiments, the CH1 domain is wildtype IgG2 CH1 domain, e.g., having the amino acid sequence: AST-KGPSVFPLAPCSRSTSESTAALGCLVKDYFPEPV TVSWNSGALTSGVHTFPAVLQSS GLYSLSSVVTVPSS N*F*GTQTYTCNVDHKPSNTKVDKTV (SEQ ID NO: 7). In certain embodiments, the CH1 domain is a variant of SEQ ID NO: 7 and comprises 1-10, 1-5, 1-2 or 1 amino acid substitutions or deletions relative to SEQ ID NO: 7. As further described in the Examples, it has been shown herein that an IgG2 CH1 domain or variants thereof confer enhanced properties to antibodies relative to IgG1 antibodies and even more enhanced properties when the antibodies also comprise an IgG2 hinge. In certain embodiments, IgG2 CH1 variants do not comprise an amino acid substitution or deletion at one or more of the following amino acid residues: C131, R133, E137 and S138, which amino acid residues are shown in bold and underlined in SEQ ID NO: 7 shown above. For example, a modified heavy chain constant region may comprise an IgG2 CH1 domain in which neither of R133, E137 and S138 are substituted with another amino acid or are deleted or in which neither of C131, R133, E137 and S138 are substituted with another amino acid or are deleted. In certain embodiments, C131 is substituted with another amino acid, e.g., C131S, which substitution triggers the antibody to adopt conformation B. Both conformation A and conformation B antibodies having modified heavy chain constant regions have been shown herein to have enhanced activities relative to the same antibody with an IgG1 constant region.

In certain embodiments, N192 and/or F193 (shown as italicized and underlined residues in SEQ ID NO: 7 shown above) are substituted with another amino acid, e.g., with the corresponding amino acids in IgG1, i.e., N192S and/or F193L.

In certain embodiments, one or more amino acid residues of an IgG2 CH1 domain are substituted with the corresponding amino acid residues in IgG4. For example, N192 may be N192S; F193 may be F193L; C131 may be C131K; and/or T214 may be T214R.

An antibody may comprise a modified heavy chain constant region comprising an IgG2 CH1 domain or variant thereof and IgG2 hinge or variant thereof. The hinge and CH1 domain may be a combination of any IgG2 hinge and IgG2 CH1 domain described herein. In certain embodiments, the IgG2 CH1 and hinge comprise the following amino acid sequence ASTKGPSVFPLAPCSRSTS ESTAALGCLVKDYFPEPVTVSWNSGALTSGVHTFPAV LQSS GLYSLSSVVTVPSSNFGTQTYTCNVDH KPSNT-KVDKTVERKCCVECPPCPAPPVAG (SEQ ID NO: 133), or an amino acid sequence that differs therefrom in at most 1-10 amino acids. The amino acid variants are as described for the hinge and CH1 domains above.

In certain embodiments, antibodies comprise at least an IgG2 hinge, and optionally also an IgG2 CH1 domain or fragment or derivative of the hinge and/or CH1 domain and the antibody has adopted form (of conformation) A (see, e.g., Allen et al. (2009) Biochemistry 48:3755). In certain embodiments, antibodies comprise at least an IgG2 hinge, and optionally also an IgG2 CH1 domain or fragment or derivative of the hinge and/or CH1 domain and the antibody has adopted form B (see, e.g., Allen et al. (2009) *Biochemistry* 48:3755).

In certain embodiments, a modified heavy chain constant region comprises a CH2 domain that is a wildtype CH2 domain of the IgG1, IgG2, IgG3 or IgG4 isotype ("IgG1 CH2 domain," "IgG2 CH2 domain," "IgG3 CH2 domain," or "IgG4 CH2 domain," respectively. A CH2 domain may also be a variant of a wildtype CH2 domain, e.g., a variant of a wildtype IgG1, IgG2, IgG3 or IgG4 CH2 domain. Exemplary variants of CH2 domains include variants that modulate a biological activity of the Fc region of an antibody, such as ADCC or CDC or modulate the half-life of the antibody or its stability. In one embodiment, the CH2 domain is a human IgG1 CH2 domain with an A330S and/or P331S mutation, wherein the CH2 domain has reduced effector function relative to the same CH2 mutation without the mutations. A CH2 domain may have enhanced effector function. CH2 domains may comprise one or more of the following mutations: SE (S267E), SELF (S267E/L328F), SDIE (S239D/I332E), SEFF, GASDALIE (G236A/S239D/A330L/I332E), and/or one or more mutations at the following amino acids: E233, G237, P238, H268, P271L328 and A330. Other mutations are further set forth herein elsewhere.

In certain embodiments, a modified heavy chain constant region comprises a CH3 domain that is a wildtype CH3 domain of the IgG1, IgG2, IgG3 or IgG4 isotype ("IgG1 CH3 domain," "IgG2 CH3 domain," "IgG3 CH3 domain," or "IgG4 CH3 domain," respectively. A CH3 domain may also be a variant of a wildtype CH3 domain, e.g., a variant of a wildtype IgG1, IgG2, IgG3 or IgG4 CH3 domain. Exemplary variants of CH3 domains include variants that modulate a biological activity of the Fc region of an antibody, such as ADCC or CDC or modulate the half-life of the antibody or its stability.

Generally, variants of the CH1, hinge, CH2 or CH3 domains may comprise 1, 2, 3, 4, 5, 6, 7, 8, 9, 10 or more mutations, and/or at most 10, 9, 8, 7, 6, 5, 4, 3, 2 or 1 mutation, or 1-10 or 1-5 mutations, or comprise an amino acid sequence that is at least about 75%, 80%, 85%, 90%, 95%, 96%, 97%, 98%, or 99% identical to that of the corresponding wildtype domain (CH1, hinge, CH2, or CH3 domain, respectively), provided that the heavy chain constant region comprising the specific variant retains the necessary biological activity.

Table 5 sets forth exemplary human heavy chain constant regions comprising a human CH1, hinge, CH2 and/or CH3 domains, wherein each domain is either a wildtype domain or a variant thereof that provides the desired biological activity to the heavy chain constant region. An unfilled cell in Table 5 indicates that the domain is present or not, and if present can be of any isotype, e.g., IgG1, IgG2, IgG3 or IgG4. For example, an antibody comprising the heavy chain constant region 1 in Table 5 is an antibody that comprises a heavy chain constant region comprising at least an IgG2 hinge, and which may also comprise a CH1, CH2 and/or CH3 domain, and if present, which CH1, CH2 and/or CH3 domain is of an IgG1, IgG2, IgG3 or IgG4 isotype. As another example for understanding Table 5, an antibody comprising a heavy chain constant region 8 is an antibody comprising a heavy chain constant region comprising an IgG1 CH1 domain, and IgG2 hinge, an IgG1 CH2 domain, and which may or may not also comprise an CH3 domain, which is present, may be of an IgG1, IgG2, IgG3 or IgG4 isotype.

TABLE 5

| MHCCR* | CH1 | Hinge | CH2 | CH3 |
|---|---|---|---|---|
| 1 |  | IgG2 |  |  |
| 2 | IgG1 | IgG2 |  |  |
| 3 | IgG2 | IgG2 |  |  |
| 4 |  | IgG2 | IgG1 |  |
| 5 |  | IgG2 | IgG2 |  |
| 6 |  | IgG2 |  | IgG1 |
| 7 |  | IgG2 |  | IgG2 |
| 8 | IgG1 | IgG2 | IgG1 |  |
| 9 | IgG1 | IgG2 | IgG2 |  |
| 10 | IgG2 | IgG2 | IgG1 |  |
| 11 | IgG2 | IgG2 | IgG2 |  |
| 12 | IgG1 | IgG2 |  | IgG1 |
| 13 | IgG1 | IgG2 |  | IgG2 |
| 14 | IgG2 | IgG2 |  | IgG1 |
| 15 | IgG2 | IgG2 |  | IgG2 |
| 16 |  | IgG2 | IgG1 | IgG1 |
| 17 |  | IgG2 | IgG1 | IgG2 |
| 18 |  | IgG2 | IgG2 | IgG1 |
| 19 |  | IgG2 | IgG2 | IgG2 |
| 20 | IgG1 | IgG2 | IgG1 | IgG1 |
| 21 | IgG1 | IgG2 | IgG1 | IgG2 |
| 22 | IgG1 | IgG2 | IgG2 | IgG1 |
| 23 | IgG1 | IgG2 | IgG2 | IgG2 |
| 24 | IgG2 | IgG2 | IgG1 | IgG1 |
| 25 | IgG2 | IgG2 | IgG1 | IgG2 |
| 26 | IgG2 | IgG2 | IgG2 | IgG1 |
| 27 | IgG2 | IgG2 | IgG2 | IgG2 |

*Modified heavy chain constant region

In certain embodiments, an antibody comprising a heavy chain constant region shown in Table 5 has an enhanced biological activity relative to the same antibody comprising a heavy chain constant region that does not comprise that specific heavy chain constant region or relative to the same antibody that comprises an IgG1 constant region.

In certain embodiments, a method for improving the biological activity of an antibody that comprises a non-IgG2 hinge and/or non-IgG2 CH1 domain comprises providing an antibody that comprises a non-IgG2 hinge and/or a non-IgG2 CH1 domain, and replacing the non-IgG2 hinge and the non-IgG2 CH1 domain with an IgG2 hinge and an IgG2 CH1 domain, respectively. A method for improving the biological activity of an antibody that does not comprise a modified heavy chain constant region, may comprise providing an antibody that does not comprise a modified heavy chain constant region, and replacing its heavy chain constant region with a modified heavy chain constant region.

Exemplary modified heavy chain constant regions are provided in Table 6, which sets forth the identity of each of the domains.

TABLE 6

| Modified heavy chain constant region | CH1 | Hinge | CH2 | CH3 | SEQ ID NO of whole MHCCR |
|---|---|---|---|---|---|
| IgG1-IgG2-IgG1 | IgG1 wildtype SEQ ID NO: 2 | IgG2/IgG1 SEQ ID NO: 22 | IgG1 wildtype SEQ ID NO: 4 | IgG1 wildtype SEQ ID NO: 5 | SEQ ID NO: 26 |
| IgG1-IgG2-IgG12 | IgG1 wildtype SEQ ID NO: 2 | IgG2 wildtype SEQ ID NO: 8 | IgG1 wildtype SEQ ID NO: 4 | IgG1 wildtype SEQ ID NO: 5 | SEQ ID NO: 27 |
| IgG1-IgG2CS-IgG1 | IgG1 wildtype SEQ ID NO: 2 | IgG2C219S/IgG1 SEQ ID NO: 23 | IgG1 wildtype SEQ ID NO: 4 | IgG1 wildtype SEQ ID NO: 5 | SEQ ID NO: 32 |
| IgG1-IgG2CS-IgG12 | IgG1 wildtype SEQ ID NO: 2 | IgG2 C219S SEQ ID NO: 21 | IgG1 wildtype SEQ ID NO: 4 | IgG1 wildtype SEQ ID NO: 5 | SEQ ID NO: 33 |
| IgG2-IgG1 | IgG2 wildtype SEQ ID NO: 7 | IgG2/IgG1 SEQ ID NO: 22 | IgG1 wildtype SEQ ID NO: 4 | IgG1 wildtype SEQ ID NO: 5 | SEQ ID NO: 28 |
| IgG2-IgG12 | IgG2 wildtype SEQ ID NO: 7 | IgG2 wildtype SEQ ID NO: 8 | IgG1 wildtype SEQ ID NO: 4 | IgG1 wildtype SEQ ID NO: 5 | SEQ ID NO: 29 |
| IgG2CS-IgG1 | IgG2 wildtype SEQ ID NO: 7 | IgG2C219S/IgG1 SEQ ID NO: 23 | IgG1 wildtype SEQ ID NO: 4 | IgG1 wildtype SEQ ID NO: 5 | SEQ ID NO: 34 |
| IgG2CS-IgG12 | IgG2 wildtype SEQ ID NO: 7 | IgG2 C219S SEQ ID NO: 21 | IgG1 wildtype SEQ ID NO: 4 | IgG1 wildtype SEQ ID NO: 5 | SEQ ID NO: 35 |
| IgG1CH1-IgG2Hinge-IgG1CH2 (A330S, P331S)-IgG1CH3 or IgG1-IgG2-IgG1.1 | IgG1 wildtype SEQ ID NO: 2 | IgG2 wildtype SEQ ID NO: 8 | IgG1 A330S/P331S SEQ ID NO: 24 | IgG1 wildtype SEQ ID NO: 5 | SEQ ID NO: 30 |
| IgG1CH1-IgG2Hinge(C219S)-IgG1CH2(A330S, P331S)-IgG1CH3 or IgG1-IgG2CS-IgG1.1 | IgG1 wildtype SEQ ID NO: 2 | IgG2 C219S SEQ ID NO: 21 | IgG1 A330S/P331S SEQ ID NO: 24 | IgG1 wildtype SEQ ID NO: 5 | SEQ ID NO: 36 |
| IgG2-IgG1.1 | IgG2 wildtype SEQ ID NO: 7 | IgG2 wildtype SEQ ID NO: 8 | IgG1 A330S/P331S SEQ ID NO: 24 | IgG1 wildtype SEQ ID NO: 5 | SEQ ID NO: 31 |
| IgG2CS-IgG1.1 | IgG2 wildtype SEQ ID NO: 7 | IgG2 C219S SEQ ID NO: 21 | IgG1 A330S/P331S SEQ ID NO: 24 | IgG1 wildtype SEQ ID NO: 5 | SEQ ID NO: 37 |

In certain embodiments, an antibody comprises a modified heavy chain constant region comprising an IgG2 hinge comprising any one of SEQ ID NO: 8, 21, 22, 23, 126-132, 134-136 and 137 or a variant thereof, such as an IgG2 hinge comprising an amino acid sequence that (i) differs from any one of SEQ ID NO: 8, 21, 22, 23, 126-132, 134-136 and 137 in 1, 2, 3, 4 or 5 amino acids substitutions, additions or deletions; (ii) differs from any one of SEQ ID NO: 8, 21, 22, 23, 126-132, 134-136 and 137 in at most 5, 4, 3, 2, or 1 amino acids substitutions, additions or deletions; (iii) differs from any one of SEQ ID NO: 8, 21, 22, 23, 126-132, 134-136 and 137 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to any one of SEQ ID NO: 8, 21, 22, 23, 126-132, 134-136 or 137, wherein in any of (i)-(iv), an amino acid substitution may be a conservative amino acid substitution or a non-conservative amino acid substitution; and wherein the modified heavy chain constant region has an enhanced biological activity relative to that of another heavy chain constant region, e.g., a heavy chain constant region that comprises a non-IgG2 hinge or relative to the same modified heavy chain constant region that comprises a non-IgG2 hinge.

In certain embodiments, a hinge comprises a sequence that is a variant of any one of SEQ ID NO: 8, 21, 22, 23, 126-132, 134-136 and 137, wherein R217 (second amino acid in wildtype IgG2 hinge (SEQ ID NO: 8) is not deleted or substituted with another amino acid. In certain embodiments in which a hinge is a variant of any one of SEQ ID NO: 8, 21, 22, 23, 126-132, 134-136 and 137, the hinge has a stiffness that is similar to that of wildtype IgG2.

In certain embodiments, an antibody comprises a modified heavy chain constant region comprising an IgG1 CH1 domain comprising SEQ ID NO: 2 or an IgG2 CH1 domain comprising SEQ ID NO: 7, or a variant of SEQ ID NO: 2 or 7, which variant (i) differs from SEQ ID NO: 2 or 7 in 1, 2, 3, 4 or 5 amino acids substitutions, additions or deletions; (ii) differs from SEQ ID NO: 2 or 7 in at most 5, 4, 3, 2, or 1 amino acids substitutions, additions or deletions; (iii) differs from SEQ ID NO: 2 or 7 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 2 or 7, wherein in any of (i)-(iv), an amino acid substitution may be a conservative amino acid substitution or a non-conservative amino acid substitution; and wherein the modified heavy chain constant region has an enhanced biological activity relative to that of another heavy chain constant region, e.g., a heavy chain constant region that comprises a non-IgG2 hinge or relative to the same modified heavy chain constant region that comprises a non-IgG2 hinge.

In certain embodiments, an antibody comprises a modified heavy chain constant region comprising an IgG1 CH2 domain comprising SEQ ID NO: 4 or 24, or a variant of SEQ ID NO: 4 or 24, which variant (i) differs from SEQ ID NO: 4 or 24 in 1, 2, 3, 4 or 5 amino acids substitutions, additions or deletions; (ii) differs from SEQ ID NO: 4 or 24 in at most 5, 4, 3, 2, or 1 amino acids substitutions, additions or deletions; (iii) differs from SEQ ID NO: 4 or 24 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 4 or 24, wherein in any of (i)-(iv), an amino acid substitution may be a conservative amino acid substitution or a non-conservative amino acid substitution; and wherein the modified heavy chain constant region has an enhanced biological activity relative to that of another heavy chain constant region, e.g., a heavy chain constant region that comprises a non-IgG2 hinge or relative to the same modified heavy chain constant region that comprises a non-IgG2 hinge.

In certain embodiments, an antibody comprises a modified heavy chain constant region comprising an IgG1 CH3 domain comprising SEQ ID NO: 5, or a variant of SEQ ID NO: 5, which variant (i) differs from SEQ ID NO: 5 in 1, 2, 3, 4 or 5 amino acids substitutions, additions or deletions; (ii) differs from SEQ ID NO: 5 in at most 5, 4, 3, 2, or 1 amino acids substitutions, additions or deletions; (iii) differs from SEQ ID NO: 5 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 5, wherein in any of (i)-(iv), an amino acid substitution may be a conservative amino acid substitution or a non-conservative amino acid substitution; and wherein the modified heavy chain constant region has an enhanced biological activity relative to that of another heavy chain constant region, e.g., a heavy chain constant region that comprises a non-IgG2 hinge or relative to the same modified heavy chain constant region that comprises a non-IgG2 hinge.

Modified heavy chain constant regions may also comprise a combination of the CH1, hinge, CH2 and CH3 domains described above.

In certain embodiments, an antibody comprises a modified heavy chain constant region described herein or a variant of a modified heavy chain constant region described herein, which variant (i) differs from a modified heavy chain constant region described herein in 1, 2, 3, 4, 5, 6, 7, 8, 9, 10 or more amino acids substitutions, additions or deletions; (ii) differs from a modified heavy chain constant region described herein in at most 10, 9, 8, 7, 6, 5, 4, 3, 2, or 1 amino acids substitutions, additions or deletions; (iii) differs from a modified heavy chain constant region described herein in 1-5, 1-3, 1-2, 2-5, 3-5, 1-10, or 5-10 amino acids substitutions, additions or deletions and/or (iv) comprises an amino acid sequence that is at least about 75%, 80%, 85%, 90%, 95%, 96%, 97%, 98% or 99% identical to a modified heavy chain constant region described herein, wherein in any of (i)-(iv), an amino acid substitution may be a conservative amino acid substitution or a non-conservative amino acid substitution; and wherein the modified heavy chain constant region has an enhanced biological activity relative to that of another heavy chain constant region, e.g., a heavy chain constant region that comprises a non-IgG2 hinge or relative to the same modified heavy chain constant region that comprises a non-IgG2 hinge.

In certain embodiments, an antibody comprises a modified heavy chain constant region comprising any one of SEQ ID NO: 26-37, 54-56, 78-125 and 152-168 or a variant of any one of SEQ ID NO: 26-37, 54-56, 78-125 and 152-168, which variant (i) differs from any one of SEQ ID NO: 26-37, 54-56, 78-125 and 152-168 in 1, 2, 3, 4, 5, 6, 7, 8, 9, 10 or more amino acids substitutions, additions or deletions; (ii) differs from any one of SEQ ID NO: 26-37, 54-56, 78-125 and 152-168 in at most 10, 9, 8, 7, 6, 5, 4, 3, 2, or 1 amino acids substitutions, additions or deletions; (iii) differs from any one of SEQ ID NO: 26-37, 54-56, 78-125 and 152-168 in 1-5, 1-3, 1-2, 2-5, 3-5, 1-10, or 5-10 amino acids substitutions, additions or deletions and/or (iv) comprises an amino acid sequence that is at least about 75%, 80%, 85%, 90%, 95%, 96%, 97%, 98% or 99% identical to any one of SEQ ID NO: 26-37, 54-56, 78-125 and 152-168, wherein in any of (i)-(iv), an amino acid substitution may be a conservative amino acid substitution or a non-conservative amino acid substitution; and wherein the modified heavy chain constant region has an enhanced biological activity relative to that of another heavy chain constant region, e.g., a heavy chain constant region that comprises a non-IgG2 hinge or relative to the same modified heavy chain constant region that comprises a non-IgG2 hinge.

Modified heavy chain constant regions may have (i) similar, reduced or increased effector function (e.g., binding to an FcγR) relative to a wildtype heavy chain constant region and or (ii) similar, reduced or increased half-life (or binding to the FcRn receptor) relative to a wildtype heavy chain constant region.

II. Antibodies with Modified Heavy Chain Constant Regions and Target Antigens Thereof Modified heavy chain constant regions can be used in a wide range of antibodies, such as antibodies that require internalization (e.g., antibody drug conjugates (ADCs), and anti-CD73 antibodies), agonist activity (e.g., antibodies that are effective in modulating immune responses, e.g., in stimulating T cell activation, such as agonist anti-GITR antibodies), antagonist activity (e.g., antibodies that inhibit or block a protein that inhibits an immune response, e.g., T cell activation, such as an antagonist PD-1 antibody), ADCC, signal transduction, or anti-tumor activity. For example, internalization of a cell surface inhibitory receptor may limit its ability to interact with its receptor(s) and decrease cell function(s).

In one embodiment, antibodies comprising a modified heavy chain constant domain are antibodies that require their internalization for activity (e.g., antibodies that are specific for cell surface receptors) by, e.g., inducing receptor-mediated endocytosis when they bind to the cell surface. Such antibodies may be used as vehicles for targeted delivery of drugs, toxins, enzymes or DNA for therapeutic applicationsTherefore, increasing the internalization properties of these antibodies is desirable. Exemplary antibodies that may benefit from effective internalization are antibody drug conjugates. Various assays for measuring the internalization properties of an antibody are known in the art and described herein. These assays utilize, for example, a wide range of dyes for antibody labeling that can be used in wash or quench-based assays to monitor internalization. Antibody internalization can also be monitored in no-wash assays which rely on fluorescent labels.

In one embodiment, antibodies comprising a modified heavy chain constant domain are antibodies that require the internalization of the antigen to which they bind, e.g., a cell surface molecule, such as a receptor or a ligand, for activity. Thus, antibodies to cell surface proteins that require to be downregulated for biological (e.g., therapeutic) activity can use a modified heavy chain constant region described herein.

In certain embodiments, antibodies comprising a modified heavy chain constant domain bind to cell surface molecules and agonize or antagonize the biological activity of the cell surface molecule, e.g., a cell surface molecule on an immune cell, e.g., a T cell, Teff cell, Th1 cell, Th2 cell, CD4+ T cell, CD8+ T cell, Treg cell, dendritic cell, macrophage, monocyte, Langerhans cell, NK cell, myeloid derived suppressor cell, B cell or any other immune cell. The cell surface molecule may be a stimulatory, e.g., co-stimulatory molecule (e.g., GITR, OX40, CD137, CD40, ICOS and other TNFR family members), and the antibody may further stimulate the activity (an agonist antibody) or the antibody may inhibit the activity (an antagonist antibody). The cell surface molecule may be an inhibitory molecule (e.g., CTLA-4, PD-1, PD-L1, LAG-3, TIM-3), and the antibody may further stimulate the activity (an agonist antibody) or the antibody may inhibit the activity (an antagonist antibody).

In certain embodiments, antibodies comprising a modified heavy chain constant domain are agonist antibodies of stimulatory (or co-stimulatory) molecules that, e.g., boost the immune system of a subject, e.g., by inducing IL-2 and/or IFN-γ secretion from T cells (e.g., anti-GITR antibodies). Other agonist antibodies have been shown to activate APCs, promote antitumor T-cell responses, and/or foster cytotoxic myeloid cells with the potential to control cancer in the absence of T-cell immunity. Agonist antibodies of stimulatory molecules are different from antagonist antibodies of inhibitory molecules, which block negative immune checkpoint such as anti-CTLA-4 or anti-PD-1. Agonist activity, such as T cell proliferation, can be measured using a variety of methods known in the art.

In certain embodiments, antibodies comprising a modified heavy chain constant domain are antagonist antibodies of checkpoint inhibitors boost the immune response of a subject by blocking or inhibiting negative immune checkpoint, such as anti-CTLA-4 or anti-PD-1 antibodies, e.g., by targeting the inhibitory receptor expressed on activated T-cells. Antagonist activity, such as inhibition of T cell proliferation can be measured using a variety of methods known in the art.

In one embodiment, the antibody is (i) an agonist of a co-stimulatory receptor or (ii) an antagonist of an inhibitory signal on, e.g., T cells, both of which may result in amplifying antigen-specific T cell responses (immune checkpoint regulators). In certain embodiments, an antibody is (i) an antagonist of a co-stimulatory receptor or (ii) an agonist of an inhibitory signal, e.g., on T cells. Most of the co-stimulatory and co-inhibitory molecules are members of the immunoglobulin super family (IgSF), and antibodies having modified heavy chain constant regions may bind to any of them. One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6, and antibodies having modified heavy chain constant regions may bind to any of them. Another family of membrane bound ligands that bind to co-stimulatory or co-inhibitory receptors is the TNF family of molecules that bind to cognate TNF receptor (TNFR) family members, which include CD40 and CD40L, OX-40, OX-40L, CD70, CD27L, CD30, CD30L, 4-1BBL, CD137, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTα, LTβ, LTβR, Lymphotoxin α 1132, FAS, FASL (CD178), DR3 (TNFRSF25), RELT, DR6, TROY, NGFR (see, e.g., Tansey (2009) Drug Discovery Today 00:1). Thus, the antibodies described herein can bind to any of these surface molecules, and they can be, e.g., (i) agonists or antagonists (or inhibitors or blocking agents) of proteins of the IgSF family or B7 family or the TNFR family that inhibit T cell activation or antagonists of cytokines that inhibit T cell activation (e.g., IL-6, IL-10, TGF-β, VEGF; "immunosuppressive cytokines") and/or (ii) agonists or antagonists of stimulatory receptors of the IgSF family, B7 family or the TNF family or of cytokines that stimulate T cell activation, for modulating, e.g, stimulating, an immune response, e.g., for treating proliferative diseases, such as cancer.

Accordingly, an antibody with a modified heavy chain constant domain may be used as one of the following agents:
(1) An agonist of a protein that stimulates, e.g., T cell activation, such as B7-1, B7-2, CD28, 4-1BB (CD137), 4-1BBL, GITR, ICOS, ICOS-L, OX40, OX40L, CD70, CD27, CD40, DR3 or CD28H; or
(2) An antagonist (inhibitor or blocking agent) of a protein that inhibits T cell activation (e.g., immune checkpoint inhibitors), such as CTLA-4, PD-1, PD-L1, PD-L2, and LAG-3, as described above, and any of the following proteins: TIM-3, Galectin 9, CEACAM-1, BTLA, CD69, Galectin-1, TIGIT, CD113, GPR56, VISTA, 2B4, CD48, GARP, CD73, PD1H, LAIR1, TIM-1, TIM-4, CD39.

Other antibodies include antagonists of inhibitory receptors on NK cells and agonists of activating receptors on NK cells, e.g., KIR, TIGIT, NKG2A.

Generally, antibodies that may benefit from a modified heavy chain constant region include, e.g., agonist antibodies that ligate positive costimulatory receptors, blocking antibodies that attenuate signaling through inhibitory receptors, antagonist antibodies, and antibodies that increase systemically the frequency of anti-tumor T cells, antibodies that overcome distinct immune suppressive pathways within the tumor microenvironment (e.g., block inhibitory receptor engagement (e.g., PD-L1/PD-1 interactions), deplete or inhibit Tregs (e.g., an anti-CD25 monoclonal antibody, inhibit metabolic enzymes such as IDO, or reverse/prevent T cell anergy or exhaustion) and antibodies that trigger innate immune activation and/or inflammation at tumor sites. An increased internalization of inhibitory receptors may translate into a lower level of a potential inhibitor.

In certain embodiments, an antibody comprising a modified heavy chain constant region is an antibody that is conjugated to a therapeutic agent to form an immunoconjugate, such as an antibody drug conjugate (ADC), which immunoconjugate requires internalization for its activity. In an ADC, the antibody functions as a targeting agent for directing the ADC to a target cell expressing its antigen, such as an antigen on a cancer cell. In this case, the antigen may be a tumor associated antigen, i.e., one that is uniquely expressed or overexpressed by the cancer cell. Once there, the drug is released, either inside the target cell or in its vicinity, to act as a therapeutic agent. For a review on the mechanism of action and use of ADCs in cancer therapy, see Schrama et al., *Nature Rev. Drug Disc.* 2006, 5, 147.

For cancer treatment, the therapeutic agent or drug of an ADC preferably is a cytotoxic drug that causes death of the targeted cancer cell. Cytotoxic drugs that can be used in ADCs include the following types of compounds and their analogs and derivatives:

(a) enediynes such as calicheamicin (see, e.g., Lee et al., *J. Am. Chem. Soc.* 1987, 109, 3464 and 3466) and uncialamycin (see, e.g., Davies et al., WO 2007/038868 A2 (2007) and Chowdari et al., U.S. Pat. No. 8,709,431 B2 (2012));

(b) tubulysins (see, e.g., Domling et al., U.S. Pat. No. 7,778,814 B2 (2010); Cheng et al., U.S. Pat. No. 8,394,922 B2 (2013); and Cong et al., US 2014/0227295 A1;

(c) CC-1065 and duocarmycin (see, e.g., Boger, U.S. Pat. No. 6,5458,530 B1 (2003); Sufi et al., U.S. Pat. No. 8,461,117 B2 (2013); and Zhang et al., US 2012/0301490 A1 (2012));

(d) epothilones (see, e.g., Vite et al., US 2007/0275904 A1 (2007) and U.S. RE42930 E (2011));

(e) auristatins (see, e.g., Senter et al., U.S. Pat. No. 6,844,869 B2 (2005) and Doronina et al., U.S. Pat. No. 7,498,298 B2 (2009));

(f) pyrrolobezodiazepine (PBD) dimers (see, e.g., Howard et al., US 2013/0059800 A1 (2013); US 2013/0028919 A1 (2013); and WO 2013/041606 A1 (2013)); and (g) maytansinoids such as DM1 and DM4 (see, e.g., Chari et al., U.S. Pat. No. 5,208,020 (1993) and Amphlett et al., U.S. Pat. No. 7,374,762 B2 (2008)).

In ADCs, the antibody and therapeutic agent may be conjugated via a linker, e.g., a cleavable linker, such as a peptidyl, disulfide, or hydrazone linker. For example, the linker may be a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295; the disclosures of which are incorporated herein by reference.

Exemplary targets of ADCs that may be enhanced with a modified heavy chain constant region include B7H4 (Korman et al., US 2009/0074660 A1); CD19 (Rao-Naik et al., U.S. Pat. No. 8,097,703 B2); CD22 (King et al., US 2010/0143368 A1); CD30 (Keler et al., U.S. Pat. No. 7,387,776 B2 (2008); CD70 (Terrett et al., U.S. Pat. No. 8,124,738 B2); CTLA-4 (Korman et al., U.S. Pat. No. 6,984,720 B1 (2006)); PD-1 (Korman et al., U.S. Pat. No. 8,008,449 B2 (2011); PSMA (Huang et al., US 2009/0297438 A1 and Cardarelli et al., U.S. Pat. No. 7,875,278 B2); PTK7 (Terrett et al., US 2010/0034826 A1); glypican-3 (Terrett et al., US 2010/0209432 (A1)); RG1 (Harkins et al., U.S. Pat. No. 7,335,748 B2 (2008)); mesothelin (Terrett et al., U.S. Pat. No. 8,268,970 B2 (2012)); and CD44 (Xu et al., US 2010/0092484 A1).

III. Methods of Enhancing the Biological Activity of Antibodies

Provided herein are methods for enhancing the biological activity of certain antibodies, such as the one or more of the following biological activities:

(a) increased or altered internalization by a cell;
(b) increased or altered agonist activity;
(c) increased or altered antagonist or blocking activity;
(d) enhanced ADCC;
(d) generation of a new property;
(e) increased or altered signal transduction;
(f) formation of larger antibody/antigen cross-linked complexes;
(g) increased clustering or oligomerization of the target cell surface molecule;
(h) increased stimulation or enhancement of an immune response; and/or
(i) increased inhibition of an immune response.

A method for enhancing a biological activity of an antibody may comprise replacing the heavy chain constant region or a portion thereof, e.g., the hinge and/or CH1 domain, with a modified heavy chain constant region or portion thereof, e.g., an IgG2 hinge and/or IgG2 CH1 domain.

In certain embodiments, a method for improving the biological activity of an antibody comprises (i) providing an antibody that does not comprise a modified heavy chain constant region as described herein; and (ii) replacing the heavy chain constant region of the antibody with a modified heavy chain constant region, or a portion thereof, that enhances the biological activity of the antibody. In certain embodiments, a method for improving the biological activity of an antibody comprises (i) providing an antibody that comprises a non-IgG2 hinge (e.g., an IgG1 hinge, an IgG3 hinge or an IgG4 hinge); and (ii) replacing the non-IgG2 hinge of the antibody with an IgG2 hinge. In certain embodiments, a method for improving the biological activity of an antibody comprises (i) providing an antibody that comprises a non-enhancing IgG2 hinge; and (ii) replacing the non-enhancing IgG2 hinge of the antibody with an IgG2 hinge. A "non-enhancing IgG2 hinge" is a variant IgG2 hinge that differs from an IgG2 hinge in such a way that it no longer has the required characteristic for enhancing the biologic activity of an antibody, e.g., a variant hinge that no longer has the stiffness of a wildtype IgG2 hinge.

Exemplary methods for enhancing the biological activity of an antibody comprise (i) providing an antibody that comprises a non-IgG2 hinge or a non-enhancing IgG2 hinge, and (ii) replacing the hinge with a hinge comprising SEQ ID NO: 8, 21, 22, 23, 126-132, 134-136 or 137 or variants thereof, e.g., the variants described herein. Methods for enhancing the biological activity of an antibody may also comprise (i) providing an antibody that comprises heavy chain constant region that is not a modified heavy chain constant region, and (ii) replacing the heavy chain constant region with a modified heavy chain constant region. Replacing the heavy chain constant region may comprise replacing the CH1, hinge, CH2 and/or CH3 domain. For example, a heavy chain constant region may be modified, by replacing the hinge with an IgG2 hinge or variant thereof, and/or by replacing the CH1 domain with an IgG1 or IgG2 CH1 domain or variant thereof. In certain embodiments, the hinge is replaced with an IgG2 hinge and the CH2 domain is replaced with an IgG1 CH2 domain. In certain embodiments, the hinge is replaced with an IgG2 hinge and the CH3 domain is replaced with an IgG1 CH3 domain. In certain embodiments, the hinge is replaced with an IgG2 hinge, the CH1 is replaced with an IgG2 hinge, the CH2 domain is replaced with an IgG1 CH2 domain and the CH3 domain is replaced with an IgG1 CH3 domain. In certain embodiments, a heavy chain constant region is replaced with a modified heavy chain regions 1-27 set forth in Table 5 above or the heavy chain constant regions set forth in Table 6 or described herein.

Also provided herein are methods for enhancing the biological activity of an IgG1 or IgG2 antibody, comprising deleting 1-10 amino acids in the hinge of the IgG1 or IgG2 antibody, respectively. For example, one or more of amino acids 5219, C22, D221, K222, T223, H224 and T225 can be deleted. In one embodiment, all of amino acids 5219, C22, D221, K222, T223, H224 and T225 are deleted.

Replacing the heavy chain constant region of an antibody to enhance its biological activity is preferably not accompanied by a reduction or a significant reduction of its binding activity to the target antigen. As described in the Examples, substituting the heavy chain constant region of anti-GITR and anti-CD73 antibodies did not significantly change their affinity for the human GITR and human CD73 antigens, respectively.

It will be understood that when referring to replacing a domain of a specific isotype with the same domain of a different isotype, it is not necessary to literally replace the domain, but rather, it may only be necessary to change the amino acids that are different between the two isotypes.

Standard assays to evaluate the binding ability of the antibodies toward an antigen of various species are known in the art and are further described herein, and include for example, ELISAs, Western blots, and RIAs. Suitable assays are described in detail in the Examples. The binding kinetics (e.g., binding affinity) of the antibodies also can be assessed by standard assays known in the art, such as by BIACORE® SPR analysis. Assays to evaluate the properties of antibodies having modified constant regions (e.g., ligand binding, T cell proliferation, cytokine production) are described in further detail infra and in the Examples.

Exemplary antibodies that can be modified as described herein include, e.g., antibodies for treating cancer, such as: Yervoy™ (ipilimumab) or Tremelimumab (to CTLA-4), galiximab (to B7.1), BMS-936558 (to PD-1), CT-011 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4).

Other antibodies that can be modified as described herein include PD-1 and PD-L1 antagonist antibodies. An exemplary anti-PD-1 antibody that may be modified as described herein is nivolumab (BMS-936558); an antibody that comprises the CDRs or variable regions of one of antibodies 17D8, 2D3, 4H1, 5C4, 7D3, 5F4 and 4A11 described in WO 2006/121168; MK-3475 (Lambrolizumab) described in WO2012/145493; AMP-514 described in WO 2012/145493; CT-011 (Pidilizumab; previously CT-AcTibody or BAT; see, e.g., Rosenblatt et al. (2011) J. Immunotherapy 34:409); those described in WO 2009/014708, WO 03/099196, WO 2009/114335, WO 2011/066389, WO 2011/161699, WO 2012/145493, WO2013/173223, U.S. Pat. Nos. 7,635,757 and 8,217,149, and U.S. Patent Publication No. 2009/0317368.

Further antibodies that may be modified include anti-PD-L1 antibodies, e.g., BMS-936559 (referred to as 12A4 in WO 2007/005874 and U.S. Pat. No. 7,943,743); an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943,743; MEDI4736 (also known as Anti-B7-H1); MPDL3280A (also known as RG7446); any of the anti-PD-L1 antibodies disclosed in WO2013/173223, WO2011/066389, WO2012/145493, U.S. Pat. Nos. 7,635,757 and 8,217,149 and U.S. Publication No. 2009/145493.

Other antibodies that may be modified include anti-CTLA-4 antibodies, e.g., Yervoy™ (ipilimumab or antibody 10D1, described in PCT Publication WO 01/14424); tremelimumab (formerly ticilimumab, CP-675,206); monoclonal or an anti-CTLA-4 antibody described in any of the following publications: WO 98/42752; WO 00/37504; U.S. Pat. No. 6,207,156; Hurwitz et al. (1998) Proc. Natl. Acad. Sci. USA 95(17):10067-10071; Camacho et al. (2004) J. Clin. Oncology 22(145): Abstract No. 2505 (antibody CP-675206); and Mokyr et al. (1998) Cancer Res. 58:5301-5304; and any of the anti-CTLA-4 antibodies disclosed in WO2013/173223.

Other antibodies that may be modified include anti-LAG-3 antibodies, e.g., BMS-986016; IMP731 described in US 2011/007023; and IMP-321.

Other antibodies that may be modified include anti-GITR agonist antibodies, e.g., the anti-GITR antibody 6C8 or humanized versions thereof, described in WO2006/105021; an antibody described in WO2011/028683; and an antibody described in JP2008278814.

Antibodies that target other antigens, including those described elsewhere herein, may also be modified. For example, anti-Her2 antibodies that require internalization, e.g., trastuzumab (Herceptin), may be modified as described herein.

IV. Additional Heavy Chain Constant Domain Modifications

In addition to the modifications described herein to antibodies to enhance their biological activity, further mutations can be made, e.g., to the CH1, hinge, CH2 or CH3 domain, to effect, e.g., the effector function, binding to FcγRs, or stability of the antibodies.

Fcs and Modified Fcs

Antibodies described herein may comprise an Fc comprising one or more modifications, typically to alter one or more functional properties of the antibody, such as serum half-life, complement fixation, Fc receptor binding, and/or antigen-dependent cellular cytotoxicity. For example, one may make modifications in the Fc region in order to generate an Fc variant with (a) increased or decreased antibody-dependent cell-mediated cytotoxicity (ADCC), (b) increased or decreased complement mediated cytotoxicity (CDC), (c) increased or decreased affinity for C and/or (d) increased or decreased affinity for a Fc receptor relative to the parent Fc. Such Fc region variants will generally comprise at least one amino acid modification in the Fc region. Combining amino acid modifications is thought to be particularly desirable.

For example, the variant Fc region may include two, three, four, five, etc substitutions therein, e.g. of the specific Fc region positions identified herein. Exemplary Fc sequence variants are disclosed herein, and are also provided at U.S. Pat. Nos. 5,624,821; 6,277,375; 6,737,056; 6,194,551; 7,317,09; 8,101,720; PCT Patent Publications WO 00/42072; WO 01/58957; WO 04/016750; WO 04/029207; WO 04/035752; WO 04/074455; WO 04/099249; WO 04/063351; WO 05/070963; WO 05/040217 WO 05/092925 and WO 06/020114.

Reducing Effector Function

ADCC activity may be reduced by modifying the Fc region. In certain embodiments, sites that affect binding to Fc receptors may be removed (e.g., by mutation), preferably sites other than salvage receptor binding sites. In other embodiments, an Fc region may be modified to remove an ADCC site. ADCC sites are known in the art; see, for example, Sarmay et al. (1992) Molec. Immunol. 29 (5): 633-9 with regard to ADCC sites in IgG1. In one embodiment, the G236R and L328R variant of human IgG1 effectively eliminates FcγR binding. Horton et al. (2011) J. Immunol. 186:4223 and Chu et al. (2008) Mol. Immunol. 45:3926. In other embodiments, the Fc having reduced binding to FcγRs comprised the amino acid substitutions L234A, L235E and G237A. Gross et al. (2001) Immunity 15:289.

CDC activity may also be reduced by modifying the Fc region. Mutations at IgG1 positions D270, K322, P329 and P331, specifically alanine mutations D270A, K322A, P329A and P331A, significantly reduce the ability of the corresponding antibody to bind C1q and activate complement. Idusogie et al. (2000) J. Immunol. 164:4178; WO 99/51642. Modification of position 331 of IgG1 (e.g. P331S) has been shown to reduce complement binding. Tao et al. (1993) J. Exp. Med. 178:661 and Canfield & Morrison (1991) J. Exp. Med. 173:1483. In another example, one or more amino acid residues within amino acid positions 231 to 239 are altered to thereby reduce the ability of the antibody to fix complement. WO 94/29351.

In some embodiments, the Fc with reduced complement fixation has the amino acid substitutions A330S and P331S. Gross et al. (2001) Immunity 15:289.

For uses where effector function is to be avoided altogether, e.g. when antigen binding alone is sufficient to generate the desired therapeutic benefit, and effector function only leads to (or increases the risk of) undesired side effects, IgG4 antibodies may be used, or antibodies or fragments lacking the Fc region or a substantial portion thereof can be devised, or the Fc may be mutated to eliminate glycosylation altogether (e.g. N297A). Alternatively, a hybrid construct of human IgG2 ($C_H1$ domain and hinge region) and human IgG4 ($C_H2$ and $C_H3$ domains) has been generated that is devoid of effector function, lacking the ability to bind the FcγRs (like IgG2) and unable to activate complement (like IgG4). Rother et al. (2007) Nat. Biotechnol. 25:1256. See also Mueller et al. (1997) Mol. Immunol. 34:441; Labrijn et al. (2008) Curr. Op. Immunol. 20:479 (discussing Fc modifications to reduce effector function generally).

In other embodiments, the Fc region is altered by replacing at least one amino acid residue with a different amino acid residue to reduce all effector function(s) of the antibody. For example, one or more amino acids selected from amino acid residues 234, 235, 236, 237, 297, 318, 320 and 322 can be replaced with a different amino acid residue such that the antibody has decreased affinity for an effector ligand but retains the antigen-binding ability of the parent antibody. The effector ligand to which affinity is altered can be, for example, an Fc receptor (residues 234, 235, 236, 237, 297) or the C1 component of complement (residues 297, 318, 320, 322). U.S. Pat. Nos. 5,624,821 and 5,648,260, both by Winter et al.

WO 88/007089 proposed modifications in the IgG Fc region to decrease binding to FcγRI to decrease ADCC (234A; 235E; 236A; G237A) or block binding to complement component C1q to eliminate CDC (E318A or V/K320A and K322A/Q). See also Duncan & Winter (1988) Nature 332:563; Chappel et al. (1991) Proc. Nat'l Acad. Sci. (USA) 88:9036; and Sondermann et al. (2000) Nature 406:267 (discussing the effects of these mutations on FcγRIII binding).

Fc modifications reducing effector function also include substitutions, insertions, and deletions at positions 234, 235, 236, 237, 267, 269, 325, and 328, such as 234G, 235G, 236R, 237K, 67R, 269R, 325L, and 328R. An Fc variant may comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V. These and other modifications are reviewed in Strohl (2009) Current Opinion in Biotechnology 20:685-691. Effector functions (both ADCC and complement activation) can be reduced, while maintaining neonatal FcR binding (maintaining half-life), by mutating IgG residues at one or more of positions 233-236 and 327-331, such as E233P, L234V, L235A, optionally G236Δ, A327G, A330S and P331S in IgG1; E233P, F234V, L235A, optionally G236Δ in IgG4; and A330S and P331S in IgG2. See Armour et al. (1999) Eur. J. Immunol. 29:2613; WO 99/58572. Other mutations that reduce effector function include L234A and L235A in IgG1 (Alegre et al. (1994) Transplantation 57:1537); V234A and G237A in IgG2 (Cole et al. (1997) J. Immunol. 159:3613; see also U.S. Pat. No. 5,834,597); and S228P and L235E for IgG4 (Reddy et al. (2000) J. Immunol. 164:1925). Another combination of mutations for reducing effector function in a human IgG1 include L234F, L235E and P331S. Oganesyan et al. (2008) Acta Crystallogr. D. Biol. Crystallogr. 64:700. See generally Labrijn et gal. (2008) Curr. Op. Immunol. 20:479. Additional mutations found to decrease effector function in the context of an Fc (IgG1) fusion protein (abatacept) are C226S, C229S and P238S (EU residue numbering). Davis et al. (2007) J. Immunol. 34:2204.

Other Fc variants having reduced ADCC and/or CDC are disclosed at Glaesner et al. (2010) Diabetes Metab. Res. Rev. 26:287 (F234A and L235A to decrease ADCC and ADCP in an IgG4); Hutchins et al. (1995) Proc. Nat'l Acad. Sci. (USA) 92:11980 (F234A, G237A and E318A in an IgG4); An et al. (2009) MAbs 1:572 and U.S. Pat. App. Pub. 2007/0148167 (H268Q, V309L, A330S and P331S in an IgG2); McEarchern et al. (2007) Blood 109:1185 (C226S, C229S, E233P, L234V, L235A in an IgG1); Vafa et al. (2014) Methods 65:114 (V234V, G237A, P238S, H268A, V309L, A330S, P331S in an IgG2).

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S. Gross et al. (2001) Immunity 15:289. These five substitutions may be combined with N297A to eliminate glycosylation as well.

Enhancing Effector Function

Alternatively, ADCC activity may be increased by modifying the Fc region. With regard to ADCC activity, human IgG1≥IgG3»IgG4≥IgG2, so an IgG1 constant domain, rather than an IgG2 or IgG4, might be chosen for use in a drug where ADCC is desired. Alternatively, the Fc region may be modified to increase antibody dependent cellular cytotoxicity (ADCC) and/or to increase the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. See WO 2012/142515; see also WO 00/42072. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F/324T. For example, human IgG1Fcs comprising the G236A variant, which can optionally be combined with I332E, have been shown to increase the FcγIIA/FcγIIB binding affinity ratio approximately 15-fold. Richards et al. (2008) *Mol. Cancer Therap.* 7:2517; Moore et al. (2010) *mAbs* 2:181. Other modifications for enhancing FcγR and complement interactions include but are not limited to substitutions 298A, 333A, 334A, 326A, 247I. 339D, 339Q, 280H, 290S, 298D, 298V, 243L, 292P, 300L, 396L, 305I, and 396L. These and other modifications are reviewed in Stroh (2009) *Current Opinion in Biotechnology* 20:685-691. Specifically, both ADCC and CDC may be enhanced by changes at position E333 of IgG1, e.g. E333A. Shields et al. (2001) *J. Biol. Chem.* 276:6591. The use of P247I and A339D/Q mutations to enhance effector function in an IgG1 is disclosed at WO 2006/020114, and D280H, K290S S298D/V is disclosed at WO 2004/074455. The K326A/W and E333A/S variants have been shown to increase effector function in human IgG1, and E333S in IgG2. Idusogie et al. (2001) *J. Immunol.* 166:2571.

Specifically, the binding sites on human IgG1 for FcγR1, FcγRII, FcγRIII and FcRn have been mapped, and variants with improved binding have been described. Shields et al. (2001) *J. Biol. Chem.* 276:6591-6604. Specific mutations at positions 256, 290, 298, 333, 334 and 339 were shown to improve binding to FcγRIII, including the combination mutants T256A/S298A, S298A/E333A, S298A/K224A and S298A/E333A/K334A (having enhanced FcγRIIIa binding and ADCC activity). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys. Lazar et al. (2006) *Proc. Nat'l Acad Sci.* (USA) 103:4005; Awan et al. (2010) *Blood* 115:1204; Desjarlais & Lazar (2011) *Exp. Cell Res.* 317:1278. Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys. Lazar et al. (2006) *Proc. Nat'l Acad Sci.* (USA) 103:4005. In addition, IgG1 mutants containing L235V, F243L, R292P, Y300L, V305I and P396L mutations which exhibited enhanced binding to FcγRIIIa and concomitantly enhanced ADCC activity in transgenic mice expressing human FcγRIIIa in models of B cell malignancies and breast cancer have been identified. Stavenhagen et al. (2007) *Cancer Res.* 67:8882; U.S. Pat. No. 8,652,466; Nordstrom et al. (2011) *Breast Cancer Res.* 13:R123.

Different IgG isotypes also exhibit differential CDC activity (IgG3>IgG1>>IgG2≈IgG4). Dangl et al. (1988) *EMBO J.* 7:1989. For uses in which enhanced CDC is desired, it is also possible to introduce mutations that increase binding to C1q. The ability to recruit complement (CDC) may be enhanced by mutations at K326 and/or E333 in an IgG2, such as K326W (which reduces ADCC activity) and E333S, to increase binding to C1q, the first component of the complement cascade. Idusogie et al. (2001) *J. Immunol.* 166:2571. Introduction of S267E/H268F/S324T (alone or in any combination) into human IgG1 enhances C1q binding. Moore et al. (2010) *mAbs* 2:181. The Fc region of the IgG1/IgG3 hybrid isotype antibody "113F" of Natsume et al. (2008) *Cancer Res.* 68:3863 (FIG. 1 therein) also confers enhanced CDC. See also Michaelsen et al. (2009) *Scand. J. Immunol.* 70:553 and Redpath et al. (1998) *Immunology* 93:595.

Additional mutations that can increase or decrease effector function are disclosed at Dall'Acqua et al. (2006) *J. Immunol.* 177:1129. See also Carter (2006) *Nat. Rev. Immunol.* 6:343; Presta (2008) *Curr. Op. Immunol.* 20:460.

Fc variants that enhance affinity for the inhibitory receptor FcγRIIb may also be used, e.g. to enhance apoptosis-inducing or adjuvant activity. Li & Ravetch (2011) *Science* 333:1030; Li & Ravetch (2012) *Proc. Nat'l Acad. Sci* (USA) 109:10966; U.S. Pat. App. Pub. 2014/0010812. Such variants may provide an antibody with immunomodulatory activities related to FcγRIIb+ cells, including for example B cells and monocytes. In one embodiment, the Fc variants provide selectively enhanced affinity to FcγRIIb relative to one or more activating receptors. Modifications for altering binding to FcγRIIb include one or more modifications at a position selected from the group consisting of 234, 235, 236, 237, 239, 266, 267, 268, 325, 326, 327, 328, and 332, according to the EU index. Exemplary substitutions for enhancing FcγRIIb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγRIIb include 235Y/267E, 236D/267E, 239D/268D, 239D/267E, 267E/268D, 267E/268E, and 267E/328F. Specifically, the S267E, G236D, S239D, L328F and I332E variants, including the S267E+L328F double variant, of human IgG1 are of particular value in specifically enhancing affinity for the inhibitory FcγRIIb receptor. Chu et al. (2008) *Mol. Immunol.* 45:3926; U.S. Pat. App. Pub. 2006/024298; WO 2012/087928. Enhanced specificity for FcγRIIb (as distinguished from FcγRIIa$^{R131}$) may be obtained by adding the P238D substitution. Mimoto et al. (2013) *Protein. Eng. Des. & Selection* 26:589; WO 2012/115241.

Glycosylation

Glycosylation of an antibody is modified to increase or decrease effector function. For example, an aglycoslated antibody can be made that lacks all effector function by mutating the conserved asparagine residue at position 297 (e.g. N297A), thus abolishing complement and FcγRI binding. Bolt et al. (1993) *Eur. J. Immunol.* 23:403. See also Tao & Morrison (1989) *J. Immunol.* 143:2595 (using N297Q in IgG1 to eliminate glycosylation at position 297).

Although aglycosylated antibodies generally lack effector function, mutations can be introduced to restore that function. Aglycosylated antibodies, e.g. those resulting from N297A/C/D/or H mutations or produced in systems (e.g. *E. coli*) that do not glycosylate proteins, can be further mutated to restore FcγR binding, e.g. S298G and/or T299A/G/or H (WO 2009/079242), or E382V and M428I (Jung et al. (2010) *Proc. Nat'l Acad. Sci* (USA) 107:604).

Additionally, an antibody with enhanced ADCC can be made by altering the glycosylation. For example, removal of fucose from heavy chain Asn297-linked oligosaccharides has been shown to enhance ADCC, based on improved binding to FcγRIIIa. Shields et al. (2002) JBC 277:26733; Niwa et al. (2005) *J. Immunol. Methods* 306: 151; Cardarelli et al. (2009) *Clin. Cancer Res.* 15:3376 (MDX-1401); Cardarelli et al. (2010) *Cancer Immunol. Immunotherap.* 59:257 (MDX-1342). Such low fucose antibodies may be produced, e.g., in knockout Chinese hamster ovary (CHO) cells lacking fucosyltransferase (FUT8) (Yamane-Ohnuki et al. (2004) *Biotechnol. Bioeng.* 87:614), or in other cells that generate afucosylated antibodies. See, e.g., Zhang et al. (2011) *mAbs* 3:289 and Li et al. (2006) *Nat. Biotechnol.* 24:210 (both describing antibody production in glycoengineered *Pichia pastoris*); Mossner et al. (2010) *Blood* 115: 4393; Shields et al. (2002) *J. Biol. Chem.* 277:26733; Shinkawa et al. (2003) *J. Biol. Chem.* 278:3466; EP 1176195B1. ADCC can also be enhanced as described in PCT Publication WO 03/035835, which discloses use of a variant CHO cell line, Lec13, with reduced ability to attach fucose to Asn(297)-linked carbohydrates, also resulting in hypofucosylation of antibodies expressed in that host cell (see also Shields, R. L. et al. (2002) *J. Biol. Chem.* 277: 26733-26740). Alternatively, fucose analogs may be added to culture medium during antibody production to inhibit incorporation of fucose into the carbohydrate on the antibody. WO 2009/135181.

Increasing bisecting GlcNac structures in antibody-linked oligosaccharides also enhances ADCC. PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

Additional glycosylation variants have been developed that are devoid of galactose, sialic acid, fucose and xylose residues (so-called GNGN glycoforms), which exhibit enhanced ADCC and ADCP but decreased CDC, as well as others that are devoid of sialic acid, fucose and xylose (so-called G1/G2 glycoforms), which exhibit enhanced ADCC, ADCP and CDC. U.S. Pat. App. Pub. No. 2013/0149300. Antibodies having these glycosylation patterns are optionally produced in genetically modified *N. benthamiana* plants in which the endogenous xylosyl and fucosyl transferase genes have been knocked-out.

Glycoengineering can also be used to modify the anti-inflammatory properties of an IgG construct by changing the α2,6 sialyl content of the carbohydrate chains attached at Asn297 of the Fc regions, wherein an increased proportion of α2,6 sialylated forms results in enhanced anti-inflammatory effects. See Nimmerjahn et al. (2008) *Ann. Rev. Immunol.* 26:513. Conversely, reduction in the proportion of antibodies having α2,6 sialylated carbohydrates may be useful in cases where anti-inflammatory properties are not wanted. Methods of modifying α2,6 sialylation content of antibodies, for example by selective purification of α2,6 sialylated forms or by enzymatic modification, are provided at U.S. Pat. Appl. Pub. No. 2008/0206246. In other embodiments, the amino acid sequence of the Fc region may be modified to mimic the effect of α2,6 sialylation, for example by inclusion of an F241A modification. WO 2013/095966.

Antibodies described herein can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J. Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N—X—S/T sequence.

Biological Half-Life

In certain embodiments, the antibody is modified to increase its biological half-life. Various approaches are possible. For example, this may be done by increasing the binding affinity of the Fc region for FcRn. In one embodiment, the antibody is altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary Fc variants that increase binding to FcRn and/or improve pharmacokinetic properties include substitutions at positions 259, 308, and 434, including for example 259I, 308F, 428L, 428M, 434S, 434H, 434F, 434Y, and 434M. Other variants that increase Fc, binding to FcRn include: 250E, 250Q, 428L, 428F, 250Q/428L (Hinton et al., 2004, J. Biol, Chem, 279(8): 6213-6216, Hinton et all. 2006 Journal of Immunology 176:346-356), 256A, 272A, 305A, 307A, 31 1A, 312A, 378Q, 380A, 382A, 434A (Shields et al, Journal of Biological Chemistry, 2001, 276 (9):6591-6604), 252F, 252Y, 252W, 254T, 256Q, 256E, 256D, 433R, 434F, 434Y, 252Y/254T/256E, 433K/434F/436H (Del' Acqua et al. Journal of immunology, 2002, 169:5171-5180, Dall'Acqua et al., 2006, Journal of Biological Chemistry 281:23514-23524). See U.S. Pat. No. 8,367, 805.

Modification of certain conserved residues in IgG Fc (I253/H310/Q311/H433/N434), such as the N434A variant (Yeung et al. (2009) *J. Immunol.* 182:7663), has been proposed as a way to increase FcRn affinity, thus increasing the half-life of the antibody in circulation. WO 98/023289. The combination Fc variant comprising M428L and N434S has been shown to increase FcRn binding and increase serum half-life up to five-fold. Zalevsky et al. (2010) *Nat. Biotechnol.* 28:157. The combination Fc variant comprising T307A, E380A and N434A modifications also extends half-life of IgG1 antibodies. Petkova et al. (2006) *Int. Immunol.* 18:1759, In addition, combination Fc variants comprising M252Y/M428L, M428L/N434H, M428L/N434F, M428L/N434Y, M428L/N434A, M428L/N434M, and M428L/N434S variants have also been shown to extend half-life. WO 2009/086320.

Further, a combination Fc variant comprising M252Y, S254T and T256E, increases half-life-nearly 4-fold. Dall'Acqua et al. (2006) *J. Biol. Chem.* 281:23514. A related IgG1 modification providing increased FcRn affinity but reduced pH dependence (M252Y S254T/T256E/H433K/N434F) has been used to create an IgG1 construct ("MST-HN Abdeg") for use as a competitor to prevent binding of other antibodies to FcRn, resulting in increased clearance of that other antibody, either endogenous IgG (e.g. in an autoimmune setting) or another exogenous (therapeutic) mAb. Vaccaro et al. (2005) *Nat. Biotechnol.* 23:1283; WO 2006/130834.

Other modifications for increasing FcRn binding are described in Yeung et al. (2010) *J. Immunol* 182:7663-7671; U.S. Pat. Nos. 6,277,375; 6,821,505; WO 97/34631; WO 2002/060919.

In certain embodiments, hybrid IgG isotypes may be used to increase FcRn binding, and potentially increase half-life. For example, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339I, 356E, 358M, 384S, 392N, 397M, 422I, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more substitutions, e.g., one or more of the following amino acid substitutions; 233E, 234L, 235L, −236G (referring to an insertion of a glycine at position 236), and 327A. See U.S. Pat. No. 8,629,113. A hybrid of IgG1/IgG2/IgG4 sequences has been generated that purportedly increases serum half-life and improves expression. U.S. Pat. No. 7,867,491 (sequence number 18 therein).

The serum half-life of the antibodies of the present invention can also be increased by pegylation. An antibody can be pegylated to, for example, increase the biological (e.g., serum) half-life of the antibody. To pegylate an antibody, the antibody, or fragment thereof, typically is reacted with a polyethylene glycol (PEG) reagent, such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivative other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0154316 by Nishimura et al. and EP 0401384 by Ishikawa et al.

Alternatively, under some circumstances it may be desirable to decrease the half-life of an antibody of the present invention, rather than increase it. Modifications such as I253A (Hornick et al. (2000) *J. Nucl. Med.* 41:355) and H435A/R I253A or H310A (Kim et al. (2000) *Eur. J. Immunol.* 29:2819) in Fc of human IgG1 can decrease FcRn binding, thus decreasing half-life (increasing clearance) for use in situations where rapid clearance is preferred, such a medical imaging. See also Kenanova et al. (2005) *Cancer Res.* 65:622. Other means to enhance clearance include formatting the antigen binding domains of the present invention as antibody fragments lacking the ability to bind FcRn, such as Fab fragments. Such modification can reduce the circulating half-life of an antibody from a couple of weeks to a matter of hours. Selective PEGylation of antibody fragments can then be used to fine-tune (increase) the half-life of the antibody fragments if necessary. Chapman et al. (1999) *Nat. Biotechnol.* 17:780. Antibody fragments may also be fused to human serum albumin, e.g. in a fusion protein construct, to increase half-life. Yeh et al. (1992) *Proc. Nat'l Acad. Sci.* 89:1904. Alternatively, a bispecific antibody may be constructed with a first antigen binding domain of the present invention and a second antigen binding domain that binds to human serum albumin (HSA). See Int'l Pat. Appl. Pub. WO 2009/127691 and patent references cited therein. Alternatively, specialized polypeptide sequences can be added to antibody fragments to increase half-life, e.g. "XTEN" polypeptide sequences. Schellenberger et al. (2009) *Nat. Biotechnol.* 27:1186; Int'l Pat. Appl. Pub. WO 2010/091122.

Stability

A potential protease cleavage site in the hinge of IgG1 constructs can be eliminated by D221G and K222S modifications, increasing the stability of the antibody. WO 2014/043344.

In certain embodiments, the antibodies described herein do not contain asparagine isomerism sites. The deamidation of asparagine may occur on N-G or D-G sequences and may result in the creation of an isoaspartic acid residue that may introduce a kink into the polypeptide chain and may decrease its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an antibody that contains a pI value that falls in the normal range. This can be achieved either by selecting antibodies with a pI in the normal range or by mutating charged surface residues.

Each antibody will have a characteristic melting temperature, with a higher melting temperature indicating greater overall stability in vivo (Krishnamurthy R and Manning M C (2002) *Curr Pharm Biotechnol* 3:361-71). Generally, it is preferred that the $T_{M1}$ (the temperature of initial unfolding) be greater than 60° C., preferably greater than 65° C., even more preferably greater than 70° C. The melting point of an antibody can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9).

In a preferred embodiment, antibodies are selected that do not degrade rapidly. Degradation of an antibody can be measured using capillary electrophoresis (CE) and MALDI-MS (Alexander A J and Hughes D E (1995) *Anal Chem* 67:3626-32).

When using an IgG4 constant domain, it is usually preferable to include the substitution S228P, which mimics the hinge sequence in IgG1 and thereby stabilizes IgG4 molecules, e.g. reducing Fab-arm exchange between the therapeutic antibody and endogenous IgG4 in the patient being treated. Labrijn et al. (2009) *Nat. Biotechnol.* 27:767; Reddy et al. (2000) *J. Immunol.* 164:1925. Similarly, in IgG2 hinge containing antibodies a C219S and/or C220S mutation stabilizes the antibody comprising an IgG2 hinge.

Aggregation

In another preferred embodiment, antibodies are selected that have minimal aggregation effects, which can lead to the triggering of an unwanted immune response and/or altered pharmacokinetic properties. Generally, antibodies are acceptable with aggregation of 25% or less, preferably 20% or less, even more preferably 15% or less, even more preferably 10% or less and even more preferably 5% or less. Aggregation can be measured by several techniques, including size-exclusion column (SEC), high performance liquid chromatography (HPLC), and light scattering.

V. Non-Antibody Proteins and Antibody Derivatives

The invention described herein may also be applied to molecules that are not full length antibodies, provided that they comprise a hinge. For example, IgG fusion proteins with an enhanced biologic activity may be made. Accordingly, provided herein are fusion proteins comprising an active moiety linked, e.g., covalently linked, to an IgG constant region, e.g., an Fc region, comprising an IgG2 hinge and optionally a CH2 and CH3 domains or portions thereof. The Fc may be any Fc of a modified heavy chain constant region described herein, such as the Fc portions of the modified heavy chain constant regions set forth in Tables 5 and 6.

Antibodies described herein may also be used for forming bispecific molecules. An antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. Antibodies described herein may be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

VI. Compositions

Further provided are compositions, e.g., a pharmaceutical compositions, containing one or a combination of antibodies, or antigen-binding portion(s) thereof, described herein, formulated together with a pharmaceutically acceptable carrier. Such compositions may include one or a combination of (e.g., two or more different) antibodies, or immunoconjugates or bispecific molecules described herein. For example, a pharmaceutical composition described herein can comprise a combination of antibodies (or immunoconjugates or bispecifics) that bind to different epitopes on the target antigen or that have complementary activities.

In certain embodiments, a composition comprises an antibody described herein at a concentration of at least 1 mg/ml, 5 mg/ml, 10 mg/ml, 50 mg/ml, 100 mg/ml, 150 mg/ml, 200 mg/ml, 1-300 mg/ml, or 100-300 mg/ml.

Pharmaceutical compositions described herein also can be administered in combination therapy, i.e., combined with other agents. For example, the combination therapy can include an antibody described herein combined with at least one other anti-cancer and/or T-cell stimulating (e.g., activating) agent. Examples of therapeutic agents that can be used in combination therapy are described in greater detail below in the section on uses of the antibodies described herein.

In some embodiments, therapeutic compositions disclosed herein can include other compounds, drugs, and/or agents used for the treatment of cancer. Such compounds, drugs, and/or agents can include, for example, chemotherapy drugs, small molecule drugs or antibodies that stimulate the immune response to a given cancer. In some instances, therapeutic compositions can include, for example, one or more of an anti-CTLA-4 antibody, an anti-PD-1 antibody, an anti-PDL-1 antibody, an anti-OX40 (also known as CD134, TNFRSF4, ACT35 and/or TXGP1L) antibody, or an anti-LAG-3 antibody.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an antibody described herein include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions described herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an antibody described herein preferably results in a decrease in severity of disease symptoms, an increase in frequency and duration of disease symptom-free periods, or a prevention of impairment or disability due to the disease affliction. In the context of cancer, a therapeutically effective dose preferably prevents further deterioration of physical symptoms associated with cancer. Symptoms of cancer are well-known in the art and include, for example, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

A therapeutically effective dose may prevent or delay onset of cancer, such as may be desired when early or preliminary signs of the disease are present. Laboratory tests utilized in the diagnosis of cancer include chemistries, hematology, serology and radiology. Accordingly, any clinical or biochemical assay that monitors any of the foregoing may be used to determine whether a particular treatment is a therapeutically effective dose for treating cancer. One of ordinary skill in the art would be able to determine such amounts based on such factors as the subject's size, the severity of the subject's symptoms, and the particular composition or route of administration selected.

A composition described herein can be administered via one or more routes of administration using one or more of a variety of methods known in the art. As will be appreciated by the skilled artisan, the route and/or mode of administration will vary depending upon the desired results. Preferred routes of administration for antibodies described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the antibodies described herein can be formulated to ensure proper distribution in vivo. For example, the blood-brain barrier (BBB) excludes many highly hydrophilic compounds. To ensure that the therapeutic compounds described herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

VII. Uses and Methods

The antibodies, antibody compositions and methods described herein have numerous in vitro and in vivo utilities involving, for example, the treatment of various disorders, e.g., cancers. For example, antibodies described herein can be administered to cells in culture, in vitro or ex vivo, or to human subjects, e.g., in vivo. Accordingly, provided herein are methods of treatment of a subject comprising administering to the subject an antibody comprising a modified heavy chain constant region, such that treatment occurs. Also provided herein are methods of modifying an immune response in a subject comprising administering to the subject an antibody such that the immune response in the subject is modified. Preferably, the response is enhanced, stimulated or up-regulated. However, in other embodiments, an immune response is inhibited.

Preferred subjects include human patients in whom enhancement of an immune response would be desirable. The methods are particularly suitable for treating human patients having a disorder that can be treated by augmenting an immune response (e.g., the T-cell mediated immune response). In a particular embodiment, the methods are particularly suitable for treatment of cancer in vivo. In one embodiment, the subject is a tumor-bearing subject and an immune response against the tumor is stimulated. A tumor may be a solid tumor or a liquid tumor, e.g., a hematological malignancy. In certain embodiments, a tumor is an immunogenic tumor. In certain embodiments, a tumor is non-immunogenic. In certain embodiments, a tumor is PD-L1 positive. In certain embodiments a tumor is PD-L1 negative. A subject may also be a virus-bearing subject and an immune response against the virus is stimulated.

Further provided are methods for inhibiting growth of tumor cells in a subject comprising administering to the subject an antibody described herein such that growth of the tumor is inhibited in the subject. Also provided are methods of treating viral infection in a subject comprising administering to the subject an antibody described herein such that the viral infection is treated in the subject.

Also encompassed herein are methods for depleting Treg cells from the tumor microenvironment of a subject having a tumor, e.g., cancerous tumor, comprising administering to the subject a therapeutically effective amount of an antibody described herein that comprises an Fc that stimulates depletion of $T_{reg}$ cells in the tumor microenvironment. An Fc may, e.g., be an Fc with effector function or enhanced effector function, such as binding or having enhanced binding to one or more activating Fc receptors.

In certain embodiments, an antibody comprising a modified heavy chain constant region binds to a stimulatory molecule and inhibits its activity, i.e., is an antagonist of a stimulatory molecule, or the antibody binds to an inhibitory molecule and stimulates its activity, i.e., is an agonist of an inhibitory molecule. Such antibodies may be used for treating disease in which the immune system or an immune response should be downregulated, e.g., autoimmune diseases or to prevent transplant rejections.

Cancer

Provided herein are methods for treating a subject having cancer, comprising administering to the subject antibody described herein, such that the subject is treated, e.g., such that growth of cancerous tumors is inhibited or reduced and/or that the tumors regress. For example, activation of GITR by anti-GITR antibodies can enhance the immune response to cancerous cells in the patient. The antibody can be used alone to inhibit the growth of cancerous tumors. Alternatively, the antibody can be used in conjunction with another agent, e.g., other immunogenic agents, standard cancer treatments, or other antibodies, as described below.

Cancers whose growth may be inhibited using the antibodies described herein include cancers typically responsive to immunotherapy. Non-limiting examples of cancers for treatment include squamous cell carcinoma, small-cell lung cancer, non-small cell lung cancer, squamous non-small cell lung cancer (NSCLC), non NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of luekemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (M0), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein may also be used for treatment of metastatic cancers, refractory cancers (e.g., cancers refractory to previous immunotherapy, e.g., with a blocking CTLA-4 or PD-1 antibody), and recurrent cancers.

Combination Therapies

In addition to the therapies provided above, the antibodies described herein can also be used in combination with another therapy. For example, for cancer treatment, an antibody described herein may be administered to a subject who is also receiving another cancer treatement, such as chemotherapy, radiation, surgery or gene therapy.

Methods of treatment may include coadministration of an antibody described herein (e.g., an antagonist antibody, agonist antibody, and ADC having a modified heavy chain constant region) with another molecule, e.g., antibody (e.g., an antagonist antibody, agonist antibody, and ADC). An antibody described herein that stimulates the immune system may be administered with another molecule that stimulates the immune system, e.g., a molecule that is an agonist of a co-stimulatory molecule or an inhibitor of an inhibitory molecule.

An antibody as described herein alone or with one or more additional immune stimulating antibodies (e.g., CTLA-4 and/or PD-1 and/or PD-L1 and/or LAG-3 blockade) can be combined with standard cancer treatments. For example, an antibody described herein alone or with one or more additional antibodies can be effectively combined with chemotherapeutic regimes. In these instances, it may be possible to reduce the dose of other chemotherapeutic reagent administered with the combination of the instant disclosure (Mokyr et al. (1998) *Cancer Research* 58: 5301-5304). An example of such a combination is a combination of an antibody described herein, with or without and an additional antibody, further in combination with decarbazine or IL-2 for the treatment of melanoma.

An antibody described herein may be combined with an anti-neoplastic antibody, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), and the like. Antibodies described herein may also be combined with one or more of the following chemotherapeutic agents: camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxorubicin, 5-fu, or camptothecin+apo21/TRAIL (a 6× combo)); a proteasome inhibitor (e.g., bortezomib or MG132); a Bcl-2 inhibitor (e.g., BH3I-2' (bcl-xl inhibitor), indoleamine dioxygenase-1 (IDO1) inhibitor (e.g., INCB24360), AT-101 (R-(−)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., *Nat Med* 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., Avastin), synthetic triterpenoids (see Hyer et al., *Cancer Research* 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), Trastuzumab, Cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK3β inhibitors, IAP inhibitors and/or genotoxic drugs.

The antibodies and combination antibody therapies described herein can further be used in combination with one or more anti-proliferative cytotoxic agents. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN™) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Suitable anti-proliferative agents for combining with antibodies described herein, without limitation, taxanes, paclitaxel (paclitaxel is commercially available as TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

Combination treatments can be administered simultaneously or sequentially. In certain examples, combinations are fixed dose combinations.

In cases where it is desirable to render aberrantly proliferative cells quiescent in conjunction with or prior to treatment with the antibodies described herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX™, can also be administered to the patient. When employing the methods or compositions described herein, other agents used in the modulation of tumor growth or metastasis in a clinical setting, such as antimimetics, can also be administered as desired.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The present disclosure is further illustrated by the following examples, which should not be construed as further limiting. The contents of all figures and all references, Genbank sequences, patents and published patent applications cited throughout this application are expressly incorporated herein by reference. In particular, the disclosures of PCT publications WO 09/045957, WO 09/073533, WO 09/073546, WO 09/054863 and PCT/US2013/072918, and U.S. Patent Publication No. 2011/0150892 are expressly incorporated herein by reference.

EXAMPLES

Example 1: Enhanced Internalization of Anti-CD73 Antibodies with an IgG2 Hinge Relative to the Same Antibodies with a Non-IgG2 Hinge It had been observed that hybridoma derived anti-CD73 antibody 11F11, which has an IgG2 constant region, is more potent in cellular CD73 inhibition assays than the 11F11 antibody as an IgG1 or IgG1.1 (effectorless IgG1), and more potent than other anti-CD73 antibodies having IgG1 constant regions. Based at least on this observation, it was hypothesized that increased inhibitory activity of anti-CD73 antibodies having IgG2 hinges relative to those having non-IgG2 hinges, such as IgG1 hinges, was due to increased internalization of the antibodies. To test this hypothesis, anti-CD73 antibodies having IgG1 or IgG2 constant regions or portions thereof were tested in internalization assays.

The antibodies that were used are listed in Table 7 which provides the identities of each of the domains of the constant regions (all human) of each antibody, including specific mutations if present.

TABLE 7

| Name of antibody | VH | CH1 | Hinge | CH2 | CH3 | HC SEQ ID NO[1] | LC SEQ ID NO[2] |
|---|---|---|---|---|---|---|---|
| 11F11 | 11F11 | IgG2 | IgG2 | IgG2 | IgG2 | 44 | 72 |
| 4C3 | 4C3 | IgG1 | IgG1 | IgG1 | IgG1 | 45 | 73 |
| 6D11 | 6D11 | IgG1 | IgG1 | IgG1 | IgG1 | 46 | 74 |
| CD73.10-IgG2-C219S | CD73.10 | IgG2 | IgG2 (C219S) | IgG2 | IgG2 | 47 | 72 |
| CD73.10-IgG2-C219S-IgG1.1 | CD73.10 | IgG2 | IgG2 (C219S) | IgG1.1 (A330S/P331S) | IgG2 | 48 | 72 |
| CD73.10-IgG1.1 | CD73.10 | IgG1.1 | IgG1.1 (L234A/L235E/G237A) | IgG1.1 (A330S/P331S) | IgG1.1 | 49 | 72 |
| CD73.4-IgG2-C219S | CD73.10 | IgG2 | IgG2 (C219S) | IgG2 | IgG2 | 50 | 72 |
| CD73.3-IgG1.1 | CD73.3 | IgG1.1 | IgG1.1 (L234A/L235E/G237A) | IgG1.1 (A330S/P331S) | IgG1.1 | 51 | 73 |

[1]SEQ ID NO of full length heavy chain
[2]SEQ ID NO of full length light chain

The antibodies were made by expressing the heavy and light chains in HEK293-6E cells, and culture media was harvested 5 days after transfection.

Binding of the constructs to FcγRs was measured. hCD64 and hCD32a-H131 binding data for IgG1.1 and IgG2 molecules were consistent with expected values for the different Fcs. IgG1.1f is the most inert Fc. IgG2 and IgG2-C219S showed typical FcR binding for IgG2. As expected, data for IgG2-C219S-G1.1f suggests significantly weaker binding than wild type IgG1 or IgG2, but increased binding compared to IgG1.1f.

The affinity of the antibodies for human CD73 was measured to determine whether the change of the constant region affects them. The affinities were determined by Surface Plasmon Resonance (SPR) as follows. CD73 binding kinetics and affinity were studied by surface Plasmon resonance (SPR) using a Biacore T100 instrument (GE Healthcare) at 25° C. This experiment tested the binding of the N-terminal domain of hCD73 (consisting of residues 26-336 of human CD73; termed N-hCD73) to antibodies that were captured on immobilized protein A surfaces. For these experiments, protein A (Pierce) was immobilized to a density of 3000-4000 RU on flow cells 1-4 of a CM5 sensor chip (GE Healthcare) using standard ethyl(dimethylaminopropyl) carbodiimide (EDC)/N-hydroxysuccinimide (NHS) chemistry, with ethanolamine blocking, in a running buffer of 0.01 M HEPES pH 7.4, 0.15 M NaCl, 3 mM EDTA, 0.005% v/v tween 20. Kinetic experiments were performed by first capturing antibodies (5-10 ug/ml) on the protein A surfaces using a 30 s contact time at 10 ul/min, with binding of 600, 200, 66.7, 22.2, 7.4, and 2.5 nM N-hCD73-his, using a 180 s association time and 360 s dissociation time at a flow rate of 30 ul/min. The running buffer for the kinetic experiments was 10 mM sodium phosphate, 130 mM sodium chloride, 0.05% tween 20, pH 7.1. The surfaces were regenerated after each cycle using two 30 s pulses of 10 mM glycine pH 1.5 at a flow rate of 30 µl/min. Sensogram data was double-referenced and then fitted to a 1:1 Langmuir model using Biacore T100 evaluation software v2.0.4, to determine the association rate constant (ka), the dissociation rate constant (kd), and the equilibrium dissociation constant (KD).

The results are shown in Table 8. The table compiles data from different experiments. For antibodies for which two sets of numbers are shown, each set corresponds to data obtained in a separate experiment.

TABLE 8

| mAb | Fc | ka (1/Ms) | kd (1/s) | KD (nM) |
|---|---|---|---|---|
| 11F11 | IgG2 | 2.6E+05 | 4.2E-04 | 1.6 |
|  |  | 2.9E+05 | 1.6E-04 | 0.56 |
| 4C3 | IgG1 | 2.2E+04 | 2.4E-03 | 110 |
|  |  | 2.4E+04 | 2.2E-03 | 92 |
| 6E11 | IgG1 | 5.7E+04 | 1.4E-03 | 25 |
| CD73.10 | IgG1.1 | 2.7E+05 | 1.3E-03 | 4.7 |
| CD73.10 | IgG2-C219S | 2.2E+05 | 1.4E-03 | 6.2 |
|  |  | 2.2E+05 | 1.8E-03 | 8.3 |
| CD73.10 | IgG2-C219S-IgG1.1 | 2.4E+05 | 1.4E-03 | 5.7 |
|  |  | 2.3E+05 | 1.60E-03 | 6.8 |
| CD73.4 | IgG2-C219S | 2.9E+05 | 1.6E-04 | 0.55 |
|  |  | 2.8E+05 | 3.3E-04 | 1.2 |
|  |  | 2.9E+05 | 3.7E-04 | 1.3 |
| CD73.3 | IgG1.1 | 1.6E+04 | 3.6E-03 | 220 |

The results indicate that the presence of the different constant regions in an antibody, e.g., CD73.10, did not change the affinity of the antibody to human CD73.

The internalization of anti-CD73 antibodies was measured in two different assays.

A. High-Content Internalization Assay (2 Hour Fixed Time Assay)

The anti-CD73 antibodies used to test anti-CD73 antibody dependent CD73 internalization in Calu6 cells by assessing cellular expression after 2 hours of antibody incubation. Cells (2,000 cells/well) in 20 µl of complete medium (Gibe® RPMI Media 1640 with 10% heat inactivated fetal bovine serum) were plated in 384 BD Falcon plate and grown overnight at 37° C. 5% $CO_2$ and 95% humidity. Anti-CD73 antibodies were serially diluted with PBS buffer containing 0.2% BSA, and added 5 µl/well into the cell plate. The cells were incubated with antibodies for 2 hours at 37° C. 5% $CO_2$ and 95% humidity, followed by washing once with PBS buffer, Formaldehyde (final 4% in PBS) was then added into the cell plate at 20 ul/well, and the plate was incubated at room temperature for 10 minutes. Afterwards, all liquid was aspirated and cells were washed once with 30 ul PBS. Detection antibody (2.5 µg/well of anti-CD73 Ab CD73.10.IG2C219S) was added at 15 µg/well into the fixed cell plate. The cells were incubated at 4° C. overnight. On the next day, the plate was washed twice with PBS buffer, followed by adding secondary antibody containing Alexa-488 goat anti human and DAPI, stained for 1 hour at room temperature. After 3 washes in PBS buffer, the plate was imaged on Arrayscan Vti (Cellomics, Pittsburgh, Pa.). $IC_{50}$ and Ymax were measured. Ymax was determined by comparing to 100 nM dose of 11F11 as internal maximum. All calculations were determined as a percentage of internalization compared to this control, which was set to 100%.

The results are provided in Table 9.

TABLE 9

| mAb | Constant region | Epitope bin | EC50 (nM) | Ymax |
|---|---|---|---|---|
| 11F11 | IgG2 | 1 | 0.58 | 98 |
| 4D4 | IgG2 | 1 | 0.38 | 104 |
| 10D2 | IgG1 | 1 | ND | 29 |
| 24H2 | IgG1 | 1 | 8.2 | 51 |
| 7A11 | IgG1 | 1 | 2.59 | 50 |
| CD73.4 | IgG2-C219S-IgG1.1 | 1 | 1.2 | 97 |
| CD73.10 | IgG1.1 | 1 | 6.18 | 64 |
| CD73.10 | IgG2-C219S | 1 | 0.67 | 99 |
| CD73.10 | IgG2-C219S-IgG1.1 | 1 | 0.87 | 99 |

ND = Not Detected
NA = Not Applicable

The results show that anti-CD73 antibodies having an IgG2 hinge have a lower EC50 and higher Ymax.

Kinetic internalization studies were performed to assess the rate of internalization. Several cells lines were tested: H2228 cells, HCC15 cells, Calu6 cells, and NCI-H2030. Cells (2,000 cells/well) in 20 µl of complete medium (Gibco RPMI Media 1640 with 10% heat inactivated fetal bovine serum) were plated in 384 BD Falcon plate and grown overnight at 37° C. 5% $CO_2$ and 95% humidity. CD73 antibodies were diluted with PBS buffer containing 0.2% BSA to 10 µg/ml and added 5 µl/well into the cell plate. The cells were incubated with antibodies for 0-2 hour time course at 37° C., followed by washing once with PBS buffer. The cells were subsequently fixed with formaldehyde (final 4% in PBS) at room temperature for 10 minutes, and then washed once with 30 ul PBS. Detection antibody (2.5 µg/well anti-CD73 Abs CD73.10.IG2C219S) were diluted with PBS buffer containing 0.2% BSA, and added 15 µl/well into the fixed cell plate. The plate was incubated at 4° C. for overnight. On the next day, after 3 washes in PBS buffer, Secondary antibody Alexa488-goat anti human with DAN were added. The cells were stained for 60 minutes at room temperature, after 3 washes, images were acquired using Arrayscan (Cellomics, Pittsburgh, Pa.). The results are provided in FIGS. 1A-J and Tables 10 and 11. The values in Table 10 derive from the data shown in FIGS. 1A-J.

TABLE 10

| Cell line | 11F11 (IgG2) $T_{1/2}$ (min) | 6E11 (IgG1) $T_{1/2}$ (min) | CD73.10.IgG1.1f $T_{1/2}$ (min) |
|---|---|---|---|
| Calu6 | 3.9 | 60.9 | 14.4 |
| HCC44 | 3.3 | 27.9 | 23.5 |
| H2030 | 3.3 | 40.3 | 18.3 |
| H647 | 45.7 | N/A | N/A |
| H2228 | 10.9 | 36.5 | 35.7 |
| HCC15 | 2.2 | 84.4 | 37.9 |
| SKLU1 | 6.8 | 18.0 | 17.2 |
| SKMES1 | 2.2 | 62.8 | 32.3 |
| SW900 | 10.3 | 94.9 | 43.4 |

TABLE 11

T$_{1/2}$ and % internalization of CD73 antibodies in 4 human cell lines

|  | H228 cells | | HCC15 cells | | Calu6 cells | | H2030 cells | |
|---|---|---|---|---|---|---|---|---|
|  | T$_{1/2}$ min | % internalization | T$_{1/2}$ min | % internalization | T$_{1/2}$ min | % internalization | T$_{1/2}$ min | % internalization |
| CD73.11-IgG2CS | — | — | — | — | 4.1 | 89 | 4.6 | 85 |
| CD73.10-IgG2CS | 9.7 | 93 | 2.6 | 91 | 3.0 | 91 | 3.3 | 85 |
| CD73.10-IgG2CS-IgG1.1f | 9.4 | 92 | 3.0 | 91 | 3.1 | 91 | 4.3 | 87 |
| CD73.4-IgG2CS | 13.8 | 94 | 3.1 | 94 | 6.5 | 88 | 3.7 | 89 |
| CD73.10-IgG1.1f | 35.7 | 33 | 37.9 | 71 | 14.4 | 63 | 18.3 | 67 |
| CD73.3-IgG1.1f | 16.5 | −47 | >240 | 38 | 111.4 | 79 | >120 | 27 |
| 11F11 | 10.9 | 96 | 2.2 | 94 | 3.9 | 87 | 3.3 | 90 |
| 4C3 | 7.6 | −48 | 141.5 | 28 | 0.6 | −6 | >120 | −34 |
| 6E11 | 36.5 | 13 | 84.4 | 64 | 107.4 | 68 | 40.32 | 51 |

The results indicate that 11F11 (an IgG2 antibody) internalized within minutes, reaching a plateau in 30 minutes, whereas 6E11 (an IgG1 antibody) internalized more slowly, reaching a plateau at about 1 hr (FIGS. 1A-J). Similarly, 11F11 with an IgG1 constant region internalized more slowly than 11F11 with an IgG2 constant region. This trend was observed in several cell lines (Tables 10 and 11 and FIGS. 1A-J).

B. Internalization Measured by Flow Cytometry

Anti-CD73 antibody mediated internalization of CD73 was also tested by flow cytometry. Indicated cells were incubated with 10 μg/mL of the indicated antibody for 30 minutes on ice, washed several times, and transferred to 37° C. for the indicated time. Cells were harvested at the same time after the indicated incubation time. Cells were stained with primary antibody again (same antibody used for initial incubation) followed by anti-human secondary antibody. Cells were then assayed for expression of CD73 by flow cytometry.

Figure 1E:
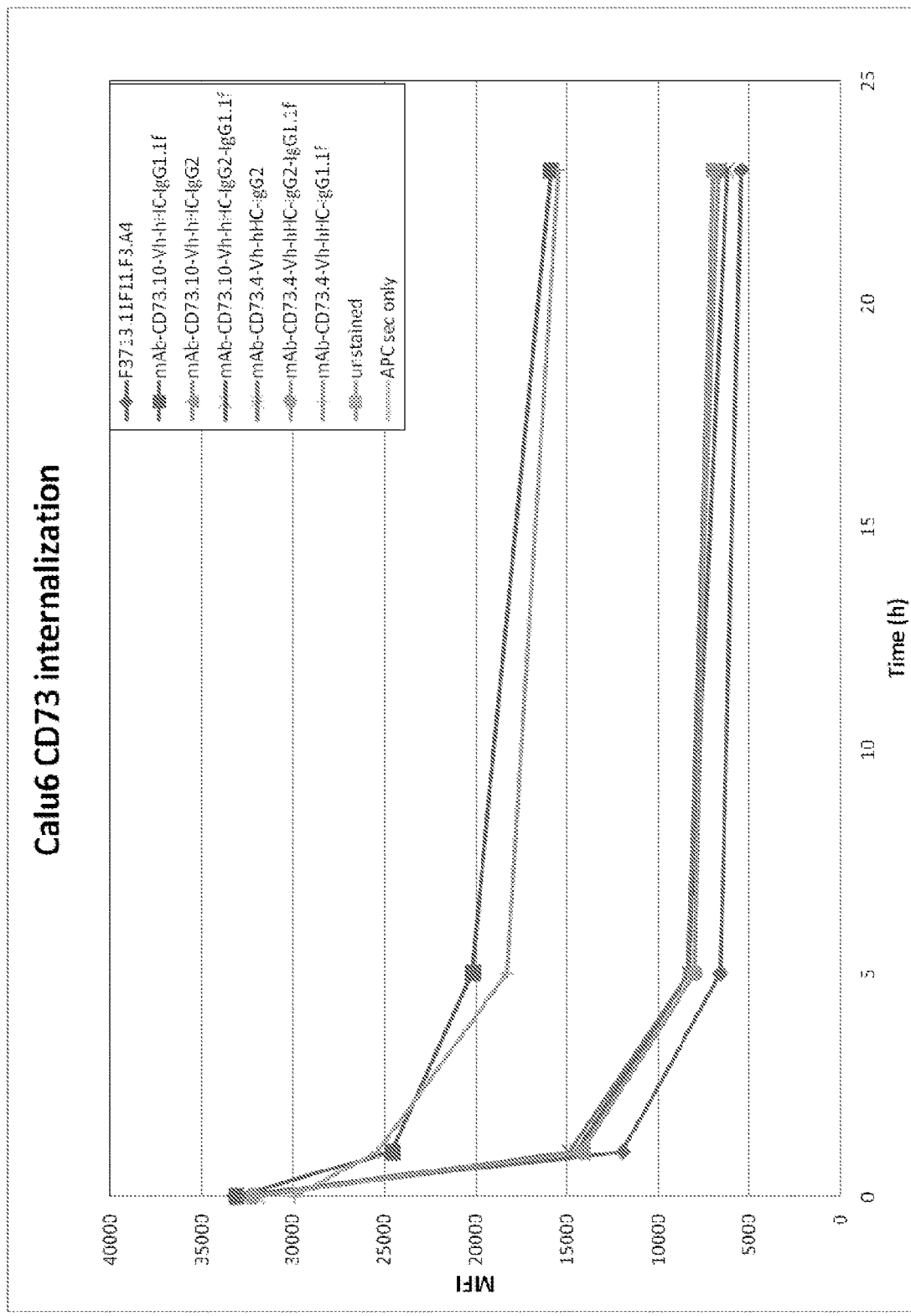
FIG. 1E shows the kinetics of antibody mediated CD73 internalization of the indicated antibodies in Calu6 cells, as measured by flow cytometry.

The results, which are shown in FIG. 1E and Table 11, are consistent with those obtained in the internalization assays described above, and indicate that, all antibodies with IgG2 hinge and CH1 induced rapid and complete internalization. The CD73 levels remained low after 22 hours post wash-out, indicating that internalization is durable.

Figure 1F:
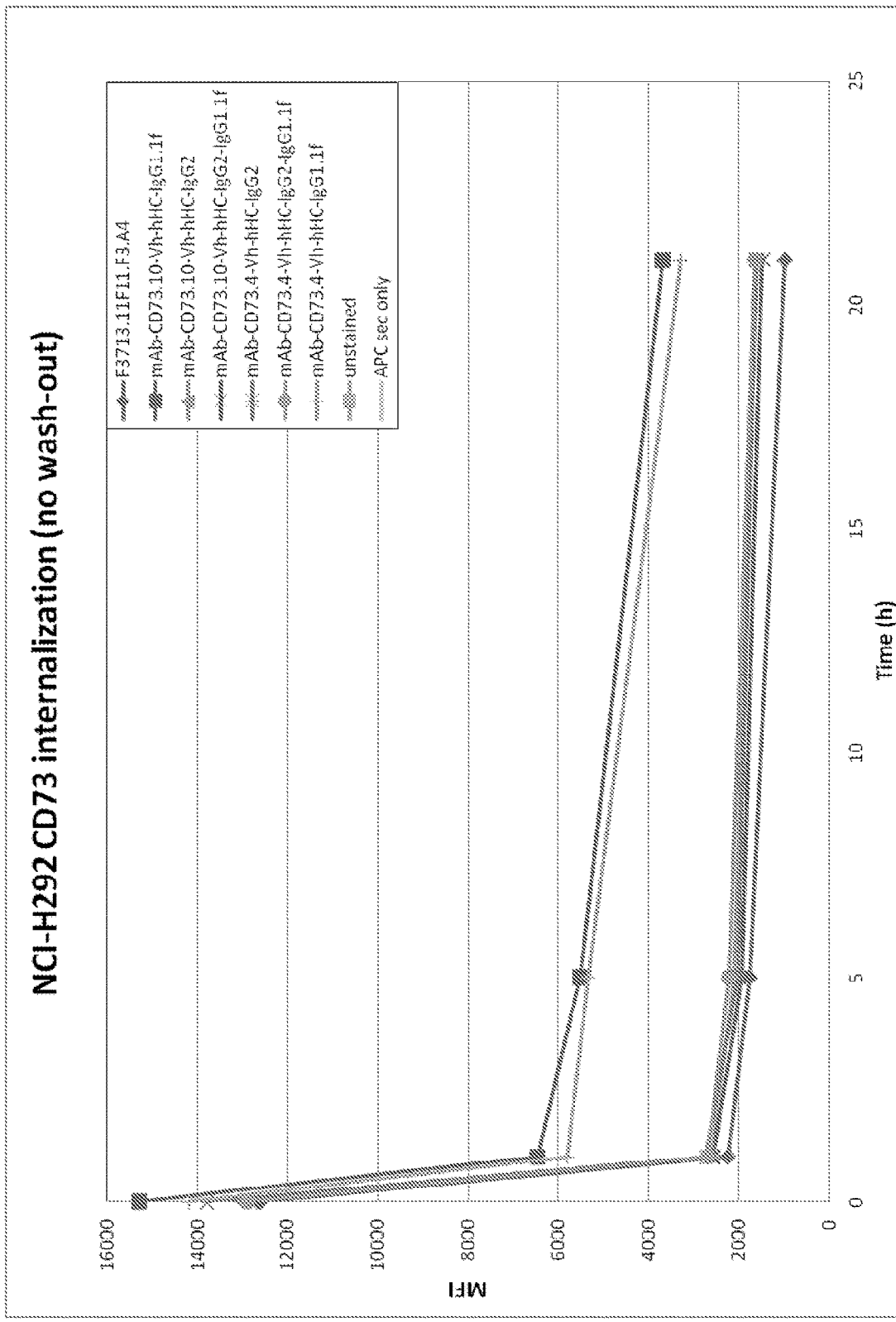
FIG. 1F shows the kinetics of antibody mediated CD73 internalization of the indicated antibodies in NCI-H292 cells (mucoepidermoid pulmonary carcinoma cell line), as measured by flow cytometry, but where the antibodies were not washed out after the first incubation of the cells with the antibodies.

Similar results shown in FIG. 1F and Table 11 were obtained in the NCI-H292 cell line in which the antibody was maintained in culture during the incubation time (no wash-out). Again, these data indicate rapid and significant internalization and maintenance of downregulation of endogenous CD73.

Figure 1G:
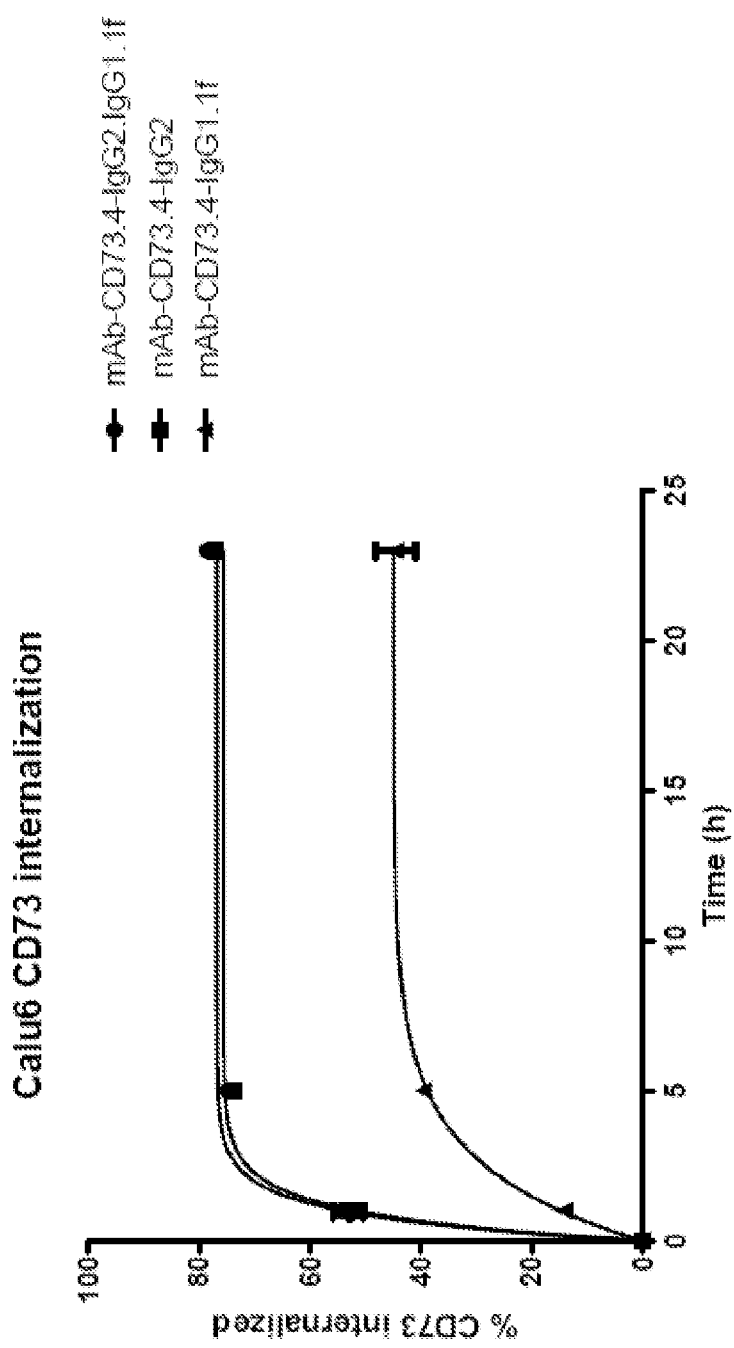
FIG. 1G shows the percentage of CD73 internalized in Calu6 cells treated with the indicated antibodies, showing antibody mediated CD73 internalization of the indicated antibodies in Calu6 cells over time.

Internalization assays were also conducted with the human SNU-C1 (colon cancer cell line) and NCI-H1437 (non-small cell lung carcinoma cell line) cells. The results, which are shown in FIGS. 1I and J, also indicate rapid internalization with a maximal level reached within 5 hours and a maximal level of internalization of about 50% for CD73.4.IgG2-C219S-IgG1.1f in SNU-C1 and 60% for NCI-H1437 cells. FIGS. 1G and H show similar kinetics of internalization of CD73.4.IgG2-C219S-IgG1.1f in Calu6 and NCI-H292 cells. For graphs, which show % of CD73 internalized, this number was obtained as follows:

$$\% \ CD73 \ \text{internalized} = 100 - \left( \frac{MFI_{t=x} - MFI_{background}}{MFI_{t=0} - MFI_{background}} \times 100 \right)$$

where for each antibody, $MFI_{t=x}$ is the MFI at a given timepoint and $MFI_{t=0}$ is maximal fluorescence at t=0, and $MFI_{background}$ is the MFI of the secondary Ab only.

TABLE 12

Figure 1H:
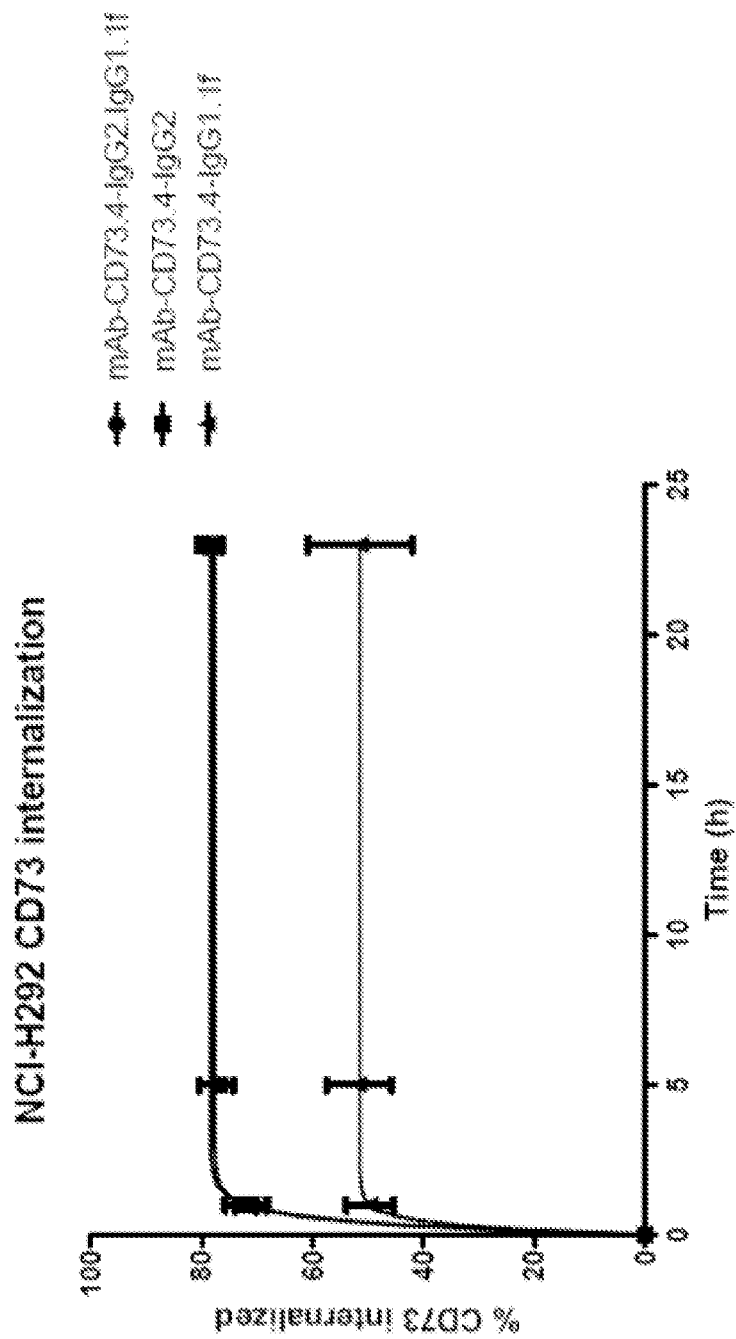
FIG. 1H shows the percentage of CD73 internalized in NCI-H292 cells treated with the indicated antibodies over time, showing antibody mediated CD73 internalization of the indicated antibodies in NCI-H292 cells over time.
Figure 1I:
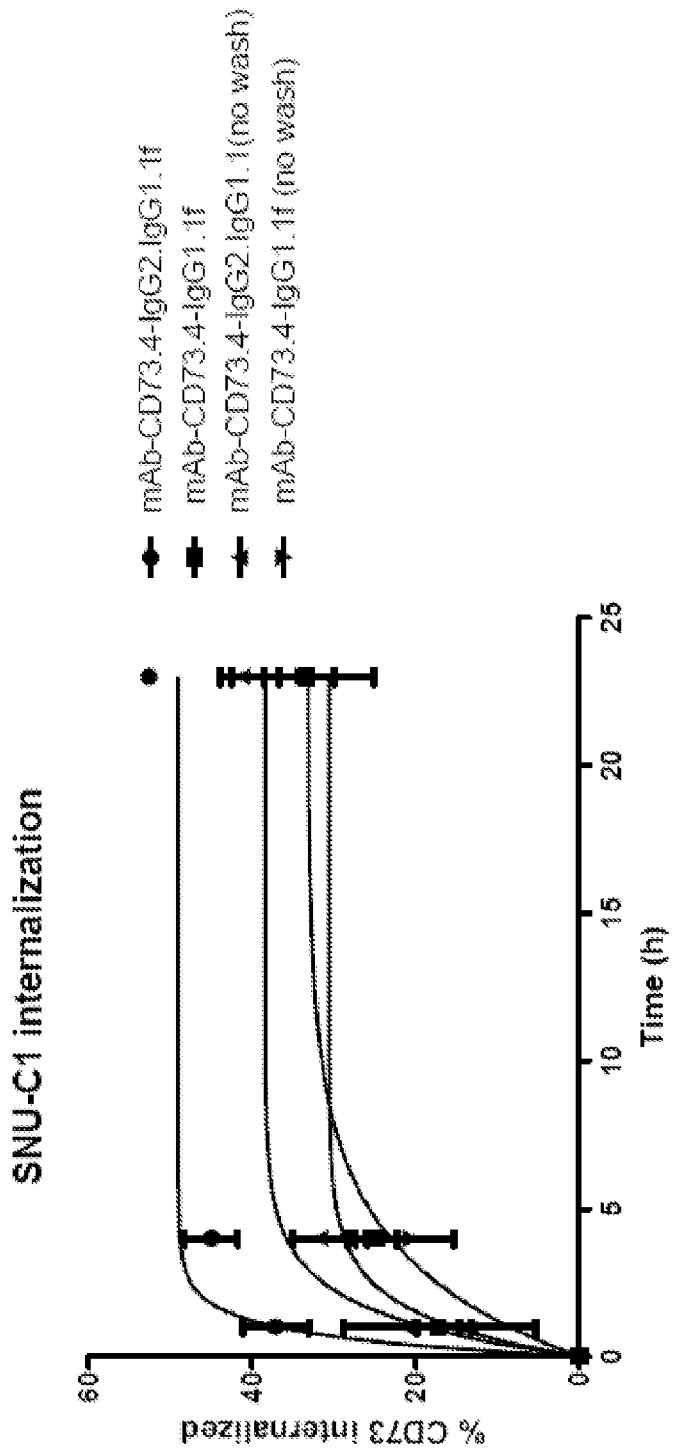
FIG. 1I shows the percentage of CD73 internalized in SNU-C1 cells (colon carcinoma cell line) treated with the indicated antibodies over time, showing antibody mediated CD73 internalization of the indicated antibodies in SNU-C1 cells over time.
Figure 1J:
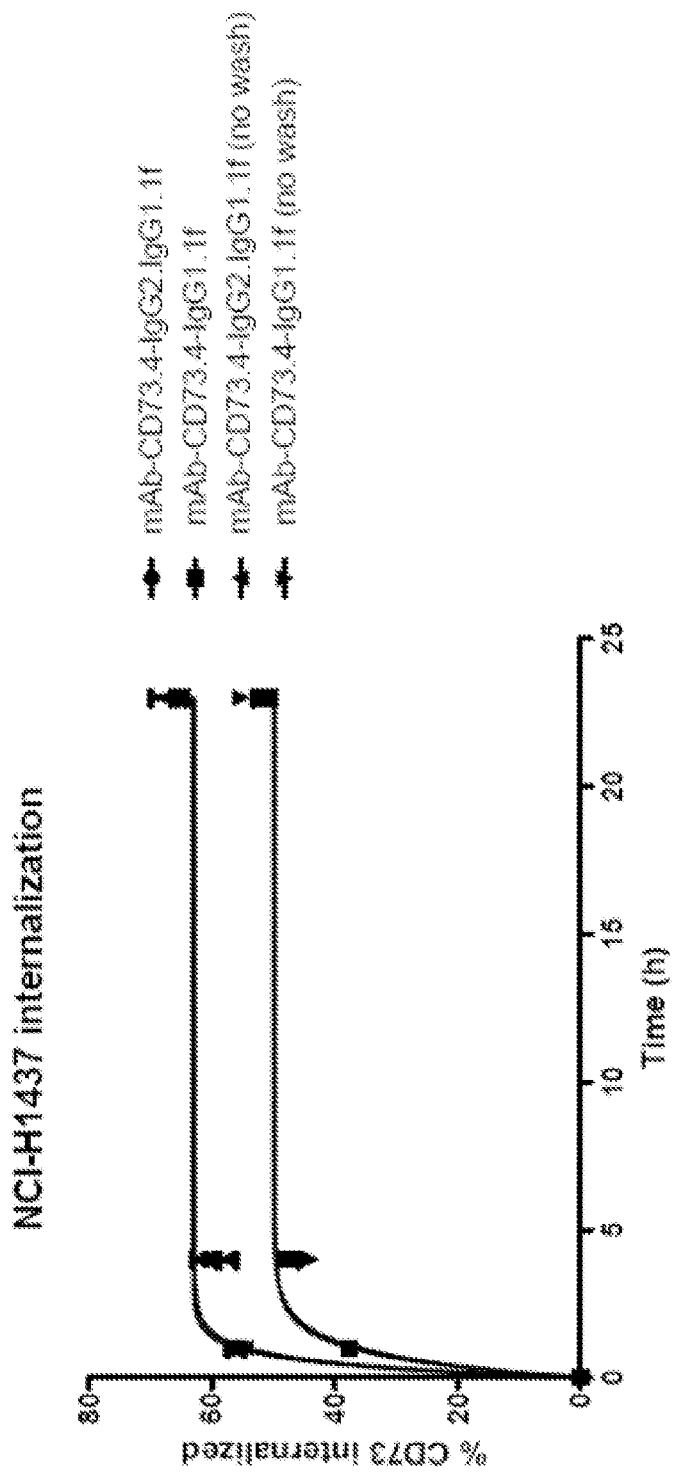
FIG. 1J shows the percentage of CD73 internalized in NCI-H1437 cells (non-small cell lung carcinoma cell line) treated with the indicated antibodies over time, showing antibody mediated CD73 internalization of the indicated antibodies in NCI-H1437 cells over time.

EC$_{50}$ of antibody mediated CD73 internalization in several cell lines (data from FIGS. 1G-I)

|  | Calu6 | | NCI-H292 | | SNU-C1 | | SNU-C1 (no wash) | | NCI-H1437 | | NCI-H1437 (no wash) | |
|---|---|---|---|---|---|---|---|---|---|---|---|---|
|  | Ymax (%) | T$_{1/2}$ (hr) | Ymax (%) | T$_{1/2}$ (hr) | Ymax (%) | T$_{1/2}$ (hr) | Ymax (%) | T$_{1/2}$ (hr) | Ymax (%) | T$_{1/2}$ (hr) | Ymax (%) | T$_{1/2}$ (hr) |
| mAb-CD73.4-IgG2-IgG1.1f | 76.8 | 0.5661 | 77.64 | 0.2633 | 48.96 | 0.4954 | 38.39 | 1.025 | 63.12 | 0.3164 | 62.78 | 0.3418 |
| mAb-CD73.4-IgG2 | 75.59 | 0.6003 | 78.42 | 0.2766 | — | — | — | — | — | — | — | — |
| mAb-CD73.4-IgG1.1f | 44.99 | 1.737 | 51.49 | 0.2087 | 30.58 | 0.9915 | 33.16 | 2.33 | 49.76 | 0.4915 | 49.95 | 0.5384 |

Thus, anti-CD73 antibodies with an IgG2 hinge internalize faster and to a greater extent relative to anti-CD73 antibodies with an IgG1 hinge.

Example 2: Enhanced Agonist Activity of GITR Antibodies with an IgG2 Hinge Relative to the Same Antibodies with an IgG1 Hinge This Example demonstrates that anti-GITR antibodies comprising an IgG2 hinge have an increased ability to induce IL-2 and IFN-γ secretion from T cells relative to the same antibodies that have an IgG1 hinge.

It had been observed in CHO-OKT3 and 3A9 assays described above that hybridoma derived antibodies, having an IgG2 constant region, are more potent in stimulating cytokine secretion than the same antibodies in which the heavy chain constant region was switched to that of IgG1 or an effectorless IgG1 (IgG1.1). Therefore, the effect of an IgG2 constant region or hinge was further tested on anti-GITR antibodies in these assays.

The heavy chain variable region of an anti-human GITR antibody (SEQ ID NO: 75) was linked to the heavy chain constant regions shown in Table 13. The light chain of the anti-GITR antibodies comprised SEQ ID NO: 77. Table 13 shows the identity of each domain of the constant regions:

TABLE 13

Heavy chain constant regions of antibodies used in this Example

| Name of antibody | CH1 | Hinge | CH2 | CH3 | SEQ ID NO* |
|---|---|---|---|---|---|
| anti-GITR | IgG2 SEQ ID NO: 7 | IgG2 SEQ ID NO: 8 | IgG2 SEQ ID NO: 9 | IgG2 SEQ ID NO: 10 | SEQ ID NO: 52 |
| anti-GITR-IgG2 | IgG2 SEQ ID NO: 7 | IgG2 SEQ ID NO: 8 | IgG2 SEQ ID NO: 9 | IgG2 SEQ ID NO: 10 | SEQ ID NO: 52 |
| anti-GITR-IgG1 | IgG1 SEQ ID NO: 2 | IgG1 SEQ ID NO: 3 | IgG1 SEQ ID NO: 4 | IgG1 SEQ ID NO: 5 | SEQ ID NO: 53 |
| anti-GITR-IgG1.1 | IgG1.1 SEQ ID NO: 2 | IgG1.1 (L234A/L235E/G237A) SEQ ID NO: 25 | IgG1.1 (A330S/P331S) SEQ ID NO: 24 | IgG1.1 SEQ ID NO: 5 | SEQ ID NO: 54 |
| anti-GITR-IgG2-IgG1 or anti-GITR.g2.g1 | IgG2 SEQ ID NO: 7 | IgG2/IgG1 hybrid SEQ ID NO: 22 | IgG1 SEQ ID NO: 4 | IgG1 SEQ ID NO: 5 | SEQ ID NO: 55 |
| anti-GITR-IgG2-IgG1.1 or anti-GITR.g2.g1.1 | IgG2 SEQ ID NO: 7 | IgG2 SEQ ID NO: 8 | IgG1.1 (A330S/P331S) SEQ ID NO: 24 | IgG1 SEQ ID NO: 5 | SEQ ID NO: 56 |

*SEQ ID NO of full-length heavy chain constant region

First, the binding affinities of these GITR antibodies were compared to those of GITR antibodies having an IgG1 hinge. The binding affinities of the anti-GITR antibodies to soluble GITR was determined by Biacore as follows. Anti-GITR antibodies were captured on human kappa coated chips (~5 KRUs; Southernbiotech cat #2060-01), and recombinant human GITR (rHGITR/Fc: R&D systems, CAT #689-GR) was flowed across the chip at concentrations of 500 nM, 250 nM, 125 nM, 62 nM, and 31 nM. The capture concentration of the mAb/volume was 2-40 μg/mL (5 μL at 10 μL/min). The antigen association time was 5 minutes at 15 μL/min, the antigen dissociation time was 6 minutes, and regeneration was performed with 50 mM HCl/50 mM NaOH (12 μL each at 100 μL/min)).

Figure 2:
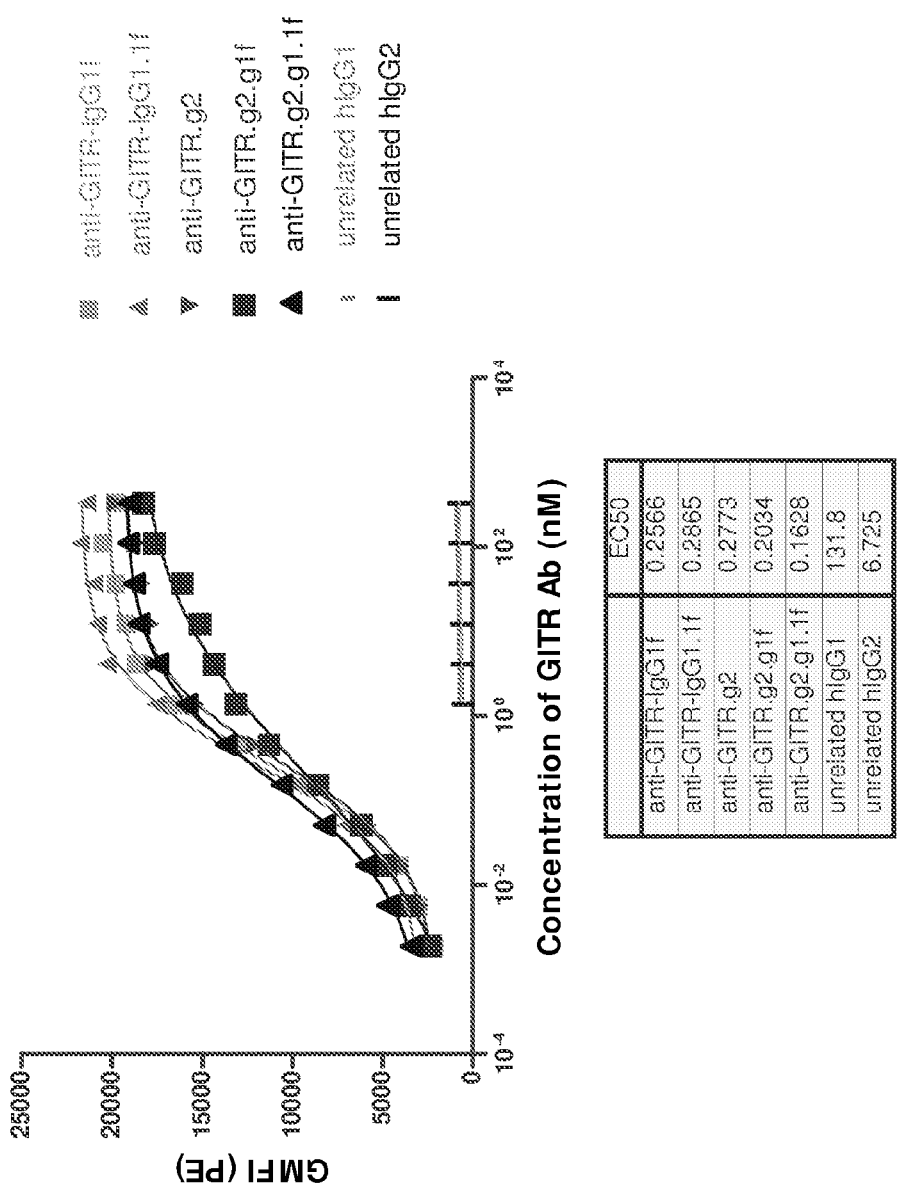
FIG. 2 shows the binding kinetics of the indicated anti-human GITR antibodies to anti-CD3 (plate coated) and CD28-activated human CD4 T cells and their corresponding EC50 values derived from the graph.

The results, which are shown in FIG. 2, indicate that all three GITR antibodies having an IgG2 hinge have similar affinities for activated T cells as GITR antibodies have IgG1 or IgG1.1 constant region.

Next, the ability of GITR antibodies having an IgG1 constant region or IgG2 hinge/IgG1 Fc domain were tested for their ability to induce IL-2 and IFN-γ secretion from human donor T cells stimulated with anti-CD3scFv (OKT3)-expressing CHO cells. The CHO cells expressed low levels of OKT3 to promote suboptimal stimulation to be able to observe agonism by anti-GITR antibodies. CD4+ T cells from a donor were stimulated with OKT3 expressing CHO cells and an anti-GITR antibody, and IL-2 and IFN-γ secretion was measured. The experiments were conducted as follows. For experiments with CD4+ T cells, CD4+ T cells were obtained from human PBMCs with RosetteSep Human CD4+ T cell enrichment cocktail (StemCell Technology #15062) according to the manufacturer's protocol. CHO cells expressing anti-CD3scFv (OKT3) (CHO-OKT3) were washed twice with RPMI medium and subjected to irradiation with a dosage of 50K Rad. Cells were harvested and resuspended in culture medium (RPMI-1640 supplemented with 10% Fetal Bovine Serum, 2 mM L-glutamine, 55 nM β-Mercaptoethanol, 1 mM sodium pyruvate, and 100 U/mL Penicillin/streptomycin) at $2.5 \times 10^5$/mL. $2.5 \times 10^4$ CHO-OKT3 cells and $1 \times 10^5$ T cells were seeded per well in a 96-well TC grade flat-bottom plate (Costar). Cells were incubated with an 8-point, 4-fold titration of GITR antibody starting at 40 μg/mL. An irrelevant hIgG1 was added at 40 μg/mL as an isotype control. A sample with cells only was included to show baseline activity without any treatment. Supernatant from each sample was harvested at day 2 for IL-2 measurement (only for assays with CD4+ T cells) (BD opt EIA Human IL-2 ELISA kit; BD Bioscience #555190) and at day 3 for IFN-γ measurement (BD optEIA human IFN-g ELISA Kit; BD Bioscience #555142).

Figure 3A:
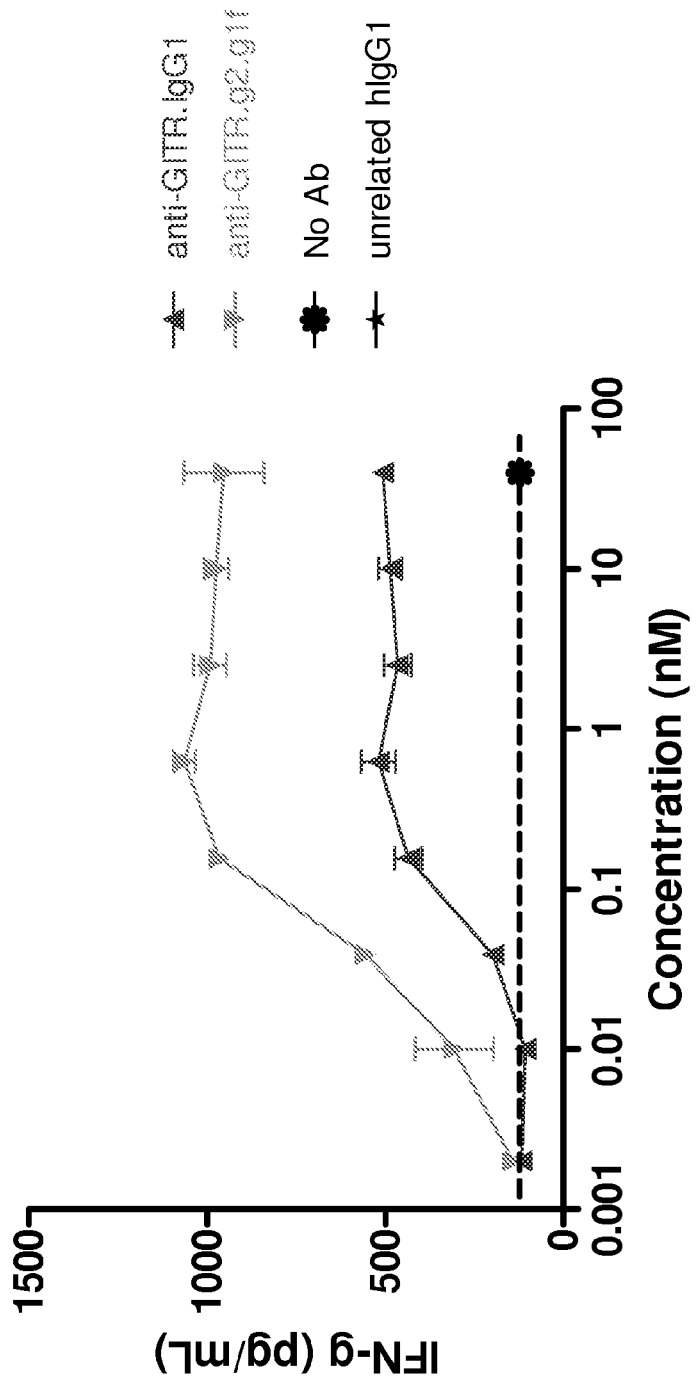
FIGS. 3A-C show the secretion of IFN-γ and IL-2 from donor CD4 T cells stimulated with soluble anti-human GITR antibodies with different heavy chain constant regions.
Figure 3B:
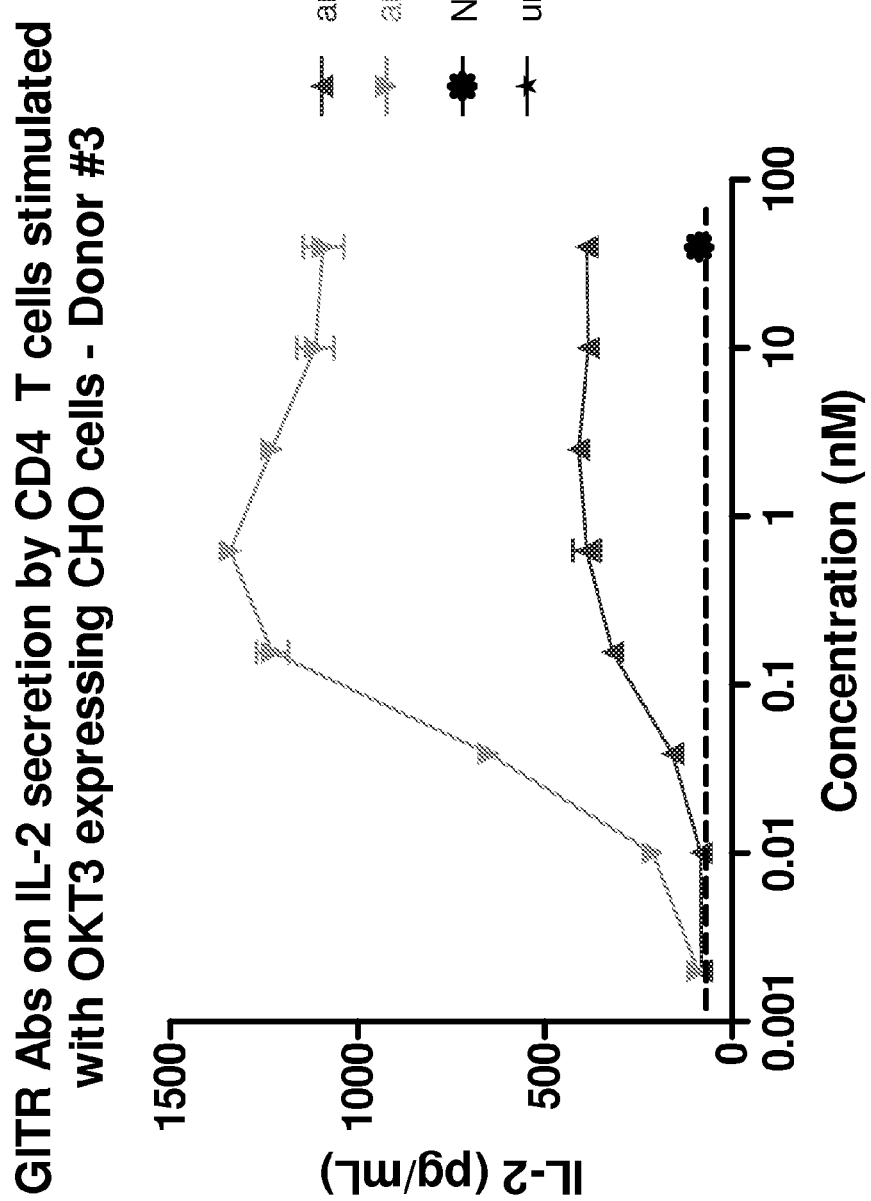
Figure 3C:
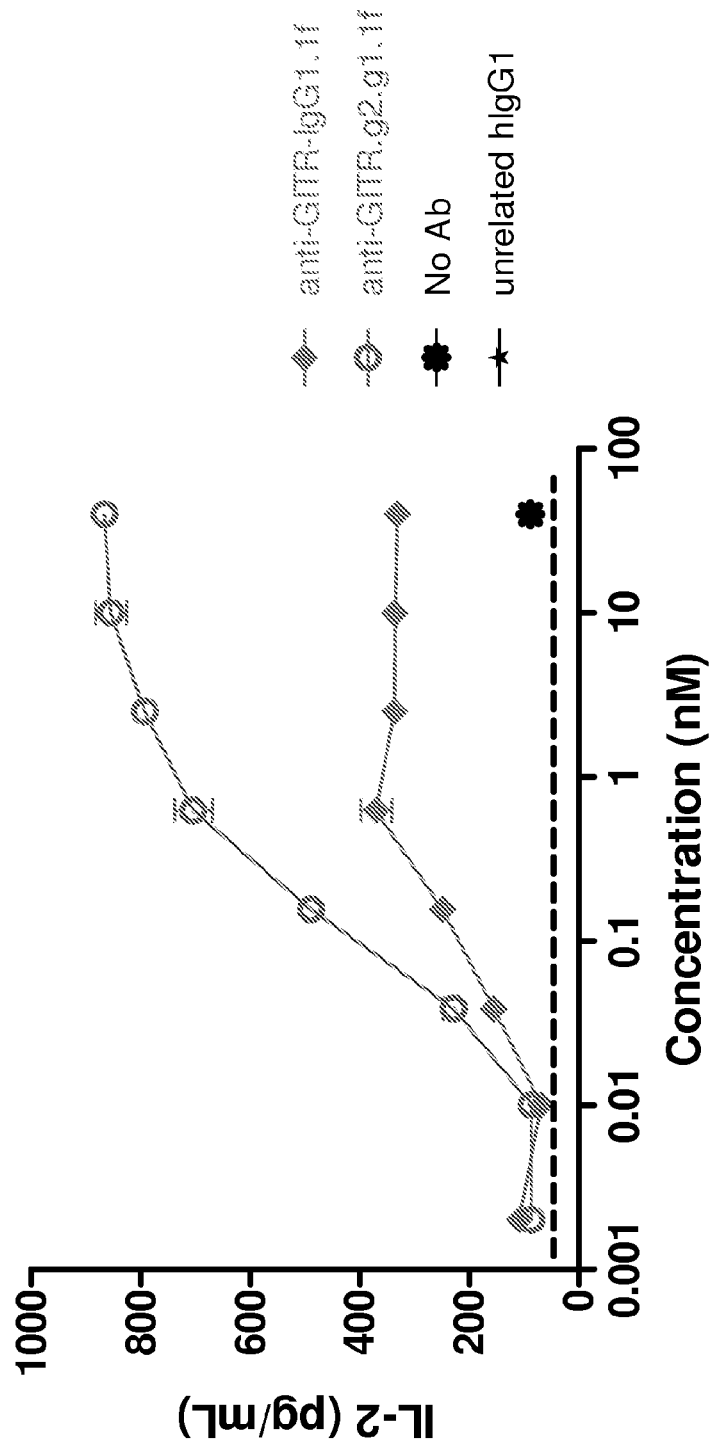

As shown in FIGS. 3A and B, the antibody with the IgG2 hinge/IgG1 Fc domain (anti-GITR.g2.g1) induced both IL-2 and IFN-γ secretion from T cells to a higher degree than the antibody with the IgG1 constant region (anti-GITR.g1). Similar results were obtained with the effectorless versions of these constant domains (FIG. 3C).

To further confirm the increased activation of T cells with the anti-GITR antibodies comprising an IgG2 hinge, IL-2 secretion in a different experimental format was tested. In this experiment, the ability of GITR antibodies to induce IL-2 secretion from 3A9-hGITR cells (mouse T cell hybridoma 3A9 cell line ectopically expressing human GITR) was tested as follows. Mouse T cell hybridoma 3A9 cell line which ectopically expresses human GITR (3A9-hGITR) was cultured on anti-CD3 monoclonal antibody-coated plates in the presence of increasing amounts of the indicated antibodies. $5 \times 10^4$ 3A9-hGITR cells were cultured on plates coated with 1 µg/ml anti-CD3 antibody (Clone 145-2C11; BD Biosciences), and treated with the indicated concentrations of antibodies for 7 hours.

Figure 4:
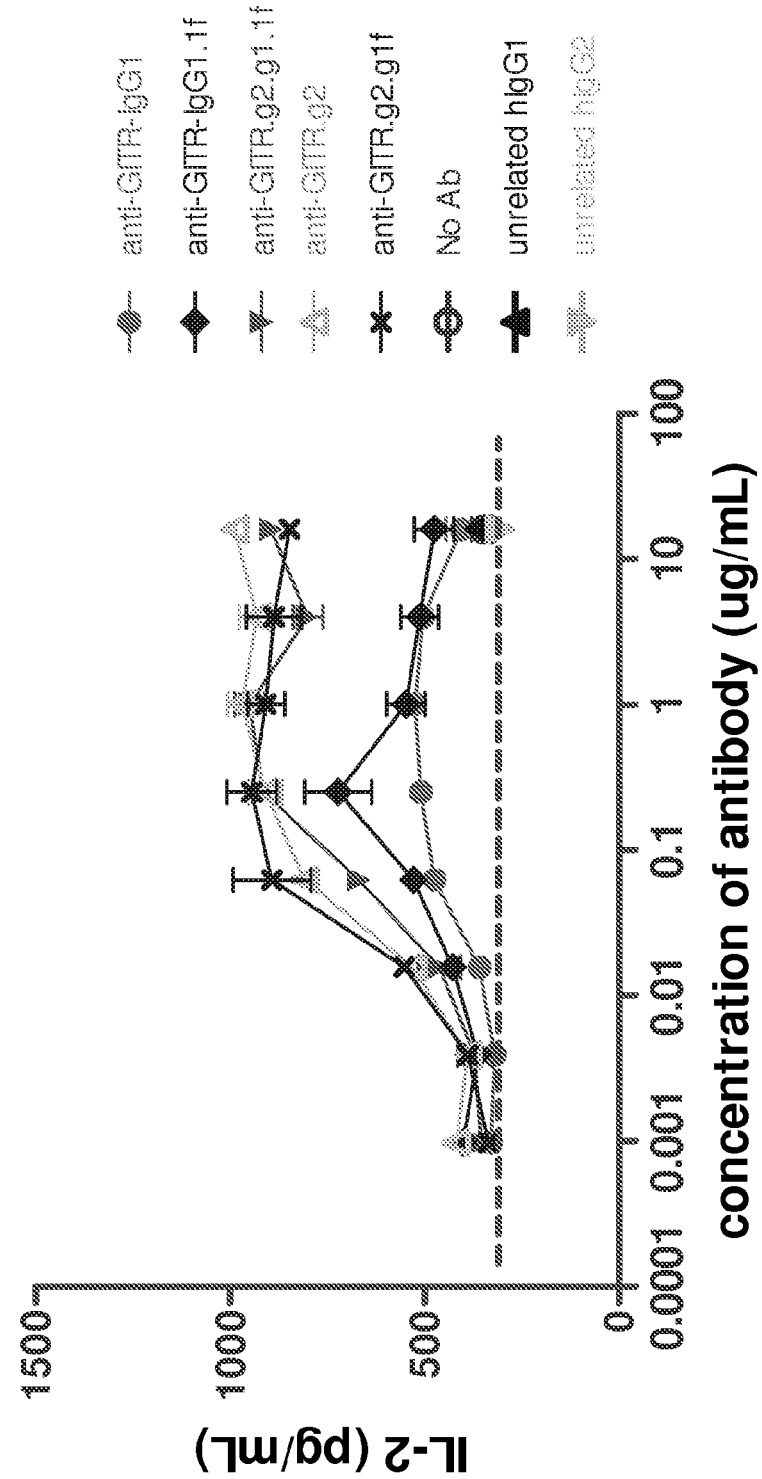
FIG. 4 shows IL-2 secretion from 3A9-hGITR cells cultured on anti-CD3 monoclonal antibody-coated plates in the presence of increasing amounts of the indicated anti-human GITR antibodies: the hybridoma anti-GITR (IgG2) and recombinant derivatives as IgG1f, IgG1.1 (effectorless), or as chimera with the IgG2 hinge.

As shown in FIG. 4, all antibodies having the IgG2 hinge (anti-GITR.g2, anti-GITR.g2.g1f, and anti-GITR.g2.g1.f) induced IL-2 secretion from 3A9-hGITR cells to a higher degree than their IgG1 constant region containing counterparts (anti-GITR.g1f and anti-GITR.g1.1f).

These results collectively suggest that anti-GITR antibodies having an IgG2 hinge and g1 or g1.1 constant regions are more potent than the same antibodies having an IgG1 hinge.

Example 3: Impact of Different Hinge/Fc Combinations on Size of Antibody/Antigen Complexes As shown in the above Examples, anti-CD73 antibodies with an IgG2 hinge are better inhibitors of CD73 cellular activity and internalize better than the same antibodies with an IgG1 hinge and anti-GITR antibodies with an IgG2 hinge are more potent agonists than the same antibodies with an IgG1 hinge. Based on this observation, and the fact that an IgG2 hinge is stiffer than an IgG1 hinge, it was hypothesized that larger complexes are formed between an antigen and antibodies having an IgG2 hinge relative to antibodies having an IgG1 hinge. The following experiment was conducted to analyze this hypothesis.

The structure and oligomeric state of CD73/antibody complexes in solution were examined by SEC-MALS and DLS. For these studies, antibodies containing either an IgG1 or IgG2 constant region, were mixed at varying molar ratios with recombinant proteins comprising either the full length extracellular domain of human-CD73 containing a C-terminal polyhistidine tag (amino acid residues 26-546 of human-CD73, termed hCD73-his) or a fragment corresponding to the N-terminal domain of human-CD73 (amino acid residues 26-336, termed N-hCD73-his).

The oligomeric state of CD73/antibody complexes were examined by size-exclusion chromatography coupled to an in-line multi-angle light scattering detector (SEC-MALS). Isocratic separations were performed on a Shodex PROTEIN KW-803 column connected to an Prominence Shimadzu UFLC in buffer containing 200 mM $K_2HPO_4$, 150 mM NaCl, pH 6.8, containing 0.02% Na azide (0.1 µm filtered) running at 0.5 mL/min. Samples were injected onto the column using a SIL-20AC Prominence Shimadzu autosampler, and data were obtained from three online detectors connected in series: a Prominence SPD-20AD diode array UV/vis spectrophotometer followed by a Wyatt miniDAWN™ TREOS Multi-Angle Light Scattering Detector then a Wyatt Optilab T-rEX Refractive Index Detector. Data were collected and analyzed using Astra (Wyatt) and Labsolutions (Shimadzu) software.

Dynamic light scattering (DLS) studies were performed on a Wyatt DynaPro plate reader in 384 well plates at 25° C. Experimental parameters were 20 acquisitions of 5 s each per measurement, and measurements were recorded in quadruplicate, with the average and standard deviation reported. Intensity autocorrelation functions were fitted using the "Regularization" algorithm in the Dynamics software (Wyatt Technologies).

A summary of the SEC-MALS and DLS is provided in FIG. 6 and FIG. 7. Analysis of the antibodies alone, shows retention times (about 16-17 min), masses (140-150 kDa), and hydrodynamic radii (5.0-5.4 nm) for each antibody that are typical for a monomeric monoclonal antibody. The data for the hCD73-his protein is consistent with the protein adopting the expected dimeric structure in solution; in particular, the mass determined from the SEC-MALS data (120 kDa) is consistent with that expected for a CD73-his dimer (117 kDa) and inconsistent with what would be expected for a hCD73-his monomer (58.5 kDa). The data for N-hCD73 is consistent with the recombinant N-domain protein being monomeric in solution (SEC-MALS measured mass=38 kDa, compared to expected monomeric mass=35.0 kDa), which is expected because the region of the full length CD73 extracellular domain that is responsible for dimerization of the protein is contained within the C-terminal domain without contribution of N-domain residues.

Equimolar mixtures of a given antibody with N-hCD73-his were found to elute as a single species in the SEC with shorter retention time than the antibody or N-hCD73-his alone, as well as larger hydrodynamic radii (Rh) by DLS, which is consistent with the formation of complexes. MALS data indicate masses for these complexes of approximately 210 kDa. This is consistent with one N-hCD73-his molecule bound to each of the two Fab domains of a given antibody to form a 1:2 antibody:N-hCD73-his complex.

Figure 5:
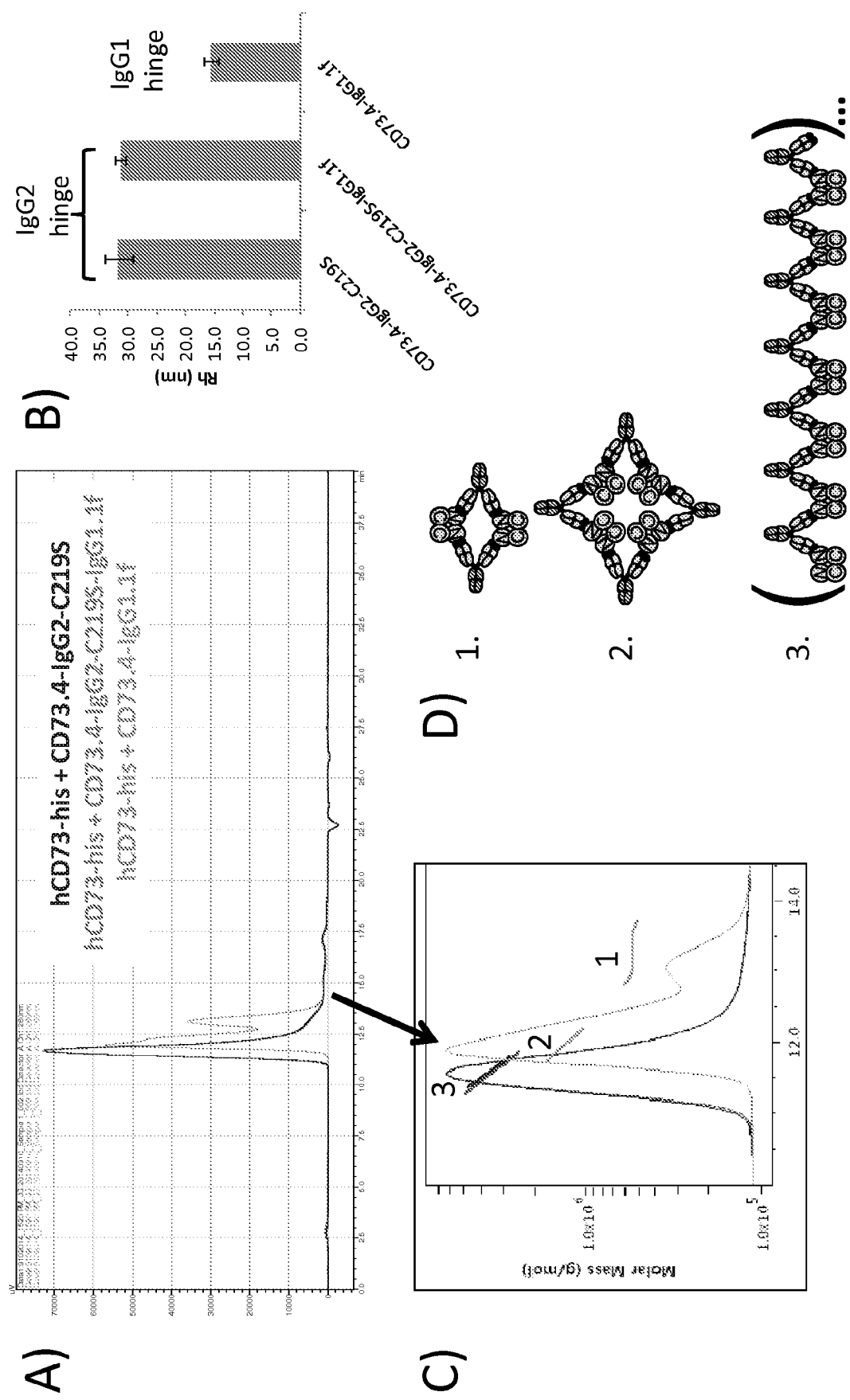
FIGS. 5A-D show the effect of an IgG2 hinge on the size of antibody/antigen complexes.

SEC-MALS data for mixtures of anti-CD73 antibodies with hCD73-his dimer shows that the mixture elutes earlier than either the hCD73-his or antibody alone, suggesting that complexes are formed. Comparing the data for mAbs that contain the same variable region but different constant domains, shows that the elution times for the complexes of hCD73-his with mAbs containing a IgG2 constant domains (IgG2-C219S, IgG2-C219S-IgG1.1f) are earlier than those for complexes of hCD73-his with mAbs containing an IgG1.1f constant domain. In addition, the MALS-determined masses for complexes of hCD73-his with mAbs containing an IgG2 constant domain are larger than those for complexes of hCD73-his with mAbs containing an IgG1 constant domain. DLS data further shows that the hydrodynamic radius of complexes of hCD73-his with mAbs containing a IgG2 constant domain are larger than those for complexes of hCD73-his with mAbs containing an IgG1 constant domain. For example, the SEC-MALS and DLS data for CD73.4 with three different constant regions (IgG2-C219S, IgG2-C219S-IgG1.1f, or IgG1.1f) is shown in FIG. 5. Here it can be seen that the complex of hCD73-his with CD73.4 containing the IgG2 constant domain have shorter retention times (FIG. 5A), larger hydrodynamic radii (FIG. 5B) and larger MALS-determined masses (FIG. 5C), as compared to the complexes of hCD73-his with CD73.4-IgG1.1f. Based on the MALS masses, a schematic model for the structure and stoichiometry of the complexes between hCD73-his and the antibodies is shown in FIG. 5D, where complexes containing CD73.4-IgG1.1f predominantly form smaller 2:2 (peak 1=~550 kDa) or 4:4 mAb/CD73 dimer complexes (peak 2=~1300 kDa), whereas CD73.4-IgG2-C219S or CD73.4-IgG2-C219S-IgG1.1f form much larger complexes (>3000 kDa) with hCD73-his, for which precise structure and stoichiometry cannot be confidently modeled.

Collectively the SEC-MALS and DLS data demonstrate that larger complexes are formed between hCD73-his and mAbs containing an IgG2 hinge region (IgG2-C219S or IgG2-C219S-IgG1.1f), compared to those containing the IgG1 hinge region (IgG1.1f).

Example 4: CH1 of IgG2 Isotype Further Improves Antibody Mediated CD73 Internalization Additional internalization assays were conducted in Calu6 and H292 cells to further discriminate the role of isotype on internalization. The internalization assays were conducted as described in Example 1A and 1B (flow cytometry protocol without the wash-out step of the antibodies), and the antibodies of varying hybrid isotypes shown in Table 14 were maintained in culture at 10 μg/mL during the incubation time. For the flow cytometry experiments, the method of Example 1B was adapted to high throughput analysis in 96 well plates (as opposed to 48 well plates) and with 50,000 cells per well.

TABLE 14

Constant regions tested with the variable regions of CD73.4:

| Constructs | SEQ ID NO of constant region | Description |
| --- | --- | --- |
| IgG1f | 78 | wild type IgG1f |
| IgG1.1f | 83 | standard inert IgG1.1f |
| IgG2.3 | 79 | IgG2 A-form (C219S) |
| IgG2.5 | 82 | IgG2 B-form (C131S) |
| IgG2.3G1-KH | 81 | CH1, upper hinge and lower hinge/upper CH2 of IgG2.3, all else IgG1f |
| IgG2.5G1-KH | 90 | CH1, upper hinge and lower hinge/upper CH2 of IgG2.5, all else IgG1f |
| IgG2.3G1-AY | 80 | CH1 and upper hinge of IgG2.3, all else IgG1f |
| IgG2.5G1-AY | 89 | CH1 and upper hinge of IgG2.5, all else IgG1f |
| IgG1-G2.3G1-KH | 93 | CH1 of IgG1, upper hinge and lower hinge/upper CH2 of IgG2.3, all else IgG1f |
| IgG1-G2.3G1-AY | 92 | CH1 of IgG1, upper hinge of IgG2.3, all else IgG1f |
| IgG2.3G1.1f-KH | 84 | CH1, upper hinge and lower hinge/upper CH2 of IgG2.3, all else IgG1.1f |
| IgG2.5G1.1f-KH | 88 | CH1, upper hinge and lower hinge/upper CH2 of IgG2.5, all else IgG1.1f |
| IgG1-deltaTHT | 85 | IgG1 with THT sequence removed from hinge |
| IgG2.3-plusTHT | 86 | IgG2.3 with THT sequence (from IgG1) added into hinge |
| IgG2.5-plusTHT | 91 | IgG2.5 with THT sequence (from IgG1) added into hinge |
| IgG2.3-plusGGG | 87 | IgG2.3 with flexible GGG sequence added into hinge |

FcγR binding was shown to be as expected for each construct, i.e., FcγR binding is driven by lower hinge/CH2 region.

Figure 8A:
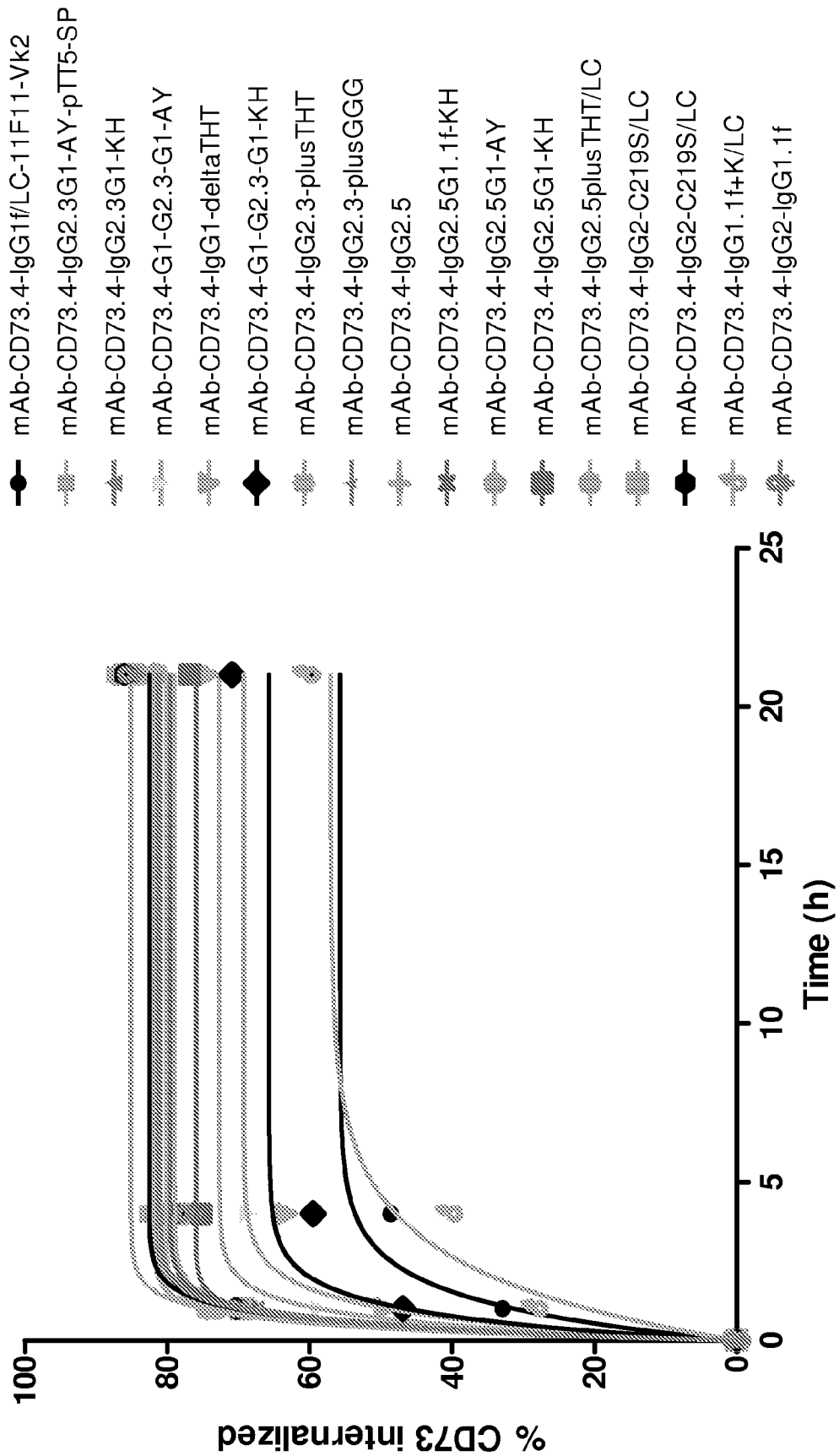
FIG. 8A shows the percentage of CD73 internalized in Calu6 cells treated with the indicated antibodies over time, showing antibody mediated CD73 internalization of the indicated antibodies in Calu6 cells over time.

The results are shown in FIGS. 8A, B and C and in Tables 15 and 16. Data shown in Table 15 were generated using the same protocol described in Example 1B (without washing out the antibodies). Data shown in Table 16 were generated using the same protocol described in Example 1A.

TABLE 15

Ymax and $T_{1/2}$ of antibody mediated CD73 internalization in Calu6 and NCI-292 cells

|  | Calu6 | | NCI-H292 | |
| --- | --- | --- | --- | --- |
|  | Ymax (%) | $T_{1/2}$ (hr) | Ymax (%) | $T_{1/2}$ (hr) |
| mAb-CD73.4-IgG1f/LC-11F11-Vk2 | 55.72 | 0.8452 | 73.05 | 0.5014 |
| mAb-CD73.4-IgG2.3G1-AY-pTT5-SP | 85.07 | 0.3326 | 90.25 | 0.272 |
| mAb-CD73.4-IgG2.3G1-KH | 81.62 | 0.3962 | 91.61 | 0.2801 |
| mAb-CD73.4-G1-G2.3-G1-AY | 72.7 | 0.4229 | 84.51 | 0.3083 |
| mAb-CD73.4-IgG1-deltaTHT | 69.27 | 0.5652 | 83.63 | 0.3441 |
| mAb-CD73.4-G1-G2.3-G1-KH | 65.67 | 0.5674 | 83.29 | 0.343 |
| mAb-CD73.4-IgG2.3-plusTHT | 81.19 | 0.3551 | 91.41 | 0.2935 |
| mAb-CD73.4-IgG2.3-plusGGG | 81.72 | 0.3355 | 91.6 | 0.2712 |
| mAb-CD73.4-IgG2.5 | 78.98 | 0.3485 | 89.56 | 0.3057 |
| mAb-CD73.4-IgG2.5G1.1f-KH | 79.63 | 0.3527 | 90.86 | 0.2993 |
| mAb-CD73.4-IgG2.5G1-AY | 81.91 | 0.2901 | 91.3 | 0.2452 |
| mAb-CD73.4-IgG2.5G1-KH | 76 | 0.2837 | 90.75 | 0.256 |
| mAb-CD73.4-IgG2.5plusTHT/LC | 80.15 | 0.2869 | 89.6 | 0.2565 |
| mAb-CD73.4-IgG2-C219S/LC | 82.35 | 0.3725 | 88.91 | 0.2866 |
| mAb-CD73.4-IgG2-C219S/LC | 82.54 | 0.3639 | 87.66 | 0.2845 |
| mAb-CD73.4-IgG1.1f+K/LC | 57.07 | 1.519 | 70.4 | 0.4969 |
| mAb-CD73.4-IgG2CS-IgG1.1f | 80.98 | 0.3508 | 90.35 | 0.2764 |

TABLE 16

Internalization characteristics of CD73.4 with various constant regions in Calu6 cells

|  | Internalization | |
| --- | --- | --- |
| CD73_mAb_Clones | Max | Speed |
| CD73.4-IgG1f/LC-11F11-Vk2 | + | + |
| CD73.4-Vh-hHC-IgG2.3G1-AY-pTT5-SP5 | ++++ | ++++ |

TABLE 16-continued

Internalization characteristics of CD73.4 with various constant regions in Calu6 cells

| CD73_mAb_Clones | Internalization | |
|---|---|---|
| | Max | Speed |
| CD73.4-Vh-hHC-IgG2.3G1-KH | ++++ | +++ |
| CD73.4-Vh-hHC-G1-G2.3-G1-AY | ++ | ++ |
| CD73.4-Vh-hHC-G1-G2.3-G1-KH | ++ | ++ |
| CD73.4-Vh-hHC-IgG1-deltaTHT | ++ | +++ |
| CD73.4-Vh-hHC-IgG2.3-plusTHT | ++++ | ++++ |
| CD73.4-Vh-hHC-IgG2.3-plusGGG | ++++ | ++++ |
| CD73.4-Vh-hHC-IgG2.5 | ++++ | ++++ |
| CD73.4-Vh-hHC-IgG2.5G1.1f-KH | ++ | ++++ |
| CD73.4-Vh-hHC-IgG2.5G1-AY | +++ | ++++ |
| CD73.4-Vh-hHC-IgG2.5G1-KH | +++ | ++++ |
| CD73.4-Vh-hHC-IgG2.5plusTHT/LC | ++++ | ++++ |
| CD73.4-Vh-hHC-IgG2-C219S/LC | ++++ | ++++ |
| CD73.4-Vh-hHC-IgG2-C219S/LC | ++++ | ++++ |
| CD73.4-Vh-hHC-IgG1.1f+K/LC | + | + |
| CD73.4-Vh-hCh-IgG2-C219S-IgG1.1f | ++++ | ++++ |

Figure 8B:
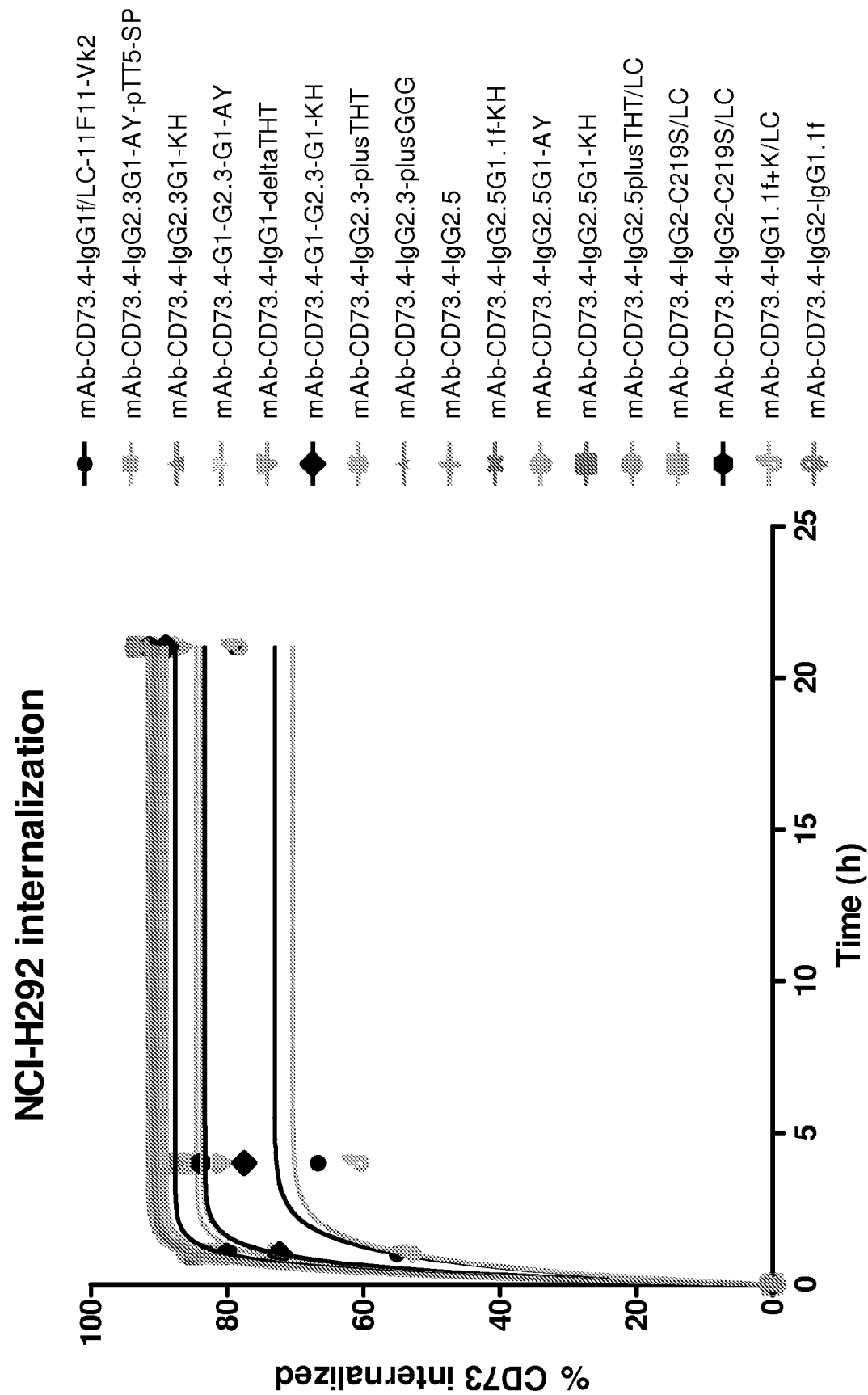
FIG. 8B shows the percentage of CD73 internalized in NCI-H292 cells treated with the indicated antibodies over time, showing antibody mediated CD73 internalization of the indicated antibodies in Calu6 cells over time.
Figure 8C:
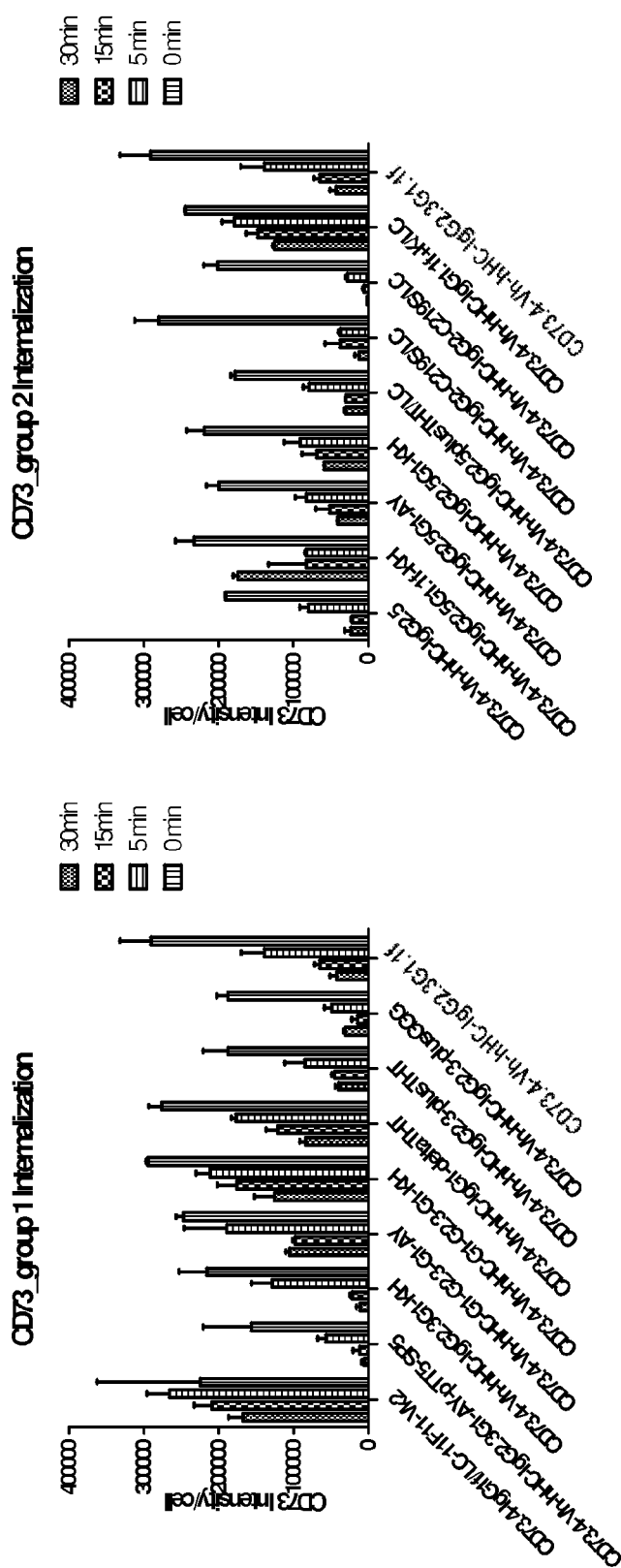
FIG. 8C shows the level of CD73 on the surface of Calu6 cells treated with 5 μg/ml of the indicated antibodies for 0, 5, 15 or 30 minutes.

FIGS. 8A-C and Tables 15 and 16 indicate that antibodies having a hinge and CH1 domain of the IgG2 isotype are most efficient at driving internalization of CD73, whereas the antibodies that have an IgG1 hinge and CH1 domain correspond to the lower curves in the figure, i.e., lower extent of internalization. In addition, antibodies with only the hinge from IgG2 have an increased internalization compared to a human IgG1 hinge. Thus, antibodies having a hinge and CH1 domain of the IgG2 isotype have superior internalization characteristics relative to the antibodies with an IgG1 isotype.

Thus, anti-CD73 antibody mAb-CD73.4-IgG2CS-IgG1.1f (having an IgG2 hinge with C219S substitution and an IgG2 CH1 domain) induced rapid internalization dependent on cell line tested. The $T_{1/2}$ for internalization ranged from minutes to under an hour. Most cell lines tested had a $T_{1/2}$ under 10 minutes. A nearly complete internalization was induced for some cell lines and most tested had at least a 50% reduction in surface CD73 expression which typically reached maximal levels by 5 hours, much shorter in some cases.

Example 5: IgG2 CH1 Enhances GITR Ab Induced IL-2 Secretion by CD4+ T Cells

This Example shows that a CH1 domain of the IgG2 isotype enhances anti-GITR antibody induced T cell activity, relative to the antibody with a CH1 domain of the IgG1 isotype.

The same modified heavy chain constant regions that were used in Example 4 were linked to the variable regions of the anti-GITR antibody (of Example 2). Donor CD4+ T cells were incubated with OKT3-scFv expressing CHO cells and the various anti-GITR antibodies, and the level of IL-2 secreted was measured. This was conducted as described in Example 2.

Figure 9:
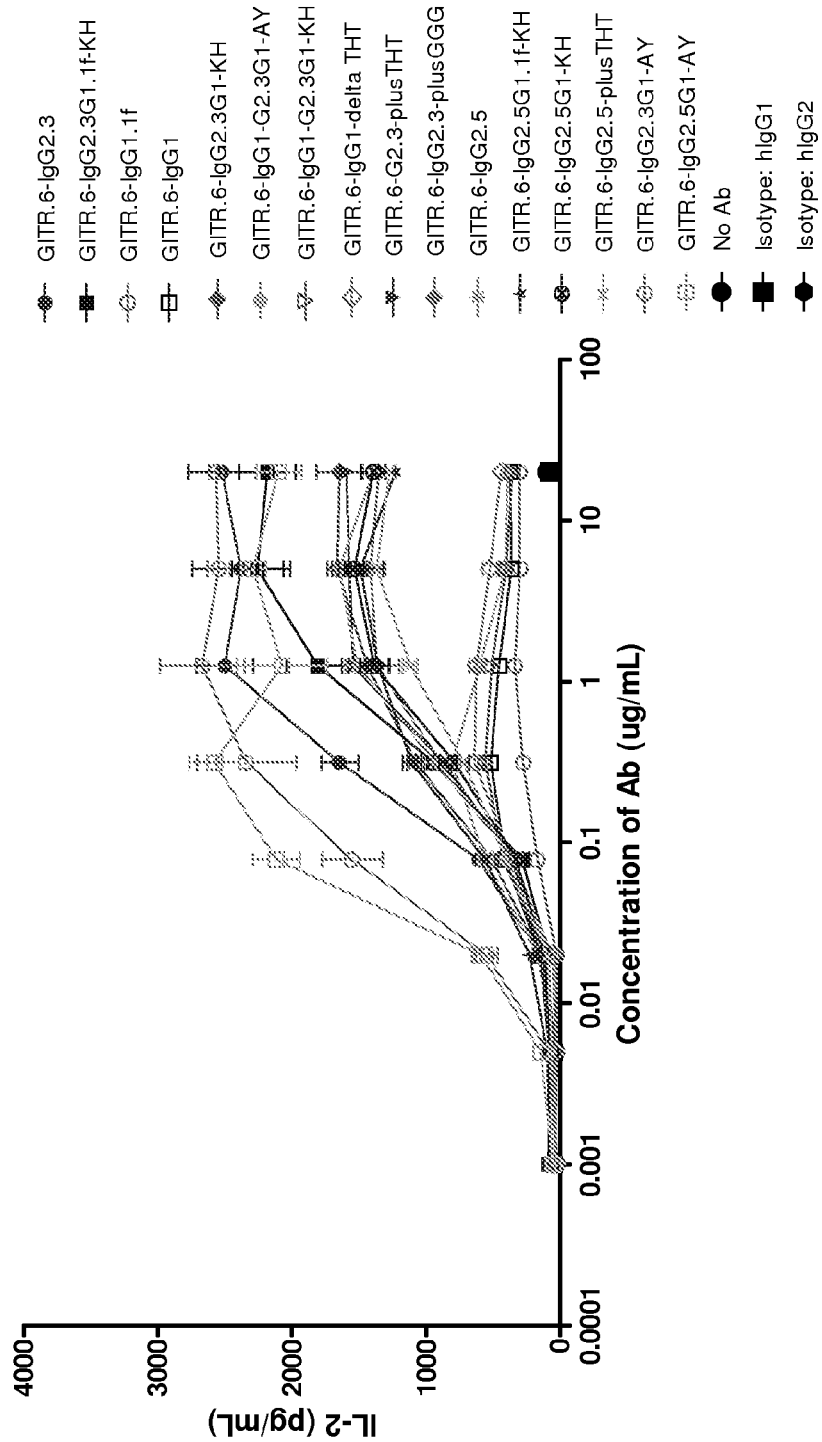
FIG. 9 shows the level of IL-2 secreted by CD4+ T cells co-cocultured with CHO-OKT3 cells in the presence of an anti-GITR antibody having the indicated constant regions.

The results, which are shown in FIG. 9, indicate that all anti-GITR antibodies having a CH1 domain of the IgG2 isotype, in addition to a hinge of the IgG2 isotype, are more effective at stimulating IL-2 secretion from CD4+ T cells than thos having an IgG1 hinge and CH1.

Thus, this Example shows that the presence of an IgG2 hinge and IgG2 CH1 domain in an agonist anti-GITR antibody further enhances the agonist activity of the antibody relative to the same antibody that does not have a hinge and/or a CH1 domain of the IgG2 isotype. An antibody having both a hinge and a CH1 domain of the IgG2 isotype has a stronger agonist effect relative to an antibody having a hinge, but not CH1, of the IgG2 isotypeAdditionally, an antibody with a CH1 domain from IgG2 has a stronger agonist activity than an antibody with with a CH1 domin from IgG1 isotype. An antibody with a hinge from IgG2 and a CH1 domain from IgG1 has stronger agonist activity than an antibody with a CH1 and hinge from IgG1 isotype.

Example 6: Relevance of Certain Amino Acid Residues in IgG2 CH1 and Hinge in Improving Antibody Mediated CD73 Internalization Anti-CD73 antibodies (CD73.4) with the heavy chain constant regions shown in Table 17 were prepared and tested as described above in antibody mediated CD73 internalization assays.

TABLE 17

Heavy chain constant regions that were fused to anti-CD73 variable regions

| Description | Constructs | SEQ ID NO of constant region |
|---|---|---|
| CH1 domain of IgG2, with all else IgG1. | G2-G1-G1-G1 | 94 |
| Also, Cys > Ser mutant to reduce potential disulfide heterogeneity: | G2.5-G1-G1-G1 | 95 |
| CH1 domain of IgG1 with all else IgG2.3: | G1-G2.3-G2-G2 | 96 |
| Swap CH1 regions in IgG1 with those of IgG2, either separate or together: | G1-KRGEGSSNLF | 97 |
| | G1-KRGEGS | 98 |
| | G1-SNLF | 99 |
| | IgG1-ITNDRTPR | 100 |
| | G1-SNLFPR | 101 |
| Swap CH1 regions in IgG2 with those of IgG1, either separate or together: | G2-RKEGSGNSFL | 102 |
| | G2-RKEGSG | 103 |
| | G2-NSFL | 104 |
| | IgG2-TIDNTRRP | 105 |
| | G2-NSFLRP | 106 |
| IgG1 with CH2 domain residues of IgG2: | G1-G1-G2-G1-AY | 107 |
| | G1-G1-G2-G1-KH | 108 |
| IgG2 with CH2 domain residues of IgG1: | G2-G2.3-G1-G2-KH | 109 |
| | G2.5-G2.3-G1-G2-KH | 110 |
| | G2-G2.3-G1-G2-AY | 111 |
| | G2.5-G2.3-G1-G2-AY | 112 |

TABLE 17-continued

Heavy chain constant regions that were fused to anti-CD73 variable regions

| Description | Constructs | SEQ ID NO of constant region |
|---|---|---|
| Swap hinge regions between IgG1 and IgG2: | G1-G2.3-G1-G1-KH | 113 |
| | G2-G1-G2-G2-AY | 114 |
| | G2.5-G1-G2-G2-AY | 115 |
| | G1-G2-G1-G1-AY | 116 |
| | G2-G1-G2-G2-KH | 117 |
| | G2.5-G1-G2-G2-KH | 118 |
| Hinge truncations | IgG1-deltaHinge | 119 |
| | IgG2-deltaHinge | 120 |
| | IgG2.5-deltaHinge | 121 |
| | IgG1-deltaG237 | 122 |
| | IgG2-plusG237 | 123 |
| Other | IgG2.4 | 124 |
| | IgG2.3/4 | 125 |

Figure 10:
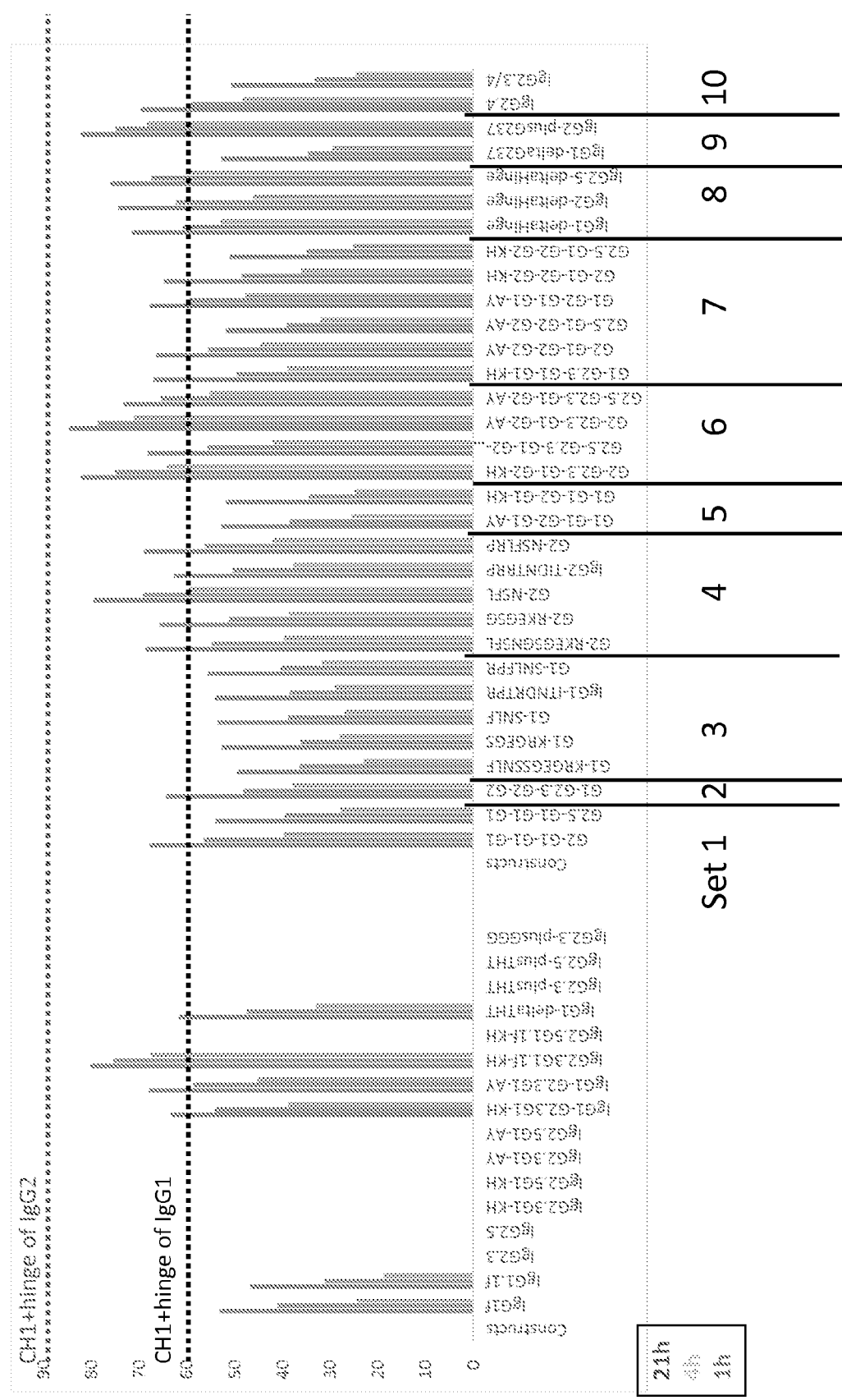
FIG. 10 shows the percentage of antibody mediated CD73 internalization at 1, 4 or 21 hours after the addition of each of the shown antibodies. The bars for each antibody are shown in the order of 21 hours (on the left), 4 hours (middle) and 1 hour (right).

The results, which are shown in FIG. 10, provide the following information in the context of CD73 internalization:

CH2 domain does not appear to have an impact as shown by
  a) very little difference in internalization ability was observed between the antibodies comprising a modified heavy chain constant region with format "AY" (having the IgG2 hinge ERKCCVECPPCPAPPVAG (SEQ ID NO: 8) relative to those with format "KH" (ERKCCVECPPCPAPELLGG (SEQ ID NO: 22) (Set 5, 6 and 7);
  b) CH2 swaps are comparable to wiltype G1 or G2 (Sets 5 and 6); and
  c) residue 237 has no impact on internalization: neither the addition of a "G" residue to an IgG2 hinge nor the deletion of the C terminal "G" in an IgG1 hinge affected internalization (Set 9).

This suggests that the CH2 domain does not impact internalization (i.e., the CH2 domain can be from IgG1 or IgG2);

Swapping the CH1 regions indicated in Set 3 (KRGEGSSNLF; KRGEGS; SNLF; ITNDRTPR and SNLFPR) in IgG1 with those of IgG2 provides little benefit, i.e., the internalization remains similar to that of IgG1; see Set 3);

Swapping the CH1 regions indicated in Set 4 (RKEGS-GNSFL; RKEGSG; NSFL; TIDNTRRP and NSFLRP) in IgG2 with those of IgG1 has variable impact: changing NSFL has no impact, whereas the other 2 regions (RKEGSG & RP) are involved (see Set 4). Based on the results of Sets 3 and 4, it appears that there is an interaction between the CH1 region and the hinge, with RKEGSG and RP regions being more important than NSFL region;

The hinge region impacts internalization, i.e., the hinge of IgG2 provides better internalization relative to the hinge of IgG1 (see Sets 7 and 8). In addition, IgG1 with a deletion (G1-delta-hinge) improves internalization over IgG1. IgG2 with a deletion (G2-delta-hinge) provides a similar level of internalization relative to that of an IgG2 hinge. This suggests that the hinge region impacts internalization, which effect is enhanced by an IgG2 CH1 (G2-G1-G2-G2-AY is comparable to G1-G2-G1-G1-AY);

IgG2.4 (C220S) has similar or reduced internalization compared to IgG2.3 (C219S). IgG2.3/4 (C219S/C220S) has much reduced internalization compared to IgG2.3 or IgG2.4 alone (see Set 10). This suggests that internalization of an antibody with an IgG2 hinge and C219S is about the same as that of an IgG2 hinge with C220S, both of which are much better than that of an IgG2 hinge with both C219S and C220S;

IgG2.5 (C131S mutation) has reduced internalization compared to constructs with C131 (see Sets 1, 6 and 7).

Thus, these results indicate that the CH1 domain and the hinge are both relevant in the antibody mediated CD73 internalization, and that an antibody having the IgG2 sequences from these domains is internalized with better efficacy relative to an antibody having these regions from IgG1.

Example 7: Antibodies Having an IgG2 Hinge and/or CH1 Domain Form High Molecular Weight Complexes CD73.4 antibodies having the heavy chain constant regions set forth in Table 14 were also tested for formation of high molecular weight complexes by SEC-MALS and DLS experiments, as described in Example 3.

Figure 11C:
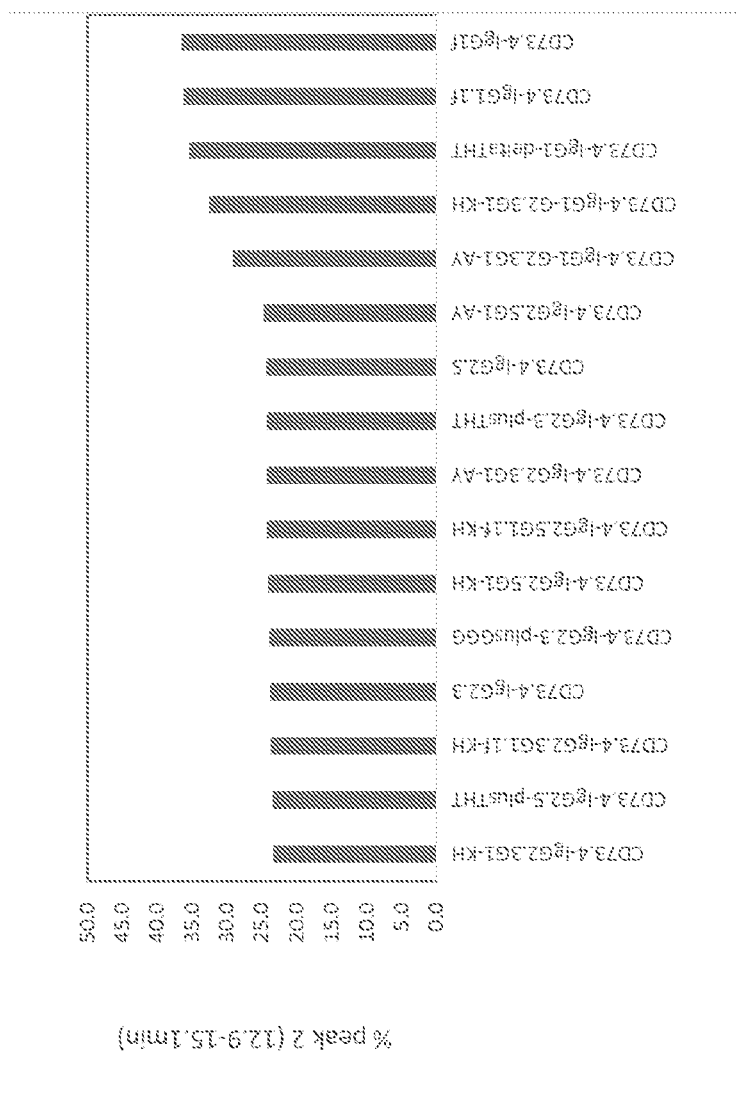
FIG. 11C shows the percentage of the UV chromatogram signal area for peak 2 of FIG. 11B, plotted for the 16 different antibody/CD73-his complexes. Data is sorted from left to right in order of increasing peak area.

Three out of the 16 antibodies in this study were were previously tested: CD73.4-IgG1.1f, CD73.4-IgG2-C219S (also called CD73.4-IgG2.3), and CD73.4-IgG2-C219S-IgG1.1f (also called CD73.4-IgG2.3G1.1f-KH). SEC-MALS and DLS data of the antibodies alone showed retention times, masses, and hydrodynamic radii for each antibody that are typical for a monomeric monoclonal antibody. Equimolar complexes of each antibody (5.5 uM) with hCD73-his (5.5 uM) showed slower retention times for all complexes as compared to antibody or hCD73-his alone indicating the formation of complexes. An overlay of the SEC chromatogram data for each of the 16 complexes is shown in FIG. 11A. The chromatogram data can be divided into 4 distinct peaks, which are shown in FIG. 11B. Peak 1 contains the largest species, with MALS-determined masses suggesting complexes with mass equivalent of greater than 4:4 hCD73-his:mAb complexes. Peak 2 contains species with MALS-determined masses suggesting complexes of about 2:2 hCD73-his:mAb complexes. Peak 3 is a minor species with low signal and MALS-determined masses suggesting about 1:1 hCD73-his:mAb complexes. Peak 4 corresponds to the elution of the mAbs alone with MALS-determined masses consistent with free antibody. To quantitate the relative amounts of each species, the 4 peaks of each chromatogram were integrated as peak 1 (<12.9 min), peak 2 (12.9-15.1 min), peak 3 (15.1-16.7 min), peak 4 (16.7-19.3 min). The integration also included an additional integrated range called peak 5 (>19.3 min) to account for any low molecular weight species, which were found to be negligible (<3.5% for all complexes). The percentage of each species from this integration is summarized in Table 18. All complexes contained a similar small percentage of peak 3 (about 6-9%), but variable amounts of the other peaks. Most notable is that all complexes between hCD73-his and antibodies containing a CH1 domain from hIgG1 had a significantly greater percentage of smaller complexes (peak 2), whereas those containing CH1 domain from hIgG2 had a greater percentage of larger complexes (peak 1) (Table 18 and FIG. 11C). This suggests an important role for not only the hinge region but also the CH1 domain in higher order complex formation.

First, antibodies binding to various targets were made that contain modified IgG1 Fc domains including the substitutions S267E (SE) and S267E/L328F (SELF), as well as various combinations of the mutations P238D, P271G, H268D, A330R, G237D, E233D, referred to as V4, V7, V8,

TABLE 18

Retention times of CD73.4 antibodies with modified heavy chain constant regions

| | UV % | | | | |
|---|---|---|---|---|---|
| Complexes | Peak1 <12.9 min | Peak2 12.9-15.1 min | Peak3 15.1-16.7 min | Peak4 16.7-19.3 min | Peak5 >19.3 min |
| CD73.4-IgG2.3 + hCD73-his | 37.0 | 23.8 | 7.7 | 28.6 | 2.9 |
| CD73.4-IgG2.3G1.1f-KH + hCD73-his | 36.0 | 23.8 | 7.9 | 29.3 | 3.0 |
| CD73.4-IgG1.1f + hCD73-his | 28.4 | 36.2 | 7.4 | 25.6 | 2.3 |
| CD73.4-IgG1f + hCD73-his | 26.0 | 36.5 | 7.5 | 27.8 | 2.2 |
| CD73.4-IgG2.3G1-AY + hCD73-his | 30.2 | 24.3 | 8.1 | 34.4 | 3.0 |
| CD73.4-IgG2.3G1-KH + hCD73-his | 34.9 | 23.4 | 7.9 | 30.7 | 3.0 |
| CD73.4-IgG1-G2.3G1-AY + hCD73-his | 14.6 | 29.2 | 6.4 | 48.3 | 1.6 |
| CD73.4-IgG1-G2.3G1-KH + hCD73-his | 23.8 | 32.6 | 7.0 | 34.5 | 2.1 |
| CD73.4-IgG1-deltaTHT + hCD73-his | 28.3 | 35.4 | 7.0 | 26.9 | 2.4 |
| CD73.4-IgG2.3-plusTHT + hCD73-his | 30.6 | 24.3 | 8.3 | 33.7 | 3.2 |
| CD73.4-IgG2.3-plusGGG + hCD73-his | 30.0 | 23.9 | 8.2 | 34.9 | 2.9 |
| CD73.4-IgG2.5 + hCD73-his | 31.7 | 24.4 | 8.4 | 32.5 | 3.1 |
| CD73.4-IgG2.5G1.1f-KH + hCD73-his | 30.7 | 24.3 | 8.9 | 32.7 | 3.4 |
| CD73.4-IgG2.5G1-AY + hCD73-his | 26.3 | 24.8 | 8.1 | 38.3 | 2.6 |
| CD73.4-IgG2.5G1-KH + hCD73-his | 21.4 | 24.1 | 7.0 | 45.6 | 1.9 |
| CD73.4-IgG2.5-plusTHT + hCD73-his | 32.6 | 23.5 | 8.3 | 32.6 | 3.0 |

Example 8: Fc Receptor Binding for Antibodies with Engineered Constant Domains

This Example demonstrates that antibodies having modified heavy chain constant regions comprising the CH1 and hinge of IgG2 bind to FcγRs when they contain CH2 and CH3 domains of IgG1.

In addition to antigen binding by the variable domains, antibodies can engage Fc-gamma receptors (FcgRs) through interaction with the constant domains. These interactions mediate effector functions such as antibody-dependent cellular cytotoxicity (ADCC) and antibody-dependent cellular phagocytosis (ADCP). Effector function activity is high for the IgG1 isotype, but very low or absent for IgG2 and IgG4 due to these isotypes having lower affinity for FcgRs. In addition, the effector function of IgG1 can be modified through mutation of amino acid residues within the constant regions to alter FcgR affinity and selectivity.

The binding of antibodies to Fc gamma receptors (FcγRs or FcgRs) was studied using biosensor technologies including Biacore surface plasmon resonance (SPR) and Fortebio Biolayer Interferometry (BLI). SPR studies were performed on a Biacore T100 instrument (GE Healthcare) at 25° C. The Fab fragment from a murine anti-6×His antibody was immobilized on a CM5 sensor chip using EDC/NHS to a density of ~3000 RU. Various his-tagged FcgRs (7 ug/ml) were captured via the C-terminal his-tag using a contact time of 30 s at 10 ul/min, and the binding of 1.0 uM antibody was evaluated in a running buffer of 10 mM NaPO4, 130 mM NaCl, 0.05% p20 (PBS-T) pH 7.1. FcgRs used for these experiments included CD64 (FcgRI), CD32a-H131 (FcgRIIa-H131), CD32a-R131 (FcgRIIa-R131), CD32b (FcgRIIb), CD16a-V158 (FcgRIIIa-V158), CD16b-NA1 (FcgRIIIb-NA1), and CD16B-NA2 (FcgRIIIb-NA2). BLI experiments were performed on a Fortebio Octet RED instrument (Pall, Fortebio) at 25° C. in 10 mM NaPO4, 130 mM NaCl, 0.05% p20 (PBS-T) pH 7.1. Antibodies were captured out of undiluted expression supernatants on protein A coated sensors, followed by the binding of 1 uM hCD32a-H131, hCD32a-R131, hCD32b, hCD16a-V158, or 0.1 uM hCD64 analytes.

Figure 12:
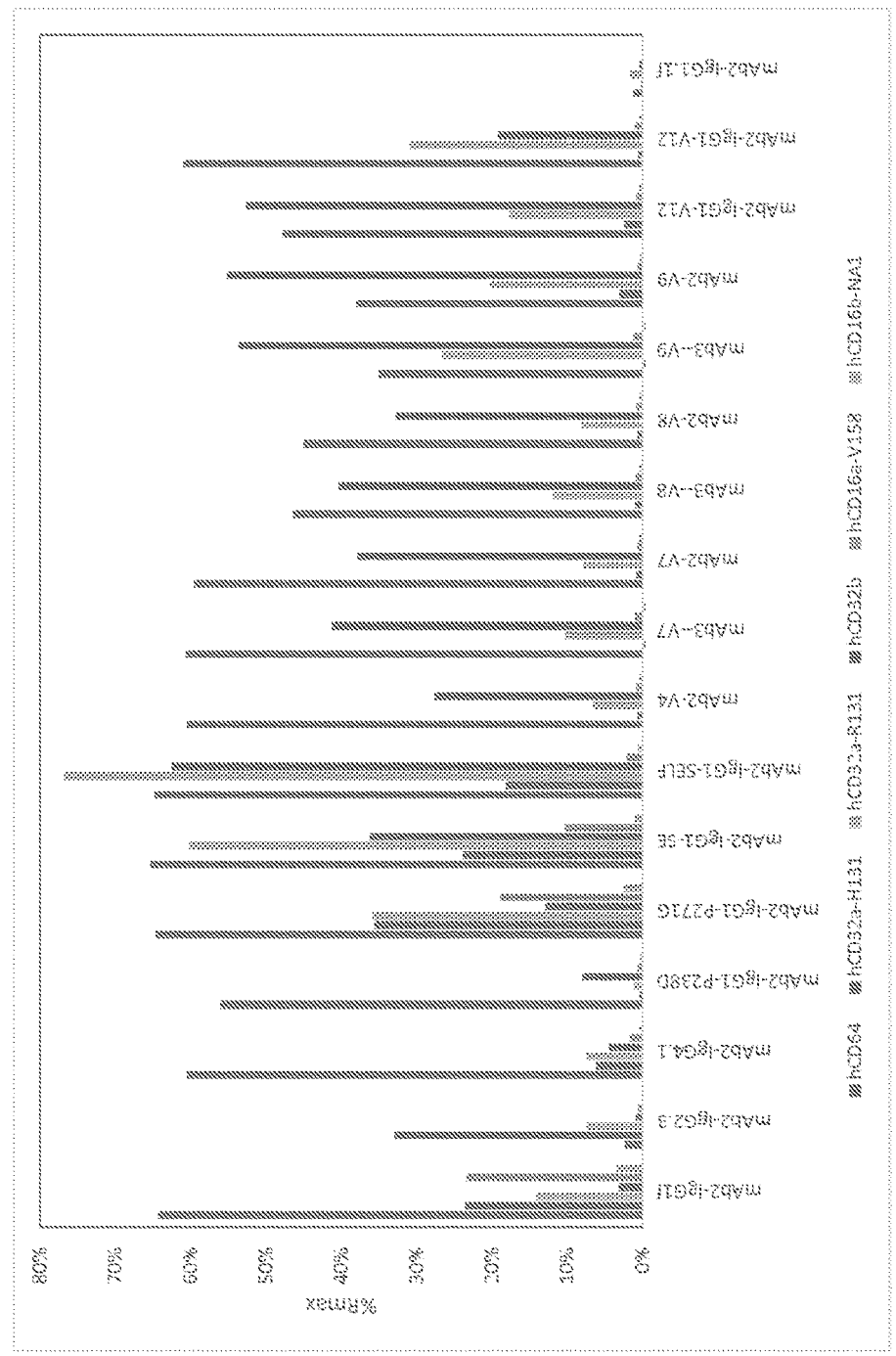
FIG. 12 shows antibody binding to anti-his Fab captured FcγR-his proteins. Binding responses are plotted as a percentage of the theoretical Rmax assuming a 1:1 mAb:FcγR binding stoichiometry. The bars for each antibody are shown in the order provided by the color legends at the bottom of the slide.

V9 and V12. The binding of these antibodies was studied by Biacore SPR with comparison to IgG1f, IgG2.3 (IgG2-C219S) and IgG4.1 (IgG4-S228P) antibodies, as well as an IgG1.1f antibody which has been engineered to reduce binding to all FcgRs. The results, which are shown in FIG. 12, demonstrate the expected FcgR binding properties for IgG1f, IgG2.3 and IgG4.1 and the mutated IgG1 antibodies, including increased CD32a-H131, CD32a-R131 and CD32b binding for SE and SELF, as well as increased selectivity of the V4, V7, V8, V9 and V12 mutants for CD32b over CD32a-H131 and CD32a-R131, FIG. 12.

Figure 13:
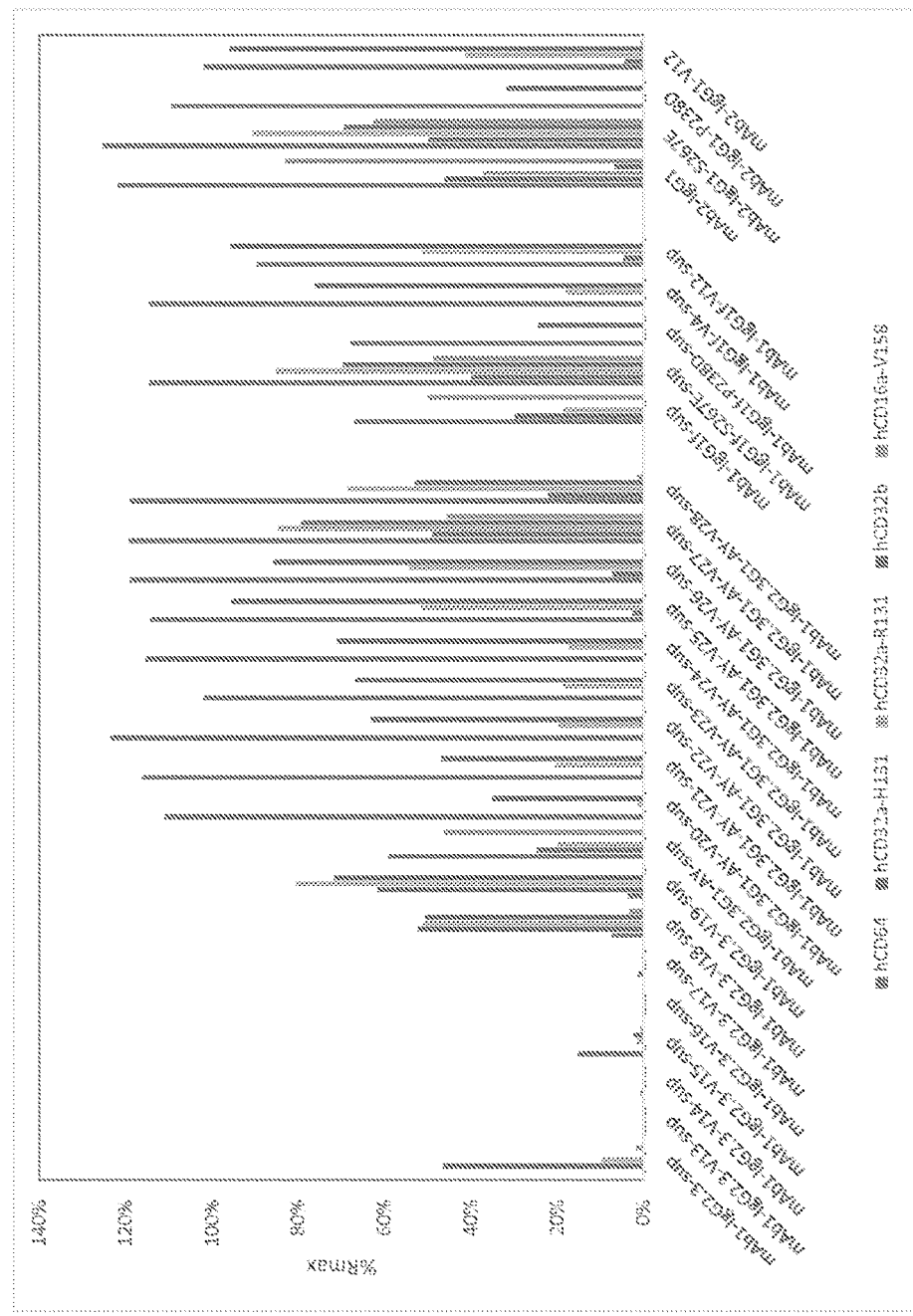
FIG. 13 shows antibody binding to anti-his Fab captured FcgR-his proteins. Binding responses are plotted as a percentage of the theoretical Rmax assuming a 1:1 mAb:FcγR binding stoichiometry. The bars for each antibody are shown in the order provided by the color legends at the bottom of the slide.

The next set of constructs were used to engineer effector function into the otherwise effector function negative IgG2 isotype. For this study, the mutations described above were introduced in the context of IgG2.3 constant region, or an IgG2.3/IgG1f hybrid termed IgG2.3G1-AY, Table 19. Antibodies were expressed at small scale as supernatants, and tested for binding to FcgRs using Fortebio Octet BioLayer Interferometry biosensor technology. Since the antibodies were present at low concentration in the supernatants, the experiment was performed by capturing antibodies out of the supernatants using protein A coated sensors, followed by binding of FcgR analytes in solution. Purified and supernatant control IgG1f including wild type IgG1, SE, P238D, V4 and V12 antibodies were also included for comparison, and each of these control antibodies demonstrated expected FcgR binding properties, FIG. 13. The IgG2.3 antibody also demonstrated the expected binding profile, with appreciable binding to only CD32a-H131. However, all mutations to introduce S267E, L328F, P238D, P271G, H268D, A330R, G237D, or E233D mutations into IgG2.3 failed to recapitulate the FcgR affinity of the corresponding engineered IgG1 mAbs, FIG. 13. In contrast, the IgG2.3G1-AY construct was able to fully preserve the FcgR binding properties of wild type IgG1, while retaining the CH1 and hinge regions of IgG2.3. In addition, all IgG2.3G1-AY mutants containing S267E, L328F, P238D, P271G, H268D, A330R, G237D, and E233D demonstrated FcgR binding properties comparable to the IgG1 version mAbs containing the same mutations, FIG. 13. This demonstrates the successful engineering of antibodies with CH1 and hinge regions of IgG2 combined with effector function of wild type or mutant IgG1.

TABLE 19

Engineered IgG2 constructs

| Set | ID | Construct | Seq ID# |
|---|---|---|---|
| 1 | IgG2.3 | hHC-IgG2-C219S | 79 |
|  | IgG2.3-V13 | hHC-IgG2-C219S - P238D | 152 |
|  | IgG2.3-V14 | hHC-IgG2-C219S - P238D, P271G | 153 |
|  | IgG2.3-V15 | hHC-IgG2-C219S - P238D, H268D, P271G | 154 |
|  | IgG2.3-V16 | hHC-IgG2-C219S - P238D, P271G, A330R | 155 |
|  | IgG2.3-V17 | hHC-IgG2-C219S - P238D, H268D, P271G, A330R | 156 |
|  | IgG2.3-V18 | hHC-IgG2-C219S - S267E | 157 |
|  | IgG2.3-V19 | hHC-IgG2-C219S - S267E, L328F | 158 |
| 2 | IgG2.3G1 | hHC-IgG2-C219S/hHC-IgG1f | 159 |
|  | IgG2.3G1-AY-V20 | hHC-IgG2-C219S/hHC-IgG1f - P238D | 160 |
|  | IgG2.3G1-AY-V21 | hHC-IgG2-C219S/hHC-IgG1f - P238D, P271G | 161 |
|  | IgG2.3G1-AY-V22 | hHC-IgG2-C219S/hHC-IgG1f - P238D, H268D, P271G | 162 |
|  | IgG2.3G1-AY-V23 | hHC-IgG2-C219S/hHC-IgG1f - P238D, P271G, A330R | 163 |
|  | IgG2.3G1-AY-V24 | hHC-IgG2-C219S/hHC-IgG1f - P238D, H268D, P271G, A330R | 164 |
|  | IgG2.3G1-AY-V25 | hHC-IgG2-C219S/hHC-IgG1f - G237D, P238D, H268D, P271G, A330R | 165 |
|  | IgG2.3G1-AY-V26 | hHC-IgG2-C219S/hHC-IgG1f - E233D, G237D, P238D, H268D, P271G, A330R | 166 |
|  | IgG2.3G1-AY-V27 | hHC-IgG2-C219S/hHC-IgG1f - S267E | 167 |
|  | IgG2.3G1-AY-V28 | hHC-IgG2-C219S/hHC-IgG1f - S267E, L328F | 168 |

Figure 14A:
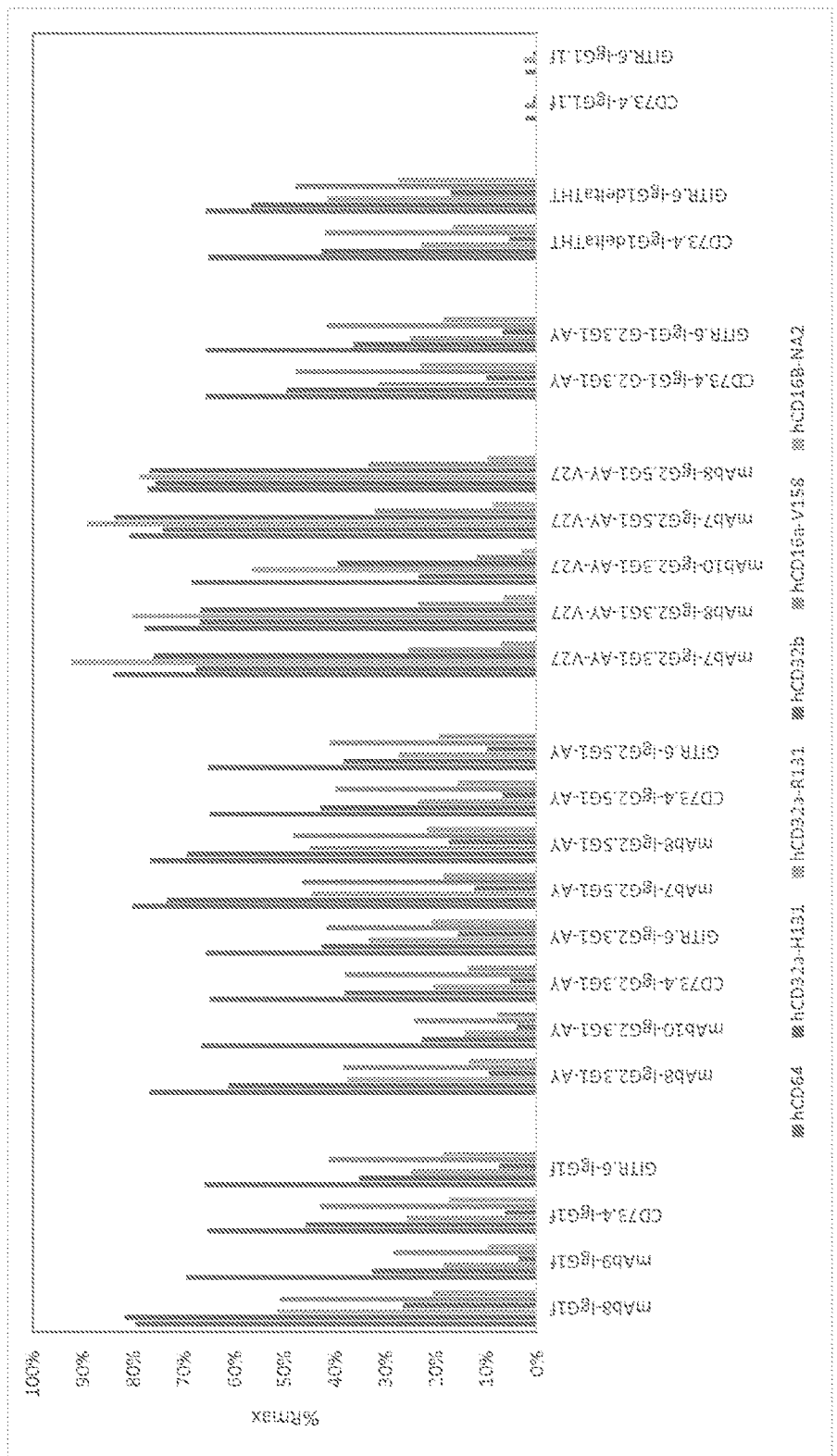
FIG. 14A shows antibody binding to anti-his Fab captured FcγR-his proteins. Binding responses are plotted as a percentage of the theoretical Rmax assuming a 1:1 mAb:FcγR binding stoichiometry. The bars for each antibody are shown in the order provided by the color legends at the bottom of the slide.
Figure 14B:
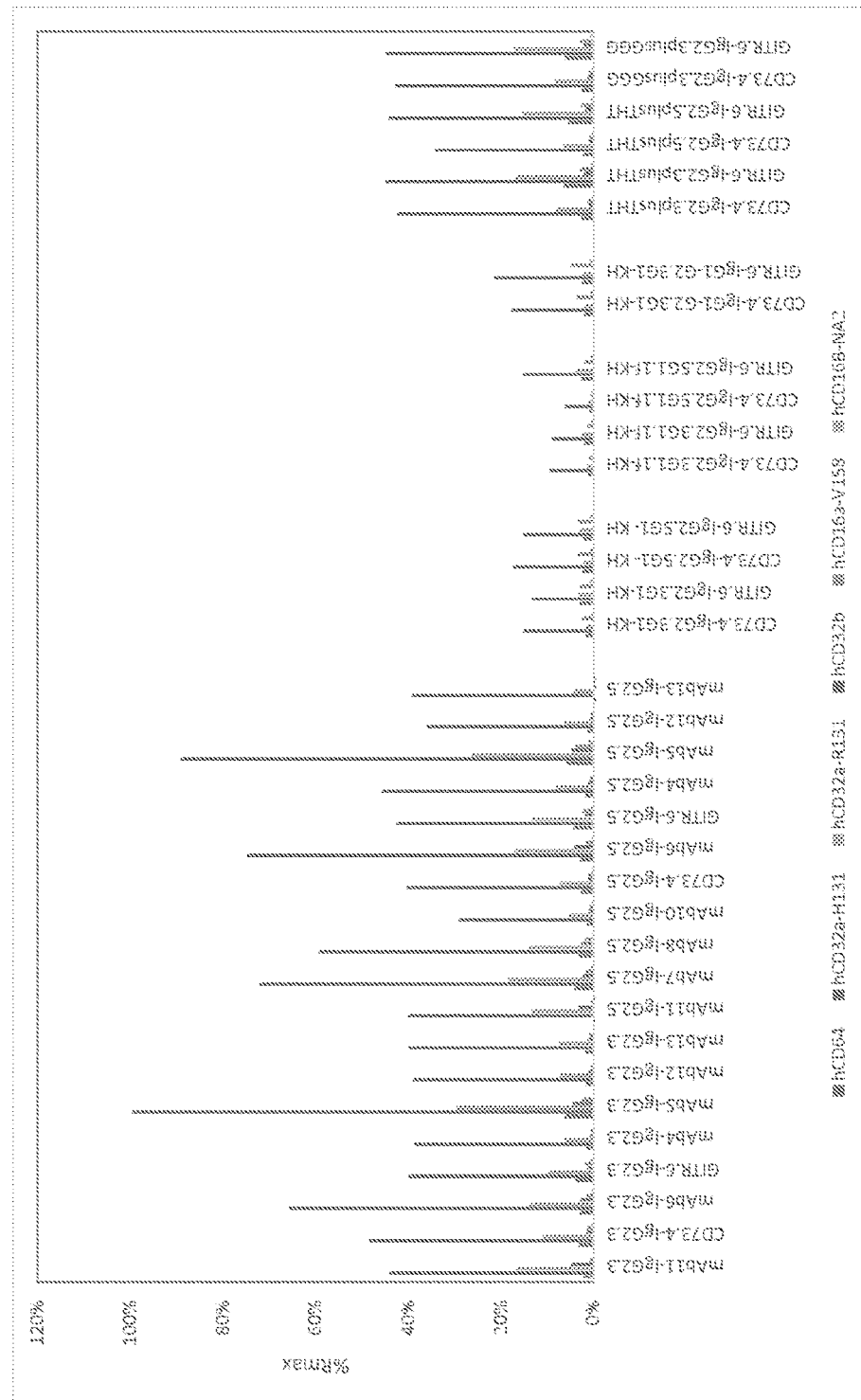
FIG. 14B shows antibody binding to anti-his Fab captured FcγR-his proteins. Binding responses are plotted as a percentage of the theoretical Rmax assuming a 1:1 mAb:FcγR binding stoichiometry. The bars for each antibody are shown in the order provided by the color legends at the bottom of the slide.

This engineering strategy was further explored by producing other antibodies formatted with IgG2.3G1-AY, IgG2.3G1-AY-S267E (IgG2.3G1-AY-V27), as well as IgG2-B-form variants (IgG2.5G1-AY and IgG2.5G1-AY-V27), and other hybrid antibodies containing different combinations of IgG1 and IgG2 constant domains, and testing the binding of these antibodies to anti-his Fab captured his-tagged FcgRs using Biacore SPR technology. In agreement with the Octet supernatant data, the SPR data showed that the IgG2.3G1-AY and IgG2.3G1-AY-V27 antibodies had comparable FcgR binding properties to IgG1f and IgG1f-S267E respectively, despite containing the CH1 and hinge regions of an A-form IgG2 antibody (IgG2.3) (FIGS. 14A and B and Table 20). Similar data was also obtained using IgG2.5G1-AY and IgG2.5G1-AY-V27 antibodies, demonstrating the successful engineering of B-form IgG2 antibodies (containing C131S mutation termed IgG2.5) having IgG1f or modified IgG1f like effector functions. Data for several other antibodies with IgG2.3G1-AY, IgG2.3G1-AY-V27, IgG2.5G1-AY, or IgG2.5G1-AY-V27 constant regions but different variable regions shows that this engineering strategy is broadly applicable to other antibodies independent of the variable domains (FIGS. 14A and B and Table 20). Other constructs that demonstrate IgG1f-like FcgR binding properties are IgG1-G2.3G1-AY, and IgG1deltaTHT, whereas several of the modified constant region constructs were unable to retain IgG1f-like FcgR binding properties, including IgG2.3G1-KH, IgG2.5G1-KH, IgG2.3plusTHT, IgG2.5plusTHT and IgG2.3plusGGG constructs, (FIGS. 14A and B and Table 2W.

TABLE 20

% Rmax values for 1 uM antibodies binding to anti-his Fab captured FcgR-his proteins

| mAb | hCD64 | hCD32a-H131 | hCD32a-R131 | hCD32b | hCD16a-V158 | hCD16B-NA2 |
|---|---|---|---|---|---|---|
| mAb8-IgG1f | 80% | 82% | 51% | 27% | 51% | 21% |
| mAb9-IgG1f | 70% | 33% | 19% | 4% | 28% | 10% |
| CD73.4-IgG1f | 65% | 46% | 26% | 6% | 43% | 17% |
| GITR.6-IgG1f | 66% | 35% | 25% | 8% | 41% | 19% |
| CD73.4-IgG1.1f | 2% | 0% | 2% | 1% | 0% | 0% |
| GITR.6-IgG1.1f | 2% | 0% | 3% | 1% | 0% | 0% |
| mAb11-IgG2.3 | 2% | 44% | 17% | 5% | 1% | 0% |
| CD73.4-IgG2.3 | 3% | 48% | 11% | 1% | 1% | 0% |
| mAb6-IgG2.3 | 3% | 66% | 14% | 3% | 1% | 0% |
| GITR.6-IgG2.3 | 4% | 40% | 10% | 1% | 2% | 0% |
| mAb4-IgG2.3 | 1% | 39% | 6% | 1% | 1% | 0% |
| mAb5-IgG2.3 | 6% | 100% | 30% | 4% | 3% | 0% |
| mAb12-IgG2.3 | 2% | 39% | 7% | 1% | 1% | 0% |
| mAb13-IgG2.3 | 2% | 40% | 7% | 1% | 1% | 0% |
| mAb11-IgG2.5 | 0% | 40% | 13% | 3% | 0% | -1% |
| mAb7-IgG2.5 | 4% | 72% | 19% | 2% | 2% | 0% |
| mAb8-IgG2.5 | 3% | 59% | 14% | 3% | 2% | 0% |
| mAb10-IgG2.5 | 1% | 29% | 5% | 1% | 1% | 0% |
| CD73.4-IgG2.5 | 3% | 40% | 7% | 1% | 1% | 0% |

TABLE 20-continued

% Rmax values for 1 uM antibodies binding to anti-his Fab captured FcgR-his proteins

| mAb | hCD64 | hCD32a-H131 | hCD32a-R131 | hCD32b | hCD16a-V158 | hCD16B-NA2 |
|---|---|---|---|---|---|---|
| mAb6-IgG2.5 | 3% | 75% | 17% | 4% | 2% | 0% |
| GITR.6-IgG2.5 | 4% | 43% | 13% | 2% | 2% | 1% |
| mAb4-IgG2.5 | 2% | 46% | 8% | 1% | 1% | 0% |
| mAb5-IgG2.5 | 6% | 89% | 26% | 5% | 4% | 1% |
| mAb12-IgG2.5 | 1% | 36% | 6% | 1% | 1% | 0% |
| mAb13-IgG2.5 | −2% | 39% | 4% | −2% | 0% | −2% |
| mAb8-IgG2.3G1-AY | 77% | 61% | 38% | 10% | 38% | 13% |
| mAb10-IgG2.3G1-AY | 67% | 23% | 14% | 4% | 24% | 8% |
| CD73.4-IgG2.3G1-AY | 65% | 38% | 20% | 5% | 38% | 14% |
| GITR.6-IgG2.3G1-AY | 66% | 43% | 33% | 16% | 42% | 21% |
| mAb7-IgG2.5G1-AY | 80% | 73% | 45% | 12% | 47% | 19% |
| mAb8-IgG2.5G1-AY | 77% | 70% | 45% | 17% | 48% | 22% |
| CD73.4-IgG2.5G1-AY | 65% | 43% | 24% | 7% | 40% | 16% |
| GITR.6-IgG2.5G1-AY | 65% | 38% | 27% | 10% | 41% | 19% |
| CD73.4-IgG2.3G1-KH | 2% | 15% | 2% | 0% | 2% | 0% |
| GITR.6-IgG2.3G1-KH | 3% | 13% | 3% | 0% | 3% | 1% |
| CD73.4-IgG2.5G1-KH | 2% | 17% | 2% | 0% | 3% | 0% |
| GITR.6-IgG2.5G1-KH | 2% | 15% | 3% | 0% | 3% | 1% |
| CD73.4-IgG2.3G1.1f-KH | 1% | 10% | 1% | 0% | 1% | 0% |
| GITR.6-IgG2.3G1.1f-KH | 2% | 9% | 2% | 0% | 1% | 0% |
| CD73.4-IgG2.5G1.1f-KH | 1% | 6% | 1% | 0% | 1% | 0% |
| GITR.6-IgG2.5G1.1f-KH | 3% | 15% | 4% | 0% | 2% | 0% |
| mAb7-IgG2.3G1-AY-V27 | 84% | 68% | 92% | 76% | 26% | 7% |
| mAb8-IgG2.3G1-AY-V27 | 78% | 67% | 80% | 67% | 24% | 7% |
| mAb10-IgG2.3G1-AY-V27 | 69% | 24% | 57% | 40% | 12% | 3% |
| mAb7-IgG2.5G1-AY-V27 | 81% | 74% | 89% | 84% | 32% | 9% |
| mAb8-IgG2.5G1-AY-V27 | 77% | 76% | 79% | 77% | 33% | 10% |
| CD73.4-IgG1-G2.3G1-AY | 66% | 50% | 31% | 10% | 48% | 23% |
| GITR.6-IgG1-G2.3G1-AY | 66% | 36% | 25% | 7% | 42% | 19% |
| CD73.4-IgG1-G2.3G1-KH | 2% | 18% | 2% | 0% | 4% | 1% |
| GITR.6-IgG1-G2.3G1-KH | 2% | 21% | 2% | 0% | 5% | 1% |
| CD73.4-IgG1deltaTHT | 65% | 43% | 23% | 6% | 42% | 17% |
| GITR.6-IgG1deltaTHT | 66% | 57% | 42% | 17% | 48% | 27% |
| CD73.4-IgG2.3plusTHT | 3% | 42% | 8% | 1% | 1% | 0% |
| GITR.6-IgG2.3plusTHT | 6% | 45% | 17% | 2% | 3% | 1% |
| CD73.4-IgG2.5plusTHT | 2% | 34% | 7% | 1% | 1% | 0% |
| GITR.6-IgG2.5plusTHT | 5% | 44% | 15% | 2% | 3% | 1% |
| CD73.4-IgG2.3plusGGG | 3% | 43% | 8% | 1% | 1% | 0% |
| GITR.6-IgG2.3plusGGG | 6% | 45% | 17% | 2% | 3% | 1% |

Taken together these data show that the sequence immediately C-terminal to the conserved CPPCPAP motif in the hinge region confers FcgR-mediated effector function, whereas the CH1 and upper portions of the hinge of the antibody can be replaced with IgG2 or modified IgG2 sequences, to potentially combine the effector functions of IgG1 and modified IgG1 with the superior internalization or signaling properties of antibodies containing IgG2 CH1 and/or hinge regions.

Example 9: GITR Agonist Ab Internalization is Enhanced in Antibodies Having an IgG2 Hinge and CH1 Domain To induce GITR expression, cells were incubated for 72 h at 37° C. with 20 ng/ml anti-CD3+1000 ng/ml CD28. As an alternate method of T-cell activation, large batches of activated CD4+ T-cells were prepared by a three stage culture protocol. Briefly, CD4+ T-cells were stimulated with plate bound CD3 (1.5 ug/ml) supplemented with 1 ug/ml soluble CD28 for 72 h at 37° C., expanded in culture for 14 days in the presence of 20 u/ml IL2 and finally exposed to another round of activation by addition of 10 ug/ml PHA, 2 u/ml IL2 and 1 ug/ml CD28 for 72 h at 37° C. Stimulated T cells were seeded into 384 well PDL imaging plates for 2 h to adhere the cells, cooled for 15 min at 4° C., and then alexa 488 labeled GITR antibodies were added separately for 1 h. Plates were finally imaged by HCS and the data were reported as total intensity per cell.

Three different GITR antibodies have been evaluated using the above mentioned T cell activation methods. They are GITR.6 antibody as a G1 isotype and an inert (IgG1.1) isotype unable to bind to Fc receptors, as well as a chimera with the IgG2 hinge in place of the IgG1 hinge.

Figure 15:
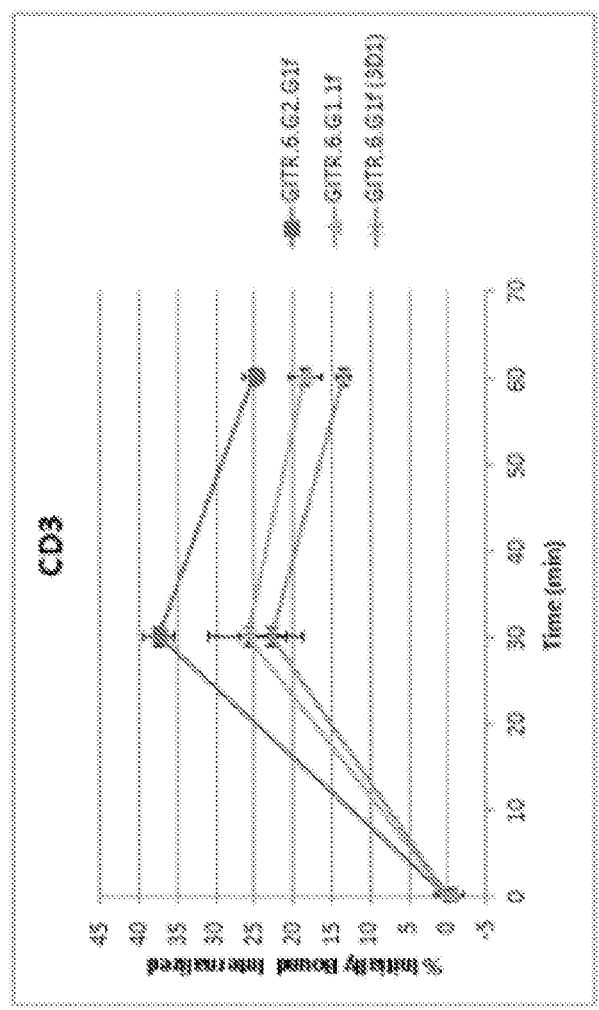
FIG. 15 shows an internalization time course analysis of anti-GITR antibodies.

GITR antibody induced internalization was assessed in CD3 stimulated CD4+ T-cells using the alexa quench assay format. Freshly obtained CD4 positive T cells were incubated under as described above to induce GITR expression. After stimulation, cells were resuspended into fresh media and plated for internalization assays as follows. Cells were incubated with antibody as described above, washed with warm media and incubated at 37° C. for the indicated times prior to fixation and quenching. Internalized antibody was measured as increased fluorescence above the small unquenchable signal observed at time zero and then normalized against the total fluorescence "unquenched control" initially bound to the cells. As shown in FIG. 15, GITR ligation resulted in rapid internalization peaking between 30-60 minutes for each antibody tested while control antibodies were found to maintain localization to the plasma membrane. The results indicate that the IgG2 hinge region enhances GITR ligation induced internalization.

Figure 16:
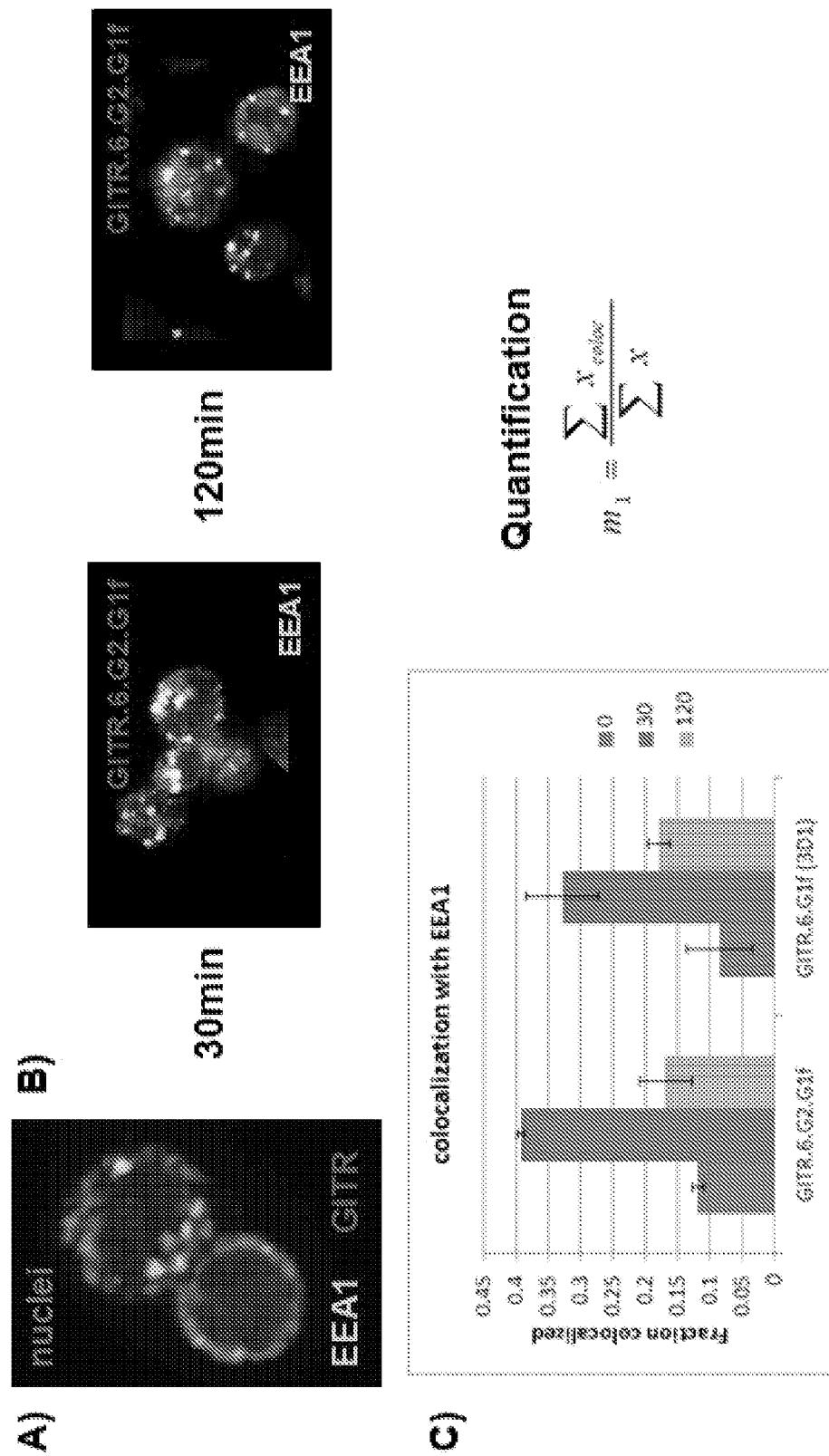
FIG. 16A shows GITR and early endosome marker EEA2 co-localization analysis at time zero.
FIG. 16B shows GITR and early endosome marker EEA2 co-localization analysis at time 30 and 120 minutes.
FIG. 16C shows the results of quantification of endosomal co-localization shown in FIGS. 16A and B plotted as the ratio of colocalized pixel intensity relative to total staining.

To further dissect the detailed mechanisms of internalization and associated dynamics, antibody endocytosis and delivery into early endosome compartments was analyzed. In this experiment, cells were subjected to pulse chase analysis with unlabeled antibodies. Upon fixation, cells were permeabilized and stained for the early endosome marker EEA1 (cell signaling technology), washed and then detected with alexa fluor-488 conjugated anti-rabbit secondary antibody (EEA1) and alexa fluor-647 conjugated anti-human antibody (GITR). Plates were imaged on an Opera confocal system with a 60× water immersion objective. The results indicated clear segregation between the membrane bound anti-GITR antibody staining and intracellular EEA1 signal. Upon warming the cultures, clustering for some antibodies was detected that appears to co-localize with endosomal proteins. Quantification of endosomal co-localization was performed using HCS Studio Software and the results are plotted as the ratio of colocalized pixel intensity relative to total staining (FIG. 16). The colocalization of GITR antibody and early endosome is most prominent at 30 minutes. At this tested time point, GITR.6.G2.G1f showed a higher fraction colocalized than the GITR.6.G1f antibody. The colocalization results correlate with the observations made using the alexa quenching method described above and support a model suggesting the G2 hinge has potential advantage over G1 for inducing GITR internalization.

Example 10: GITR Agonist Ab Signaling in T Cell Receptor Activated CD4+ and CD8+ T Cells is Enhanced in Antibodies Having an IgG2 Hinge and CH1 Domain To further investigate the mechanisms for anti-GITR agonist antibodies, several signaling pathways involved in T cell activation, such as NFkB and P38 signaling pathways, were monitored.

CD4+ and CD8+ T cells from a healthy donor (M6576) were activated with plate-coated 0.4 µg/ml anti-CD3 and 0.4 µg/ml anti-CD28. After 3 days, cells were collected and plated onto 384-well image plates for signaling activation. After cells settled in the plate for 2 hours, they were treated with GITR antibodies for 15 minutes and the signaling events were terminated by adding formaldehyde to a final of 10% into the assays plate. Then the cells were permeabilized and stained with phosphor-p65 NFKB antibody for signaling detection. As shown in FIG. 17, GITR.6.G2 and GITR.6.G2.G1f antibodies had higher signaling responses compared to the GITR.6.G1f in both CD4+ and CD8+ T cells. Although there is no direct evidence of linking internalization and signaling pathway activation, it is intriguing to note that G2 isotype seems to improve both aspects of antibody functional activities compared to the IgG1 for GITR.6.

To quantify the signaling activities for each antibody, both EC50 and Emax for each antibody were calculated, since both parameters are critical to capture the full extent of the signaling event. The response level of GITR.6.G2.G1f is chosen to be the 100% control, and all other antibodies were normalized against it. As shown in Table 21 for both CD4+ and CD8+ T cell populations activated by anti-CD3 and anti-CD28 antibodies, there were a range of activities for GITR antibodies in terms of both potency (EC50s) and efficacy (Emax %). Although GITR.6.G2, GITR.6.G2.G1f and GITR.6.G1f showed similar potencies (EC50s) around 10 nM range, the efficacy (Emax) was quite different for different isotypes, suggesting G1 antibody does not signal as effectively as the G2 or chimeric isotypes.

TABLE 21

Summary of the GITR HuMab NFKB Signaling activities in TCR Activated CD4+ and CD8+ T Cells

| Antibody | CD4+ T cells | | CD8+ T cells | |
|---|---|---|---|---|
| | EC50 (nM) | Emax (%) | EC50 (nM) | Emax (%) |
| GITR.6.G2 | 12.8 | 69 | 9.00 | 85 |
| GITR.6.G2.G1f | 9.00 | 100 | 3.77 | 92 |
| GITR.6.G1f | 7.3 | 10.8 | 20.05 | 27 |
| hIgG1 Isotype Control | Inactive | 4 | Inactive | 6 |

Figure 18:
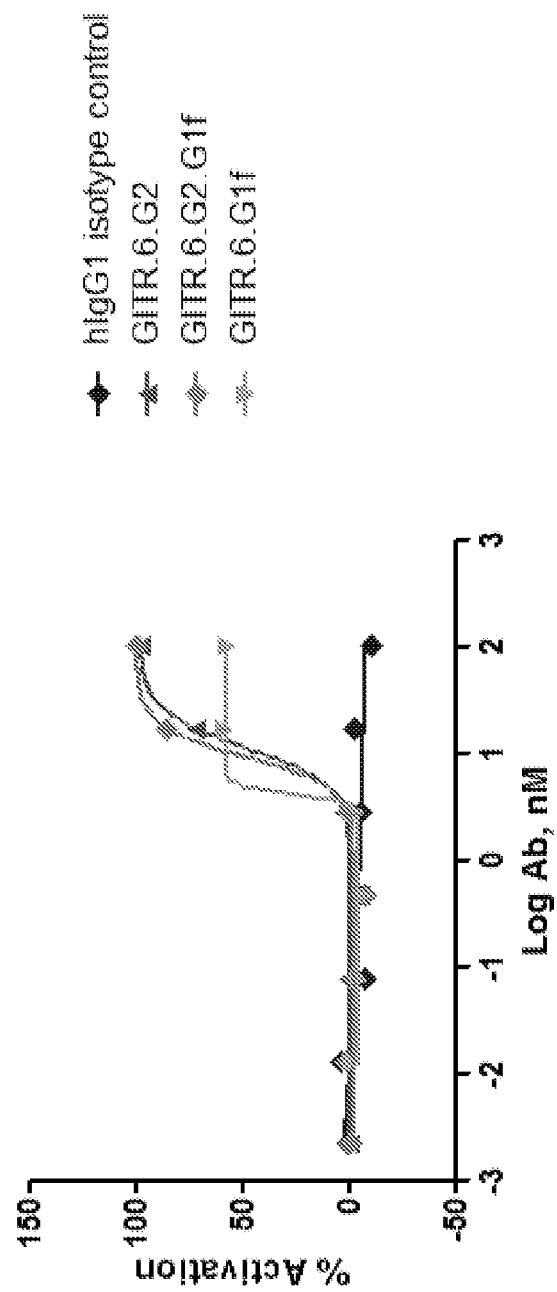
FIG. 18 shows P38 activation in CD4+ T cells treated with the indicated anti-GITR antibodies.
Figure 19:
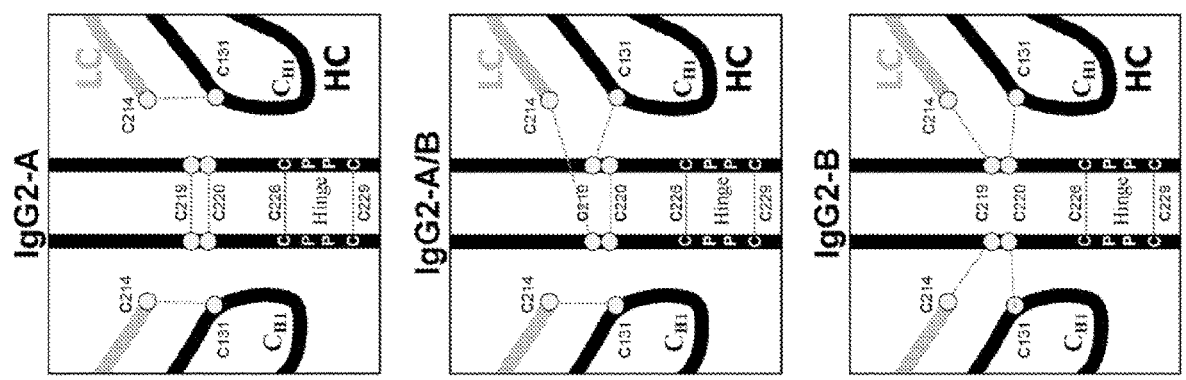
FIG. 19 shows the configuration of the disulfide bonds in IgG2 antibodies having conformation A, B or A/B.
Figure 20A:
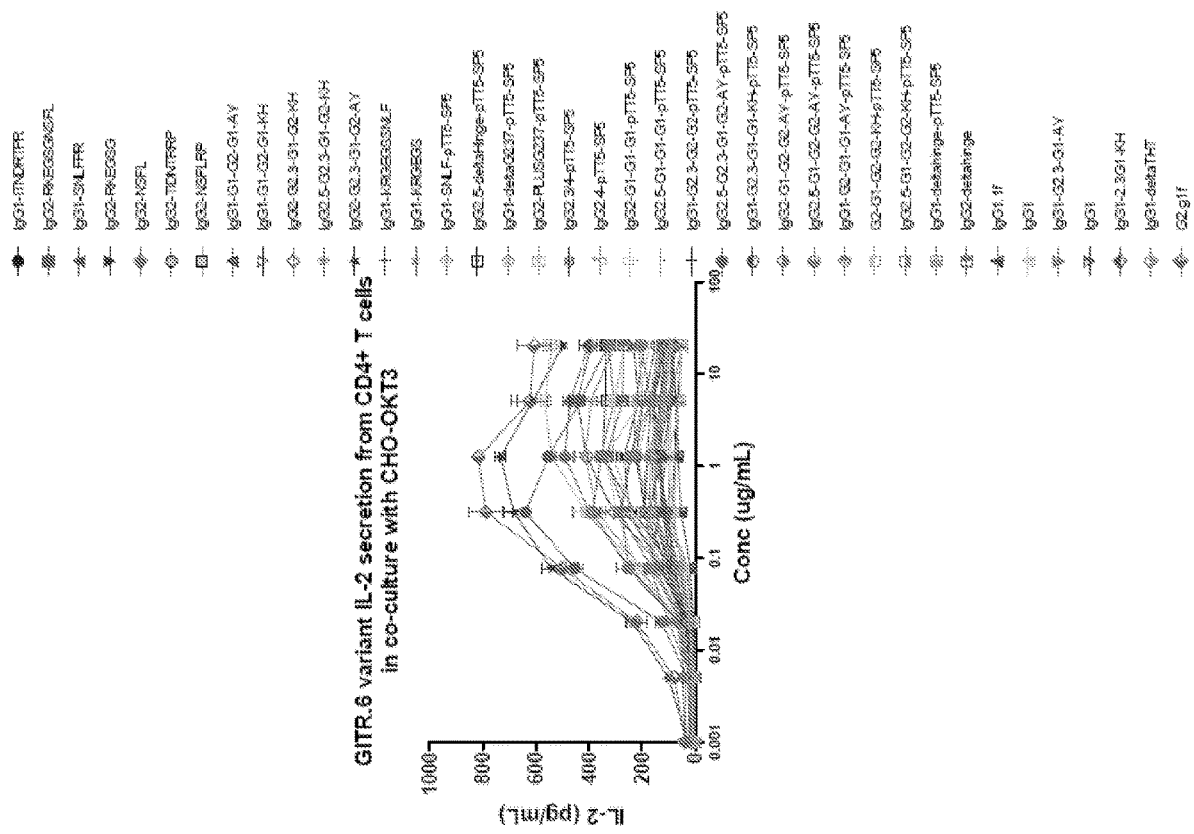
FIG. 20A shows the level of IL-2 secreted by CD4+ T cells co-cocultured with CHO-OKT3 cells in the presence of different concentrations of an anti-GITR antibody having the indicated constant regions.
Figure 20B:
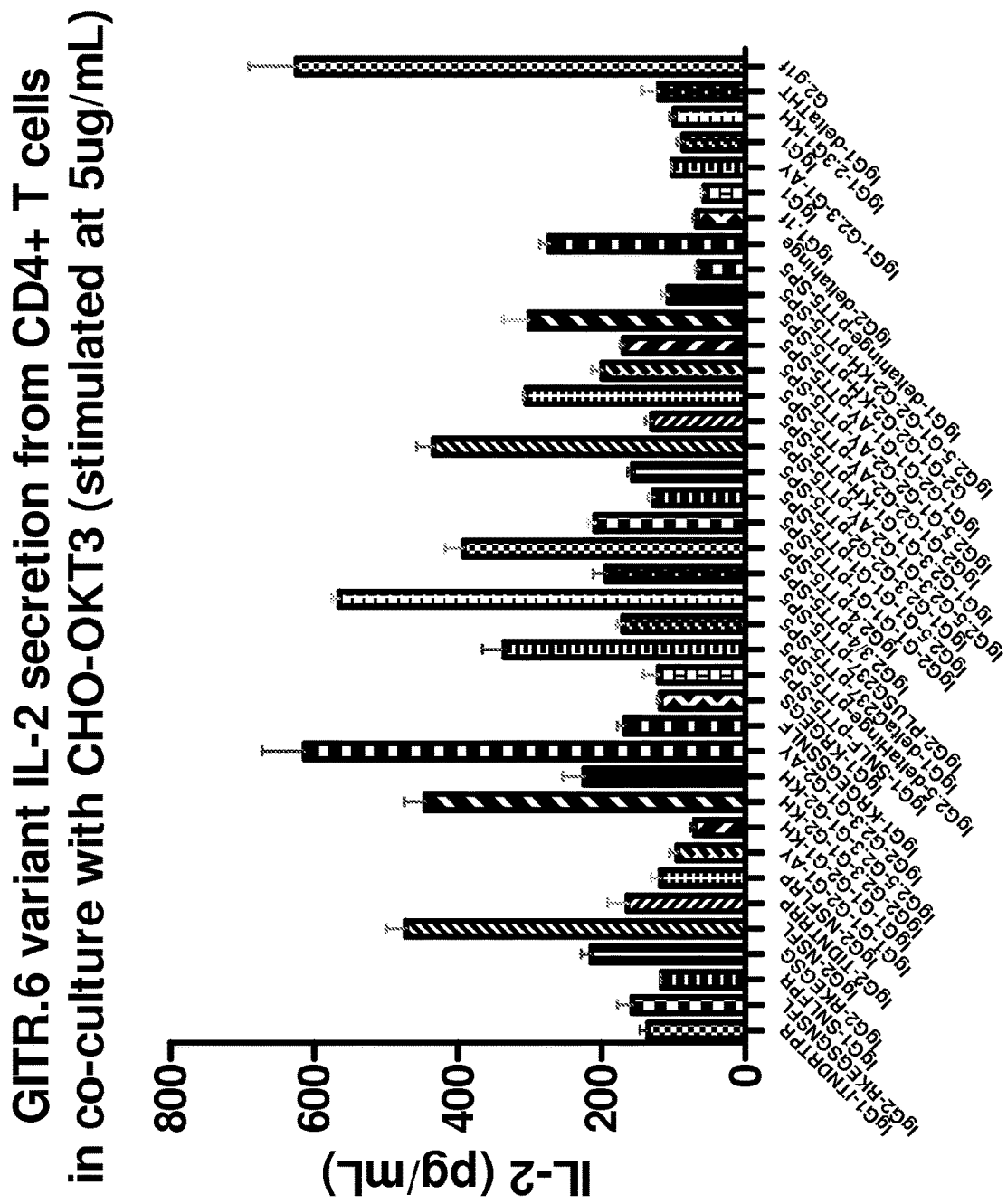
FIG. 20B shows the level of IL-2 secreted by CD4+ T cells co-cocultured with CHO-OKT3 cells in the presence of 5 μg/ml of an anti-GITR antibody having the indicated constant regions (same experiment as that in FIG. 20A).
Figure 20C:
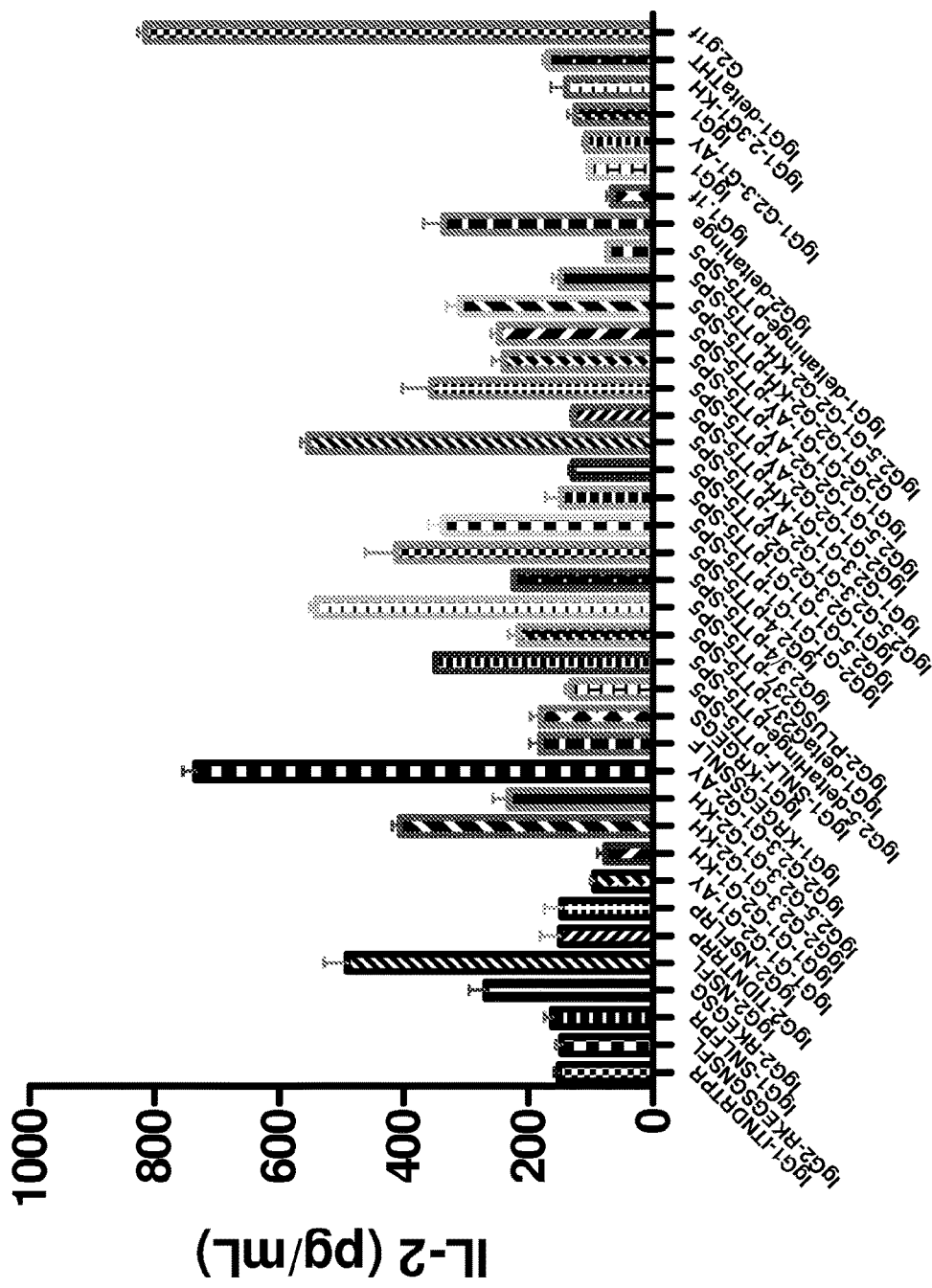
FIG. 20C shows the level of IL-2 secreted by CD4+ T cells co-cocultured with CHO-OKT3 cells in the presence of 1.25 μg/ml of an anti-GITR antibody having the indicated constant regions (same experiment as that in FIG. 20A).
Figure 20D:
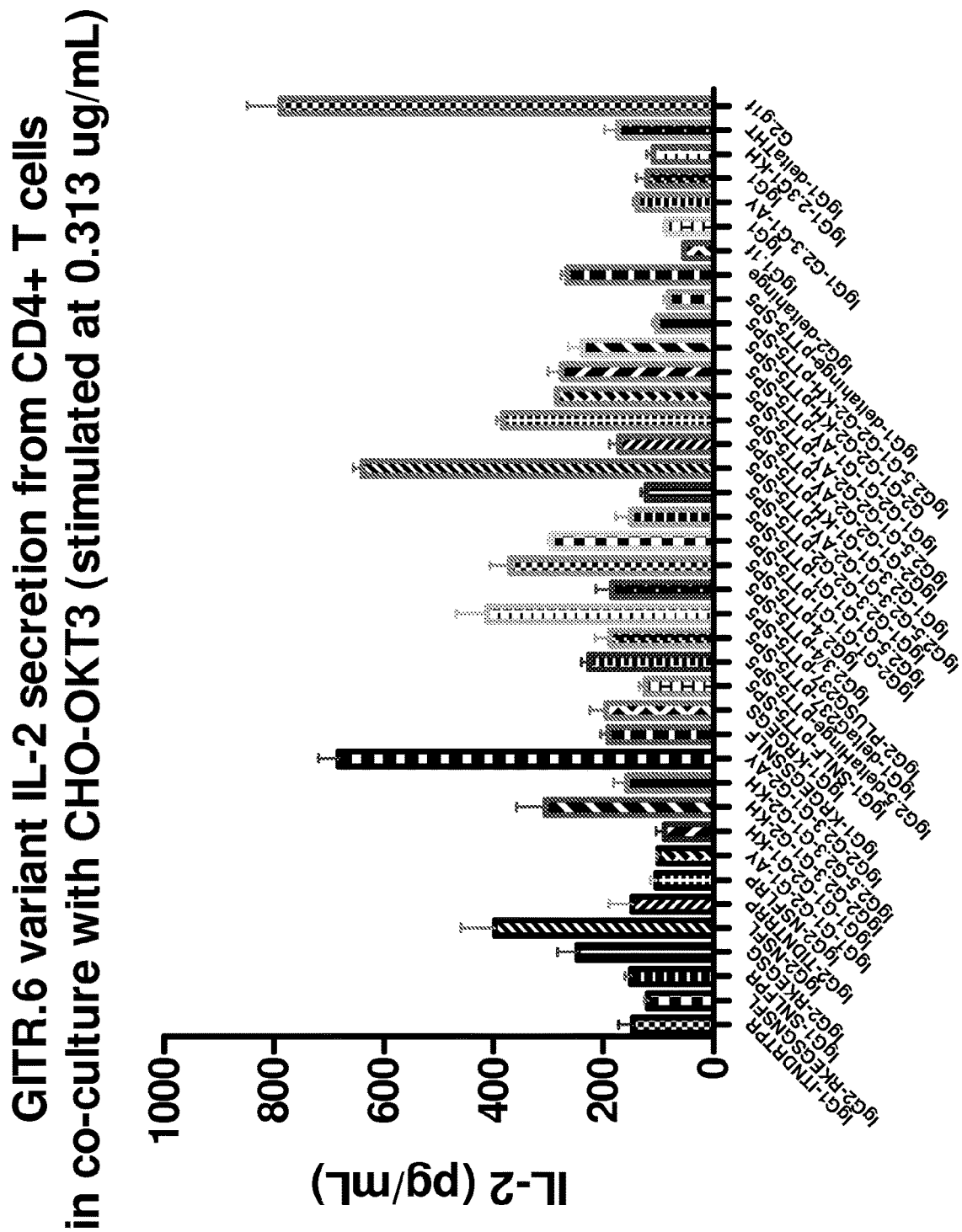
FIG. 20D shows the level of IL-2 secreted by CD4+ T cells co-cocultured with CHO-OKT3 cells in the presence of 0.313 μg/ml of an anti-GITR antibody having the indicated constant regions (same experiment as that in FIG. 20A).

To further confirm if the signaling difference of GITR.6.G2 and GITR.6.G2.G1f compared to GITR.6.G1f is limited to NFkB signaling only or if it holds true for other signaling events as well, a P38MAPK signaling readout was explored. As shown in FIG. 18, GITR.6.G2 and GITR.6.G2.G1f antibodies had higher signaling responses compared to the GITR.6.G1f antibody in a CD4+ cell p38 MAPK activation assay. Therefore the better signaling activities for GITR.6 G2 isotype compared with G1 isotype is not only limited to NFkB signaling.

In addition to enhanced agonist activity and internalization, it was also shown that modified heavy chain constant regions can impart enhanced ADCC (to, e.g., an agonist of a stimulatory receptor), as well as provide a new activity to an antibody. For example, it was found that changing the constant heavy chain domain of an antibody that binds to an inhibitory cell surface molecule and prevents the inhibitory activity of the cell surface molecule (an antagonist) to a modified heavy chain constant region described herein, resulted in the antibody losing its ability to be an antagonist, and instead endowed it with agonist activity (of the inhibitory activity).

Example 11: Confirmation of Disulfide Bonds of IgG2.3 and IgG2.5 Constructs

The disulfide bond structures in an antibody comprising the constant domain IgG2.3 (A form), IgG2.3G1 (A form) and IgG2.5 (B-form) were confirmed to be correct by comparison of non-reduced to reduced Lys-C digests.

The antibody samples were digested with Lys-C which specifically cleaves peptide bonds on the carboxyl-terminal side of Lysine (K, Lys) residues. Peptides in the digest were separated using a Waters ACQUITY BEH C18 column, 1.7 µm, 2.1×150 mm, reverse phase HPLC column and detected with an ultraviolet (UV) detector at 214 nm and Thermo LTQ mass spectrometer.

Lys-C enzymatic digestion and reduction of disulfide bonds: To a vial containing 100 µg of the antibody sample, 120 µL denature buffer was added, resulting in a 3.7M GuHCl, 0.2M Tris pH 7.0 solution. The mixture was incubated at 55° C. for 30 minutes. Alkylation of protein was done by adding 1 µl 50 mM Iodoacetamide in the above solution, then incubation in the dark at room temperature for 30 minutes. Alkylated sample was diluted with 80 µL dH2O and Waco Lys-C was added at enzyme to substrate ratio as 1:10. The antibodies were digested overnight in the dark at room temperature. After digestion, a 100 µL aliquot was removed from the Lys-C digested sample and 10 µL of 0.5M DTT was added in. This sample was incubated at room temperature for 1 hour to reduce the disulfide bonds.

The results obtained are as follows:

Disulfide structure of the IgG2.3 and IgG2.3G1 antibodies (A form): Within the Fab region of the heavy chain Cys22

(H) is linked to Cys98 (H) and Cys151 (H) is linked to Cys 207(H). Within the Fc region of the heavy chain Cys265(H) is linked to Cys325 (H) and Cys371 (H) is linked to Cys429 (H). Within the Fab region of the light chain Cys23 (L) is linked to Cys88 (L) and Cys134 (L) is linked to Cys194 (L). The C-terminal of light chain Cys214 (L) is linked to the heavy chain at Cys138 (H). The hinge region of the heavy chain contains three cysteine residues Cys227 (H), Cys230 (H) and Cys233 (H), which provide three inter-chain disulfide bonds. The most likely linkage is Cys227 (H) to Cys227 (H), Cys230 (H) to Cys230 (H) and Cys233 (H) to Cys233 (H) which is the correct theoretical disulfide arrangement of IgG2 A form.

Disulfide structure of the IgG2.5 antibody (B form): Within the Fab region of the heavy chain Cys22 (H) is linked to Cys98 (H) and Cys151 (H) is linked to Cys 207(H). Within the Fc region of the heavy chain Cys264(H) is linked to Cys324 (H) and Cys370 (H) is linked to Cys428 (H). Within the Fab region of the light chain Cys23 (L) is linked to Cys88 (L) and Cys134 (L) is linked to Cys194 (L). The hinge region of the heavy chain contains four cysteine residues Cys226(H), Cys227 (H), Cys230 (H) and Cys233 (H). The C-terminal of light chain Cys214 (L) is linked to a cysteine residue of heavy chain in the hinge region, and rest three cysteine residues provide three inter-chain disulfide bonds. The most likely linkage is Cys214 (L) to Cys226 (H), then Cys227 (H) to Cys227 (H), Cys230 (H) to Cys230 (H) and Cys233 (H) to Cys233 (H), which is the correct theoretical disulfide arrangement of IgG2 B form. Additionally, the disulfide linkages in the hinge region were confirmed using electron transfer dissociation (ETD) triggered tandem mass spectrometry using an ion trap mass spectrometer.

Example 12: Relevance of Certain Amino Acid Residues in IgG2 CH1 and Hinge in Improving GITR Agonism on T Cells Anti-GITR antibodies (GITR.6) with the heavy chain constant regions shown in Table 17 were prepared and tested in IL-2 production assays as described in Example 2, but in which supernatants were harvested at 40 hours rather than 48 hours.

The results, which are shown in FIG. 20A-D, were largely in agreement with the CD73 internalization results (see FIG. 10) obtained with anti-CD73 antibodies having the same heavy chain constant regions as those used in this Example.

SEQUENCE TABLE

| SEQ ID NO | Description | Sequence |
|---|---|---|
| 1 | Full-length IgG1 wild-type | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSCDKTHTCPP CPAPELLGGPSVFLFPPKPKDTLMISRTPEVTCVVVDV SHEDPEVKFNWYVDGVEVHNAKTKPREEQYNSTYR VVSVLTVLHQDWLNGKEYKCKVSNKALPAPIEKTIS KAKGQPREPQVYTLPPSREEMTKNQVSLTCLVKGFY PSDIAVEWESNGQPENNYKTTPPVLDSDGSFFLYSKL TVDKSRWQQGNVFSCSVMHEALHNHYTQKSLSLSPGK |
| 2 | CH1 IgG1 wild-type | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKV |
| 3 | Hinge IgG1 wild-type | EPKSCDKTHTCPPCPAPELLGG |
| 4 | CH2 IgG1 wild-type | PSVFLFPPKPKDTLMISRTPEVTCVVVDVSHEDPEVKF NWYVDGVEVHNAKTKPREEQYNSTYRVVSVLTVLH QDWLNGKEYKCKVSNKALPAPIEKTISKAK |
| 5 | CH3 IgG1 wild-type | GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPGK |
| 6 | Full-length IgG2 wild-type | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PPVAGPSVFLFPPKPKDTLMISRTPEVTCVVVDVSHE DPEVQFNWYVDGVEVHNAKTKPREEQFNSTFRVVSV LTVVHQDWLNGKEYKCKVSNKGLPAPIEKTISKTKG QPREPQVYTLPPSREEMTKNQVSLTCLVKGFYPSDIA VEWESNGQPENNYKTTPPMLDSDGSFFLYSKLTVDK SRWQQGNVFSCSVMHEALHNHYTQKSLSLSPGK |
| 7 | CH1 IgG2 wild-type | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTV |
| 8 | Hinge IgG2 wild-type | ERKCCVECPPCPAPPVAG |
| 9 | CH2 IgG2 wild-type | PSVFLFPPKPKDTLMISRTPEVTCVVVDVSHEDPEVQF NWYVDGVEVHNAKTKPREEQFNSTFRVVSVLTVVH QDWLNGKEYKCKVSNKGLPAPIEKTISKTK |

SEQUENCE TABLE

| SEQ ID NO | Description | Sequence |
|---|---|---|
| 10 | CH3 IgG2 wild-type | GQPREPQVYTLPPSREEMTKNQVSLTCLVKGFYPSDI AVEWESNGQPENNYKTTPPMLDSDGSFFLYSKLTVD KSRWQQGNVFSCSVMHEALHNHYTQKSLSLSPGK |
| 11 | Full-length IgG3 wild-type | ASTKGPSVFPLAPCSRSTSGGTAALGCLVKDYFPEPV TVSWNSGALTSGVHTFPAVLQSSGLYSLSSVVTVPSS SLGTQTYTCNVNHKPSNTKVDKRVELKTPLGDTTHT CPRCPEPKSCDTPPPCPRCPEPKSCDTPPPCPRCPEPKS CDTPPPCPRCPAPELLGGPSVFLFPPKPKDTLMISRTPE VTCVVVDVSHEDPEVQFKWYVDGVEVHNAKTKPRE EQYNSTFRVVSVLTVLHQDWLNGKEYKCKVSNKAL PAPIEKTISKTKGQPREPQVYTLPPSREEMTKNQVSLT CLVKGFYPSDIAVEWESSGQPENNYNTTPPMLDSDGS FFLYSKLTVDKSRWQQGNIFSCSVMHEALHNRFTQK SLSLSPGK |
| 12 | CH1 IgG3 wild-type | ASTKGPSVFPLAPCSRSTSGGTAALGCLVKDYFPEPV TVSWNSGALTSGVHTFPAVLQSSGLYSLSSVVTVPSS SLGTQTYTCNVNHKPSNTKVDKRV |
| 13 | Hinge IgG3 wild-type | ELKTPLGDTTHTCPRCPE |
| 14 | CH2 IgG3 wild-type | PKSCDTPPPCPRCPEPKSCDTPPPCPRCPEPKSCDTPPP CPRCPAPELLGGPSVFLFPPKPKDTLMISRTPEVTCVV VDVSHEDPEVQFKWYVDGVEVHNAKTKPREEQYNS TFRVVSVLTVLHQDWLNGKEYKCKVSNKALPAPIEK TISKTK |
| 15 | CH3 IgG3 wild-type | GQPREPQVYTLPPSREEMTKNQVSLTCLVKGFYPSDI AVEWESSGQPENNYNTTPPMLDSDGSFFLYSKLTVD KSRWQQGNIFSCSVMHEALHNRFTQKSLSLSPGK |
| 16 | Full-length IgG4 wild-type | ASTKGPSVFPLAPCSRSTSESTAALGCLVKDYFPEPVT VSWNSGALTSGVHTFPAVLQSSGLYSLSSVVTVPSSS LGTKTYTCNVDHKPSNTKVDKRVESKYGPPCPSCPA PEFLGGPSVFLFPPKPKDTLMISRTPEVTCVVVDVSQE DPEVQFNWYVDGVEVHNAKTKPREEQFNSTYRVVS VLTVLHQDWLNGKEYKCKVSNKGLPSSIEKTISKAK GQPREPQVYTLPPSQEEMTKNQVSLTCLVKGFYPSDI AVEWESNGQPENNYKTTPPVLDSDGSFFLYSRLTVD KSRWQEGNVFSCSVMHEALHNHYTQKSLSLSLGK |
| 17 | CH1 IgG4 wild-type | ASTKGPSVFPLAPCSRSTSESTAALGCLVKDYFPEPVT VSWNSGALTSGVHTFPAVLQSSGLYSLSSVVTVPSSS LGTKTYTCNVDHKPSNTKVDKRV |
| 18 | Hinge IgG4 wild-type | ESKYGPPCPSCPAPEFLGG |
| 19 | CH2 IgG4 wild-type | PSVFLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAK |
| 20 | CH3 IgG4 wild-type | GQPREPQVYTLPPSQEEMTKNQVSLTCLVKGFYPSDI AVEWESNGQPENNYKTTPPVLDSDGSFFLYSRLTVD KSRWQEGNVFSCSVMHEALHNHYTQKSLSLSLGK |
| 21 | Modified IgG2 Hinge (C219S) | ERKSCVECPPCPAPPVAG |
| 22 | IgG2/IgG1 hybrid hinge | ERKCCVECPPCPAPELLGG |
| 23 | IgG2 C219S/IgG1 hybrid hinge | ERKSCVECPPCPAPELLGG |
| 24 | Modified CH2 IgG1 (A330S/P331S) | PSVFLFPPKPKDTLMISRTPEVTCVVVDVSHEDPEVKF NWYVDGVEVHNAKTKPREEQYNSTYRVVSVLTVLH QDWLNGKEYKCKVSNKALPSSIEKTISKAK |
| 25 | IgG1.1 Hinge (L234A/L235E/G237A) | EPKSCDKTHTCPPCPAPEAEGA |

SEQUENCE TABLE

| SEQ ID NO | Description | Sequence |
|---|---|---|
| 26 | IgG1-IgG2-IgG1 (IgG1-IgG2/IgG1(SEQ#22)-IgG1-IgG1) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKV<u>ERKCCVECPPCP APELL</u>GGPSVFLFPPKPKDTLMISRTPEVTCVVVDVSH EDPEVKFNWYVDGVEVHNAKTKPREEQYNSTYRVV SVLTVLHQDWLNGKEYKCKVSNKALPAPIEKTISKA KGQPREPQVYTLPPSR<u>EE</u>MTKNQVSLTCLVKGFYPSD IAVEWESNGQPENNYKTTPPVLDSDGSFFLYSKLTVD KSRWQQGNVFSCSVMHEALHNHYTQKSLSLSPG |
| 27 | IgG1-IgG2-IgG12 (IgG1-IgG2(SEQ#8)-IgG1-IgG1) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKV<u>ERKCCVECPPCP APPVAG</u>PSVFLFPPKPKDTLMISRTPEVTCVVVDVSH EDPEVKFNWYVDGVEVHNAKTKPREEQYNSTYRVV SVLTVLHQDWLNGKEYKCKVSNKALPAPIEKTISKA KGQPREPQVYTLPPSR<u>EE</u>MTKNQVSLTCLVKGFYPSD IAVEWESNGQPENNYKTTPPVLDSDGSFFLYSKLTVD KSRWQQGNVFSCSVMHEALHNHYTQKSLSLSPG |
| 28 | IgG2-IgG1 (IgG2-IgG2/IgG1(SEQ#22)-IgG1-IgG1) | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTV<u>ERKCCVECPPCPA PELL</u>GGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSR<u>EE</u>MTKNQVSLTCLVKGFYPSDI AVEWESNGQPENNYKTTPPVLDSDGSFFLYSKLTVD KSRWQQGNVFSCSVMHEALHNHYTQKSLSLSPG |
| 29 | IgG2-IgG12 (IgG2-IgG2(SEQ#8)-IgG1-IgG1) | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTV<u>ERKCCVECPPCPA PPVAG</u>PSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSREE<u>M</u>TKNQVSLTCLVKGFYPSDI AVEWESNGQPENNYKTTPPVLDSDGSFFLYSKLTVD KSRWQQGNVFSCSVMHEALHNHYTQKSLSLSPG |
| 30 | IgG1-IgG2-IgG1.1 (IgG1-IgG2(SEQ#8)-IgG1(A330S/P331S)-IgG1) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKV<u>ERKCCVECPPCP APPVAG</u>PSVFLFPPKPKDTLMISRTPEVTCVVVDVSH EDPEVKFNWYVDGVEVHNAKTKPREEQYNSTYRVV SVLTVLHQDWLNGKEYKCKVSNKALPSSIEKTISKAK GQPREPQVYTLPPSR<u>EE</u>MTKNQVSLTCLVKGFYPSDI AVEWESNGQPENNYKTTPPVLDSDGSFFLYSKLTVD KSRWQQGNVFSCSVMHEALHNHYTQKSLSLSPG |
| 31 | IgG2-IgG1.1 (IgG2-IgG2(SEQ#8)-IgG1(A330S/P331S)-IgG1) | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTV<u>ERKCCVECPPCPA PPVAG</u>PSVFLFPPKPKDTLMISRTPEVTCVVVDVSHE DPEVKFNWYVDGVEVHNAKTKPREEQYNSTYRVVS VLTVLHQDWLNGKEYKCKVSNKALPSSIEKTISKAK GQPREPQVYTLPPSR<u>EE</u>MTKNQVSLTCLVKGFYPSDI AVEWESNGQPENNYKTTPPVLDSDGSFFLYSKLTVD KSRWQQGNVFSCSVMHEALHNHYTQKSLSLSPGK |
| 32 | IgG1-IgG2CS-IgG1 (IgG1-IgG2(C219S)-IgG1-IgG1) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKV<u>ERKSCVECPPCPA PPVAG</u>PSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSR<u>EE</u>MTKNQVSLTCLVKGFYPSDI AVEWESNGQPENNYKTTPPVLDSDGSFFLYSKLTVD KSRWQQGNVFSCSVMHEALHNHYTQKSLSLSPG |

| SEQ ID NO | Description | Sequence |
|---|---|---|
| 33 | IgG1-IgG2CS-IgG12 (IgG1-IgG2(C219S)-IgG1-IgG1) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKV<u>ERKSCVECPPCPA PPVAG</u>PSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSR<u>EEM</u>TKNQVSLTCLVKGFYPSDI AVEWESNGQPENNYKTTPPVLDSDGSFFLYSKLTVD KSRWQQGNVFSCSVMHEALHNHYTQKSLSLSPG |
| 34 | IgG2CS-IgG1 (IgG2-IgG2(C219S)-IgG1-IgG1) | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTV<u>ERKSCVECPPCPA PPVAG</u>PSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSR<u>EEM</u>TKNQVSLTCLVKGFYPSDI AVEWESNGQPENNYKTTPPVLDSDGSFFLYSKLTVD KSRWQQGNVFSCSVMHEALHNHYTQKSLSLSPG |
| 35 | IgG2CS-IgG12 (IgG2-IgG2(C219S)-IgG1-IgG1) | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTV<u>ERKSCVECPPCPA PPVAG</u>PSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSR<u>EEM</u>TKNQVSLTCLVKGFYPSDI AVEWESNGQPENNYKTTPPVLDSDGSFFLYSKLTVD KSRWQQGNVFSCSVMHEALHNHYTQKSLSLSPG |
| 36 | IgG1-IgG2CS-IgG1.1 (IgG1-IgG2(C219S)-IgG1(A330S/P331S)-IgG1) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKV<u>ERKSCVECPPCPA PPVAG</u>PSVFLFPPKPKDTLMISRTPEVTCVVVDVSHE DPEVKFNWYVDGVEVHNAKTKPREEQYNSTYRVVS VLTVLHQDWLNGKEYKCKVSNKALP<u>SSI</u>EKTISKAK GQPREPQVYTLPPSR<u>EEM</u>TKNQVSLTCLVKGFYPSDI AVEWESNGQPENNYKTTPPVLDSDGSFFLYSKLTVD KSRWQQGNVFSCSVMHEALHNHYTQKSLSLSPG |
| 37 | IgG2CS-IgG1.1 (IgG2-IgG2(C219S)-IgG1(A330S/P331S)-IgG1) | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTV<u>ERKSCVECPPCPA PPVAG</u>PSVFLFPPKPKDTLMISRTPEVTCVVVDVSHE DPEVKFNWYVDGVEVHNAKTKPREEQYNSTYRVVS VLTVLHQDWLNGKEYKCKVSNKALP<u>SSI</u>EKTISKAK GQPREPQVYTLPPSR<u>EEM</u>TKNQVSLTCLVKGFYPSDI AVEWESNGQPENNYKTTPPVLDSDGSFFLYSKLTVD KSRWQQGNVFSCSVMHEALHNHYTQKSLSLSPG |
| 38 | Ab 11F11 VH | QVQLVESGGGVVQPGRSLRLSCATSGFTFSNYGMHW VRQAPGKGLEWVAVILYDGSNKYYPDSVKGRFTISR DNSKNTLYLQMNSLRAEDTAVYYCARGGSSWYPDS FDIWGQGTMVTVSS |
| 39 | Ab 4C3 VH | EVQLVESGGGLVQPGRSLRLSCAASGFTFDDYAMHW VRQAPGKGLEWVSGISWKSGSIGYADSVKGRFTISRD NAKNSLYLQMNSLRAEDTALYYCVKGYYVILTGLD YWGQGTLVTVSS |
| 40 | Ab CD73.10 VH | QVQLVESGGGVVQPGRSLRLSCA<u>A</u>SGFTFSNYGMH WVRQAPGKGLEWVAVI<u>WYDE</u>SNKYYPDSVKGRFTI SRDNSKNTLYLQMNSLRAEDTAVYYCARGGSSWYP DSFDIWGQGTMVTVSS |
| 41 | Ab CD73.3 VH (4C3/V94A) | EVQLVESGGGLVQPGRSLRLSCAASGFTFDDYAMHW VRQAPGKGLEWVSGISWKSGSIGYADSVKGRFTISRD NAKNSLYLQMNSLRAEDT<u>V</u>LYYCVKGYYVILTGLD YWGQGTLVTVSS |
| 42 | Ab 6E11 VH | EVQLVESGGALVQPGRSLRLSCAASGFTFDDYAMHW VRQAPGKGLEWVSGITWNSGGIGYADSVKGRFTISR |

| SEQ ID NO | Description | Sequence |
|---|---|---|
| | | DNAKNSLYLQMNSLRAEDTALYYCAKDRYYSSWLL FDNWGQGILVTVSS |
| 43 | Ab CD73.4 VH | QVQLVESGGGVVQPGRSLRLSCAASGFTFSNYGMH WVRQAPGKGLEWVAVILYDGSNKYYPDSVKGRFTIS RDNSKNTLYLQMNSLRAEDTAVYYCARGGSSWYPD SFDIWGQGTMVTVSS |
| 44 | Ab 11F11 full-length HC | QVQLVESGGGVVQPGRSLRLSCATSGFTFSNYGMHW VRQAPGKGLEWVAVILYDGSNKYYPDSVKGRFTISR DNSKNTLYLQMNSLRAEDTAVYYCARGGSSWYPDS FDIWGQGTMVTVSSASTKGPSVFPLAPCSRSTSESTA ALGCLVKDYFPEPVTVSWNSGALTSGVHTFPAVLQS SGLYSLSSVVTVPSSNFGTQTYTCNVDHKPSNTKVDK TVERKCCVECPPCPAPPVAGPSVFLFPPKPKDTLMISR TPEVTCVVVDVSHEDPEVQFNWYVDGVEVHNAKTK PREEQFNSTFRVVSVLTVVHQDWLNGKEYKCKVSNK GLPAPIEKTISKTKGQPREPQVYTLPPSREEMTKNQVS LTCLVKGFYPSDIAVEWESNGQPENNYKTTPPMLDS DGSFFLYSKLTVDKSRWQQGNVFSCSVMHEALHNH YTQKSLSLSPGK |
| 45 | Ab 4C3 full-length HC | EVQLVESGGGLVQPGRSLRLSCAASGFTFDDYAMHW VRQAPGKGLEWVSGISWKSGSIGYADSVKGRFTISRD NAKNSLYLQMNSLRAEDTALYYCVKGYYVILTGLD YWGQGTLVTVSSASTKGPSVFPLAPSSKSTSGGTAAL GCLVKDYFPEPVTVSWNSGALTSGVHTFPAVLQSSG LYSLSSVVTVPSSSLGTQTYICNVNHKPSNTKVDKKV EPKSCDKTHTCPPCPAPELLGGPSVFLFPPKPKDTLMI SRTPEVTCVVVDVSHEDPEVKFNWYVDGVEVHNAK TKPREEQYNSTYRVVSVLTVLHQDWLNGKEYKCKV SNKALPAPIEKTISKAKGQPREPQVYTLPPSRDELTKN QVSLTCLVKGFYPSDIAVEWESNGQPENNYKTTPPVL DSDGSFFLYSKLTVDKSRWQQGNVFSCSVMHEALHN HYTQKSLSLSPGK |
| 46 | Ab 6E11 full-length HC | EVQLVESGGALVQPGRSLRLSCAASGFTFDDYAMHW VRQAPGKGLEWVSGITWNSGGIGYADSVKGRFTISR DNAKNSLYLQMNSLRAEDTALYYCAKDRYYSSWLL FDNWGQGILVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVDK KVEPKSCDKTHTCPPCPAPELLGGPSVFLFPPKPKDTL MISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSRDELT KNQVSLTCLVKGFYPSDIAVEWESNGQPENNYKTTPP VLDSDGSFFLYSKLTVDKSRWQQGNVFSCSVMHEAL HNHYTQKSLSLSPGK |
| 47 | Ab CD73.10-IgG2-C219S full-length HC | QVQLVESGGGVVQPGRSLRLSCA<u>A</u>SGFTFSNYGMH WVRQAPGKGLEWVAVI<u>WYDE</u>SNKYYPDSVKGRFTI SRDNSKNTLYLQMNSLRAEDTAVYYCARGGSSWYP DSFDIWGQGTMVTVSSASTKGPSVFPLAPCSRSTSEST AALGCLVKDYFPEPVTVSWNSGALTSGVHTFPAVLQ SSGLYSLSSVVTVPSSNFGTQTYTCNVDHKPSNTKVD KTV<u>ERKSCVECPPCPAPPVAG</u>PSVFLFPPKPKDTLMIS RTPEVTCVVVDVSHEDPEVQFNWYVDGVEVHNAKT KPREEQFNSTFRVVSVLTVVHQDWLNGKEYKCKVSN KGLPAPIEKTISKTKGQPREPQVYTLPPSREEMTKNQV SLTCLVKGFYPSDIAVEWESNGQPENNYKTTPPMLDS DGSFFLYSKLTVDKSRWQQGNVFSCSVMHEALHNH YTQKSLSLSPG |
| 48 | Ab CD73.10-IgG2-C219S-IgG1.1 full-length HC | QVQLVESGGGVVQPGRSLRLSCA<u>A</u>SGFTFSNYGMH WVRQAPGKGLEWVAVI<u>WYDE</u>SNKYYPDSVKGRFTI SRDNSKNTLYLQMNSLRAEDTAVYYCARGGSSWYP DSFDIWGQGTMVTVSSASTKGPSVFPLAPCSRSTSEST AALGCLVKDYFPEPVTVSWNSGALTSGVHTFPAVLQ SSGLYSLSSVVTVPSSNFGTQTYTCNVDHKPSNTKVD KTV<u>ERKSCVECPPCPAPPVAG</u>PSVFLFPPKPKDTLMIS RTPEVTCVVVDVSHEDPEVKFNWYVDGVEVHNAKT KPREEQYNSTYRVVSVLTVLHQDWLNGKEYKCKVS |

SEQUENCE TABLE

| SEQ ID NO | Description | Sequence |
|---|---|---|
| | | NKALPSSIEKTISKAKGQPREPQVYTLPPSREEMTKNQ VSLTCLVKGFYPSDIAVEWESNGQPENNYKTTPPML DSDGSFFLYSKLTVDKSRWQQGNVFSCSVMHEALHN HYTQKSLSLSPG |
| 49 | Ab CD73.10-IgG1.1 full-length HC (IgG1.1-IgG1.1(L234A/L235E/G237A)-IgG1.1(A330S/P331S)-IgG1.1) | QVQLVESGGGVVQPGRSLRLSCAASGFTFSNYGMH WVRQAPGKGLEWVAVIWYDESNKYYPDSVKGRFTI SRDNSKNTLYLQMNSLRAEDTAVYYCARGGSSWYP DSFDIWGQGTMVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKV DKKVEPKSCDKTHTCPPCPAPEAEGAPSVFLFPPKPK DTLMISRTPEVTCVVVDVSHEDPEVKFNWYVDGVEV HNAKTKPREEQYNSTYRVVSVLTVLHQDWLNGKEY KCKVSNKALPSSIEKTISKAKGQPREPQVYTLPPSREE MTKNQVSLTCLVKGFYPSDIAVEWESNGQPENNYKT TPPVLDSDGSFFLYSKLTVDKSRWQQGNVFSCSVMH EALHNHYTQKSLSLSPG |
| 50 | Ab CD73.4-IgG2-C219S full-length HC | QVQLVESGGGVVQPGRSLRLSCAASGFTFSNYGMH WVRQAPGKGLEWVAVILYDGSNKYYPDSVKGRFTIS RDNSKNTLYLQMNSLRAEDTAVYYCARGGSSWYPD SFDIWGQGTMVTVSSASTKGPSVFPLAPCSRSTSESTA ALGCLVKDYFPEPVTVSWNSGALTSGVHTFPAVLQS SGLYSLSSVVTVPSSNFGTQTYTCNVDHKPSNTKVDK TVERKSCVECPPCPAPPVAGPSVFLFPPKPKDTLMISR TPEVTCVVVDVSHEDPEVQFNWYVDGVEVHNAKTK PREEQFNSTFRVVSVLTVVHQDWLNGKEYKCKVSNK GLPAPIEKTISKTKGQPREPQVYTLPPSREEMTKNQVS LTCLVKGFYPSDIAVEWESNGQPENNYKTTPPMLDS DGSFFLYSKLTVDKSRWQQGNVFSCSVMHEALHNH YTQKSLSLSPG |
| 51 | Ab CD73.3-IgG1.1 full-length HC (IgG1.1-IgG1.1(L234A/L235E/G237A)-IgG1.1(A330S/P331S)-IgG1.1) | EVQLVESGGGLVQPGRSLRLSCAASGFTFDDYAMHW VRQAPGKGLEWVSGISWKSGSIGYADSVKGRFTISRD NAKNSLYLQMNSLRAEDTVLYYCVKGYYVILTGLD YWGQGTLVTVSSASTKGPSVFPLAPSSKSTSGGTAAL GCLVKDYFPEPVTVSWNSGALTSGVHTFPAVLQSSG LYSLSSVVTVPSSSLGTQTYICNVNHKPSNTKVDKKV EPKSCDKTHTCPPCPAPEAEGAPSVFLFPPKPKDTLMI SRTPEVTCVVVDVSHEDPEVKFNWYVDGVEVHNAK TKPREEQYNSTYRVVSVLTVLHQDWLNGKEYKCKV SNKALPSSIEKTISKAKGQPREPQVYTLPPSREEMTKN QVSLTCLVKGFYPSDIAVEWESNGQPENNYKTTPPVL DSDGSFFLYSKLTVDKSRWQQGNVFSCSVMHEALHN HYTQKSLSLSPG |
| 52 | Full-length heavy chain constant region IgG2-IgG2-IgG2-IgG2 | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PPVAGPSVFLFPPKPKDTLMISRTPEVTCVVVDVSHE DPEVQFNWYVDGVEVHNAKTKPREEQFNSTFRVVSV LTVVHQDWLNGKEYKCKVSNKGLPAPIEKTISKTKG QPREPQVYTLPPSREEMTKNQVSLTCLVKGFYPSDIA VEWESNGQPENNYKTTPPMLDSDGSFFLYSKLTVDK SRWQQGNVFSCSVMHEALHNHYTQKSLSLSPGK |
| 53 | Full-length heavy chain constant region IgG1-IgG1-IgG1-IgG1 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSCDKTHTCPP CPAPELLGGPSVFLFPPKPKDTLMISRTPEVTCVVVDV SHEDPEVKFNWYVDGVEVHNAKTKPREEQYNSTYR VVSVLTVLHQDWLNGKEYKCKVSNKALPAPIEKTIS KAKGQPREPQVYTLPPSREEMTKNQVSLTCLVKGFY PSDIAVEWESNGQPENNYKTTPPVLDSDGSFFLYSKL TVDKSRWQQGNVFSCSVMHEALHNHYTQKSLSLSPGK |
| 54 | Full-length heavy chain constant region IgG1-IgG1.1(L234A/L235E/G237A)-IgG1.1 (A330S/P331S)-IgG1 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSCDKTHTCPP CPAPEAEGAPSVFLFPPKPKDTLMISRTPEVTCVVVD VSHEDPEVKFNWYVDGVEVHNAKTKPREEQYNSTY RVVSVLTVLHQDWLNGKEYKCKVSNKALPSSIEKTIS |

| SEQ ID NO | Description | Sequence |
|---|---|---|
| | | KAKGQPREPQVYTLPPSREEMTKNQVSLTCLVKGFY PSDIAVEWESNGQPENNYKTTPPVLDSDGSFFLYSKL TVDKSRWQQGNVFSCSVMHEALHNHYTQKSLSLSPG |
| 55 | Full-length heavy chain constant region IgG2-IgG2/IgG1 hybrid-IgG1-IgG1 | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PELLGGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPG |
| 56 | Full-length heavy chain constant region IgG2-IgG2-IgG1.1(A330/P331S)-IgG1 | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PPVAGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPSSIEKTISKAK GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPG |
| 57 | Table 2 - hinge domain | VDKRV |
| 58 | Table 2 - hinge domain | VDKTV |
| 59 | Table 2 - hinge domain | EPKSCDKTHT |
| 60 | Table 2 - hinge domain | ERK |
| 61 | Table 2 - hinge domain | ELKTPLGDTTHT |
| 62 | Table 2 - hinge domain | EPKS |
| 63 | Table 2 - hinge domain | ESKYGPP |
| 64 | Table 2 - hinge domain | CPPCP |
| 65 | Table 2 - hinge domain | CCVECPPCP |
| 66 | Table 2 - hinge domain | CPRCP |
| 67 | Table 2 - hinge domain | EPKSCDTPPPCPRCP |
| 68 | Table 2 - hinge domain | CDTPPPCPRCP |
| 69 | Table 2 - hinge domain | CPSCP |
| 70 | Table 2 - hinge domain | APELLGG |
| 71 | Table 2 - hinge domain | APPVAG |
| 72 | Light chain 11F11 | DIQMTQSPSSLSASVGDRVTITCRASQGISSWLAWYQ QKPEKAPKSLIYAASSLQSGVPSRFSGSGSGTDFTLTIS SLQPEDFATYYCQQYNSYPLTFGGGTKVEIKRTVAAP SVFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGEC |
| 73 | Light chain 4C3 | EIVLTQSPGTLSLSPGERATLSCRASQSVSSYLAWYQ QKPGQAPRLLIYGASSRATGIPDRFSGSGSGTDFTLTIS RLEPEDFAVYYCQQYGSSPLTFGGGTKVEIKRTVAAP SVFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGEC |
| 74 | Light chain 6D11 | EIVLTQSPGTLSLSPGERATLSCRASQSVSSSYLAWYQ QKPGQAPRLLIYGASSRATGIPDRFSGSGSGTDFTLTIS RLEPEDFAVYYCQHYGSSFTFGPGTKVDIKRTVAAPS |

SEQUENCE TABLE

| SEQ ID NO | Description | Sequence |
|---|---|---|
| | | VFIFPPSDEQLKSGTASVVCLLNNFYPREAKVQWKVD NALQSGNSQESVTEQDSKDSTYSLSSTLTLSKADYEK HKVYACEVTHQGLSSPVTKSFNRGEC |
| 75 | Anti-GITR AbVH | QVQLVESGGGVVQPGRSLRLSCAASGFTFSSYGMHW VRQAPGKGLEWVAVIWYEGSNKYYADSVKGRFTISR DNSKNTLYLQMNSLRAEDTAVYYCARGGSMVRGDY YYGMDVWGQGTTVTVSS |
| 76 | Anti-GITR Ab VL | AIQLTQSPSSLSASVGDRVTITCRASQGISSALAWYQQ KPGKAPKLLIYDASSLESGVPSRFSGSGSGTDFTLTISS LQPEDFATYYCQQFNSYPYTFGQGTKLEIK |
| 77 | Anti-GITR Ab LC | AIQLTQSPSSLSASVGDRVTITCRASQGISSALAWYQQ KPGKAPKLLIYDASSLESGVPSRFSGSGSGTDFTLTISS LQPEDFATYYCQQFNSYPYTFGQGTKLEIKRTVAAPS VFIFPPSDEQLKSGTASVVCLLNNFYPREAKVQWKVD NALQSGNSQESVTEQDSKDSTYSLSSTLTLSKADYEK HKVYACEVTHQGLSSPVTKSFNRGEC |
| 78 | IgG1f | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPSVFLFPPKPKDTLMISRTPEVTCVVVDV SHEDPEVKFNWYVDGVEVHNAKTKPREEQYNSTYR VVSVLTVLHQDWLNGKEYKCKVSNKALPAPIEKTIS KAKGQPREPQVYTLPPSREEMTKNQVSLTCLVKGFY PSDIAVEWESNGQPENNYKTTPPVLDSDGSFFLYSKL TVDKSRWQQGNVFSCSVMHEALHNHYTQKSLSLSPGK |
| 79 | IgG2.3 | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKSCVECPPCPA PPVAGPSVFLFPPKPKDTLMISRTPEVTCVVVDVSHE DPEVQFNWYVDGVEVHNAKTKPREEQFNSTFRVVSV LTVVHQDWLNGKEYKCKVSNKGLPAPIEKTISKTKG QPREPQVYTLPPSREEMTKNQVSLTCLVKGFYPSDIA VEWESNGQPENNYKTTPPMLDSDGSFFLYSKLTVDK SRWQQGNVFSCSVMHEALHNHYTQKSLSLSPGK |
| 80 | IgG2.3G1-AY | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKSCVECPPCPA PELLGGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPGK |
| 81 | IgG2.3G1-KH | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKSCVECPPCPA PPVAGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPGK |
| 82 | IgG2.5 | ASTKGPSVFPLAPSSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PPVAGPSVFLFPPKPKDTLMISRTPEVTCVVVDVSHE DPEVQFNWYVDGVEVHNAKTKPREEQFNSTFRVVSV LTVVHQDWLNGKEYKCKVSNKGLPAPIEKTISKTKG QPREPQVYTLPPSREEMTKNQVSLTCLVKGFYPSDIA VEWESNGQPENNYKTTPPMLDSDGSFFLYSKLTVDK SRWQQGNVFSCSVMHEALHNHYTQKSLSLSPGK |
| 83 | IgG1.1f | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP |

SEQUENCE TABLE

| SEQ ID NO | Description | Sequence |
|---|---|---|
| | | CPAPEAEGAPSVFLFPPKPKDTLMISRTPEVTCVVVD VSHEDPEVKFNWYVDGVEVHNAKTKPREEQYNSTY RVVSVLTVLHQDWLNGKEYKCKVSNKALPSSIEKTIS KAKGQPREPQVYTLPPSREEMTKNQVSLTCLVKGFY PSDIAVEWESNGQPENNYKTTPPVLDSDGSFFLYSKL TVDKSRWQQGNVFSCSVMHEALHNHYTQKSLSLSPGK |
| 84 | IgG2.3G1.1f-KH | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKSCVECPPCPA PPVAGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPSSIEKTISKAK GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPGK |
| 85 | IgG1-deltaTHT | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKCPPCPA PELLGGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPGK |
| 86 | IgG2.3-plusTHT | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKSCVETHTCPP CPAPPVAGPSVFLFPPKPKDTLMISRTPEVTCVVVDVS HEDPEVQFNWYVDGVEVHNAKTKPREEQFNSTFRV VSVLTVVHQDWLNGKEYKCKVSNKGLPAPIEKTISK TKGQPREPQVYTLPPSREEMTKNQVSLTCLVKGFYPS DIAVEWESNGQPENNYKTTPPMLDSDGSFFLYSKLTV DKSRWQQGNVFSCSVMHEALHNHYTQKSLSLSPGK |
| 87 | IgG2.3-plusGGG | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKSCVEGGGCPP CPAPPVAGPSVFLFPPKPKDTLMISRTPEVTCVVVDVS HEDPEVQFNWYVDGVEVHNAKTKPREEQFNSTFRV VSVLTVVHQDWLNGKEYKCKVSNKGLPAPIEKTISK TKGQPREPQVYTLPPSREEMTKNQVSLTCLVKGFYPS DIAVEWESNGQPENNYKTTPPMLDSDGSFFLYSKLTV DKSRWQQGNVFSCSVMHEALHNHYTQKSLSLSPGK |
| 88 | IgG2.5G1.1f-KH | ASTKGPSVFPLAPSSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PPVAGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPSSIEKTISKAK GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPGK |
| 89 | IgG2.5G1-AY | ASTKGPSVFPLAPSSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PELLGGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPGK |
| 90 | IgG2.5G1-KH | ASTKGPSVFPLAPSSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PPVAGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK |

SEQUENCE TABLE

| SEQ ID NO | Description | Sequence |
|---|---|---|
| | | GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPGK |
| 91 | IgG2.5-plusTHT | ASTKGPSVFPLAPSSRSTSESTAALGCLVKDYFPEPVT VSWNSGALTSGVHTFPAVLQSSGLYSLSSVVTVPSSN FGTQTYTCNVDHKPSNTKVDKTVERKCCVETHTCPP CPAPPVAGPSVFLFPPKPKDTLMISRTPEVTCVVVDVS HEDPEVQFNWYVDGVEVHNAKTKPREEQFNSTFRV VSVLTVVHQDWLNGKEYKCKVSNKGLPAPIEKTISK TKGQPREPQVYTLPPSREEMTKNQVSLTCLVKGFYPS DIAVEWESNGQPENNYKTTPPVLDSDGSFFLYSKLTV DKSRWQQGNVFSCSVMHEALHNHYTQKSLSLSPGK |
| 92 | IgG1-G2.3G1-AY | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVERKSCVECPPCPA PELLGGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPGK |
| 93 | IgG1-G2.3G1-KH | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVERKSCVECPPCPA PPVAGPSVFLFPPKPKDTLMISRTPEVTCVVVDVSHE DPEVKFNWYVDGVEVHNAKTKPREEQYNSTYRVVS VLTVLHQDWLNGKEYKCKVSNKALPAPIEKTISKAK GQPREPQVYTLPPSREEMTKNQVSLTCLVKGFYPSDI AVEWESNGQPENNYKTTPPVLDSDGSFFLYSKLTVD KSRWQQGNVFSCSVMHEALHNHYTQKSLSLSPGK |
| 94 | G2-G1-G1-G1 | ASTKGPSVFPLAPCSRSTSESTAALGCLVKDYFPEPVT VSWNSGALTSGV HTFPAVLQSSGLYSLSSVVTVPSSNFGTQTYTCNVDH KPSNTKVDKTVER KSCDKTHTCPPCPAPELLGGPSVFLFPPKPKDTLMISR TPEVTCVVVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC LVKGFYPSDIAVEWESNGQPENNYKTTPPVLDSDGSF FLYSKLTVDKSRW QQGNVFSCSVMHEALHNHYTQKSLSLSPGK |
| 95 | G2.5-G1-G1-G1 | ASTKGPSVFPLAPSSRSTSESTAALGCLVKDYFPEPVT VSWNSGALTSGV HTFPAVLQSSGLYSLSSVVTVPSSNFGTQTYTCNVDH KPSNTKVDKTVER KSCDKTHTCPPCPAPELLGGPSVFLFPPKPKDTLMISR TPEVTCVVVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC LVKGFYPSDIAVEWESNGQPENNYKTTPPVLDSDGSF FLYSKLTVDKSRW QQGNVFSCSVMHEALHNHYTQKSLSLSPGK |
| 96 | G1-G2.3-G2-G2 | ASTKGPSVFPLAPSSKSTSGGTAALGCLVKDYFPEPV TVSWNSGALTSGV HTFPAVLQSSGLYSLSSVVTVPSSSLGTQTYICNVNHK PSNTKVDKRVEP KSCVECPPCPAPPVAGPSVFLFPPKPKDTLMISRTPEV TCVVVDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPMLDSDGSF |

SEQUENCE TABLE

| SEQ ID NO | Description | Sequence |
|---|---|---|
| 97 | G1-KRGEGSSNLF | ASTKGPSVFPLAPSSRSTSESTAALGCLVKDYFPEPVT VSWNSGALTSGV HTFPAVLQSSGLYSLSSVVTVPSSNFGTQTYICNVNH KPSNTKVDKRVEP KSCDKTHTCPPCPAPELLGGPSVFLFPPKPKDTLMISR TPEVTCVVVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC LVKGFYPSDIAVEWESNGQPENNYKTTPPVLDSDGSF FLYSKLTVDKSRW QQGNVFSCSVMHEALHNHYTQKSLSLSPGK |
| 98 | G1-KRGEGS | ASTKGPSVFPLAPSSRSTSESTAALGCLVKDYFPEPVT VSWNSGALTSGV HTFPAVLQSSGLYSLSSVVTVPSSSLGTQTYICNVNHK PSNTKVDKRVEP KSCDKTHTCPPCPAPELLGGPSVFLFPPKPKDTLMISR TPEVTCVVVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC LVKGFYPSDIAVEWESNGQPENNYKTTPPVLDSDGSF FLYSKLTVDKSRW QQGNVFSCSVMHEALHNHYTQKSLSLSPGK |
| 99 | G1-SNLF | ASTKGPSVFPLAPSSKSTSGGTAALGCLVKDYFPEPV TVSWNSGALTSGV HTFPAVLQSSGLYSLSSVVTVPSSNFGTQTYICNVNH KPSNTKVDKRVEP KSCDKTHTCPPCPAPELLGGPSVFLFPPKPKDTLMISR TPEVTCVVVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC LVKGFYPSDIAVEWESNGQPENNYKTTPPVLDSDGSF FLYSKLTVDKSRW QQGNVFSCSVMHEALHNHYTQKSLSLSPGK |
| 100 | IgG1-ITNDRTPR | ASTKGPSVFPLAPSSKSTSGGTAALGCLVKDYFPEPV TVSWNSGALTSGV HTFPAVLQSSGLYSLSSVVTVPSSSLGTQTYTCNVDH KPSNTKVDKTVER KSCDKTHTCPPCPAPELLGGPSVFLFPPKPKDTLMISR TPEVTCVVVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC LVKGFYPSDIAVEWESNGQPENNYKTTPPVLDSDGSF FLYSKLTVDKSRW QQGNVFSCSVMHEALHNHYTQKSLSLSPGK |
| 101 | G1-SNLFPR | ASTKGPSVFPLAPSSKSTSGGTAALGCLVKDYFPEPV TVSWNSGALTSGV HTFPAVLQSSGLYSLSSVVTVPSSNFGTQTYICNVNH KPSNTKVDKRVER KSCDKTHTCPPCPAPELLGGPSVFLFPPKPKDTLMISR TPEVTCVVVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC LVKGFYPSDIAVEWESNGQPENNYKTTPPVLDSDGSF FLYSKLTVDKSRW QQGNVFSCSVMHEALHNHYTQKSLSLSPG |

SEQUENCE TABLE

| SEQ ID NO | Description | Sequence |
|---|---|---|
| 102 | G2-RKEGSGNSFL | ASTKGPSVFPLAPCSKSTSGGTAALGCLVKDYFPEPV TVSWNSGALTSGV HTFPAVLQSSGLYSLSSVVTVPSSSLGTQTYTCNVDH KPSNTKVDKTVER KSCVECPPCPAPPVAGPSVFLFPPKPKDTLMISRTPEV TCVVVDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPGK |
| 103 | G2-RKEGSG | ASTKGPSVFPLAPCSKSTSGGTAALGCLVKDYFPEPV TVSWNSGALTSGV HTFPAVLQSSGLYSLSSVVTVPSSNFGTQTYTCNVDH KPSNTKVDKTVER KSCVECPPCPAPPVAGPSVFLFPPKPKDTLMISRTPEV TCVVVDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPGK |
| 104 | G2-NSFL | ASTKGPSVFPLAPCSRSTSESTAALGCLVKDYFPEPVT VSWNSGALTSGV HTFPAVLQSSGLYSLSSVVTVPSSSLGTQTYTCNVDH KPSNTKVDKTVER KSCVECPPCPAPPVAGPSVFLFPPKPKDTLMISRTPEV TCVVVDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPGK |
| 105 | IgG2-TIDNTRRP | ASTKGPSVFPLAPCSRSTSESTAALGCLVKDYFPEPVT VSWNSGALTSGV HTFPAVLQSSGLYSLSSVVTVPSSNFGTQTYICNVNH KPSNTKVDKRVEP KSCVECPPCPAPPVAGPSVFLFPPKPKDTLMISRTPEV TCVVVDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPGK |
| 106 | G2-NSFLRP | ASTKGPSVFPLAPCSRSTSESTAALGCLVKDYFPEPVT VSWNSGALTSGV HTFPAVLQSSGLYSLSSVVTVPSSSLGTQTYTCNVDH KPSNTKVDKTVEP KSCVECPPCPAPPVAGPSVFLFPPKPKDTLMISRTPEV TCVVVDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPGK |
| 107 | G1-G1-G2-G1-AY | ASTKGPSVFPLAPSSKSTSGGTAALGCLVKDYFPEPV TVSWNSGALTSGV HTFPAVLQSSGLYSLSSVVTVPSSSLGTQTYICNVNHK |

| SEQ ID NO | Description | Sequence |
|---|---|---|
| | | PSNTKVDKRVEP KSCDKTHTCPPCPAPELLGGPSVFLFPPKPKDTLMISR TPEVTCVVVDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPVLDSDGSF FLYSKLTVDKSRW QQGNVFSCSVMHEALHNHYTQKSLSLSPGK |
| 108 | G1-G1-G2-G1-KH | ASTKGPSVFPLAPSSKSTSGGTAALGCLVKDYFPEPV TVSWNSGALTSGV HTFPAVLQSSGLYSLSSVVTVPSSSLGTQTYICNVNHK PSNTKVDKRVEP KSCDKTHTCPPCPAPPVAGPSVFLFPPKPKDTLMISRT PEVTCVVVDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPVLDSDGSF FLYSKLTVDKSRW QQGNVFSCSVMHEALHNHYTQKSLSLSPGK |
| 109 | G2-G2.3-G1-G2-KH | ASTKGPSVFPLAPCSRSTSESTAALGCLVKDYFPEPVT VSWNSGALTSGV HTFPAVLQSSGLYSLSSVVTVPSSNFGTQTYTCNVDH KPSNTKVDKTVER KSCVECPPCPAPPVAGPSVFLFPPKPKDTLMISRTPEV TCVVVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPGK |
| 110 | G2.5-G2.3-G1-G2-KH | ASTKGPSVFPLAPSSRSTSESTAALGCLVKDYFPEPVT VSWNSGALTSGV HTFPAVLQSSGLYSLSSVVTVPSSNFGTQTYTCNVDH KPSNTKVDKTVER KSCVECPPCPAPPVAGPSVFLFPPKPKDTLMISRTPEV TCVVVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPGK |
| 111 | G2-G2.3-G1-G2-AY | ASTKGPSVFPLAPCSRSTSESTAALGCLVKDYFPEPVT VSWNSGALTSGV HTFPAVLQSSGLYSLSSVVTVPSSNFGTQTYTCNVDH KPSNTKVDKTVER KSCVECPPCPAPELLGGPSVFLFPPKPKDTLMISRTPE VTCVVVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPG |
| 112 | G2.5-G2.3-G1-G2-AY | ASTKGPSVFPLAPSSRSTSESTAALGCLVKDYFPEPVT VSWNSGALTSGV HTFPAVLQSSGLYSLSSVVTVPSSNFGTQTYTCNVDH KPSNTKVDKTVER KSCVECPPCPAPELLGGPSVFLFPPKPKDTLMISRTPE VTCVVVDVS |

SEQUENCE TABLE

| SEQ ID NO | Description | Sequence |
|---|---|---|
| | | HEDPEVKFNWYVDGVEVHNAKTKPREEQYNSTYRV<br>VSVLTVLHQDWLNGK<br>EYKCKVSNKALPAPIEKTISKAKGQPREPQVYTLPPSR<br>EEMTKNQVSLTC<br>LVKGFYPSDIAVEWESNGQPENNYKTTPPMLDSDGSF<br>FLYSKLTVDKSRW<br>QQGNVFSCSVMHEALHNHYTQKSLSLSPGK |
| 113 | G1-G2.3-G1-G1-KH | ASTKGPSVFPLAPSSKSTSGGTAALGCLVKDYFPEPV<br>TVSWNSGALTSGV<br>HTFPAVLQSSGLYSLSSVVTVPSSSLGTQTYICNVNHK<br>PSNTKVDKRVEP<br>KSCVECPPCPAPPVAGPSVFLFPPKPKDTLMISRTPEV<br>TCVVVDVS<br>HEDPEVKFNWYVDGVEVHNAKTKPREEQYNSTYRV<br>VSVLTVLHQDWLNGK<br>EYKCKVSNKALPAPIEKTISKAKGQPREPQVYTLPPSR<br>EEMTKNQVSLTC<br>LVKGFYPSDIAVEWESNGQPENNYKTTPPVLDSDGSF<br>FLYSKLTVDKSRW<br>QQGNVFSCSVMHEALHNHYTQKSLSLSPGK |
| 114 | G2-G1-G2-G2-AY | ASTKGPSVFPLAPCSRSTSESTAALGCLVKDYFPEPVT<br>VSWNSGALTSGV<br>HTFPAVLQSSGLYSLSSVVTVPSSNFGTQTYTCNVDH<br>KPSNTKVDKTVER<br>KSCDKTHTCPPCPAPELLGGPSVFLFPPKPKDTLMISR<br>TPEVTCVVVDVS<br>HEDPEVQFNWYVDGVEVHNAKTKPREEQFNSTFRV<br>VSVLTVVHQDWLNGK<br>EYKCKVSNKGLPAPIEKTISKTKGQPREPQVYTLPPSR<br>EEMTKNQVSLTC<br>LVKGFYPSDIAVEWESNGQPENNYKTTPPMLDSDGSF<br>FLYSKLTVDKSRW<br>QQGNVFSCSVMHEALHNHYTQKSLSLSPGK |
| 115 | 2.5-G1-G2-G2-AY | ASTKGPSVFPLAPSSRSTSESTAALGCLVKDYFPEPVT<br>VSWNSGALTSGV<br>HTFPAVLQSSGLYSLSSVVTVPSSNFGTQTYTCNVDH<br>KPSNTKVDKTVER<br>KSCDKTHTCPPCPAPELLGGPSVFLFPPKPKDTLMISR<br>TPEVTCVVVDVS<br>HEDPEVQFNWYVDGVEVHNAKTKPREEQFNSTFRV<br>VSVLTVVHQDWLNGK<br>EYKCKVSNKGLPAPIEKTISKTKGQPREPQVYTLPPSR<br>EEMTKNQVSLTC<br>LVKGFYPSDIAVEWESNGQPENNYKTTPPMLDSDGSF<br>FLYSKLTVDKSRW<br>QQGNVFSCSVMHEALHNHYTQKSLSLSPGK |
| 116 | G1-G2-G1-G1-AY | ASTKGPSVFPLAPSSKSTSGGTAALGCLVKDYFPEPV<br>TVSWNSGALTSGV<br>HTFPAVLQSSGLYSLSSVVTVPSSSLGTQTYICNVNHK<br>PSNTKVDKRVEP<br>KSCVECPPCPAPELLGGPSVFLFPPKPKDTLMISRTPE<br>VTCVVVDVS<br>HEDPEVKFNWYVDGVEVHNAKTKPREEQYNSTYRV<br>VSVLTVLHQDWLNGK<br>EYKCKVSNKALPAPIEKTISKAKGQPREPQVYTLPPSR<br>EEMTKNQVSLTC<br>LVKGFYPSDIAVEWESNGQPENNYKTTPPVLDSDGSF<br>FLYSKLTVDKSRW<br>QQGNVFSCSVMHEALHNHYTQKSLSLSPGK |
| 117 | G2-G1-G2-G2-KH | ASTKGPSVFPLAPCSRSTSESTAALGCLVKDYFPEPVT<br>VSWNSGALTSGV<br>HTFPAVLQSSGLYSLSSVVTVPSSNFGTQTYTCNVDH<br>KPSNTKVDKTVER<br>KSCDKTHTCPPCPAPPVAGPSVFLFPPKPKDTLMISRT<br>PEVTCVVVDVS<br>HEDPEVQFNWYVDGVEVHNAKTKPREEQFNSTFRV<br>VSVLTVVHQDWLNGK<br>EYKCKVSNKGLPAPIEKTISKTKGQPREPQVYTLPPSR |

SEQUENCE TABLE

| SEQ ID NO | Description | Sequence |
|---|---|---|
| | | EEMTKNQVSLTC LVKGFYPSDIAVEWESNGQPENNYKTTPPMLDSDGSF FLYSKLTVDKSRW QQGNVFSCSVMHEALHNHYTQKSLSLSPG |
| 118 | G2.5-G1-G2-G2-KH | ASTKGPSVFPLAPSSRSTSESTAALGCLVKDYFPEPVT VSWNSGALTSGV HTFPAVLQSSGLYSLSSVVTVPSSNFGTQTYTCNVDH KPSNTKVDKTVER KSCDKTHTCPPCPAPPVAGPSVFLFPPKPKDTLMISRT PEVTCVVVDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPGK |
| 119 | IgG1-deltaHinge | ASTKGPSVFPLAPSSKSTSGGTAALGCLVKDYFPEPV TVSWNSGALTSGV HTFPAVLQSSGLYSLSSVVTVPSSSLGTQTYICNVNHK PSNTKVDKRVEP KCPPCPAPELLGGPSVFLFPPKPKDTLMISRTPEVTCV VVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC LVKGFYPSDIAVEWESNGQPENNYKTTPPVLDSDGSF FLYSKLTVDKSRW QQGNVFSCSVMHEALHNHYTQKSLSLSPGK |
| 120 | IgG2-deltaHinge | ASTKGPSVFPLAPCSRSTSESTAALGCLVKDYFPEPVT VSWNSGALTSGV HTFPAVLQSSGLYSLSSVVTVPSSNFGTQTYTCNVDH KPSNTKVDKTVER KCPPCPAPPVAGPSVFLFPPKPKDTLMISRTPEVTCVV VDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPGK |
| 121 | IgG2.5-deltaHinge | ASTKGPSVFPLAPSSRSTSESTAALGCLVKDYFPEPVT VSWNSGALTSGV HTFPAVLQSSGLYSLSSVVTVPSSNFGTQTYTCNVDH KPSNTKVDKTVER KCPPCPAPPVAGPSVFLFPPKPKDTLMISRTPEVTCVV VDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPGK |
| 122 | IgG1-deltaG237 | ASTKGPSVFPLAPSSKSTSGGTAALGCLVKDYFPEPV TVSWNSGALTSGV HTFPAVLQSSGLYSLSSVVTVPSSSLGTQTYICNVNHK PSNTKVDKRVEP KSCDKTHTCPPCPAPELLGPSVFLFPPKPKDTLMISRT PEVTCVVVDVS HEDPEVKFNWYVDGVEVHNAKTKPREEQYNSTYRV VSVLTVLHQDWLNGK EYKCKVSNKALPAPIEKTISKAKGQPREPQVYTLPPSR EEMTKNQVSLTC |

SEQUENCE TABLE

| SEQ ID NO | Description | Sequence |
|---|---|---|
| | | LVKGFYPSDIAVEWESNGQPENNYKTTPPVLDSDGSF FLYSKLTVDKSRW QQGNVFSCSVMHEALHNHYTQKSLSLSPG |
| 123 | IgG2-plusG237 | ASTKGPSVFPLAPCSRSTSESTAALGCLVKDYFPEPVT VSWNSGALTSGV HTFPAVLQSSGLYSLSSVVTVPSSNFGTQTYTCNVDH KPSNTKVDKTVER KSCVECPPCPAPPVAGGPSVFLFPPKPKDTLMISRTPE VTCVVVDVS HEDPEVQFNWYVDGVEVHNAKTKPREEQFNSTFRV VSVLTVVHQDWLNGK EYKCKVSNKGLPAPIEKTISKTKGQPREPQVYTLPPSR EEMTKNQVSLTC LVKGFYPSDIAVEWESNGQPENNYKTTPPMLDSDGSF FLYSKLTVDKSRW QQGNVFSCSVMHEALHNHYTQKSLSLSPGK |
| 124 | IgG2.4 | ASTKGP SVFPLAPCSR STSESTAALG CLVKDYFPEP VTVSWNSGAL TSGVHTFPAV LQSSGLYSLS SVVTVPSSNF GTQTYTCNVD HKPSNTKVDK TVERKCSVEC PPCPAPPVAG PSVFLFPPKP KDTLMISRTP EVTCVVVDVS HEDPEVQFNW YVDGVEVHNA KTKPREEQFN STFRVVSVLT VVHQDWLNGK EYKCKVSNKG LPAPIEKTIS KTKGQPREPQ VYTLPPSREE MTKNQVSLTC LVKGFYPSDI AVEWESNGQP ENNYKTTPPM LDSDGSFFLY SKLTVDKSRW QQGNVFSCSV MHEALHNHYT QKSLSLSPGK |
| 125 | IgG2.3/4 | ASTKGP SVFPLAPCSR STSESTAALG CLVKDYFPEP VTVSWNSGAL TSGVHTFPAV LQSSGLYSLS SVVTVPSSNF GTQTYTCNVD HKPSNTKVDK TVERKSSVEC PPCPAPPVAG PSVFLFPPKP KDTLMISRTP EVTCVVVDVS HEDPEVQFNW YVDGVEVHNA KTKPREEQFN STFRVVSVLT VVHQDWLNGK EYKCKVSNKG LPAPIEKTIS KTKGQPREPQ VYTLPPSREE MTKNQVSLTC LVKGFYPSDI AVEWESNGQP ENNYKTTPPM LDSDGSFFLY SKLTVDKSRW QQGNVFSCSV MHEALHNHYT QKSLSLSPGK |
| 126 | Hinge IgG2 C220S | ERKCSVECPPCPAPPVAG |
| 127 | IgG2/IgG1 hybrid hinge C220S | ERKCSVECPPCPAPELLGG |
| 128 | Wildtype IgG2 hinge portion | ERKCCVECPPCPAP |
| 129 | IgG2 hinge portion C219S | ERKSCVECPPCPAP |
| 130 | IgG2 hinge portion C220S | ERKCSVECPPCPAP |
| 131 | IgG2 hinge portion C219X | ERKXCVECPPCPAP |
| 132 | IgG2 hinge portion C220X | ERKCXVECPPCPAP |
| 133 | IgG2 CH1 + IgG2 hinge (wildtype) | ASTKGPSVFPLAPCSRSTSESTAALGCLVKDYFPEPVT VSWNSGALTSGVHTFPAVLQSSGLYSLSSVVTVPSSN FGTQTYTCNVDHKPSNTKVDKTVERKCCVECPPCPA PPVAG |
| 134 | IgG2 with C219X | ERKXCVECPPCPAPPVAG |
| 135 | IgG2 with C220X | ERKCXVECPPCPAPPVAG |

SEQUENCE TABLE

| SEQ ID NO | Description | Sequence |
|---|---|---|
| 136 | IgG2/IgG1 hybrid with C219X | ERKXCVECPPCPAPELLGG |
| 137 | IgG2/IgG1 hybrid with C220X | ERKCVECPPCPAPELLGG |
| 138 | IgG2/IgG1 hybrid deltaG | ERKCCVECPPCPAPELLG |
| 139 | IgG2/IgG1 hybrid with C219S deltaG | ERKSCVECPPCPAPELLG |
| 140 | IgG2/IgG1 hybrid with C220S deltaG | ERKCSVECPPCPAPELLG |
| 141 | IgG2/IgG1 hybrid with C219X deltaG | ERKXCVECPPCPAPELLG |
| 142 | IgG2/IgG1 hybrid with C220X deltaG | ERKCXVECPPCPAPELLG |
| 143 | Wildtype IgG2 with C-terminal X | ERKCCVECPPCPAPPVAGX |
| 144 | IgG2 with C219S with C-terminal X | ERKSCVECPPCPAPPVAGX |
| 145 | IgG2 with C220S with C-terminal X | ERKCSVECPPCPAPPVAGX |
| 146 | IgG2 with C219X with C-terminal X | ERKXCVECPPCPAPPVAGX |
| 147 | IgG2 with C220X with C-terminal X | ERKCXVECPPCPAPPVAGX |
| 148 | IgG2 hinge portion | PVAG |
| 149 | IgG1 hinge portion | SCDKTHT |
| 150 | IgG1 hinge portion 1 | ELLG |
| 151 | IgG1 hinge portion 2 | ELLGG |
| 152 | IgG2.3-V13 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPPVAGDSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 153 | IgG2.3-V14 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPPVAGDSVFLFPPKPKDTLMISRTPEVTCVVVDVSHEDGEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 154 | IgG2.3-V15 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPPVAGDSVFLFPPKPKDTLMISRTPEVTCVVVDVSDEDGEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |

SEQUENCE TABLE

| SEQ ID NO | Description | Sequence |
|---|---|---|
| 155 | IgG2.3-V16 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPPVAGDSVFLFPPKPKDTLMISRTPEVTCVVVDVSHEDGEVQFNWYVDGVEVHNAKTKPREEQFNSTFRVVSVLTVVHQDWLNGKEYKCKVSNKGLPRPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 156 | IgG2.3-V17 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPPVAGDSVFLFPPKPKDTLMISRTPEVTCVVVDVSDEDGEVQFNWYVDGVEVHNAKTKPREEQFNSTFRVVSVLTVVHQDWLNGKEYKCKVSNKGLPRPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 157 | IgG2.3-V18 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPPVAGPSVFLFPPKPKDTLMISRTPEVTCVVVDVEHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 158 | IgG2.3-V19 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPPVAGPSVFLFPPKPKDTLMISRTPEVTCVVVDVEHEDPEVQFNWYVDGVEVHNAKTKPREEQFNSTFRVVSVLTVVHQDWLNGKEYKCKVSNKGFPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 159 | IgG2.3G1 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 160 | IgG2.3G1-V20 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPELLGGDSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 161 | IgG2.3G1-V21 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPAPELLGGDSVFLFPPKPKDTLMISRTPEVTCVVVDVSHEDGEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 162 | IgG2.3G1-V22 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKSCVECPPCPA |

SEQUENCE TABLE

| SEQ ID NO | Description | Sequence |
|---|---|---|
| | | PELLGGDSVFLFPPKPKDTLMISRTPEVTCVVVDVSD<br>EDGEVKFNWYVDGVEVHNAKTKPREEQYNSTYRVV<br>SVLTVLHQDWLNGKEYKCKVSNKALPAPIEKTISKA<br>KGQPREPQVYTLPPSREEMTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPGK |
| 163 | IgG2.3G1-V23 | ASTKGPSVFPLAPCSRSTSESTAALGCLVKDYFPEPVT<br>VSWNSGALTSGVHTFPAVLQSSGLYSLSSVVTVPSSN<br>FGTQTYTCNVDHKPSNTKVDKTVERKSCVECPPCPA<br>PELLGGDSVFLFPPKPKDTLMISRTPEVTCVVVDVSH<br>EDGEVKFNWYVDGVEVHNAKTKPREEQYNSTYRVV<br>SVLTVLHQDWLNGKEYKCKVSNKALPRPIEKTISKA<br>KGQPREPQVYTLPPSREEMTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPGK |
| 164 | IgG2.3G1-V24 | ASTKGPSVFPLAPCSRSTSESTAALGCLVKDYFPEPVT<br>VSWNSGALTSGVHTFPAVLQSSGLYSLSSVVTVPSSN<br>FGTQTYTCNVDHKPSNTKVDKTVERKSCVECPPCPA<br>PELLGGDSVFLFPPKPKDTLMISRTPEVTCVVVDVSD<br>EDGEVKFNWYVDGVEVHNAKTKPREEQYNSTYRVV<br>SVLTVLHQDWLNGKEYKCKVSNKALPRPIEKTISKA<br>KGQPREPQVYTLPPSREEMTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPGK |
| 165 | IgG2.3G1-V25 | ASTKGPSVFPLAPCSRSTSESTAALGCLVKDYFPEPVT<br>VSWNSGALTSGVHTFPAVLQSSGLYSLSSVVTVPSSN<br>FGTQTYTCNVDHKPSNTKVDKTVERKSCVECPPCPA<br>PELLGDDSVFLFPPKPKDTLMISRTPEVTCVVVDVSD<br>EDGEVKFNWYVDGVEVHNAKTKPREEQYNSTYRVV<br>SVLTVLHQDWLNGKEYKCKVSNKALPRPIEKTISKA<br>KGQPREPQVYTLPPSREEMTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPGK |
| 166 | IgG2.3G1-V26 | ASTKGPSVFPLAPCSRSTSESTAALGCLVKDYFPEPVT<br>VSWNSGALTSGVHTFPAVLQSSGLYSLSSVVTVPSSN<br>FGTQTYTCNVDHKPSNTKVDKTVERKSCVECPPCPA<br>PDLLGGDDSVFLFPPKPKDTLMISRTPEVTCVVVDVSD<br>EDGEVKFNWYVDGVEVHNAKTKPREEQYNSTYRVV<br>SVLTVLHQDWLNGKEYKCKVSNKALPRPIEKTISKA<br>KGQPREPQVYTLPPSREEMTKNQVSLTCLVKGFYPSD<br>IAVEWESNGQPENNYKTTPPVLDSDGSFFLYSKLTVD<br>KSRWQQGNVFSCSVMHEALHNHYTQKSLSLSPGK |
| 167 | IgG2.3G1-V27 | ASTKGPSVFPLAPCSRSTSESTAALGCLVKDYFPEPVT<br>VSWNSGALTSGVHTFPAVLQSSGLYSLSSVVTVPSSN<br>FGTQTYTCNVDHKPSNTKVDKTVERKSCVECPPCPA<br>PELLGGPSVFLFPPKPKDTLMISRTPEVTCVVVDVEHE<br>DPEVKFNWYVDGVEVHNAKTKPREEQYNSTYRVVS<br>VLTVLHQDWLNGKEYKCKVSNKALPAPIEKTISKAK<br>GQPREPQVYTLPPSREEMTKNQVSLTCLVKGFYPSDI<br>AVEWESNGQPENNYKTTPPVLDSDGSFFLYSKLTVD<br>KSRWQQGNVFSCSVMHEALHNHYTQKSLSLSPGK |
| 168 | IgG2.3G1-V28 | ASTKGPSVFPLAPCSRSTSESTAALGCLVKDYFPEPVT<br>VSWNSGALTSGVHTFPAVLQSSGLYSLSSVVTVPSSN<br>FGTQTYTCNVDHKPSNTKVDKTVERKSCVECPPCPA<br>PELLGGPSVFLFPPKPKDTLMISRTPEVTCVVVDVEHE<br>DPEVKFNWYVDGVEVHNAKTKPREEQYNSTYRVVS<br>VLTVLHQDWLNGKEYKCKVSNKAFPAPIEKTISKAK<br>GQPREPQVYTLPPSREEMTKNQVSLTCLVKGFYPSDI<br>AVEWESNGQPENNYKTTPPVLDSDGSFFLYSKLTVD<br>KSRWQQGNVFSCSVMHEALHNHYTQKSLSLSPGK |

Those skilled in the art will recognize or be able to ascertain, using no more than routine experimentation, many equivalents of the specific embodiments described herein described herein. Such equivalents are intended to be encompassed by the following claims.

We claim:

1. A method of preparing an antibody comprising a modified heavy chain constant region, comprising the steps of:
   (a) providing an antibody comprising a hinge and/or a CH1 domain that is not an IgG2 hinge and/or IgG2 CH1 domain;
   (b) replacing the hinge and/or the CH1 domain with an IgG2 hinge and/or IgG2 CH1 domain, respectively, wherein the modified heavy chain constant region comprises a CH1 domain, a hinge, a CH2 domain, and a CH3 domain in order from N- to C-terminus, wherein:
   (i) the hinge comprises the amino acid sequence of SEQ ID NO: 129, SEQ ID NO: 21, SEQ ID NO: 23, SEQ ID NO: 130, or SEQ ID NO: 127;
   (ii) the CH1 domain comprises the amino acid sequence of SEQ ID NO: 7;
   (iii) the CH2 domain comprises the amino acid sequence of SEQ ID NO: 4 or the amino acid sequence of SEQ ID NO: 24; and
   (iv) the CH3 domain comprises the amino acid sequence of SEQ ID NO: 5 or SEQ ID NO: 5 with the amino acid substitutions E356D and M358L according to the EU index as in Kabat;
   or wherein the modified heavy chain constant region comprising the CH1 domain, the hinge, the CH2 domain, and the CH3 domain as defined in (i), (ii), (iii) and (iv) lacks the C-terminal GK or K.

2. A method of increasing internalization of an antibody by a cell, comprising:
   (a) providing an antibody comprising a hinge and/or a CH1 domain that is not an IgG2 hinge and/or IgG2 CH1 domain;
   (b) replacing the hinge and/or the CH1 domain with an IgG2 hinge and/or IgG2 CH1 domain, respectively, thereby modifying the heavy chain constant region of the antibody so that it comprises a CH1 domain, a hinge, a CH2 domain, and a CH3 domain in order from N- to C-terminus, wherein:
   (i) the hinge comprises the amino acid sequence of SEQ ID NO: 129, SEQ ID NO: 21, SEQ ID NO: 23, SEQ ID NO: 130, or SEQ ID NO: 127;
   (ii) the CH1 domain comprises the amino acid sequence of SEQ ID NO: 7;
   (iii) the CH2 domain comprises the amino acid sequence of SEQ ID NO: 4 or the amino acid sequence of SEQ ID NO: 24; and
   (iv) the CH3 domain comprises the amino acid sequence of SEQ ID NO: 5 or SEQ ID NO: 5 with the amino acid substitutions E356D and M358L according to the EU index as in Kabat;
   or wherein the modified heavy chain constant region comprising the CH1 domain, the hinge, the CH2 domain, and the CH3 domain as defined in (i), (ii), (iii) and (iv) lacks the C-terminal GK or K.

3. A method of increasing the agonist activity of an antibody, comprising:
   (a) providing an antibody comprising a hinge and/or a CH1 domain that is not an IgG2 hinge and/or IgG2 CH1 domain;
   (b) replacing the hinge and/or the CH1 domain with an IgG2 hinge and/or IgG2 CH1 domain, respectively, thereby modifying the heavy chain constant region of the antibody so that it comprises a CH1 domain, a hinge, a CH2 domain, and a CH3 domain in order from N- to C-terminus, wherein:
   (i) the hinge comprises the amino acid sequence of SEQ ID NO: 129, SEQ ID NO: 21, SEQ ID NO: 23, SEQ ID NO: 130, or SEQ ID NO: 127;
   (ii) the CH1 domain comprises the amino acid sequence of SEQ ID NO: 7;
   (iii) the CH2 domain comprises the amino acid sequence of SEQ ID NO: 4 or the amino acid sequence of SEQ ID NO: 24; and
   (iv) the CH3 domain comprises the amino acid sequence of SEQ ID NO: 5 or SEQ ID NO: 5 with the amino acid substitutions E356D and M358L according to the EU index as in Kabat;

or wherein the modified heavy chain constant region comprising the CH1 domain, the hinge, the CH2 domain, and the CH3 domain as defined in (i), (ii), (iii) and (iv) lacks the C-terminal GK or K.

4. The method of claim 1, wherein the antibody comprises a modified heavy chain constant region selected from the group consisting of SEQ ID NOs: 34, 35, 37, 80, 81, 84 and 159.

5. The method of claim 2, wherein the antibody comprises a modified heavy chain constant region selected from the group consisting of SEQ ID NOs: 34, 35, 37, 80, 81, 84 and 159.

6. The method of claim 3, wherein the antibody comprises a modified heavy chain constant region selected from the group consisting of SEQ ID NOs: 34, 35, 37, 80, 81, 84 and 159.

\* \* \* \* \*

SEQUENCE LISTING

<160> NUMBER OF SEQ ID NOS: 170

<210> SEQ ID NO 1
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Full length IgG1 wild type

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

```
                305                 310                 315                 320
Gln Lys Ser Leu Ser Leu Ser Pro Gly Lys
                    325                 330

<210> SEQ ID NO 2
<211> LENGTH: 98
<212> TYPE: PRT
<213> ORGANISM: Homo sapiens
<220> FEATURE:
<221> NAME/KEY: misc_feature
<222> LOCATION: (1)..(98)
<223> OTHER INFORMATION: CH1 IgG1 wild type

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 3
<211> LENGTH: 22
<212> TYPE: PRT
<213> ORGANISM: Homo sapiens
<220> FEATURE:
<221> NAME/KEY: misc_feature
<222> LOCATION: (1)..(22)
<223> OTHER INFORMATION: Hinge IgG1 wild type

<400> SEQUENCE: 3

Glu Pro Lys Ser Cys Asp Lys Thr His Thr Cys Pro Pro Cys Pro Ala
1               5                   10                  15

Pro Glu Leu Leu Gly Gly
            20

<210> SEQ ID NO 4
<211> LENGTH: 103
<212> TYPE: PRT
<213> ORGANISM: Homo sapiens
<220> FEATURE:
<221> NAME/KEY: misc_feature
<222> LOCATION: (1)..(103)
<223> OTHER INFORMATION: CH2 IgG1 wild type

<400> SEQUENCE: 4

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
        35                  40                  45

Asn Ala Lys Thr Lys Pro Arg Glu Glu Gln Tyr Asn Ser Thr Tyr Arg
    50                  55                  60
```

```
Val Val Ser Val Leu Thr Val Leu His Gln Asp Trp Leu Asn Gly Lys
 65                  70                  75                  80

Glu Tyr Lys Cys Lys Val Ser Asn Lys Ala Leu Pro Ala Pro Ile Glu
                 85                  90                  95

Lys Thr Ile Ser Lys Ala Lys
            100
```

<210> SEQ ID NO 5
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: CH3 IgG1 wild type

<400> SEQUENCE: 5

```
Gly Gln Pro Arg Glu Pro Gln Val Tyr Thr Leu Pro Pro Ser Arg Glu
 1                5                  10                  15

Glu Met Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

<210> SEQ ID NO 6
<211> LENGTH: 326
<212> TYPE: PRT
<213> ORGANISM: Homo sapiens
<220> FEATURE:
<221> NAME/KEY: misc_feature
<222> LOCATION: (1)..(326)
<223> OTHER INFORMATION: Full length IgG2 wild type

<400> SEQUENCE: 6

```
Ala Ser Thr Lys Gly Pro Ser Val Phe Pro Leu Ala Pro Cys Ser Arg
 1                5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
```

```
                130                 135                 140
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 7
<211> LENGTH: 98
<212> TYPE: PRT
<213> ORGANISM: Homo sapiens
<220> FEATURE:
<221> NAME/KEY: misc_feature
<222> LOCATION: (1)..(98)
<223> OTHER INFORMATION: CH1 IgG2 wild type

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 8
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: Hinge IgG2 wild type
```

```
<400> SEQUENCE: 8

Glu Arg Lys Cys Cys Val Glu Cys Pro Pro Cys Pro Ala Pro Pro Val
1               5                   10                  15

Ala Gly

<210> SEQ ID NO 9
<211> LENGTH: 103
<212> TYPE: PRT
<213> ORGANISM: Homo sapiens
<220> FEATURE:
<221> NAME/KEY: misc_feature
<222> LOCATION: (1)..(103)
<223> OTHER INFORMATION: CH2 IgG2 wild type

<400> SEQUENCE: 9

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Gln Phe Asn Trp Tyr Val Asp Gly Val Glu Val His
        35                  40                  45

Asn Ala Lys Thr Lys Pro Arg Glu Glu Gln Phe Asn Ser Thr Phe Arg
    50                  55                  60

Val Val Ser Val Leu Thr Val Val His Gln Asp Trp Leu Asn Gly Lys
65                  70                  75                  80

Glu Tyr Lys Cys Lys Val Ser Asn Lys Gly Leu Pro Ala Pro Ile Glu
                85                  90                  95

Lys Thr Ile Ser Lys Thr Lys
            100

<210> SEQ ID NO 10
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: CH3 IgG2 wild type

<400> SEQUENCE: 10

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 11
<211> LENGTH: 377
<212> TYPE: PRT
<213> ORGANISM: Homo sapiens
```

```
<220> FEATURE:
<221> NAME/KEY: misc_feature
<222> LOCATION: (1)..(377)
<223> OTHER INFORMATION: Full length IgG3 wild type

<400> SEQUENCE: 11
```

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Cys | Ser | Arg |
| 1 | | | | 5 | | | | | 10 | | | | | 15 |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Thr | Cys | Asn | Val | Asn | His | Lys | Pro | Ser | Asn | Thr | Lys | Val | Asp | Lys |
| | | | | 85 | | | | | 90 | | | | | 95 | |
| Arg | Val | Glu | Leu | Lys | Thr | Pro | Leu | Gly | Asp | Thr | Thr | His | Thr | Cys | Pro |
| | | | 100 | | | | | 105 | | | | | 110 | | |
| Arg | Cys | Pro | Glu | Pro | Lys | Ser | Cys | Asp | Thr | Pro | Pro | Cys | Pro | Arg |
| | | 115 | | | | | 120 | | | | | 125 | | | |
| Cys | Pro | Glu | Pro | Lys | Ser | Cys | Asp | Thr | Pro | Pro | Cys | Pro | Arg | Cys |
| | 130 | | | | | 135 | | | | | 140 | | | | |
| Pro | Glu | Pro | Lys | Ser | Cys | Asp | Thr | Pro | Pro | Cys | Pro | Arg | Cys | Pro |
| 145 | | | | | 150 | | | | | 155 | | | | | 160 |
| Ala | Pro | Glu | Leu | Leu | Gly | Gly | Pro | Ser | Val | Phe | Leu | Phe | Pro | Pro | Lys |
| | | | | 165 | | | | | 170 | | | | | 175 | |
| Pro | Lys | Asp | Thr | Leu | Met | Ile | Ser | Arg | Thr | Pro | Glu | Val | Thr | Cys | Val |
| | | | 180 | | | | | 185 | | | | | 190 | | |
| Val | Val | Asp | Val | Ser | His | Glu | Asp | Pro | Glu | Val | Gln | Phe | Lys | Trp | Tyr |
| | | 195 | | | | | 200 | | | | | 205 | | | |
| Val | Asp | Gly | Val | Glu | Val | His | Asn | Ala | Lys | Thr | Lys | Pro | Arg | Glu | Glu |
| | 210 | | | | | 215 | | | | | 220 | | | | |
| Gln | Tyr | Asn | Ser | Thr | Phe | Arg | Val | Val | Ser | Val | Leu | Thr | Val | Leu | His |
| 225 | | | | | 230 | | | | | 235 | | | | | 240 |
| Gln | Asp | Trp | Leu | Asn | Gly | Lys | Glu | Tyr | Lys | Cys | Lys | Val | Ser | Asn | Lys |
| | | | | 245 | | | | | 250 | | | | | 255 | |
| Ala | Leu | Pro | Ala | Pro | Ile | Glu | Lys | Thr | Ile | Ser | Lys | Thr | Lys | Gly | Gln |
| | | | 260 | | | | | 265 | | | | | 270 | | |
| Pro | Arg | Glu | Pro | Gln | Val | Tyr | Thr | Leu | Pro | Pro | Ser | Arg | Glu | Glu | Met |
| | | 275 | | | | | 280 | | | | | 285 | | | |
| Thr | Lys | Asn | Gln | Val | Ser | Leu | Thr | Cys | Leu | Val | Lys | Gly | Phe | Tyr | Pro |
| | 290 | | | | | 295 | | | | | 300 | | | | |
| Ser | Asp | Ile | Ala | Val | Glu | Trp | Glu | Ser | Ser | Gly | Gln | Pro | Glu | Asn | Asn |
| 305 | | | | | 310 | | | | | 315 | | | | | 320 |
| Tyr | Asn | Thr | Thr | Pro | Met | Leu | Asp | Ser | Asp | Gly | Ser | Phe | Phe | Leu |
| | | | | 325 | | | | | 330 | | | | | 335 | |
| Tyr | Ser | Lys | Leu | Thr | Val | Asp | Lys | Ser | Arg | Trp | Gln | Gln | Gly | Asn | Ile |
| | | | 340 | | | | | 345 | | | | | 350 | | |
| Phe | Ser | Cys | Ser | Val | Met | His | Glu | Ala | Leu | His | Asn | Arg | Phe | Thr | Gln |
| | | 355 | | | | | 360 | | | | | 365 | | | |
| Lys | Ser | Leu | Ser | Leu | Ser | Pro | Gly | Lys |
| | 370 | | | | | 375 | | |

<210> SEQ ID NO 12
<211> LENGTH: 98
<212> TYPE: PRT
<213> ORGANISM: Homo sapiens
<220> FEATURE:
<221> NAME/KEY: misc_feature
<222> LOCATION: (1)..(98)
<223> OTHER INFORMATION: CH1 IgG3 wild type

<400> SEQUENCE: 12

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 13
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: Hinge IgG3 wild type

<400> SEQUENCE: 13

Glu Leu Lys Thr Pro Leu Gly Asp Thr Thr His Thr Cys Pro Arg Cys
1               5                   10                  15

Pro Glu

<210> SEQ ID NO 14
<211> LENGTH: 154
<212> TYPE: PRT
<213> ORGANISM: Homo sapiens
<220> FEATURE:
<221> NAME/KEY: misc_feature
<222> LOCATION: (1)..(154)
<223> OTHER INFORMATION: CH2 IgG3 wild type

<400> SEQUENCE: 14

Pro Lys Ser Cys Asp Thr Pro Pro Pro Cys Pro Arg Cys Pro Glu Pro
1               5                   10                  15

Lys Ser Cys Asp Thr Pro Pro Pro Cys Pro Arg Cys Pro Glu Pro Lys
            20                  25                  30

Ser Cys Asp Thr Pro Pro Pro Cys Pro Arg Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Gln Phe Lys Trp Tyr Val Asp Gly Val
                85                  90                  95

```
Glu Val His Asn Ala Lys Thr Lys Pro Arg Glu Gln Tyr Asn Ser
            100                 105                 110

Thr Phe Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
130                 135                 140

Pro Ile Glu Lys Thr Ile Ser Lys Thr Lys
145                 150
```

```
<210> SEQ ID NO 15
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: CH3 IgG3 wild type

<400> SEQUENCE: 15
```

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105
```

```
<210> SEQ ID NO 16
<211> LENGTH: 327
<212> TYPE: PRT
<213> ORGANISM: Homo sapiens
<220> FEATURE:
<221> NAME/KEY: misc_feature
<222> LOCATION: (1)..(327)
<223> OTHER INFORMATION: Full length IgG4 wild type

<400> SEQUENCE: 16
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
```

```
                115                 120                 125
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 17
<211> LENGTH: 98
<212> TYPE: PRT
<213> ORGANISM: Homo sapiens
<220> FEATURE:
<221> NAME/KEY: misc_feature
<222> LOCATION: (1)..(98)
<223> OTHER INFORMATION: CH1 IgG4 wild type

<400> SEQUENCE: 17

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 18
<211> LENGTH: 19
<212> TYPE: PRT
<213> ORGANISM: Homo sapiens
<220> FEATURE:
```

```
<221> NAME/KEY: misc_feature
<222> LOCATION: (1)..(19)
<223> OTHER INFORMATION: Hinge IgG4 wild type

<400> SEQUENCE: 18

Glu Ser Lys Tyr Gly Pro Pro Cys Pro Ser Cys Pro Ala Pro Glu Phe
1               5                   10                  15

Leu Gly Gly

<210> SEQ ID NO 19
<211> LENGTH: 103
<212> TYPE: PRT
<213> ORGANISM: Homo sapiens
<220> FEATURE:
<221> NAME/KEY: misc_feature
<222> LOCATION: (1)..(103)
<223> OTHER INFORMATION: CH2 IgG4 wild type

<400> SEQUENCE: 19

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser Gln Glu
            20                  25                  30

Asp Pro Glu Val Gln Phe Asn Trp Tyr Val Asp Gly Val Glu Val His
        35                  40                  45

Asn Ala Lys Thr Lys Pro Arg Glu Glu Gln Phe Asn Ser Thr Tyr Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Gly Leu Pro Ser Ser Ile Glu
                85                  90                  95

Lys Thr Ile Ser Lys Ala Lys
            100

<210> SEQ ID NO 20
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: CH3 IgG4 wild type

<400> SEQUENCE: 20

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 21
```

```
<211> LENGTH: 18
<212> TYPE: PRT
<213> ORGANISM: Artificial Sequence
<220> FEATURE:
<223> OTHER INFORMATION: Synthetic: Modified IgG2 Hinge (C219S)

<400> SEQUENCE: 21

Glu Arg Lys Ser Cys Val Glu Cys Pro Pro Cys Pro Ala Pro Pro Val
1               5                   10                  15
Ala Gly

<210> SEQ ID NO 22
<211> LENGTH: 19
<212> TYPE: PRT
<213> ORGANISM: Artificial Sequence
<220> FEATURE:
<223> OTHER INFORMATION: Synthetic: IgG2/IgG1 hybrid hinge

<400> SEQUENCE: 22

Glu Arg Lys Cys Cys Val Glu Cys Pro Pro Cys Pro Ala Pro Glu Leu
1               5                   10                  15
Leu Gly Gly

<210> SEQ ID NO 23
<211> LENGTH: 19
<212> TYPE: PRT
<213> ORGANISM: Artificial Sequence
<220> FEATURE:
<223> OTHER INFORMATION: Synthetic: IgG2 C219S/IgG1 hybrid hinge

<400> SEQUENCE: 23

Glu Arg Lys Ser Cys Val Glu Cys Pro Pro Cys Pro Ala Pro Glu Leu
1               5                   10                  15
Leu Gly Gly

<210> SEQ ID NO 24
<211> LENGTH: 103
<212> TYPE: PRT
<213> ORGANISM: Artificial Sequence
<220> FEATURE:
<223> OTHER INFORMATION: Synthetic: Modified CH2 IgG1 (A330S/P331S)

<400> SEQUENCE: 24

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
        35                  40                  45

Asn Ala Lys Thr Lys Pro Arg Glu Glu Gln Tyr Asn Ser Thr Tyr Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ser Ser Ile Glu
                85                  90                  95

Lys Thr Ile Ser Lys Ala Lys
            100

<210> SEQ ID NO 25
<211> LENGTH: 22
<212> TYPE: PRT
<213> ORGANISM: Artificial Sequence
```

<220> FEATURE:
<223> OTHER INFORMATION: Synthetic: IgG1.1 Hinge (L234A/L235E/G237A)

<400> SEQUENCE: 25

```
Glu Pro Lys Ser Cys Asp Lys Thr His Thr Cys Pro Pro Cys Pro Ala
1               5                   10                  15

Pro Glu Ala Glu Gly Ala
            20
```

<210> SEQ ID NO 26
<211> LENGTH: 326
<212> TYPE: PRT
<213> ORGANISM: Artificial Sequence
<220> FEATURE:
<223> OTHER INFORMATION: Synthetic: IgG1 IgG2 IgG1 (IgG1 IgG2/IgG1
    (SEQ#22) IgG1 IgG1)

<400> SEQUENCE: 26

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65              70                  75                  80

Tyr Ile Cys Asn Val Asn His Lys Pro Ser Asn Thr Lys Val Asp Lys
                85                  90                  95

Lys Val Glu Arg Lys Cys Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Pro Gly
                325

<210> SEQ ID NO 27
<211> LENGTH: 325
<212> TYPE: PRT
<213> ORGANISM: Artificial Sequence
<220> FEATURE:
<223> OTHER INFORMATION: Synthetic: IgG1 IgG2 IgG12 (IgG1 IgG2(SEQ#8)
      IgG1 IgG1)

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325
```

<210> SEQ ID NO 28
<211> LENGTH: 326
<212> TYPE: PRT
<213> ORGANISM: Artificial Sequence
<220> FEATURE:
<223> OTHER INFORMATION: Synthetic: IgG2 IgG1 (IgG2 IgG2/IgG1(SEQ#22) IgG1 IgG1)

<400> SEQUENCE: 28

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly
                325
```

<210> SEQ ID NO 29
<211> LENGTH: 325
<212> TYPE: PRT

<213> ORGANISM: Artificial Sequence
<220> FEATURE:
<223> OTHER INFORMATION: Synthetic: IgG2 IgG12 (IgG2 IgG2(SEQ#8) IgG1 IgG1)

<400> SEQUENCE: 29

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325
```

<210> SEQ ID NO 30
<211> LENGTH: 325
<212> TYPE: PRT
<213> ORGANISM: Artificial Sequence
<220> FEATURE:
<223> OTHER INFORMATION: Synthetic: IgG1 IgG2 IgG1.1 (IgG1 IgG2(SEQ#8) IgG1(A330S/P331S) IgG1)

```
<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
            165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 31
<211> LENGTH: 326
<212> TYPE: PRT
<213> ORGANISM: Artificial Sequence
<220> FEATURE:
<223> OTHER INFORMATION: Synthetic: IgG2 IgG1.1 (IgG2 IgG2(SEQ#8)
      IgG1(A330S/P331S) IgG1)

<400> SEQUENCE: 31

Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 32
<211> LENGTH: 325
<212> TYPE: PRT
<213> ORGANISM: Artificial Sequence
<220> FEATURE:
<223> OTHER INFORMATION: Synthetic: IgG1 IgG2CS IgG1 (IgG1 IgG2(C219S)
      IgG1 IgG1)

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
            325

<210> SEQ ID NO 33
<211> LENGTH: 325
<212> TYPE: PRT
<213> ORGANISM: Artificial Sequence
<220> FEATURE:
<223> OTHER INFORMATION: Synthetic: IgG1 IgG2CS IgG12 (IgG1 IgG2(C219S)
      IgG1 IgG1)

<400> SEQUENCE: 33

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95
Lys Val Glu Arg Lys Ser Cys Val Glu Cys Pro Pro Cys Pro Ala Pro
                100                 105                 110
Pro Val Ala Gly Pro Ser Val Phe Leu Phe Pro Pro Lys Pro Lys Asp
                115                 120                 125
Thr Leu Met Ile Ser Arg Thr Pro Glu Val Thr Cys Val Val Val Asp
            130                 135                 140
Val Ser His Glu Asp Pro Glu Val Lys Phe Asn Trp Tyr Val Asp Gly
145                 150                 155                 160
Val Glu Val His Asn Ala Lys Thr Lys Pro Arg Glu Glu Gln Tyr Asn
                165                 170                 175
Ser Thr Tyr Arg Val Val Ser Val Leu Thr Val Leu His Gln Asp Trp
                180                 185                 190
Leu Asn Gly Lys Glu Tyr Lys Cys Lys Val Ser Asn Lys Ala Leu Pro
                195                 200                 205
Ala Pro Ile Glu Lys Thr Ile Ser Lys Ala Lys Gly Gln Pro Arg Glu
            210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
                260                 265                 270
Thr Pro Pro Val Leu Asp Ser Asp Gly Ser Phe Phe Leu Tyr Ser Lys
            275                 280                 285
Leu Thr Val Asp Lys Ser Arg Trp Gln Gln Gly Asn Val Phe Ser Cys
            290                 295                 300
Ser Val Met His Glu Ala Leu His Asn His Tyr Thr Gln Lys Ser Leu
305                 310                 315                 320
Ser Leu Ser Pro Gly
                325

<210> SEQ ID NO 34
<211> LENGTH: 326
<212> TYPE: PRT
<213> ORGANISM: Artificial Sequence
<220> FEATURE:
<223> OTHER INFORMATION: Synthetic: IgG2CS IgG1 (IgG2 IgG2(C219S) IgG1
      IgG1)

<400> SEQUENCE: 34

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
```

```
Thr Val Glu Arg Lys Ser Cys Val Glu Cys Pro Pro Cys Pro Ala Pro
            100                 105                 110

Glu Leu Leu Gly Gly Pro Ser Val Phe Leu Phe Pro Lys Pro Lys Asp
            115                 120                 125

Thr Leu Met Ile Ser Arg Thr Pro Glu Val Thr Cys Val Val Val Asp
        130                 135                 140             145

Val Ser His Glu Asp Pro Glu Val Lys Phe Asn Trp Tyr Val Asp Gly
150                 155                 160

Val Glu Val His Asn Ala Lys Thr Lys Pro Arg Glu Glu Gln Tyr Asn
            165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
            195                 200                 205

Ala Pro Ile Glu Lys Thr Ile Ser Lys Ala Lys Gly Gln Pro Arg Glu
        210                 215                 220             225

Pro Gln Val Tyr Thr Leu Pro Pro Ser Arg Glu Glu Met Thr Lys Asn
230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300             305

Ser Val Met His Glu Ala Leu His Asn His Tyr Thr Gln Lys Ser Leu
310                 315                 320

Ser Leu Ser Pro Gly
                325

<210> SEQ ID NO 35
<211> LENGTH: 325
<212> TYPE: PRT
<213> ORGANISM: Artificial Sequence
<220> FEATURE:
<223> OTHER INFORMATION: Synthetic: IgG2CS IgG12 (IgG2 IgG2(C219S) IgG1
      IgG1)

<400> SEQUENCE: 35

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125
```

```
Thr Leu Met Ile Ser Arg Thr Pro Glu Val Thr Cys Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 36
<211> LENGTH: 325
<212> TYPE: PRT
<213> ORGANISM: Artificial Sequence
<220> FEATURE:
<223> OTHER INFORMATION: Synthetic: IgG1 IgG2CS IgG1.1 (IgG1 IgG2(C219S)
      IgG1(A330S/P331S) IgG1)

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Asp
    130                 135                 140

Val Ser His Glu Asp Pro Glu Val Lys Phe Asn Trp Tyr Val Asp Gly
```

```
            145                 150                 155                 160
Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
                180                 185                 190

Leu Asn Gly Lys Glu Tyr Lys Cys Lys Val Ser Asn Lys Ala Leu Pro
                195                 200                 205

Ser Ser Ile Glu Lys Thr Ile Ser Lys Ala Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Val Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 37
<211> LENGTH: 325
<212> TYPE: PRT
<213> ORGANISM: Artificial Sequence
<220> FEATURE:
<223> OTHER INFORMATION: Synthetic: IgG2CS IgG1.1 (IgG2 IgG2(C219S)
      IgG1(A330S/P331S) IgG1)

<400> SEQUENCE: 37

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175
```

```
Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 38
<211> LENGTH: 121
<212> TYPE: PRT
<213> ORGANISM: Artificial Sequence
<220> FEATURE:
<223> OTHER INFORMATION: Synthetic: Ab 11F11 VH

<400> SEQUENCE: 38

Gln Val Gln Leu Val Glu Ser Gly Gly Gly Val Val Gln Pro Gly Arg
1               5                   10                  15

Ser Leu Arg Leu Ser Cys Ala Thr Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Leu Tyr Asp Gly Ser Asn Lys Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Ser Trp Tyr Pro Asp Ser Phe Asp Ile Trp Gly
            100                 105                 110

Gln Gly Thr Met Val Thr Val Ser Ser
        115                 120

<210> SEQ ID NO 39
<211> LENGTH: 120
<212> TYPE: PRT
<213> ORGANISM: Artificial Sequence
<220> FEATURE:
<223> OTHER INFORMATION: Synthetic: Ab 4C3 VH

<400> SEQUENCE: 39

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

```
Ala Met His Trp Val Arg Gln Ala Pro Gly Lys Gly Leu Glu Trp Val
            35                  40                  45

Ser Gly Ile Ser Trp Lys Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Gly Tyr Tyr Val Ile Leu Thr Gly Leu Asp Tyr Trp Gly Gln
                100                 105                 110

Gly Thr Leu Val Thr Val Ser Ser
            115                 120

<210> SEQ ID NO 40
<211> LENGTH: 121
<212> TYPE: PRT
<213> ORGANISM: Artificial Sequence
<220> FEATURE:
<223> OTHER INFORMATION: Synthetic: Ab CD73.10 VH

<400> SEQUENCE: 40

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Val Ile Trp Tyr Asp Glu Ser Asn Lys Tyr Tyr Pro Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Ser Trp Tyr Pro Asp Ser Phe Asp Ile Trp Gly
                100                 105                 110

Gln Gly Thr Met Val Thr Val Ser Ser
            115                 120

<210> SEQ ID NO 41
<211> LENGTH: 120
<212> TYPE: PRT
<213> ORGANISM: Artificial Sequence
<220> FEATURE:
<223> OTHER INFORMATION: Synthetic: Ab CD73.3 VH  (4C3 / V94A)

<400> SEQUENCE: 41

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Lys Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Val Leu Tyr Tyr Cys
```

85                  90                  95
Val Lys Gly Tyr Tyr Val Ile Leu Thr Gly Leu Asp Tyr Trp Gly Gln
                100                 105                 110

Gly Thr Leu Val Thr Val Ser Ser
        115                 120

<210> SEQ ID NO 42
<211> LENGTH: 121
<212> TYPE: PRT
<213> ORGANISM: Artificial Sequence
<220> FEATURE:
<223> OTHER INFORMATION: Synthetic: Ab 6E11 VH

<400> SEQUENCE: 42

Glu Val Gln Leu Val Glu Ser Gly Gly Ala Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Thr Trp Asn Ser Gly Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Arg Tyr Tyr Ser Ser Trp Leu Leu Phe Asp Asn Trp Gly
                100                 105                 110

Gln Gly Ile Leu Val Thr Val Ser Ser
        115                 120

<210> SEQ ID NO 43
<211> LENGTH: 121
<212> TYPE: PRT
<213> ORGANISM: Artificial Sequence
<220> FEATURE:
<223> OTHER INFORMATION: Synthetic: Ab CD73.4 VH

<400> SEQUENCE: 43

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Val Ile Leu Tyr Asp Gly Ser Asn Lys Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Ser Trp Tyr Pro Asp Ser Phe Asp Ile Trp Gly
                100                 105                 110

Gln Gly Thr Met Val Thr Val Ser Ser
        115                 120

<210> SEQ ID NO 44
<211> LENGTH: 447

```
<212> TYPE: PRT
<213> ORGANISM: Artificial Sequence
<220> FEATURE:
<223> OTHER INFORMATION: Synthetic: Ab 11F11 full length HC

<400> SEQUENCE: 44

Gln Val Gln Leu Val Glu Ser Gly Gly Val Val Gln Pro Gly Arg
1               5                   10                  15

Ser Leu Arg Leu Ser Cys Ala Thr Ser Gly Phe Thr Phe Ser Asn Tyr
            20                  25                  30

Gly Met His Trp Val Arg Gln Ala Pro Gly Lys Gly Leu Glu Trp Val
            35                  40                  45

Ala Val Ile Leu Tyr Asp Gly Ser Asn Lys Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Ser Trp Tyr Pro Asp Ser Phe Asp Ile Trp Gly
            100                 105                 110

Gln Gly Thr Met Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
    195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380
```

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 45
<211> LENGTH: 450
<212> TYPE: PRT
<213> ORGANISM: Artificial Sequence
<220> FEATURE:
<223> OTHER INFORMATION: Synthetic: Ab 4C3 full length HC

<400> SEQUENCE: 45

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Lys Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Gly Tyr Tyr Val Ile Leu Thr Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 46
<211> LENGTH: 451
<212> TYPE: PRT
<213> ORGANISM: Artificial Sequence
<220> FEATURE:
<223> OTHER INFORMATION: Synthetic: Ab 6E11 full length HC

<400> SEQUENCE: 46

Glu Val Gln Leu Val Glu Ser Gly Gly Ala Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Gly Gly Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Arg Tyr Tyr Ser Ser Trp Leu Leu Phe Asp Asn Trp Gly
            100                 105                 110

Gln Gly Ile Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 47
<211> LENGTH: 446
<212> TYPE: PRT
<213> ORGANISM: Artificial Sequence
<220> FEATURE:
<223> OTHER INFORMATION: Synthetic: Ab CD73.10 IgG2 C219S full length
      HC

<400> SEQUENCE: 47

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Glu Ser Asn Lys Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Ser Trp Tyr Pro Asp Ser Phe Asp Ile Trp Gly
            100                 105                 110

Gln Gly Thr Met Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 48
<211> LENGTH: 446
<212> TYPE: PRT
<213> ORGANISM: Artificial Sequence
<220> FEATURE:
<223> OTHER INFORMATION: Synthetic: Ab CD73.10 IgG2 C219S IgG1.1 full
      length HC

<400> SEQUENCE: 48

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr

```
               20                  25                  30
Gly Met His Trp Val Arg Gln Ala Pro Gly Lys Gly Leu Glu Trp Val
            35                  40                  45
Ala Val Ile Trp Tyr Asp Glu Ser Asn Lys Tyr Tyr Pro Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Gly Ser Ser Trp Tyr Pro Asp Ser Phe Asp Ile Trp Gly
            100                 105                 110
Gln Gly Thr Met Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
            195                 200                 205
Lys Pro Ser Asn Thr Lys Val Asp Lys Thr Val Glu Arg Lys Ser Cys
            210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
            290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
            435                 440                 445
```

<210> SEQ ID NO 49
<211> LENGTH: 450
<212> TYPE: PRT
<213> ORGANISM: Artificial Sequence
<220> FEATURE:
<223> OTHER INFORMATION: Synthetic: Ab CD73.10 IgG1.1 full length HC
      (IgG1.1 IgG1.1(L234A/L235E/G237A) IgG1.1(A330S/P331S) IgG1.1)

<400> SEQUENCE: 49

```
Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
                35                  40                  45

Ala Val Ile Trp Tyr Asp Glu Ser Asn Lys Tyr Tyr Pro Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Ser Trp Tyr Pro Asp Ser Phe Asp Ile Trp Gly
                100                 105                 110

Gln Gly Thr Met Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Glu Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
```

-continued

```
                355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly
    450

<210> SEQ ID NO 50
<211> LENGTH: 446
<212> TYPE: PRT
<213> ORGANISM: Artificial Sequence
<220> FEATURE:
<223> OTHER INFORMATION: Synthetic: Ab CD73.4 IgG2 C219S full length HC

<400> SEQUENCE: 50

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Asn Tyr
            20                  25                  30
Gly Met His Trp Val Arg Gln Ala Pro Gly Lys Gly Leu Glu Trp Val
        35                  40                  45
Ala Val Ile Leu Tyr Asp Gly Ser Asn Lys Tyr Tyr Pro Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Gly Ser Ser Trp Tyr Pro Asp Ser Phe Asp Ile Trp Gly
            100                 105                 110
Gln Gly Thr Met Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
        195                 200                 205
Lys Pro Ser Asn Thr Lys Val Asp Lys Thr Val Glu Arg Lys Ser Cys
    210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
```

-continued

```
                260                 265                 270
Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
        290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445
```

<210> SEQ ID NO 51
<211> LENGTH: 449
<212> TYPE: PRT
<213> ORGANISM: Artificial Sequence
<220> FEATURE:
<223> OTHER INFORMATION: Synthetic: Ab CD73.3 IgG1.1 full length HC
      (IgG1.1 IgG1.1(L234A/L235E/G237A) IgG1.1(A330S/P331S) IgG1.1)

<400> SEQUENCE: 51

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Lys Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Val Leu Tyr Tyr Cys
                85                  90                  95

Val Lys Gly Tyr Tyr Val Ile Leu Thr Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Ala Glu Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 52
<211> LENGTH: 326
<212> TYPE: PRT
<213> ORGANISM: Artificial Sequence
<220> FEATURE:
<223> OTHER INFORMATION: Synthetic: Full length heavy chain constant
      region IgG2 IgG2 IgG2 IgG2

<400> SEQUENCE: 52

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80
```

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
        100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 53
<211> LENGTH: 330
<212> TYPE: PRT
<213> ORGANISM: Artificial Sequence
<220> FEATURE:
<223> OTHER INFORMATION: Synthetic: Full length heavy chain constant
      region IgG1 IgG1 IgG1 IgG1

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 54
<211> LENGTH: 329
<212> TYPE: PRT
<213> ORGANISM: Artificial Sequence
<220> FEATURE:
<223> OTHER INFORMATION: Synthetic: Full length heavy chain constant
      region IgG1 IgG1.1(L234A/L235E/G237A) IgG1.1 (A330S/P331S) IgG1

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
            115                 120                 125

Lys Pro Lys Asp Thr Leu Met Ile Ser Arg Thr Pro Glu Val Thr Cys

```
              130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ser Ser Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 55
<211> LENGTH: 326
<212> TYPE: PRT
<213> ORGANISM: Artificial Sequence
<220> FEATURE:
<223> OTHER INFORMATION: Synthetic: Full length heavy chain constant
      region IgG2 IgG2/IgG1 hybrid IgG1 IgG1

<400> SEQUENCE: 55

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160
```

```
Gly Val Glu Val His Asn Ala Lys Thr Lys Pro Arg Glu Glu Gln Tyr
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly
                325

<210> SEQ ID NO 56
<211> LENGTH: 325
<212> TYPE: PRT
<213> ORGANISM: Artificial Sequence
<220> FEATURE:
<223> OTHER INFORMATION: Synthetic: Full length heavy chain constant
      region IgG2 IgG2 IgG1.1(A330/P331S) IgG1

<400> SEQUENCE: 56

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190
```

Leu Asn Gly Lys Glu Tyr Lys Cys Lys Val Ser Asn Lys Ala Leu Pro
            195                 200                 205

Ser Ser Ile Glu Lys Thr Ile Ser Lys Ala Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 57
<211> LENGTH: 5
<212> TYPE: PRT
<213> ORGANISM: Artificial Sequence
<220> FEATURE:
<223> OTHER INFORMATION: Synthetic: Table 2   hinge domain

<400> SEQUENCE: 57

Val Asp Lys Arg Val
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic: Table 2   hinge domain

<400> SEQUENCE: 58

Val Asp Lys Thr Val
1               5

<210> SEQ ID NO 59
<211> LENGTH: 10
<212> TYPE: PRT
<213> ORGANISM: Artificial Sequence
<220> FEATURE:
<223> OTHER INFORMATION: Synthetic: Table 2   hinge domain

<400> SEQUENCE: 59

Glu Pro Lys Ser Cys Asp Lys Thr His Thr
1               5                   10

<210> SEQ ID NO 60
<211> LENGTH: 3
<212> TYPE: PRT
<213> ORGANISM: Artificial Sequence
<220> FEATURE:
<223> OTHER INFORMATION: Synthetic: Table 2   hinge domain

<400> SEQUENCE: 60

Glu Arg Lys
1

```
<210> SEQ ID NO 61
<211> LENGTH: 12
<212> TYPE: PRT
<213> ORGANISM: Artificial Sequence
<220> FEATURE:
<223> OTHER INFORMATION: Synthetic: Table 2  hinge domain

<400> SEQUENCE: 61

Glu Leu Lys Thr Pro Leu Gly Asp Thr Thr His Thr
1               5                   10

<210> SEQ ID NO 62
<211> LENGTH: 4
<212> TYPE: PRT
<213> ORGANISM: Artificial Sequence
<220> FEATURE:
<223> OTHER INFORMATION: Synthetic: Table 2  hinge domain

<400> SEQUENCE: 62

Glu Pro Lys Ser
1

<210> SEQ ID NO 63
<211> LENGTH: 7
<212> TYPE: PRT
<213> ORGANISM: Artificial Sequence
<220> FEATURE:
<223> OTHER INFORMATION: Synthetic: Table 2  hinge domain

<400> SEQUENCE: 63

Glu Ser Lys Tyr Gly Pro Pro
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic: Table 2  hinge domain

<400> SEQUENCE: 64

Cys Pro Pro Cys Pro
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic: Table 2  hinge domain

<400> SEQUENCE: 65

Cys Cys Val Glu Cys Pro Pro Cys Pro
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic: Table 2  hinge domain

<400> SEQUENCE: 66

Cys Pro Arg Cys Pro
1               5
```

<210> SEQ ID NO 67
<211> LENGTH: 15
<212> TYPE: PRT
<213> ORGANISM: Artificial Sequence
<220> FEATURE:
<223> OTHER INFORMATION: Synthetic: Table 2  hinge domain

<400> SEQUENCE: 67

Glu Pro Lys Ser Cys Asp Thr Pro Pro Cys Pro Arg Cys Pro
1               5                   10                  15

<210> SEQ ID NO 68
<211> LENGTH: 11
<212> TYPE: PRT
<213> ORGANISM: Artificial Sequence
<220> FEATURE:
<223> OTHER INFORMATION: Synthetic: Table 2  hinge domain

<400> SEQUENCE: 68

Cys Asp Thr Pro Pro Cys Pro Arg Cys Pro
1               5                   10

<210> SEQ ID NO 69
<211> LENGTH: 5
<212> TYPE: PRT
<213> ORGANISM: Artificial Sequence
<220> FEATURE:
<223> OTHER INFORMATION: Synthetic: Table 2  hinge domain

<400> SEQUENCE: 69

Cys Pro Ser Cys Pro
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic: Table 2  hinge domain

<400> SEQUENCE: 70

Ala Pro Glu Leu Leu Gly Gly
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic: Table 2  hinge domain

<400> SEQUENCE: 71

Ala Pro Pro Val Ala Gly
1               5

<210> SEQ ID NO 72
<211> LENGTH: 214
<212> TYPE: PRT
<213> ORGANISM: Artificial Sequence
<220> FEATURE:
<223> OTHER INFORMATION: Synthetic: Light chain 11F11

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp

```
                    20                  25                  30
Leu Ala Trp Tyr Gln Gln Lys Pro Glu Lys Ala Pro Lys Ser Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Leu
                85                  90                  95
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
            195                 200                 205
Phe Asn Arg Gly Glu Cys
    210

<210> SEQ ID NO 73
<211> LENGTH: 214
<212> TYPE: PRT
<213> ORGANISM: Artificial Sequence
<220> FEATURE:
<223> OTHER INFORMATION: Synthetic: Light chain 4C3

<400> SEQUENCE: 73

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Tyr
                20                  25                  30
Leu Ala Trp Tyr Gln Gln Lys Pro Gly Gln Ala Pro Arg Leu Leu Ile
            35                  40                  45
Tyr Gly Ala Ser Ser Arg Ala Thr Gly Ile Pro Asp Arg Phe Ser Gly
        50                  55                  60
Ser Gly Ser Gly Thr Asp Phe Thr Leu Thr Ile Ser Arg Leu Glu Pro
65                  70                  75                  80
Glu Asp Phe Ala Val Tyr Tyr Cys Gln Gln Tyr Gly Ser Ser Pro Leu
                85                  90                  95
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
```

165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 74
<211> LENGTH: 214
<212> TYPE: PRT
<213> ORGANISM: Artificial Sequence
<220> FEATURE:
<223> OTHER INFORMATION: Synthetic: Light chain 6D11

<400> SEQUENCE: 74

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 75
<211> LENGTH: 124
<212> TYPE: PRT
<213> ORGANISM: Artificial Sequence
<220> FEATURE:
<223> OTHER INFORMATION: Synthetic: Anti GITR AbVH

<400> SEQUENCE: 75

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Glu Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Ser Met Val Arg Gly Asp Tyr Tyr Tyr Gly Met Asp
                100                 105                 110

Val Trp Gly Gln Gly Thr Thr Val Thr Val Ser Ser
            115                 120

<210> SEQ ID NO 76
<211> LENGTH: 107
<212> TYPE: PRT
<213> ORGANISM: Artificial Sequence
<220> FEATURE:
<223> OTHER INFORMATION: Synthetic: Anti GITR Ab VL

<400> SEQUENCE: 76

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Tyr
                 85                  90                  95

Thr Phe Gly Gln Gly Thr Lys Leu Glu Ile Lys
                100                 105

<210> SEQ ID NO 77
<211> LENGTH: 214
<212> TYPE: PRT
<213> ORGANISM: Artificial Sequence
<220> FEATURE:
<223> OTHER INFORMATION: Synthetic: Anti GITR Ab LC

<400> SEQUENCE: 77

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Tyr
                 85                  90                  95

Thr Phe Gly Gln Gly Thr Lys Leu Glu Ile Lys Arg Thr Val Ala Ala
                100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 78
<211> LENGTH: 330
<212> TYPE: PRT
<213> ORGANISM: Artificial Sequence
<220> FEATURE:
<223> OTHER INFORMATION: Synthetic: IgG1f

<400> SEQUENCE: 78

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

-continued

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 79
<211> LENGTH: 326
<212> TYPE: PRT
<213> ORGANISM: Artificial Sequence
<220> FEATURE:
<223> OTHER INFORMATION: Synthetic: IgG2.3

<400> SEQUENCE: 79

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

Leu Thr Val Asp Lys Ser Arg Trp Gln Gln Gly Asn Val Phe Ser Cys
            290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 80
<211> LENGTH: 327
<212> TYPE: PRT
<213> ORGANISM: Artificial Sequence
<220> FEATURE:
<223> OTHER INFORMATION: Synthetic: IgG2.3G1 AY

<400> SEQUENCE: 80

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys
            325

<210> SEQ ID NO 81
<211> LENGTH: 326
<212> TYPE: PRT
<213> ORGANISM: Artificial Sequence
<220> FEATURE:
<223> OTHER INFORMATION: Synthetic: IgG2.3G1 KH

<400> SEQUENCE: 81

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 82

<211> LENGTH: 326
<212> TYPE: PRT
<213> ORGANISM: Artificial Sequence
<220> FEATURE:
<223> OTHER INFORMATION: Synthetic: IgG2.5

<400> SEQUENCE: 82

```
Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 83
<211> LENGTH: 330
<212> TYPE: PRT
<213> ORGANISM: Artificial Sequence
<220> FEATURE:
<223> OTHER INFORMATION: Synthetic: IgG1.1f

```
<400> SEQUENCE: 83

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 84
<211> LENGTH: 326
<212> TYPE: PRT
<213> ORGANISM: Artificial Sequence
<220> FEATURE:
<223> OTHER INFORMATION: Synthetic: IgG2.3G1.1f KH

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
```

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
            165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
            195                 200                 205

Ser Ser Ile Glu Lys Thr Ile Ser Lys Ala Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 85
<211> LENGTH: 327
<212> TYPE: PRT
<213> ORGANISM: Artificial Sequence
<220> FEATURE:
<223> OTHER INFORMATION: Synthetic: IgG1 deltaTHT

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
                    50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Arg Val Glu Pro Lys Ser Cys Asp Lys Cys Pro Pro Cys Pro Ala Pro
                    100                 105                 110

Glu Leu Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
            130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
            325

<210> SEQ ID NO 86
<211> LENGTH: 329
<212> TYPE: PRT
<213> ORGANISM: Artificial Sequence
<220> FEATURE:
<223> OTHER INFORMATION: Synthetic: IgG2.3 plusTHT

<400> SEQUENCE: 86

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
```

```
                    85                  90                  95
Thr Val Glu Arg Lys Ser Cys Val Glu Thr His Thr Cys Pro Pro Cys
            100                 105                 110

Pro Ala Pro Pro Val Ala Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 87
<211> LENGTH: 329
<212> TYPE: PRT
<213> ORGANISM: Artificial Sequence
<220> FEATURE:
<223> OTHER INFORMATION: Synthetic: IgG2.3 plusGGG

<400> SEQUENCE: 87

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Gly Gly Gly Cys Pro Pro Cys
            100                 105                 110

Pro Ala Pro Pro Val Ala Gly Pro Ser Val Phe Leu Phe Pro Pro Lys
```

```
            115                 120                 125
Pro Lys Asp Thr Leu Met Ile Ser Arg Thr Pro Glu Val Thr Cys Val
130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
            165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
            195                 200                 205

Gly Leu Pro Ala Pro Ile Glu Lys Thr Ile Ser Lys Thr Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
            275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                    325

<210> SEQ ID NO 88
<211> LENGTH: 326
<212> TYPE: PRT
<213> ORGANISM: Artificial Sequence
<220> FEATURE:
<223> OTHER INFORMATION: Synthetic: IgG2.5G1.1f KH

<400> SEQUENCE: 88

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
```

```
                145                 150                 155                 160
        Val Glu Val His Asn Ala Lys Thr Lys Pro Arg Glu Glu Gln Tyr Asn
                            165                 170                 175

Ser Thr Tyr Arg Val Val Ser Val Leu Thr Val Leu His Gln Asp Trp
                            180                 185                 190

Leu Asn Gly Lys Glu Tyr Lys Cys Lys Val Ser Asn Lys Ala Leu Pro
                            195                 200                 205

Ser Ser Ile Glu Lys Thr Ile Ser Lys Ala Lys Gly Gln Pro Arg Glu
                            210                 215                 220

Pro Gln Val Tyr Thr Leu Pro Pro Ser Arg Glu Glu Met Thr Lys Asn
        225                 230                 235                 240

Gln Val Ser Leu Thr Cys Leu Val Lys Gly Phe Tyr Pro Ser Asp Ile
                            245                 250                 255

Ala Val Glu Trp Glu Ser Asn Gly Gln Pro Glu Asn Asn Tyr Lys Thr
                            260                 265                 270

Thr Pro Pro Val Leu Asp Ser Asp Gly Ser Phe Phe Leu Tyr Ser Lys
                            275                 280                 285

Leu Thr Val Asp Lys Ser Arg Trp Gln Gln Gly Asn Val Phe Ser Cys
                            290                 295                 300

Ser Val Met His Glu Ala Leu His Asn His Tyr Thr Gln Lys Ser Leu
        305                 310                 315                 320

Ser Leu Ser Pro Gly Lys
                            325

<210> SEQ ID NO 89
<211> LENGTH: 327
<212> TYPE: PRT
<213> ORGANISM: Artificial Sequence
<220> FEATURE:
<223> OTHER INFORMATION: Synthetic: IgG2.5G1 AY

<400> SEQUENCE: 89

Ala Ser Thr Lys Gly Pro Ser Val Phe Pro Leu Ala Pro Ser Ser Arg
        1               5                   10                  15

Ser Thr Ser Glu Ser Thr Ala Ala Leu Gly Cys Leu Val Lys Asp Tyr
                            20                  25                  30

Phe Pro Glu Pro Val Thr Val Ser Trp Asn Ser Gly Ala Leu Thr Ser
                            35                  40                  45

Gly Val His Thr Phe Pro Ala Val Leu Gln Ser Ser Gly Leu Tyr Ser
                    50                  55                  60

Leu Ser Ser Val Val Thr Val Pro Ser Ser Asn Phe Gly Thr Gln Thr
        65                  70                  75                  80

Tyr Thr Cys Asn Val Asp His Lys Pro Ser Asn Thr Lys Val Asp Lys
                            85                  90                  95

Thr Val Glu Arg Lys Cys Cys Val Glu Cys Pro Pro Cys Pro Ala Pro
                            100                 105                 110

Glu Leu Leu Gly Gly Pro Ser Val Phe Leu Phe Pro Pro Lys Pro Lys
                            115                 120                 125

Asp Thr Leu Met Ile Ser Arg Thr Pro Glu Val Thr Cys Val Val Val
        130                 135                 140

Asp Val Ser His Glu Asp Pro Glu Val Lys Phe Asn Trp Tyr Val Asp
        145                 150                 155                 160

Gly Val Glu Val His Asn Ala Lys Thr Lys Pro Arg Glu Glu Gln Tyr
                            165                 170                 175

Asn Ser Thr Tyr Arg Val Val Ser Val Leu Thr Val Leu His Gln Asp
```

```
                180                 185                 190
Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Gly Gln Pro Arg
        210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 90
<211> LENGTH: 326
<212> TYPE: PRT
<213> ORGANISM: Artificial Sequence
<220> FEATURE:
<223> OTHER INFORMATION: Synthetic: IgG2.5G1 KH

<400> SEQUENCE: 90

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
```

```
            210                 215                 220
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 91
<211> LENGTH: 329
<212> TYPE: PRT
<213> ORGANISM: Artificial Sequence
<220> FEATURE:
<223> OTHER INFORMATION: Synthetic: IgG2.5 plusTHT

<400> SEQUENCE: 91

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
```

```
                    245                 250                 255

Ser Asp Ile Ala Val Glu Trp Glu Ser Asn Gly Gln Pro Glu Asn Asn
                260                 265                 270

Tyr Lys Thr Thr Pro Pro Met Leu Asp Ser Asp Gly Ser Phe Phe Leu
            275                 280                 285

Tyr Ser Lys Leu Thr Val Asp Lys Ser Arg Trp Gln Gln Gly Asn Val
        290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 92
<211> LENGTH: 327
<212> TYPE: PRT
<213> ORGANISM: Artificial Sequence
<220> FEATURE:
<223> OTHER INFORMATION: Synthetic: IgG1 G2.3G1 AY

<400> SEQUENCE: 92

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Arg Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
```

```
            275                 280                 285
Lys Leu Thr Val Asp Lys Ser Arg Trp Gln Gln Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Pro Gly Lys
                325

<210> SEQ ID NO 93
<211> LENGTH: 326
<212> TYPE: PRT
<213> ORGANISM: Artificial Sequence
<220> FEATURE:
<223> OTHER INFORMATION: Synthetic: IgG1 G2.3G1 KH

<400> SEQUENCE: 93

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Arg Lys Ser Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
    130                 135                 140
Val Ser His Glu Asp Pro Glu Val Lys Phe Asn Trp Tyr Val Asp Gly
145                 150                 155                 160
Val Glu Val His Asn Ala Lys Thr Lys Pro Arg Glu Glu Gln Tyr Asn
                165                 170                 175
Ser Thr Tyr Arg Val Val Ser Val Leu Thr Val Leu His Gln Asp Trp
            180                 185                 190
Leu Asn Gly Lys Glu Tyr Lys Cys Lys Val Ser Asn Lys Ala Leu Pro
        195                 200                 205
Ala Pro Ile Glu Lys Thr Ile Ser Lys Ala Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Val Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
```

Ser Leu Ser Pro Gly Lys
            325

<210> SEQ ID NO 94
<211> LENGTH: 330
<212> TYPE: PRT
<213> ORGANISM: Artificial Sequence
<220> FEATURE:
<223> OTHER INFORMATION: Synthetic: G2 G1 G1 G1

<400> SEQUENCE: 94

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 95
<211> LENGTH: 330
<212> TYPE: PRT
<213> ORGANISM: Artificial Sequence
<220> FEATURE:
<223> OTHER INFORMATION: Synthetic: G2.5 G1 G1 G1

<400> SEQUENCE: 95

```
Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 96
<211> LENGTH: 326
<212> TYPE: PRT
<213> ORGANISM: Artificial Sequence
<220> FEATURE:
<223> OTHER INFORMATION: Synthetic: G1 G2.3 G2 G2

<400> SEQUENCE: 96

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325
```

<210> SEQ ID NO 97
<211> LENGTH: 330
<212> TYPE: PRT
<213> ORGANISM: Artificial Sequence
<220> FEATURE:
<223> OTHER INFORMATION: Synthetic: G1 KRGEGSSNLF

<400> SEQUENCE: 97

```
Ala Ser Thr Lys Gly Pro Ser Val Phe Pro Leu Ala Pro Ser Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
 65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 98
<211> LENGTH: 330
<212> TYPE: PRT
<213> ORGANISM: Artificial Sequence
<220> FEATURE:
<223> OTHER INFORMATION: Synthetic: G1 KRGEGS

<400> SEQUENCE: 98

Ala Ser Thr Lys Gly Pro Ser Val Phe Pro Leu Ala Pro Ser Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 99
<211> LENGTH: 330
<212> TYPE: PRT
<213> ORGANISM: Artificial Sequence
<220> FEATURE:
<223> OTHER INFORMATION: Synthetic: G1 SNLF

<400> SEQUENCE: 99

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80
```

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 100
<211> LENGTH: 330
<212> TYPE: PRT
<213> ORGANISM: Artificial Sequence
<220> FEATURE:
<223> OTHER INFORMATION: Synthetic: IgG1 ITNDRTPR

<400> SEQUENCE: 100

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 101
<211> LENGTH: 329
<212> TYPE: PRT
<213> ORGANISM: Artificial Sequence
<220> FEATURE:
<223> OTHER INFORMATION: Synthetic: G1 SNLFPR

<400> SEQUENCE: 101

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Ile Cys Asn Val Asn His Lys Pro Ser Asn Thr Lys Val Asp Lys
                85                  90                  95

Arg Val Glu Arg Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 102
<211> LENGTH: 326
<212> TYPE: PRT
<213> ORGANISM: Artificial Sequence
<220> FEATURE:
<223> OTHER INFORMATION: Synthetic: G2 RKEGSGNSFL

<400> SEQUENCE: 102

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Ser Cys Val Glu Cys Pro Pro Cys Pro Ala Pro
        100                 105                 110

Pro Val Ala Gly Pro Ser Val Phe Leu Phe Pro Pro Lys Pro Lys Asp
    115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175
```

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 103
<211> LENGTH: 326
<212> TYPE: PRT
<213> ORGANISM: Artificial Sequence
<220> FEATURE:
<223> OTHER INFORMATION: Synthetic: G2 RKEGSG

<400> SEQUENCE: 103

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 104
<211> LENGTH: 326
<212> TYPE: PRT
<213> ORGANISM: Artificial Sequence
<220> FEATURE:
<223> OTHER INFORMATION: Synthetic: G2 NSFL

<400> SEQUENCE: 104

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

```
Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 105
<211> LENGTH: 326
<212> TYPE: PRT
<213> ORGANISM: Artificial Sequence
<220> FEATURE:
<223> OTHER INFORMATION: Synthetic: IgG2 TIDNTRRP

<400> SEQUENCE: 105

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

```
Thr Pro Pro Met Leu Asp Ser Asp Gly Ser Phe Phe Leu Tyr Ser Lys
            275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 106
<211> LENGTH: 326
<212> TYPE: PRT
<213> ORGANISM: Artificial Sequence
<220> FEATURE:
<223> OTHER INFORMATION: Synthetic: G2 NSFLRP

<400> SEQUENCE: 106

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Thr Cys Asn Val Asp His Lys Pro Ser Asn Thr Lys Val Asp Lys
                85                  90                  95
Thr Val Glu Pro Lys Ser Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
    130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
```

Ser Val Met His Glu Ala Leu His Asn His Tyr Thr Gln Lys Ser Leu
305                 310                 315                 320

Ser Leu Ser Pro Gly Lys
                325

<210> SEQ ID NO 107
<211> LENGTH: 330
<212> TYPE: PRT
<213> ORGANISM: Artificial Sequence
<220> FEATURE:
<223> OTHER INFORMATION: Synthetic: G1 G1 G2 G1 AY

<400> SEQUENCE: 107

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Gly Leu Pro Ala Pro Ile Glu Lys Thr Ile Ser Lys Thr Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 108
<211> LENGTH: 329
<212> TYPE: PRT
<213> ORGANISM: Artificial Sequence
<220> FEATURE:
<223> OTHER INFORMATION: Synthetic: G1 G1 G2 G1 KH

<400> SEQUENCE: 108

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 109
<211> LENGTH: 326
<212> TYPE: PRT
<213> ORGANISM: Artificial Sequence
<220> FEATURE:

<223> OTHER INFORMATION: Synthetic: G2 G2.3 G1 G2 KH

<400> SEQUENCE: 109

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 110
<211> LENGTH: 326
<212> TYPE: PRT
<213> ORGANISM: Artificial Sequence
<220> FEATURE:
<223> OTHER INFORMATION: Synthetic: G2.5 G2.3 G1 G2 KH

<400> SEQUENCE: 110

```
Ala Ser Thr Lys Gly Pro Ser Val Phe Pro Leu Ala Pro Ser Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 111
<211> LENGTH: 326
<212> TYPE: PRT
<213> ORGANISM: Artificial Sequence
<220> FEATURE:
<223> OTHER INFORMATION: Synthetic: G2 G2.3 G1 G2 AY

<400> SEQUENCE: 111

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Ser Cys Val Cys Pro Pro Cys Pro Ala Pro
            100                 105                 110

Glu Leu Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Ala Leu
                195                 200                 205

Pro Ala Pro Ile Glu Lys Thr Ile Ser Lys Ala Lys Gly Gln Pro Arg
            210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Met Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro Gly
                325

<210> SEQ ID NO 112
<211> LENGTH: 327
<212> TYPE: PRT
<213> ORGANISM: Artificial Sequence
<220> FEATURE:
<223> OTHER INFORMATION: Synthetic: G2.5 G2.3 G1 G2 AY

<400> SEQUENCE: 112

Ala Ser Thr Lys Gly Pro Ser Val Phe Pro Leu Ala Pro Ser Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80
```

```
Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Met Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 113
<211> LENGTH: 326
<212> TYPE: PRT
<213> ORGANISM: Artificial Sequence
<220> FEATURE:
<223> OTHER INFORMATION: Synthetic: G1 G2.3 G1 G1 KH

<400> SEQUENCE: 113

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Val Glu Cys Pro Pro Cys Pro Ala Pro
            100                 105                 110
```

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 114
<211> LENGTH: 330
<212> TYPE: PRT
<213> ORGANISM: Artificial Sequence
<220> FEATURE:
<223> OTHER INFORMATION: Synthetic: G2 G1 G2 G2 AY

<400> SEQUENCE: 114

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Gly Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 115
<211> LENGTH: 330
<212> TYPE: PRT
<213> ORGANISM: Artificial Sequence
<220> FEATURE:
<223> OTHER INFORMATION: Synthetic: G2.5 G1 G2 G2 AY

<400> SEQUENCE: 115

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

```
Glu Gln Phe Asn Ser Thr Phe Arg Val Val Ser Val Leu Thr Val Val
                180                 185                 190

His Gln Asp Trp Leu Asn Gly Lys Glu Tyr Lys Cys Lys Val Ser Asn
            195                 200                 205

Lys Gly Leu Pro Ala Pro Ile Glu Lys Thr Ile Ser Lys Thr Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 116
<211> LENGTH: 327
<212> TYPE: PRT
<213> ORGANISM: Artificial Sequence
<220> FEATURE:
<223> OTHER INFORMATION: Synthetic: G1 G2 G1 G1 AY

<400> SEQUENCE: 116

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205
```

```
Pro Ala Pro Ile Glu Lys Thr Ile Ser Lys Ala Lys Gly Gln Pro Arg
        210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 117
<211> LENGTH: 328
<212> TYPE: PRT
<213> ORGANISM: Artificial Sequence
<220> FEATURE:
<223> OTHER INFORMATION: Synthetic: G2 G1 G2 G2 KH

<400> SEQUENCE: 117

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240
```

```
Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 118
<211> LENGTH: 329
<212> TYPE: PRT
<213> ORGANISM: Artificial Sequence
<220> FEATURE:
<223> OTHER INFORMATION: Synthetic: G2.5 G1 G2 G2 KH

<400> SEQUENCE: 118

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270
```

```
Tyr Lys Thr Thr Pro Pro Met Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 119
<211> LENGTH: 323
<212> TYPE: PRT
<213> ORGANISM: Artificial Sequence
<220> FEATURE:
<223> OTHER INFORMATION: Synthetic: IgG1 deltaHinge

<400> SEQUENCE: 119

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Cys Pro Pro Cys Pro Ala Pro Glu Leu Leu Gly
            100                 105                 110

Gly Pro Ser Val Phe Leu Phe Pro Pro Lys Pro Lys Asp Thr Leu Met
        115                 120                 125

Ile Ser Arg Thr Pro Glu Val Thr Cys Val Val Val Asp Val Ser His
    130                 135                 140

Glu Asp Pro Glu Val Lys Phe Asn Trp Tyr Val Asp Gly Val Glu Val
145                 150                 155                 160

His Asn Ala Lys Thr Lys Pro Arg Glu Glu Gln Tyr Asn Ser Thr Tyr
                165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Ala Leu Pro Ala Pro Ile
        195                 200                 205

Glu Lys Thr Ile Ser Lys Ala Lys Gly Gln Pro Arg Glu Pro Gln Val
    210                 215                 220

Tyr Thr Leu Pro Pro Ser Arg Glu Glu Met Thr Lys Asn Gln Val Ser
225                 230                 235                 240

Leu Thr Cys Leu Val Lys Gly Phe Tyr Pro Ser Asp Ile Ala Val Glu
                245                 250                 255

Trp Glu Ser Asn Gly Gln Pro Glu Asn Asn Tyr Lys Thr Thr Pro Pro
            260                 265                 270

Val Leu Asp Ser Asp Gly Ser Phe Phe Leu Tyr Ser Lys Leu Thr Val
        275                 280                 285

Asp Lys Ser Arg Trp Gln Gln Gly Asn Val Phe Ser Cys Ser Val Met
    290                 295                 300
```

```
His Glu Ala Leu His Asn His Tyr Thr Gln Lys Ser Leu Ser Leu Ser
305                 310                 315                 320

Pro Gly Lys

<210> SEQ ID NO 120
<211> LENGTH: 322
<212> TYPE: PRT
<213> ORGANISM: Artificial Sequence
<220> FEATURE:
<223> OTHER INFORMATION: Synthetic: IgG2 deltaHinge

<400> SEQUENCE: 120

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Pro Pro Cys Pro Ala Pro Pro Val Ala Gly
            100                 105                 110

Pro Ser Val Phe Leu Phe Pro Pro Lys Pro Lys Asp Thr Leu Met Ile
            115                 120                 125

Ser Arg Thr Pro Glu Val Thr Cys Val Val Val Asp Val Ser His Glu
130                 135                 140

Asp Pro Glu Val Gln Phe Asn Trp Tyr Val Asp Gly Val Glu Val His
145                 150                 155                 160

Asn Ala Lys Thr Lys Pro Arg Glu Glu Gln Phe Asn Ser Thr Phe Arg
                165                 170                 175

Val Val Ser Val Leu Thr Val Val His Gln Asp Trp Leu Asn Gly Lys
            180                 185                 190

Glu Tyr Lys Cys Lys Val Ser Asn Lys Gly Leu Pro Ala Pro Ile Glu
        195                 200                 205

Lys Thr Ile Ser Lys Thr Lys Gly Gln Pro Arg Glu Pro Gln Val Tyr
    210                 215                 220

Thr Leu Pro Pro Ser Arg Glu Glu Met Thr Lys Asn Gln Val Ser Leu
225                 230                 235                 240

Thr Cys Leu Val Lys Gly Phe Tyr Pro Ser Asp Ile Ala Val Glu Trp
                245                 250                 255

Glu Ser Asn Gly Gln Pro Glu Asn Asn Tyr Lys Thr Thr Pro Pro Met
            260                 265                 270

Leu Asp Ser Asp Gly Ser Phe Phe Leu Tyr Ser Lys Leu Thr Val Asp
        275                 280                 285

Lys Ser Arg Trp Gln Gln Gly Asn Val Phe Ser Cys Ser Val Met His
    290                 295                 300

Glu Ala Leu His Asn His Tyr Thr Gln Lys Ser Leu Ser Leu Ser Pro
305                 310                 315                 320

Gly Lys
```

<210> SEQ ID NO 121
<211> LENGTH: 322
<212> TYPE: PRT
<213> ORGANISM: Artificial Sequence
<220> FEATURE:
<223> OTHER INFORMATION: Synthetic: IgG2.5 deltaHinge

<400> SEQUENCE: 121

```
Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Pro Pro Cys Pro Ala Pro Pro Val Ala Gly
            100                 105                 110

Pro Ser Val Phe Leu Phe Pro Pro Lys Pro Lys Asp Thr Leu Met Ile
        115                 120                 125

Ser Arg Thr Pro Glu Val Thr Cys Val Val Val Asp Val Ser His Glu
    130                 135                 140

Asp Pro Glu Val Gln Phe Asn Trp Tyr Val Asp Gly Val Glu Val His
145                 150                 155                 160

Asn Ala Lys Thr Lys Pro Arg Glu Glu Gln Phe Asn Ser Thr Phe Arg
                165                 170                 175

Val Val Ser Val Leu Thr Val Val His Gln Asp Trp Leu Asn Gly Lys
            180                 185                 190

Glu Tyr Lys Cys Lys Val Ser Asn Lys Gly Leu Pro Ala Pro Ile Glu
        195                 200                 205

Lys Thr Ile Ser Lys Thr Lys Gly Gln Pro Arg Glu Pro Gln Val Tyr
    210                 215                 220

Thr Leu Pro Pro Ser Arg Glu Glu Met Thr Lys Asn Gln Val Ser Leu
225                 230                 235                 240

Thr Cys Leu Val Lys Gly Phe Tyr Pro Ser Asp Ile Ala Val Glu Trp
                245                 250                 255

Glu Ser Asn Gly Gln Pro Glu Asn Asn Tyr Lys Thr Thr Pro Pro Met
            260                 265                 270

Leu Asp Ser Asp Gly Ser Phe Phe Leu Tyr Ser Lys Leu Thr Val Asp
        275                 280                 285

Lys Ser Arg Trp Gln Gln Gly Asn Val Phe Ser Cys Ser Val Met His
    290                 295                 300

Glu Ala Leu His Asn His Tyr Thr Gln Lys Ser Leu Ser Leu Ser Pro
305                 310                 315                 320

Gly Lys
```

<210> SEQ ID NO 122
<211> LENGTH: 328
<212> TYPE: PRT
<213> ORGANISM: Artificial Sequence
<220> FEATURE:
<223> OTHER INFORMATION: Synthetic: IgG1 deltaG237

<400> SEQUENCE: 122

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325
```

<210> SEQ ID NO 123
<211> LENGTH: 327
<212> TYPE: PRT
<213> ORGANISM: Artificial Sequence
<220> FEATURE:
<223> OTHER INFORMATION: Synthetic: IgG2 plusG237

<400> SEQUENCE: 123

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
```

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser His Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Phe Arg Val Val Ser Val Leu Thr Val His Gln Asp
            180                 185                 190

Trp Leu Asn Gly Lys Glu Tyr Lys Cys Lys Val Ser Asn Lys Gly Leu
        195                 200                 205

Pro Ala Pro Ile Glu Lys Thr Ile Ser Lys Thr Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Met Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 124
<211> LENGTH: 326
<212> TYPE: PRT
<213> ORGANISM: Artificial Sequence
<220> FEATURE:
<223> OTHER INFORMATION: Synthetic: IgG2.4

<400> SEQUENCE: 124

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
                    50                  55                  60
Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                     85                  90                  95

Thr Val Glu Arg Lys Cys Ser Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 125
<211> LENGTH: 326
<212> TYPE: PRT
<213> ORGANISM: Artificial Sequence
<220> FEATURE:
<223> OTHER INFORMATION: Synthetic: IgG2.3/4

<400> SEQUENCE: 125

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
```

```
                     85                  90                  95
Thr Val Glu Arg Lys Ser Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 126
<211> LENGTH: 18
<212> TYPE: PRT
<213> ORGANISM: Artificial Sequence
<220> FEATURE:
<223> OTHER INFORMATION: Synthetic: Hinge IgG2 C220S

<400> SEQUENCE: 126

Glu Arg Lys Cys Ser Val Glu Cys Pro Pro Cys Pro Ala Pro Pro Val
1               5                   10                  15

Ala Gly

<210> SEQ ID NO 127
<211> LENGTH: 19
<212> TYPE: PRT
<213> ORGANISM: Artificial Sequence
<220> FEATURE:
<223> OTHER INFORMATION: Synthetic: IgG2/IgG1 hybrid hinge C220S

<400> SEQUENCE: 127

Glu Arg Lys Cys Ser Val Glu Cys Pro Pro Cys Pro Ala Pro Glu Leu
1               5                   10                  15

Leu Gly Gly

<210> SEQ ID NO 128
```

```
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Wildtype IgG2 hinge portion

<400> SEQUENCE: 128

Glu Arg Lys Cys Cys Val Glu Cys Pro Pro Cys Pro Ala Pro
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Synthetic: IgG2 hinge portion C219S

<400> SEQUENCE: 129

Glu Arg Lys Ser Cys Val Glu Cys Pro Pro Cys Pro Ala Pro
1               5                   10

<210> SEQ ID NO 130
<211> LENGTH: 14
<212> TYPE: PRT
<213> ORGANISM: Artificial Sequence
<220> FEATURE:
<223> OTHER INFORMATION: Synthetic: IgG2 hinge portion C220S

<400> SEQUENCE: 130

Glu Arg Lys Cys Ser Val Glu Cys Pro Pro Cys Pro Ala Pro
1               5                   10

<210> SEQ ID NO 131
<211> LENGTH: 14
<212> TYPE: PRT
<213> ORGANISM: Artificial Sequence
<220> FEATURE:
<223> OTHER INFORMATION: Synthetic: IgG2 hinge portion C219X
<220> FEATURE:
<221> NAME/KEY: misc_feature
<222> LOCATION: (4)..(4)
<223> OTHER INFORMATION: Xaa is any amino acid, except cysteine

<400> SEQUENCE: 131

Glu Arg Lys Xaa Cys Val Glu Cys Pro Pro Cys Pro Ala Pro
1               5                   10

<210> SEQ ID NO 132
<211> LENGTH: 14
<212> TYPE: PRT
<213> ORGANISM: Artificial Sequence
<220> FEATURE:
<223> OTHER INFORMATION: Synthetic: IgG2 hinge portion C220X
<220> FEATURE:
<221> NAME/KEY: misc_feature
<222> LOCATION: (5)..(5)
<223> OTHER INFORMATION: Xaa is any amino acid, except cysteine

<400> SEQUENCE: 132

Glu Arg Lys Cys Xaa Val Glu Cys Pro Pro Cys Pro Ala Pro
1               5                   10

<210> SEQ ID NO 133
<211> LENGTH: 116
<212> TYPE: PRT
<213> ORGANISM: Homo sapiens
<220> FEATURE:
```

```
<221> NAME/KEY: misc_feature
<222> LOCATION: (1)..(116)
<223> OTHER INFORMATION: IgG2 CH1+IgG2 hinge (wildtype)

<400> SEQUENCE: 133

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly
            115

<210> SEQ ID NO 134
<211> LENGTH: 18
<212> TYPE: PRT
<213> ORGANISM: Artificial Sequence
<220> FEATURE:
<223> OTHER INFORMATION: Synthetic: IgG2 with C219X
<220> FEATURE:
<221> NAME/KEY: misc_feature
<222> LOCATION: (4)..(4)
<223> OTHER INFORMATION: Xaa is any amino acid, except cysteine

<400> SEQUENCE: 134

Glu Arg Lys Xaa Cys Val Glu Cys Pro Pro Cys Pro Ala Pro Pro Val
1               5                   10                  15

Ala Gly

<210> SEQ ID NO 135
<211> LENGTH: 18
<212> TYPE: PRT
<213> ORGANISM: Artificial Sequence
<220> FEATURE:
<223> OTHER INFORMATION: Synthetic: IgG2 with C220X
<220> FEATURE:
<221> NAME/KEY: misc_feature
<222> LOCATION: (5)..(5)
<223> OTHER INFORMATION: Xaa is any amino acid, except cysteine

<400> SEQUENCE: 135

Glu Arg Lys Cys Xaa Val Glu Cys Pro Pro Cys Pro Ala Pro Pro Val
1               5                   10                  15

Ala Gly

<210> SEQ ID NO 136
<211> LENGTH: 19
<212> TYPE: PRT
<213> ORGANISM: Artificial Sequence
<220> FEATURE:
<223> OTHER INFORMATION: Synthetic: IgG2/IgG1 hybrid with C219X
<220> FEATURE:
<221> NAME/KEY: misc_feature
<222> LOCATION: (4)..(4)
<223> OTHER INFORMATION: Xaa is any amino acid, except cysteine
```

```
<400> SEQUENCE: 136

Glu Arg Lys Xaa Cys Val Glu Cys Pro Pro Cys Pro Ala Pro Glu Leu
1               5                   10                  15

Leu Gly Gly

<210> SEQ ID NO 137
<211> LENGTH: 18
<212> TYPE: PRT
<213> ORGANISM: Artificial Sequence
<220> FEATURE:
<223> OTHER INFORMATION: Synthetic: IgG2/IgG1 hybrid with C220X

<400> SEQUENCE: 137

Glu Arg Lys Cys Val Glu Cys Pro Pro Cys Pro Ala Pro Glu Leu Leu
1               5                   10                  15

Gly Gly

<210> SEQ ID NO 138
<211> LENGTH: 18
<212> TYPE: PRT
<213> ORGANISM: Artificial Sequence
<220> FEATURE:
<223> OTHER INFORMATION: Synthetic: IgG2/IgG1 hybrid deltaG

<400> SEQUENCE: 138

Glu Arg Lys Cys Cys Val Glu Cys Pro Pro Cys Pro Ala Pro Glu Leu
1               5                   10                  15

Leu Gly

<210> SEQ ID NO 139
<211> LENGTH: 18
<212> TYPE: PRT
<213> ORGANISM: Artificial Sequence
<220> FEATURE:
<223> OTHER INFORMATION: Synthetic: IgG2/IgG1 hybrid with C219S deltaG

<400> SEQUENCE: 139

Glu Arg Lys Ser Cys Val Glu Cys Pro Pro Cys Pro Ala Pro Glu Leu
1               5                   10                  15

Leu Gly

<210> SEQ ID NO 140
<211> LENGTH: 18
<212> TYPE: PRT
<213> ORGANISM: Artificial Sequence
<220> FEATURE:
<223> OTHER INFORMATION: Synthetic: IgG2/IgG1 hybrid with C220S deltaG

<400> SEQUENCE: 140

Glu Arg Lys Cys Ser Val Glu Cys Pro Pro Cys Pro Ala Pro Glu Leu
1               5                   10                  15

Leu Gly

<210> SEQ ID NO 141
<211> LENGTH: 18
<212> TYPE: PRT
<213> ORGANISM: Artificial Sequence
<220> FEATURE:
<223> OTHER INFORMATION: Synthetic: IgG2/IgG1 hybrid with C219X deltaG
<220> FEATURE:
<221> NAME/KEY: misc_feature
<222> LOCATION: (4)..(4)
<223> OTHER INFORMATION: Xaa is any amino acid, except cysteine
```

-continued

<400> SEQUENCE: 141

Glu Arg Lys Xaa Cys Val Glu Cys Pro Pro Cys Pro Ala Pro Glu Leu
1               5                   10                  15

Leu Gly

<210> SEQ ID NO 142
<211> LENGTH: 18
<212> TYPE: PRT
<213> ORGANISM: Artificial Sequence
<220> FEATURE:
<223> OTHER INFORMATION: Synthetic: IgG2/IgG1 hybrid with C220X deltaG
<220> FEATURE:
<221> NAME/KEY: misc_feature
<222> LOCATION: (5)..(5)
<223> OTHER INFORMATION: Xaa is any amino acid, except cysteine

<400> SEQUENCE: 142

Glu Arg Lys Cys Xaa Val Glu Cys Pro Pro Cys Pro Ala Pro Glu Leu
1               5                   10                  15

Leu Gly

<210> SEQ ID NO 143
<211> LENGTH: 19
<212> TYPE: PRT
<213> ORGANISM: Homo sapiens
<220> FEATURE:
<221> NAME/KEY: misc_feature
<222> LOCATION: (1)..(19)
<223> OTHER INFORMATION: Wildtype IgG2 with C terminal X
<220> FEATURE:
<221> NAME/KEY: misc_feature
<222> LOCATION: (19)..(19)
<223> OTHER INFORMATION: Xaa is any amino acid, except cysteine

<400> SEQUENCE: 143

Glu Arg Lys Cys Cys Val Glu Cys Pro Pro Cys Pro Ala Pro Pro Val
1               5                   10                  15

Ala Gly Xaa

<210> SEQ ID NO 144
<211> LENGTH: 19
<212> TYPE: PRT
<213> ORGANISM: Artificial Sequence
<220> FEATURE:
<223> OTHER INFORMATION: Synthetic: IgG2 with C219S with C terminal X
<220> FEATURE:
<221> NAME/KEY: misc_feature
<222> LOCATION: (19)..(19)
<223> OTHER INFORMATION: Xaa is any amino acid, except cysteine

<400> SEQUENCE: 144

Glu Arg Lys Ser Cys Val Glu Cys Pro Pro Cys Pro Ala Pro Pro Val
1               5                   10                  15

Ala Gly Xaa

<210> SEQ ID NO 145
<211> LENGTH: 19
<212> TYPE: PRT
<213> ORGANISM: Artificial Sequence
<220> FEATURE:
<223> OTHER INFORMATION: Synthetic: IgG2 with C220S with C terminal X
<220> FEATURE:
<221> NAME/KEY: misc_feature
<222> LOCATION: (19)..(19)
<223> OTHER INFORMATION: Xaa is any amino acid, except cysteine -continued

<400> SEQUENCE: 145

Glu Arg Lys Cys Ser Val Glu Cys Pro Pro Cys Pro Ala Pro Pro Val
1               5                   10                  15

Ala Gly Xaa

<210> SEQ ID NO 146
<211> LENGTH: 19
<212> TYPE: PRT
<213> ORGANISM: Artificial Sequence
<220> FEATURE:
<223> OTHER INFORMATION: Synthetic: IgG2 with C219X with C terminal X
<220> FEATURE:
<221> NAME/KEY: misc_feature
<222> LOCATION: (4)..(4)
<223> OTHER INFORMATION: Xaa is any amino acid, except cysteine
<220> FEATURE:
<221> NAME/KEY: misc_feature
<222> LOCATION: (19)..(19)
<223> OTHER INFORMATION: Xaa is any amino acid, except cysteine

<400> SEQUENCE: 146

Glu Arg Lys Xaa Cys Val Glu Cys Pro Pro Cys Pro Ala Pro Pro Val
1               5                   10                  15

Ala Gly Xaa

<210> SEQ ID NO 147
<211> LENGTH: 19
<212> TYPE: PRT
<213> ORGANISM: Artificial Sequence
<220> FEATURE:
<223> OTHER INFORMATION: Synthetic: IgG2 with C220X with C terminal X
<220> FEATURE:
<221> NAME/KEY: misc_feature
<222> LOCATION: (5)..(5)
<223> OTHER INFORMATION: Xaa is any amino acid, except cysteine
<220> FEATURE:
<221> NAME/KEY: misc_feature
<222> LOCATION: (19)..(19)
<223> OTHER INFORMATION: Xaa is any amino acid, except cysteine

<400> SEQUENCE: 147

Glu Arg Lys Cys Xaa Val Glu Cys Pro Pro Cys Pro Ala Pro Pro Val
1               5                   10                  15

Ala Gly Xaa

<210> SEQ ID NO 148
<211> LENGTH: 4
<212> TYPE: PRT
<213> ORGANISM: Artificial Sequence
<220> FEATURE:
<223> OTHER INFORMATION: Synthetic: IgG2 hinge portion

<400> SEQUENCE: 148

Pro Val Ala Gly
1

<210> SEQ ID NO 149
<211> LENGTH: 7
<212> TYPE: PRT
<213> ORGANISM: Artificial Sequence
<220> FEATURE:
<223> OTHER INFORMATION: Synthetic: IgG1 hinge portion

<400> SEQUENCE: 149

Ser Cys Asp Lys Thr His Thr
1               5

<210> SEQ ID NO 150
<211> LENGTH: 4
<212> TYPE: PRT
<213> ORGANISM: Artificial Sequence
<220> FEATURE:
<223> OTHER INFORMATION: Synthetic: IgG1 hinge portion 1

<400> SEQUENCE: 150

Glu Leu Leu Gly
1

<210> SEQ ID NO 151
<211> LENGTH: 5
<212> TYPE: PRT
<213> ORGANISM: Artificial Sequence
<220> FEATURE:
<223> OTHER INFORMATION: Synthetic: IgG1 hinge portion 2

<400> SEQUENCE: 151

Glu Leu Leu Gly Gly
1               5

<210> SEQ ID NO 152
<211> LENGTH: 326
<212> TYPE: PRT
<213> ORGANISM: Artificial Sequence
<220> FEATURE:
<223> OTHER INFORMATION: Synthetic: IgG2.3 V13

<400> SEQUENCE: 152

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Asp Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn

```
            225                 230                 235                 240
Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 153
<211> LENGTH: 326
<212> TYPE: PRT
<213> ORGANISM: Artificial Sequence
<220> FEATURE:
<223> OTHER INFORMATION: Synthetic: IgG2.3 V14

<400> SEQUENCE: 153

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Asp Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Gly Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
```

```
                260                 265                 270
Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 154
<211> LENGTH: 326
<212> TYPE: PRT
<213> ORGANISM: Artificial Sequence
<220> FEATURE:
<223> OTHER INFORMATION: Synthetic: IgG2.3 V15

<400> SEQUENCE: 154

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Asp Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser Asp Glu Asp Gly Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
```

```
                  290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 155
<211> LENGTH: 326
<212> TYPE: PRT
<213> ORGANISM: Artificial Sequence
<220> FEATURE:
<223> OTHER INFORMATION: Synthetic: IgG2.3 V16

<400> SEQUENCE: 155

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
                100                 105                 110

Pro Val Ala Gly Asp Ser Val Phe Leu Phe Pro Pro Lys Pro Lys Asp
                115                 120                 125

Thr Leu Met Ile Ser Arg Thr Pro Glu Val Thr Cys Val Val Val Asp
                130                 135                 140

Val Ser His Glu Asp Gly Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Arg Pro Ile Glu Lys Thr Ile Ser Lys Thr Lys Gly Gln Pro Arg Glu
                210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
                290                 295                 300

Ser Val Met His Glu Ala Leu His Asn His Tyr Thr Gln Lys Ser Leu
305                 310                 315                 320

Ser Leu Ser Pro Gly Lys
```

<210> SEQ ID NO 156
<211> LENGTH: 326
<212> TYPE: PRT
<213> ORGANISM: Artificial Sequence
<220> FEATURE:
<223> OTHER INFORMATION: Synthetic: IgG2.3 V17

<400> SEQUENCE: 156

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Asp Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser Asp Glu Asp Gly Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Arg Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 157
<211> LENGTH: 326
<212> TYPE: PRT

<213> ORGANISM: Artificial Sequence
<220> FEATURE:
<223> OTHER INFORMATION: Synthetic: IgG2.3 V18

<400> SEQUENCE: 157

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Glu His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 158
<211> LENGTH: 326
<212> TYPE: PRT
<213> ORGANISM: Artificial Sequence
<220> FEATURE:
<223> OTHER INFORMATION: Synthetic: IgG2.3 V19

<400> SEQUENCE: 158

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Glu His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Phe Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 159
<211> LENGTH: 327
<212> TYPE: PRT
<213> ORGANISM: Artificial Sequence
<220> FEATURE:
<223> OTHER INFORMATION: Synthetic: IgG2.3G1

<400> SEQUENCE: 159

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

-continued

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 160
<211> LENGTH: 327
<212> TYPE: PRT
<213> ORGANISM: Artificial Sequence
<220> FEATURE:
<223> OTHER INFORMATION: Synthetic: IgG2.3G1 V20

<400> SEQUENCE: 160

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

```
Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Ser Cys Val Glu Cys Pro Pro Cys Pro Ala Pro
            100                 105                 110

Glu Leu Leu Gly Gly Asp Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 161
<211> LENGTH: 327
<212> TYPE: PRT
<213> ORGANISM: Artificial Sequence
<220> FEATURE:
<223> OTHER INFORMATION: Synthetic: IgG2.3G1 V21

<400> SEQUENCE: 161

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95
```

```
Thr Val Glu Arg Lys Ser Cys Val Glu Cys Pro Pro Cys Pro Ala Pro
            100                 105                 110

Glu Leu Leu Gly Gly Asp Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser His Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
            210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 162
<211> LENGTH: 327
<212> TYPE: PRT
<213> ORGANISM: Artificial Sequence
<220> FEATURE:
<223> OTHER INFORMATION: Synthetic: IgG2.3G1 V22

<400> SEQUENCE: 162

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Asp Ser Val Phe Leu Phe Pro Pro Lys Pro Lys
            115                 120                 125
```

```
Asp Thr Leu Met Ile Ser Arg Thr Pro Glu Val Thr Cys Val Val Val
    130                 135                 140

Asp Val Ser Asp Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
                195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 163
<211> LENGTH: 327
<212> TYPE: PRT
<213> ORGANISM: Artificial Sequence
<220> FEATURE:
<223> OTHER INFORMATION: Synthetic: IgG2.3G1 V23

<400> SEQUENCE: 163

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Asp Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Gly Val Lys Phe Asn Trp Tyr Val Asp
145                 150                 155                 160
```

```
Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Arg Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 164
<211> LENGTH: 327
<212> TYPE: PRT
<213> ORGANISM: Artificial Sequence
<220> FEATURE:
<223> OTHER INFORMATION: Synthetic: IgG2.3G1 V24

<400> SEQUENCE: 164

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Asp Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Asp Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Ala Leu
            195                 200                 205

Pro Arg Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
            325

<210> SEQ ID NO 165
<211> LENGTH: 327
<212> TYPE: PRT
<213> ORGANISM: Artificial Sequence
<220> FEATURE:
<223> OTHER INFORMATION: Synthetic: IgG2.3G1 V25

<400> SEQUENCE: 165

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Asp Asp Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Asp Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Arg Pro Ile Glu Lys Thr Ile Ser Lys Ala Lys Gly Gln Pro Arg
    210                 215                 220
```

```
Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 166
<211> LENGTH: 327
<212> TYPE: PRT
<213> ORGANISM: Artificial Sequence
<220> FEATURE:
<223> OTHER INFORMATION: Synthetic: IgG2.3G1 V26

<400> SEQUENCE: 166

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Asp Leu Leu Gly Asp Asp Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Asp Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Arg Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
            245                 250                 255
```

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 167
<211> LENGTH: 327
<212> TYPE: PRT
<213> ORGANISM: Artificial Sequence
<220> FEATURE:
<223> OTHER INFORMATION: Synthetic: IgG2.3G1 V27

<400> SEQUENCE: 167

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Glu His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

```
Lys Leu Thr Val Asp Lys Ser Arg Trp Gln Gln Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Pro Gly Lys
                325

<210> SEQ ID NO 168
<211> LENGTH: 327
<212> TYPE: PRT
<213> ORGANISM: Artificial Sequence
<220> FEATURE:
<223> OTHER INFORMATION: Synthetic: IgG2.3G1 V28

<400> SEQUENCE: 168

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Ser Cys Val Glu Cys Pro Pro Cys Pro Ala Pro
            100                 105                 110
Glu Leu Leu Gly Gly Pro Ser Val Phe Leu Phe Pro Pro Lys Pro Lys
    115                 120                 125
Asp Thr Leu Met Ile Ser Arg Thr Pro Glu Val Thr Cys Val Val Val
130                 135                 140
Asp Val Glu His Glu Asp Pro Glu Val Lys Phe Asn Trp Tyr Val Asp
145                 150                 155                 160
Gly Val Glu Val His Asn Ala Lys Thr Lys Pro Arg Glu Glu Gln Tyr
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Ala Phe
    195                 200                 205
Pro Ala Pro Ile Glu Lys Thr Ile Ser Lys Ala Lys Gly Gln Pro Arg
210                 215                 220
Glu Pro Gln Val Tyr Thr Leu Pro Pro Ser Arg Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
    275                 280                 285
Lys Leu Thr Val Asp Lys Ser Arg Trp Gln Gln Gly Asn Val Phe Ser
290                 295                 300
Cys Ser Val Met His Glu Ala Leu His Asn His Tyr Thr Gln Lys Ser
305                 310                 315                 320
```

```
Leu Ser Leu Ser Pro Gly Lys
                325

<210> SEQ ID NO 169
<211> LENGTH: 5
<212> TYPE: PRT
<213> ORGANISM: Artificial Sequence
<220> FEATURE:
<223> OTHER INFORMATION: Synthetic: linker

<400> SEQUENCE: 169

Pro Val Gly Val Val
1               5

<210> SEQ ID NO 170
<211> LENGTH: 4
<212> TYPE: PRT
<213> ORGANISM: Artificial Sequence
<220> FEATURE:
<223> OTHER INFORMATION: Synthetic: IgG2 hinge portion

<400> SEQUENCE: 170

Cys Cys Val Glu
1
```